US010415024B2

(12) United States Patent
Ostertag et al.

(10) Patent No.: US 10,415,024 B2
(45) Date of Patent: Sep. 17, 2019

(54) SITE-SPECIFIC ENZYMES AND METHODS OF USE

(71) Applicant: Poseida Therapeutics, Inc., San Diego, CA (US)

(72) Inventors: Eric M. Ostertag, San Diego, CA (US); Tseten Yeshi, Lexington, KY (US)

(73) Assignee: POSEIDA THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 14/443,361

(22) PCT Filed: Nov. 18, 2013

(86) PCT No.: PCT/US2013/070636
§ 371 (c)(1),
(2) Date: May 15, 2015

(87) PCT Pub. No.: WO2014/078819
PCT Pub. Date: May 22, 2014

(65) Prior Publication Data
US 2016/0060610 A1 Mar. 3, 2016

Related U.S. Application Data

(60) Provisional application No. 61/727,652, filed on Nov. 16, 2012, provisional application No. 61/802,066, filed on Mar. 15, 2013.

(51) Int. Cl.
*C12N 9/22* (2006.01)
*C07K 14/195* (2006.01)

(52) U.S. Cl.
CPC .............. *C12N 9/22* (2013.01); *C07K 14/195* (2013.01)

(58) Field of Classification Search
None
See application file for complete search history.

(56) References Cited

U.S. PATENT DOCUMENTS 4,554,101 A 11/1985 Hopp
4,873,192 A 10/1989 Kunkel
5,240,846 A 8/1993 Collins et al.
5,380,831 A 1/1995 Adang et al.
5,399,346 A 3/1995 Anderson et al.
5,436,146 A 7/1995 Shenk et al.
5,436,391 A 7/1995 Fujimoto et al.
5,529,774 A 6/1996 Barba et al.
5,547,932 A 8/1996 Curiel et al.
5,639,642 A 6/1997 Kjeldsen et al.
5,645,829 A 7/1997 Shockley et al.
5,656,465 A 8/1997 Panicali et al.
5,670,488 A 9/1997 Gregory et al.
5,672,344 A 9/1997 Kelley et al.
5,741,486 A 4/1998 Pathak et al.
5,817,492 A 10/1998 Saito et al.
5,830,880 A 11/1998 Sedlacek et al.
5,854,019 A 12/1998 Sedlacek et al.
5,869,040 A 2/1999 Oin
5,910,488 A 6/1999 Nabel et al.
5,911,983 A 6/1999 Barranger et al.
5,928,214 A 7/1999 Rubinstein et al.
5,928,914 A 7/1999 Leboulch et al.
6,596,509 B1 7/2003 Bauer et al.
6,824,978 B1 11/2004 Cox, III et al.
6,933,113 B2 8/2005 Case et al.
6,979,539 B2 12/2005 Cox, III et al.
7,001,768 B2 2/2006 Wolffe
7,013,219 B2 3/2006 Case et al.
7,070,934 B2 7/2006 Cox, III et al.
7,163,824 B2 1/2007 Cox, III et al.
7,220,719 B2 5/2007 Case et al.
7,262,054 B2 8/2007 Jamieson et al.
7,273,923 B2 9/2007 Jamieson et al.
7,285,416 B2 10/2007 Choo et al.
7,361,635 B2 4/2008 Miller et al.
7,521,241 B2 4/2009 Choo et al.
7,790,379 B2 9/2010 Laemmli et al.
8,586,526 B2 * 11/2013 Gregory ................. C12N 15/62 435/23
9,499,592 B2 * 11/2016 Zhang .................. C07K 14/195
2003/0138850 A1 7/2003 Mossner et al.
2005/0272107 A1 12/2005 Rabbitts et al.
2006/0099654 A1 5/2006 Huster
(Continued)

FOREIGN PATENT DOCUMENTS

CA 2246005 A1 4/2000
EP 2 522 726 A1 11/2012
(Continued)

OTHER PUBLICATIONS

Remenent et al., "RGeseeanrcho amrticlee s of three tomato pathogens within the Ralstonia solanacearum species complex reveal significant evolutionary divergence", BMC Genomics, 2010, 11:379 (1-16).*

UniProtKB Sequence information for D8N2L9 Retrieved from <http://www.uniprot.org/uniprot/D8N2L9> on Jun. 14, 2017.*

Schandry et al., "TALE-Like Effectors Are an Ancestral Feature of the Ralstonia solanacearum Species Complex and Converge in DNA Targeting Specificity", Frontiers in Plant Science; Aug. 2016, vol. 7, Article 1225, pp. 1-16. doi: 10.3389/fpls.2016.01225.*

Michelle Christian, "Targeting DNA Double-Strand Breaks with TAL Effector Nucleases", Genetics vol. 186, No. 2, Oct. 31, 2010, pp. 757-761 (and supporting information, pp. 1-8.).

Yanqiang Li, "Molecular recognition code between pathogene bacterial TAL-effectors and host target genes", Chinese Journal of Biotechnology, vol. 27, No. 8, Aug. 31, 2011, pp. 1132-1141 (English Abstract and Figure Legends provided).
(Continued)

*Primary Examiner* — Suzanne M Noakes
(74) *Attorney, Agent, or Firm* — Cooley LLP; Ivor R. Elrifi; Matthew Pavao

(57) ABSTRACT

The present invention provides polypeptides related to *Ralstonia* proteins, nucleic acids encoding the same, compositions comprising the same, kits comprising the same, non-human transgenic animals comprising the same, and methods of using the same.

8 Claims, 2 Drawing Sheets

Specification includes a Sequence Listing.

(56) References Cited

U.S. PATENT DOCUMENTS

2009/0305402 A1 12/2009 Liljedahl et al.
2012/0270273 A1 10/2012 Zhang et al.
2013/0117869 A1 5/2013 Duchateau et al.
2014/0068797 A1 3/2014 Doudna et al.
2014/0298505 A1 10/2014 Kühn
2014/0304847 A1 10/2014 Kühn
2015/0044772 A1 2/2015 Zhao
2017/0107541 A1 4/2017 Ostertag et al.
2017/0114149 A1 4/2017 Ostertag et al.
2018/0187185 A1 7/2018 Ostertag et al.

FOREIGN PATENT DOCUMENTS

WO WO 2000/071702 A1 11/2000
WO 2007060495 A1 5/2007
WO 2009095793 A1 8/2009
WO WO 2011/146121 A1 11/2011
WO WO 2012/093833 A2 7/2012
WO 2012158986 A2 11/2012
WO WO 2012/168304 A1 12/2012
WO WO 2013/152220 A2 10/2013
WO WO 2014/089290 A1 6/2014
WO WO 2015/195798 A1 12/2015

OTHER PUBLICATIONS

Bochtler M. "Structural basis of the TAL effector-DNA interaction", *Biological Chemistry*, vol. 393, No. 10, Oct. 2012, pp. 1055-1066.
De Lange O. et al. "Breaking the DNA-binding code of Ralstonia solanacearum TAL effectors provides new possibilities to generate plant resistance genes against bacterial wilt disease", *New Phytologist*, vol. 199, No. 3, May 21, 2013, pp. 773-786.
Arora & Leppla, Residues 1-254 of anthrax toxin lethal factor are sufficient to cause cellular uptake of fused polypeptides, J Biol Chem 1993 268(5):3334-41.
Ballas et al., Efficient functioning of plant promoters and poly(A) sites in Xenopus oocytes, Nucleic Acids Res 1989 17(19):7891-903.
Chevalier et al., Design activity and structure of a highly specific artificial endonuclease, Mol Cell 2002 10(4):895-905.
Choulika et al., Induction of homologous recombination in mammalian chromosomes by using the I-Scel system of *Saccharomyces cerevisiae*, Mol Cell Biol 1995 15(4):1968-73.
Della-Cioppa et al., Protein trafficking in plant cells, Plant Physiol 1987 84(4):965-8.
Derossi, The third helix of the Antennapedia homeodomain translocates through biological membranes, J Biol Chem 1994 269(14):10444-50.
Donnelly et al., Targeted delivery of peptide epitopes to class I major histocompatibility molecules by a modified Pseudomonas exotoxin, PNAS 1993 90(8):3530-4.
Elliott & O'Hare, Intercellular trafficking and protein delivery by a herpesvirus structural protein, Cell 1997 88(2):223-33.
Elroy-Stein et al., Cap-independent translation of mRNA conferred by encephalomyocarditis virus 5' sequence improves the performance of the vaccinia virus/bacteriophage T7 hybrid expression system, PNAS 1989 86(16):6126-30.
Fajardo-Sanchez et al., Computer design of obligate heterodimer meganucleases allows efficient cutting of custom DNA sequences, Nucleic Acids Res 2008 36(7):2163-73.
Fåhraeus et al., Inhibition of pRb phosphorylation and cell-cycle progression by a 20-residue peptide derived from p16CDKN2/INK4A, Curr Biol 1996 6(1):84-91.
Joshi, Putative polyadenylation signals in nuclear genes of higher plants: a compilation and analysis, Nucleic Acids Res 1987 15(23):9627-40.
Kim et al., Hybrid restriction enzymes: zinc finger fusions to Fokl cleavage domain, PNAS 1996 93(3):1156-60.
Klimpel et al., Anthrax toxin protective antigen is activated by a cell surface protease with the sequence specificity and catalytic properties of furin, PNAS 1992 89(21):10277-81.
Kunkel, Rapid and efficient site-specific mutagenesis without phenotypic selection, PNAS 1985 82(2):488-92.
Li et al., Functional domains in Fokl restriction endonuclease, PNAS 89(10):4275-4279.
Miller et al., A TALE nuclease architecture for efficient genome editing, Nat Biotechnol 2011 29(2):143-8.
Mogen et al., Upstream sequences other than AAUAAA are required for efficient messenger RNA 3'-end formation in plants, Plant Cell 1990 2(12):1261-72.
Novak et al., Functional characterization of protease-treated Bacillus anthracis protective antigen, J Biol Chem 1992 267(24):17186-93.
Perelle et al., Characterization of Clostridium perfringens iota-toxin genes and expression in *Escherichia coli*, Infect Immun 1993 61(12):5147-56.
Puchta et al., Homologous recombination in plant cells is enhanced by in vivo induction of double strand breaks into DNA by a site-specific endonuclease, Nucleic Acids Res 1993 21(22):5034-40.
Reyon et al., FLASH assembly of TALENs for high-throughput genome editing, Nat Biotechnol 2012 30(5):460-5.
Sanfaçon et al., A dissection of the cauliflower mosaic virus polyadenylaion signal. Genes Dev 1991 5(1):141-9.
Sebo et al., Cell-invasive activity of epitope-tagged adenylate cyclase of Bordetella pertussis allows in vitro presentation of a foreign epitope to CD8+ cytotoxic T cells, Infect Immun 1995 63(10):3851-7.
Segal et al., Endonuclease-induced, targeted homologous extrachromosomal recombination in Xenopus oocytes, PNAS 1995 92(3):806-10.
Stenmark et al., Peptides fused to the amino-ternimal end of diphtheria toxin are translocated to the cytosol, J Cell Biol 1991 113(5):1025-32.
Thierry et al., Cleavage of yeast and bacteriophage T7 genomes at a single site using the rare cutter endonuclease I-Sce I, Nucleic Acids Res 1991 19(1):189-90.
Salanoubat, M. et al. "Genome sequence of the plant pathogen Ralstonia solanacearum", Nature, 2002, vol. 415, p. 497-502.
Abe, R. et al. (Apr. 11, 2014) "Ultra Q-bodies: quench-based antibody probes that utilize dye-dye interactions with enhanced antigen-dependent fluorescence" *Scientific Reports*, 4:4640; DOI: 10.1038/srep04640, 9 pages.
Addgene, "TALEN Expression Vectors for REAL, REAL-Fast and FLASH" [online]. Retrieved from the Internet: www.addgene.org/talengineering/expressionvectors/, Retrieved on Aug. 22, 2018; 1 page.
Allison, R. (Oct. 15, 1986) "The nucleotide sequence of the coding region of tobacco etch virus genomic RNA: evidence for the synthesis of a single polyprotein" Virology, 154:9-20.
An, G. et al. (1986) "Transformation of Tobacco, Tomato, Potato, and *Arabidopsis thaliana* Using a Binary Ti Vector System", Plant Physiol., 81:301-305.
Asano, et al. (1994) "Transgenic plants of *Agrostis alba* obtained by electroporation-mediated direct gene transfer into protoplasts", Plant Cell Reports 13:243-246.
Auf Der Maur, A. et al. (2002) "Direct in vivo screening of intrabody libraries constructed on a highly stable single-chain framework", *Journal of Biological Chemistry*, vol. 277, No. 47, pp. 45075-45085.
Ayres, N.M. and Park, W.D. (1994) "Genetic Transformation of Rice", Critical Reviews in Plant Sciences, 13:219-239.
Baim et al. (Jun. 1991) "A chimeric mammalian transactivator based on the lac repressor that is regulated by temperature and isopropyl (β-D-thiogalactopyranoside", Proc. Natl. Acad. Sci. USA, 88:5072-5076.
Banta, S. et al. (2013) "Replacing Antibodies: Engineering New Binding Proteins" Annual Reviews Biomedical Engineering, 15:93-113.
Barcelo, P. et al. (1994) "Transgenic cereal (tritordeum) plants obtained at high efficiency by microprojectile bombardment of inflorescence tissue", Plant Journal, 5:583-592.
Barkley, M.D. et al. (1980) "Repressor Recognition of Operator and Effectors", The Operon, p. 177-220.

(56) References Cited

OTHER PUBLICATIONS

Barlos, K. et. al. (1989) "Darstellung geschützter peptid-fragmente unter einsatz substituierter triphenylmethyl-harze" Tetrahedron Lett, 30(30):3943-3946. German with English Summary on p. 3943.
Becker, D. et al. (1994) "Fertile transgenic wheat from microprojectile bombardment of scutellar tissue", Plant. Journal, 5:299-307.
Bibikova, M. et al. (May 2, 2003) "Enhancing Gene Targeting with Designed Zinc Finger Nucleases", Science, 300:764.
Bolte, S. et al. (2004) "The N-myristoylated Rab-GTPase m-Rab$_{mc}$ is involved in post-Golgi trafficking events to the lytic vacuole in plant cells", Journal of Cell Science, 117:943-954.
Borkowska, M. et al. (1994) "Transformation of diploid potato with an *Agrobacterium tumefaciens* binary vector system: I. Methodological approach" *Acta. Physiol Plant.* 16(3):225-230.
Brooks, A.I. et al. (1998) "Reproducible and efficient murine CNS gene delivery using a microprocessor-controlled injector" J. Neurosci. Methods, 80:137-147.
Brown, M. et al. (Jun. 5, 1987) "lac Repressor Can Regulate Expression from a Hybrid SV40 Early Promoter Containing a lac Operator in Animal Cells" Cell, 49:603-612.
Campbell, W.H. and G. Gowri (1990) "Codon Usage in Higher Plants, Green Algae, and Cyanobacteria" Plant Physiol, 92:1-11.
Carbonetti, N. et al. (1995) "Use of Perussis toxin Vaccine Molecule PT9K/129G to Deliver Peptide Epitopes for Stimulation of a Cytotoxic T Lymphocyte Response" Abstr. Annu. Meet. Am Soc. Microbiol., 95:295, Abstract E-86.
Casas, A.M. et al. (Dec. 1993) "Transgenic sorghum plants via microprojectile bombardment" Proc. Nat. Acad Sci. USA, 90:11212-11216.
Chee, P.P. and J.L. Slightom (1992) "Transformation of cucumber tissues by microprojectile bombardment: identification of plants containing functional and non-functional transferred genes" (1992) Gene, 118:255-260.
Christopherson, K.S. et al. (Jul. 1992) "Ecdysteroid-dependent regulation of genes in mammalian cells by a *Drosophila* ecdysone receptor and chimeric transactivators" Proc. Natl. Acad. Sci. USA, 89:6314-6318.
Christou, P. et al. (1992) "The development of a variety-independent gene-transfer method for rice" TIBTECH, 10:239-246.
Christou, P. (Mar./Apr. 1994) "Genetic engeenering of crop legumes and cereals: current status and recent advances" Agro. Food. Ind. Hi Tech., 5:17-27.
Christou, P. (Jul. 1993) "Philosophy and practive of variety-independent gene transfer into recalcitrant crops" In Vitro Cell. Dev. Biol., 29P:119-124.
Cong, L. et al. (Feb. 15, 2013) "Multiplex Genome Engineering Using CRISPR/Cas Systems", Science, 339(6121):819-823.
Cousins, Y.L. et al. (1991) "Transformation of an Australian Cotton Cultivar: Prospects for Cotton Improvement through Genetic Engineering", Aust. J. Plant Physiol., 18:481-494.
Davies, D.R. et al. (1993) "Transformation of peas" Plant Cell Rep, 12:180-183.
De Block, M. (1988) "Genotype-independent leaf disc transformation of potato (*Solanum tuberosum*) using *Agrobacterium tumefaciens*", Theor. Appl Genet. 76:767-774.
Degenkolb, J. et al. (Aug. 1991) "Structural Requirements of Tetracycline-Tet Repressor Interaction: Determination of Equilibrium Binding Constants for Tetracycline Analogs with the Tet Repressor" Antimicrob. Agents Chemother., 35:1591-1595.
Deuschle, U. et al. (Jul. 1989) "Regulated expression of foreign genes in mammalian cells under the control of coliphage T3 RNA polymerase and lac repressor" Proc. Natl. Acad. Aci. USA, 86:5400-5404.
Deuschle, U. et al. (1990) "RNA Polymerase II Transcription Blocked by *Escherichia coli* Lac Repressor" Science, 248:480-483.
D'Halluin, K. et al. (Mar. 1992) "Transformation of Sugarbeet (*Beta vulgaris* I.) and evaluation of herbicide resistance in transgenic plants" Bio/Technol, 10:309-314.
Dhir, S.K. et al. (1992) "Regeneration of Transgenic Soybean (*Glycine max*) Plants from Electroporated Protoplasts" Plant Physiol, 99:81-88. Includes "Notice of Retraction", May 10, 1993, 102:331.
Dong, J-Z. and McHughen, A. (1993) "Transgenic flax plants from *Agrobacterium* mediated transformation: incidence of chimeric regenerants and inheritance of transgenic plants" Plant Sci., 91:139-148.
Eapen, S. and L. George (1994) "*Agrobacterium tumefaciens* mediated gene transfer in peanut (*Arachis hypogaea* L.)" Plant Cell Rep., 13:582-586.
Fetter et al. (Jan. 2004) "Interactions between Plasma Membrane Aquaporins Modulate Their Water Channel Activity", Plant Cell, 16:215-228.
Fields, S. and O-k Song (Jul. 1989) "A Novel Genetic System to Detect Protein-Protein Interactions" *Nature*, vol. 340, No. 6230, pp. 245-246.
Figge, J. et al. (Mar. 11, 1988) "Stringent Regulation of Stably Integrated Chloramphenicol Acetyl Transferase Genes by *E. coli* lac Repressor in Monkey Cells", Cell, 52:713-722.
Franklin, C. I. and T.N. Trieu (May 1993) "Transformation of the forage grass caucasian bluestem via biolistic bombardment-mediated DNA transfer" Plant. Physiol. Suppl., 102(1):167, Abstract 958.
Fry, J. et al. (1987) "Transformation of *Brassica napus* with *Agrobacterium tumefaciens* based vectors", Plant Cell Rep, 6:321-325.
Fuerst, T.R. et al. (Apr. 1989) "Transfer of the inducible lac repressor/operator system from *Escherichia coli* to a vaccinia virus expression vector", Proc. Natl. Acad. Sci. USA, 86:2549-2553.
Galán, J.E. and A. Collmer (May 21, 1999) "Type III Secretion Machines: Bacterial Devices for Protein Delivery into Host Cells" Science, 284:1322-1328.
Gallie, D.R. et al. (1989) "Eukaryotic viral 5'-leader sequences act as translational enhancers in eukaryotes and prokaryotes" in *Molecular Biology of RNA*. Thomas R. Cech (Ed.), New York: Alan R. Liss, Inc.; pp. 237-256.
Gallie, D.R. et al. (1995) "The tobacco etch viral 5' leader and poly(A) tail are functionally synergistic regulators of translation" Gene, 165(2):233-238.
Gilbert, L. et al. (Jul. 18, 2013) "CRISPR-Mediated Modular RNA-Guided Regulation of Transcription in Eukaryotes" Cell, 154(2):442-451.
Gill, G. and M. Ptashne (1988) "Negative effect of the transcriptional activator GAL4" *Nature*, 334:721-724.
Golovkin, M. et al. (1993) "Production of transgenic maize plants by direct DNA uptake into embryogenic protoplasts" Plant Science, 90:41-52.
Gossen, M. and H. Bujard (Jun. 1992) "Tight control of gene expression in mammalian cells by tetracycline-responsive promoters", Proc. Natl. Acad. Sci. USA, 89:5547-5551.
Guerineau, F. et al. (1991) "Effect of deletions in the cauliflower mosaic virus polyadenylation sequence on the choice of the polyadenylation sites in tobacco protoplasts" Mol. Gen. Genet., 262:141-144.
Guglielmi, L. et al. (2011) "Selection for intrabody solubility in mammalian cells using GFP fusions". *Protein Engineering, Design & Selection*, 24(12):873-881.
Guilinger, J.P. et al. (Jun. 2014) "Fusion of catalytically inactive Cas9 to FokI nuclease improves the specificity of genome modification" *Nature Biotechnology*, vol. 32, No. 6, pp. 577-582.
Guo et al. (Dec. 1993) "Transgenic Plants Obtained From Wheat Protoplasts Transformed by PEGmediated Direct Gene Transfer", Chinese Science Bulletin, 38(24):2072-2078.
Hartman, C.L. et al. (Sep. 1994) "Herbicide resistant turfgrass (*Agrostis palustris* Huds.) by biolostic transformation", *Bio-Technology*, 12:919-923.
Hassanzadeh-Ghassabeh, G. et al. (2013) "Nanobodies and their potential applications" *Nanomedicine*, 8(6):1013-1026.
Hillen, W. and Wissmann, A. (1989) "Tet repressor-tet operator interaction", Topics Mol. Struc. Biol., 10:143-162.
Hinchee, M.A.W. et al. (1990) "Transformation and regeneration of non-solanaceous crop plants", in *Gene Manipulation in Plant Improvement II*. J.P. Gustafson (Ed.), New York: Plenum Press; p. 203-212.

(56) References Cited

OTHER PUBLICATIONS

Holliger, P. and P.J. Hudson (Sep. 2005) "Engineered antibody fragments and the rise of single domains" *Nature Biotechnology*, 23(9):1126-1136.

Hu, M.C.-T. and N. Davidson (Feb. 27, 1987) "The Inducible lac Operator-Repressor System Is Functional in Mammalian Cells", *Cell*, 48:555-566.

Jobling, S.A. et al. "Enhanced translation of chimaeric messenger RNAs containing a plant viral untranslated leader sequence", (1987) *Nature* 325:622-625.

Kato, N. et al. (Jul. 2002) "Spectral Profiling for the Simultaneous Observation of Four Distinct Fluorescent Proteins and Detection of Protein-Protein Interaction via Fluorescence Resonance Energy Transfer in Tobacco Leaf Nuclei", Plant Physiology, 129:931-942.

Kleinschmidt, C. et al. (1988) "Dynamics of Repressor-Operator Recognition: The Tn10-Encoded Tetracycline Resistance Control", *Biochemistry*, 27:1094-1104.

Kulinski, J. et al. "CEL I Enzymatic Mutation Detection Assay", *BioTechniques* (2000), 29(1):44-48.

Kunkel, T.A. et al. (1987) "Rapid and Efficient Site-Specific Mutagenesis without Phenotypic Selection" Methods in Enzymol, 154:367-382.

Kyte, J. and R.F. Doolittle (1982) "A Simple Method for Displaying the Hydropathic Character of a Protein" J. Mol. Biol. 157:105-132.

Labow, M.A. et al. (Jul. 1990) "Conversion of the lac Repressor into an Allosterically Regulated Transcriptional Activator for Mammalian Cells", Molecular and Cellular Biology, 10(7):3343-3356.

Lehninger, A.L. "The amino acid building blocks of proteins", in *Biochemistry*, Second Edition. Worth Publishers, Inc., 1975; p. 71-77.

Li, Y. et al. (Nov. 28, 2012) "Transcription activator-like effector hybrids for conditional control and rewiring of chromosomal transgene expression", *Scientific Reports*, vol. 2, No. 897, DOI: 10.1038/srep00897; 7 pages.

Li, L. et al. (Jul. 2013) "Characterization and DNA-Binding Specificities of *Ralstonia* TAL-Like Effectors" Mol Plant, 6(4):1318-1330.

Lommel, S.A. et al. (1991) "Identification of the Maize Chlorotic Mottle Virus Capsid Protein Cistron and Characterization of its Subgenomic Messenger RNA", Virology, 81:382-385.

Luo, Y. et al. (1997) "Mammalian Two-Hybrid System: A Complementary Approach to the Yeast Two-Hybrid System" *Biotechniques*, vol. 22, No. 2, pp. 350-352.

Macejak, D.G. and P. Sarnow (Sep. 5, 1991) "Internal initiation of translation mediated by the 5' leader of a cellular mRNA", Nature, 353:90-94.

Mali, L. et al. (Feb. 13, 2013) "RNA-Guided Human Genome Engineering via Cas9" *Science*, 339(6121):823-826.

Mali, P. et al. (Sep. 2013) "CAS9 transcriptional activators for target specificity screening and paired nickases for cooperative genome engineering", *Nature Biotechnology*, vol. 31, No. 9, p. 833-840.

Maynard, J. and G. Georgiou et al. (2000) "Antibody Engineering" *Annual Reviews Biomedical Engineering*, 02:339-376.

Mino, T. et al. (2009) "Efficient double-stranded DNA cleavage by artificial zinc-finger nucleases composed of one zinc-finger protein and a single-chain FokI dimer" J. Biotechnol., 140:156-161.

Mössner, E. et al. (2001) "Fast selection of antibodies without antigen purification: adaptation of the protein fragment complementation assay to select antigen-antibody pairs" *Journal of Molecular Biology*, vol. 308, No. 2, pp. 115-122.

Munroe, D. and A. Jacobson (1990) "Tales of poly(A): a review", Gene, 91:151-158.

Muramatsu, T. et al. (Jan. 1998) "In vivo electroporation: a powerful and convenient means of nonviral gene transfer to tissues of living animals (Review)" Int. J. Mol. Med., 1:55-62.

Murray, E.E. et al. (1989) "Codon usage in plant genes", Nucleic Acids Research, 17:477-498.

Oliva, B. et al. (May 1992) "Evidence that Tetracycline Analogs Whose Primary Target Is Not the Bacterial Ribosome Cause Lysis of *Escherichia coli*", Antimicrobial Agents and Chemotherapy, 36:913-919.

Phelan, A. et al. (May 1998) "Intercellular Delivery of Functional p53 by the Herpesvirus Protein VP22" Nat. Biotechnol., 16:440-443.

Proudfoot, N. (Feb. 22, 1991) "Poly(A) Signals", Cell, 64:671-674.

Reines, D. and J. Mote, Jr. (Mar. 1993) "Elongation factor SII-dependent transcription by RNA polymerase II through a sequence-specific DNA-binding protein", Proc. Natl. Acad. Sci. USA, 90:1917-1921.

Reznikoff, W.S. (1992) "The lactose operon-controlling elements: a complex paradigm", Molecular Microbiology, 6(17):2419-2422.

Ritala, A. et al. (1994) "Fertile transgenic barley by particle bombardment of immature embryos", Plant. Mol. Biol., 24:317-325.

Schwarze, S.R. et al. (Jul. 2000) "Protein Transduction: Unrestricted Delivery Into All Cells?" Trends Cell Biol, 10:290-295.

Secco, P. et al. (2009) "Antibody library selection by the β-lactamase protein fragment complementation assay", *Protein Engineering, Design and Selection*, vol. 22, No. 3, pp. 149-158.

Shulka, V.K. et al. (2009) "Precise genome modification in the crop species *Zea mays* using zinc-finger nucleases" Nature, 459:437-441.

Smolarek, D. et al. (2010) "A recombinant dromedary antibody fragment (VHH or nanobody) directed against human Duffy antigen receptor for chemokines" Cell Mol Life Sci, 67(19):3371-3387. Author Manuscript, HAL Archives Ouvertes—France [online]. Retrieved from: https://www.ncbi.nlm.nih.gov/pmc/articles/PMC2966875/?report=printable; retreived on Jun. 18, 2018, 30 pages.

Stenmark, H. et al. "Peptides Fused to the Amino-Terminal End of Diphtheria Toxin Are Translocated to the Cytosol" (1991) *J. Cell Biol.* 113:1025 1032.

Su, W.W. et al. (2004) "High-Level Secretion of Functional Green Fluorescent Protein From Transgenic Tobacco Cell Cultures: Characterization and Sensing", Biotechnol Bioeng, 85:610-619.

Tanenbaum, M. et al. (Oct. 2014) "A Protein-Tagging System for Signal Amplification in Gene Expression and Fluorescence Imaging" *CELL*, vol. 159, No. 3, pp. 635-646.

Tatusova and Madden, "Blast 2 Sequences, a new tool for comparing protein andnucleotide sequences", *FEMS Microbiology Letters* (1999), 174:247-250.

Townsend, J.A. et al. (May 21, 2009) "High-frequency modification of plant genes using engineered zinc-finger nucleases" Nature, 459:442-445.

Tsai, S. et al. (Jun. 2014) "Dimeric CRISPR RNA-guided Fokl nucleases for highly specific genome editing", *Nature Biotechnology*, vol. 32, No. 6, p. 569-577.

Urnov, F.D. et al. (Jun. 2005) "Highly efficient endogenous human gene correction using designated zinc-finger nucleases" Nature, 435:646-651.

Vannocci, T. et al. (2014) "Nuclease-stimulated homologous recombination at the human beta-globin gene", *The Journal of Gene Medicine*, vol. 16, No. 1-2, p. 1-10.

Vielemeyer, O. et al. (2010) "Characterization of single chain antibody targets through yeast two hybrid" *BMC Biotechnology*, 10:59, 13 pages.

Visintin, M. et al. (Oct. 1999) "Selection of antibodies for intracellular function using a two-hybrid in vivo system", *Proceedings of The National Academy of Sciences*, USA, vol. 96, No. 21, pp. 11723-11728.

Wan, Y. C. and P.G. Lemaux (1994) "Generation of Large Numbers of Independently Transformed Fertile Barley Plants" Plant Physiol., 104:37-48.

Wright, D.A. et al. (2005) "High-frequency homologous recombination in plants mediated by zinc-finger nucleases" The Plant Journal, 44:693-705.

Wyborski, D.L. and J.M. Short (1991) "Analysis of inducers of the *E.coli* lac repressor system in mammalian cells and whole animals", Nucleic Acids Res, 19:4647-4653.

Yao, T-P. et al. (Oct. 2, 1992) "*Drosophila* ultraspiracle modulates ecdysone receptor function via heterodimer formation" Cell, 71:63-72.

Yarranton, G.T. "Inducible vectors for expression in mammalian cells" Curr. Opin. Biotech., 3:506-511.

(56) References Cited

OTHER PUBLICATIONS

Zambretti, G.P. et al. (May 1992) "A mutant p53 protein is required for maintenance of the transformed phenotype in cells transformed with p53 plus ras cDNAs" Proc. Natl Acad. Sci. USA, 89:3952-3956.
GenBank Accession No. A34965 (Jul. 16, 1999) "62K membrane antigen ipaB—Shigella flexneri plasmid" National Center for Biotechnology Information (NCBI).gov [online]. Retrieved from: http://www.ncbi.nlm.nih.gov/protein/A34965; retrieved on Feb. 21, 2019; 2 pages.
GenBank Accession No. AAA25728 (Jul. 26, 1993) "avirulence protein [*Pseudomonas syringae*]" National Center for Biotechnology Information (NCBI).gov [online]. Retrieved from: http://www.ncbi.nlm.nih.gov/protein/AAA25728; retrieved on Feb. 15, 2019; 1 page.
GenBank Accession No. AAA26525 (Apr. 26, 1993) "IpaA protein, partial [*Shigella flexneri*]" National Center for Biotechnology Information (NCBI).gov [online]. Retrieved from: http://www.ncbi.nlm.nih.gov/protein/AAA26525; retrieved on Feb. 15, 2019; 1 page.
GenBank Accession No. AAC02071 (Oct. 4, 1999) "SopE [*Salmonella enterica* subsp. enterica serovar Typhimurium str. SL1344]" National Center for Biotechnology Information (NCBI).gov [online]. Retrieved from: http://www.ncbi.nlm.nih.gov/protein/AAC02071; retrieved on Feb. 15, 2019; 1 page.
GenBank Accession No. AAC44349 (Sep. 4, 1996) "protein tyrosine phosphatase SptP [*Salmonella enterica* subsp. enterica serovar Typhimurium str. SL1344]" National Center for Biotechnology Information (NCBI).gov [online]. Retrieved from: http://www.ncbi.nlm.nih.gov/protein/AAC44349; retrieved on Feb. 15, 2019; 2 pages.
GenBank Accession No. AAC69765 (Jul. 26, 2016) "secreted protein kinase (plasmid) [*Yersinia pestis*]" National Center for Biotechnology Information (NCBI).gov [online]. Retrieved from: http://www.ncbi.nlm.nih.gov/protein/AAC69765; retrieved on Feb. 15, 2019; 2 pages.
GenBank Accession No. AAC69766 (Jul. 26, 2016) "targeted effector protein (plasmid) [*Yersinia pestis*]" National Center for Biotechnology Information (NCBI).gov [online]. Retrieved from: http://www.ncbi.nlm.nih.gov/protein/AAC69766; retrieved on Feb. 15, 2019; 1 page.
GenBank Accession No. AAC69768 (Jul. 26, 2016) "targeted effector protein (plasmid) [*Yersinia pestis*]" National Center for Biotechnology Information (NCBI).gov [online]. Retrieved from: http://www.ncbi.nlm.nih.gov/protein/AAC69768; retrieved on Feb. 15, 2019; 2 pages.
GenBank Accession No. AAD11434 (Feb. 1, 1999) "avirulence protein AvrBs2 [*Xanthomonas euvesicatoria*]" National Center for Biotechnology Information (NCBI).gov [online]. Retrieved from: http://www.ncbi.nlm.nih.gov/protein/AAD11434; retrieved on Feb. 21, 2019; 2 pages.
GenBank Accession No. AAF21057 (Dec. 29, 1999) "invasion protein D, partial [*Salmonella typhimurium*]" National Center for Biotechnology Information (NCBI).gov [online]. Retrieved from: http://www.ncbi.nlm.nih.gov/protein/AAF21057.1; retrieved on Feb. 21, 2019; 1 page.
GenBank Accession No. AAF71481.1 (May 23, 2000) "type III effector protein [*Pseudomonas syringae* pv. syringae]" National Center for Biotechnology Information (NCBI).gov [online]. Retrieved from: http://www.ncbi.nlm.nih.gov/protein/AAF71481.1; retrieved on Feb. 21, 2019; 1 page.
GenBank Accession No. AAG03434 (Jan. 31, 2014) "exoenzyme T [*Pseudomonas aeruginosa* PAO1]" National Center for Biotechnology Information (NCBI).gov [online]. Retrieved from: http://www.ncbi.nlm.nih.gov/protein/AAG03434; retrieved on Feb. 15, 2019; 2 pages.
GenBank Accession No. AAG05579 (Jan. 31, 2014) "adenylate cyclase ExoY [*Pseudomonas aeruginosa* PAO1]" National Center for Biotechnology Information (NCBI).gov [online]. Retrieved from: http://www.ncbi.nlm.nih.gov/protein/AAG05579; retrieved on Feb. 15, 2019; 2 pages.
GenBank Accession No. AAG07228 (Jan. 31, 2014) "exoenzyme S [*Pseudomonas aeruginosa* PAO1]" National Center for Biotechnology Information (NCBI).gov [online]. Retrieved from: http://www.ncbi.nlm.nih.gov/protein/AAG07228; retrieved on Feb. 15, 2019; 2 pages.
GenBank Accession No. AF232006 (May 23, 2000) "Pseudomonas syringae pv. tomato strain DC3000 AvrE (avrE), HrpW (hrpW), and GstA (gstA) genes, complete cds; and unknown genes" National Center for Biotechnology Information (NCBI).gov [online]. Retrieved from: http://www.ncbi.nlm.nih.gov/protein/AF232006.1; retrieved on Feb. 21, 2019; 8 pages.
GenBank Accession No. BAA96815 (Jun. 22, 2000) "Tir [*Escherichia coli*]" National Center for Biotechnology Information (NCBI).gov [online]. Retrieved from: http://www.ncbi.nlm.nih.gov/protein/BAA96815; retrieved on Feb. 15, 2019; 2 pages.
GenBank Accession No. CAA34257 (Jul. 26, 2016) "avirulence protein avrBs3 (plasmid) [*Xanthomonas vesicatoria*]" National Center for Biotechnology Information (NCBI).gov [online]. Retrieved from: http://www.ncbi.nlm.nih.gov/protein/CAA34257; retrieved on Feb. 15, 2019; 2 pages.
GenBank Accession No. CAA63302 (Jul. 23, 2016) "sipA, partial [*Salmonella enterica* subsp. enterica serovar Typhi str. Ty2]" National Center for Biotechnology Information (NCBI).gov [online]. Retrieved from: http://www.ncbi.nlm.nih.gov/protein/CAA63302; retrieved on Feb. 15, 2019; 1 page.
GenBank Accession No. EFW82095 (Jan. 28, 2011) "chemotaxis-specific methylesterase [*Pseudomonas savastanoi* pv. glycinea str. B076]" National Center for Biotechnology Information (NCBI).gov [online]. Retrieved from: http://www.ncbi.nlm.nih.gov/protein/EFW82095; retrieved on Feb. 15, 2019; 2 pages.
GenBank Accession No. EFW86187 (Jan. 28, 2011) "chemotaxis-specific methylesterase [*Pseudomonas savastanoi* pv. glycinea str. race 4]" National Center for Biotechnology Information (NCBI).gov [online]. Retrieved from: http://www.ncbi.nlm.nih.gov/protein/EFW86187; retrieved on Feb. 15, 2019; 2 pages.
GenBank Accession No. EGH06695 (May 22, 2012) "chemotaxis-specific methylesterase [*Pseudomonas amygdali* pv. morsprunorum str. M302280]" National Center for Biotechnology Information (NCBI).gov [online]. Retrieved from: http://www.ncbi.nlm.nih.gov/protein/EGH06695; retrieved on Feb. 15, 2019; 2 pages.
GenBank Accession No. EGH23390 (Apr. 28, 2011) "chemotaxis-specific methylesterase [*Pseudomonas amygdali* pv. mori str. 301020]" National Center for Biotechnology Information (NCBI).gov [online]. Retrieved from: http://www.ncbi.nlm.nih.gov/protein/EGH23390; retrieved on Feb. 15, 2019; 2 pages.
GenBank Accession No. EGH31878 (May 22, 2011) "chemotaxis-specific methylesterase, partial [*Pseudomonas syringae* pv. japonica str. M301072]" National Center for Biotechnology Information (NCBI).gov [online]. Retrieved from: http://www.ncbi.nlm.nih.gov/protein/EGH31878; retrieved on Feb. 15, 2019; 2 pages.
GenBank Accession No. EGH48032 (Apr. 28, 2011) "chemotaxis-specific methylesterase, partial [*Pseudomonas syringae* pv. pisi str. 1704B]" National Center for Biotechnology Information (NCBI).gov [online]. Retrieved from: http://www.ncbi.nlm.nih.gov/protein/EGH48032; retrieved on Feb. 15, 2019; 2 pages.
GenBank Accession No. EGH54563 (Apr. 28, 2011) "chemotaxis-specific methylesterase [*Pseudomonas syringae* Cit 7]" National Center for Biotechnology Information (NCBI).gov [online]. Retrieved from: http://www.ncbi.nlm.nih.gov/protein/EGH54563; retrieved on Feb. 15, 2019; 2 pages.
GenBank Accession No. EGH56182 (Apr. 28, 2011) "amino acid adenylation, partial [*Pseudomonas syringae* Cit 7]" National Center for Biotechnology Information (NCBI).gov [online]. Retrieved from: http://www.ncbi.nlm.nih.gov/protein/EGH51682; retrieved on Feb. 15, 2019; 1 page.
GenBank Accession No. EGH61007 (Apr. 28, 2011) "chemotaxis-specific methylesterase [*Pseudomonas syringae* pv. maculicola str. ES4326]" National Center for Biotechnology Information (NCBI).gov [online]. Retrieved from: http://www.ncbi.nlm.nih.gov/protein/EGH61007; retrieved on Feb. 15, 2019; 2 pages.
GenBank Accession No. EGH66597 (Apr. 28, 2011) "chemotaxis-specific methylesterase [*Pseudomonas syringae* pv. actinidiae str. M302091]" National Center for Biotechnology Information (NCBI).

(56) References Cited

OTHER PUBLICATIONS gov [online]. Retrieved from: http://www.ncbi.nlm.nih.gov/protein/EGH66597; retrieved on Feb. 15, 2019; 2 pages.
GenBank Accession No. EGH71924 (Apr. 28, 2011) "chemotaxis-specific methylesterase, partial [*Pseudomonas syringae* pv. aceris str. M302273]" National Center for Biotechnology Information (NCBI).gov [online]. Retrieved from: http://www.ncbi.nlm.nih.gov/protein/EGH71924; retrieved on Feb. 15, 2019; 2 pages.
GenBank Accession No. EGH77388 (Apr. 28, 2011) "chemotaxis-specific methylesterase [*Pseudomonas syringae* pv. aptata str. DSM 50252]" National Center for Biotechnology Information (NCBI).gov [online]. Retrieved from: http://www.ncbi.nlm.nih.gov/protein/EGH77388; retrieved on Feb. 15, 2019; 2 pages.
GenBank Accession No. EJ092907 (Aug. 13, 2012) "response regulator receiver modulated CheB methylesterase [*Pseudomonas mendocina* DLHK]" National Center for Biotechnology Information (NCBI).gov [online]. Retrieved from: http://www.ncbi.nlm.nih.gov/protein/EJ092907; retrieved on Feb. 15, 2019; 2 pages.
GenBank Accession No. EKE17764 (Sep. 26, 2012) "hypothetical protein ACD_10C00285G0003 [uncultured bacterium]" National Center for Biotechnology Information (NCBI).gov [online]. Retrieved from: http://www.ncbi.nlm.nih.gov/protein/EKE17764; retrieved on Feb. 15, 2019; 1 page.
GenBank Accession No. J04623 (Apr. 26, 1993) "F.okeanokoites methylase (MFokI) and endonuclease (RFokI) genes, complete cds" National Center for Biotechnology Information (NCBI).gov [online]. Retrieved from: https://www.ncbi.nlm.nih.gov/nuccore/J04623.1; retrieved on Feb. 21, 2019, 2 pages.
GenBank Accession No. M28828 (Apr. 26, 1993) "F.okeanokoites fokIR and fokIM genes encoding endonuclease and methyltransferase, complete cds" National Center for Biotechnology Information (NCBI).gov [online]. Retrieved from: https://www.ncbi.nlm.nih.gov/nuccore/M28828.1/; retrieved on Feb. 21, 2019, 3 pages.
GenPept Accession No. NP_790747 (Aug. 6, 2012) "protein-glutamate methylesterase CheB [*Pseudomonas syringae* pv. tomato str. DC3000]" National Center for Biotechnology Information (NCBI).gov [online]. Retrieved from: http://www.ncbi.nlm.nih.gov/protein/NP_790747; retrieved on Feb. 20, 2019; 2 pages.
GenPept Accession No. S14242 (Oct. 8, 1999) "yopE protein—*Yersinia enterocolitica* virulence plasmid pYVe439-80" National Center for Biotechnology Information (NCBI).gov [online]. Retrieved from: https://www.ncbi.nlm.nih.gov/protein/96986?report=genpept; retrieved on Feb. 21, 2019, 2 pages.
GenPept Accession No. S15579 (Aug. 26, 1999) "ipaD protein—*Shigella dysenteriae*" National Center for Biotechnology Information (NCBI).gov [online]. Retrieved from: https://www.ncbi.nlm.nih.gov/protein/96907?report=genpept; retrieved on Feb. 21, 2019, 1 page.
GenPept Accession No. YP_233877 (Sep. 27, 2012) "chemotaxis-specific methylesterase [*Pseudomonas syringae* pv. syringae B728a]" National Center for Biotechnology Information (NCBI).gov [online]. Retrieved from: http://www.ncbi.nlm.nih.gov/protein/YP_233877; retrieved on Feb. 20, 2019; 2 pages.
GenPept Accession No. YP_273082 (Sep. 27, 2012) "chemotaxis-specific methylesterase [*Pseudomonas syringae* pv. phaseolicola 1448A]" National Center for Biotechnology Information (NCBI).gov [online]. Retrieved from: http://www.ncbi.nlm.nih.gov/protein/YP_273082; retrieved on Feb. 20, 2019; 2 pages.
GenPept Accession No. YP_001187060 (Sep. 27, 2012) "response regulator receiver modulated CheB methylesterase [*Pseudomonas mendocina* ymp]" National Center for Biotechnology Information (NCBI).gov [online]. Retrieved from: http://www.ncbi.nlm.nih.gov/protein/YP_001187060; retrieved on Feb. 20, 2019; 2 pages.
GenPept Accession No. YP_001792820 (Jan. 25, 2012) "chemotaxis-specific methylesterase [*Leptothrix cholodnii* SP-6]" National Center for Biotechnology Information (NCBI).gov [online]. Retrieved from: http://www.ncbi.nlm.nih.gov/protein/YP_001792820; retrieved on Feb. 20, 2019; 2 pages.
GenPept Accession No. YP_003847734 (Jan. 25, 2012) "response regulator receiver modulated CheB methylesterase [*Gallionella capsiferriformans* ES-2]" National Center for Biotechnology Information (NCBI).gov [online]. Retrieved from: http://www.ncbi.nlm.nih.gov/protein/YP_003847734; retrieved on Feb. 20, 2019; 2 pages.
GenPept Accession No. YP_003907367 (Jun. 18, 2012) "response regulator receiver modulated CheB methylesterase [*Burkholderia* sp. CCGE1003]" National Center for Biotechnology Information (NCBI).gov [online]. Retrieved from: http://www.ncbi.nlm.nih.gov/protein/YP_003907367; retrieved on Feb. 20, 2019; 2 pages.
GenPept Accession No. YP_004030667 (Apr. 25, 2011) "hypothetical protein RBRH_01777 (plasmid) [*Burkholderia rhizoxinica* HKI 454]" National Center for Biotechnology Information (NCBI).gov [online]. Retrieved from: http://www.ncbi.nlm.nih.gov/protein/YP_004030667; retrieved on Feb. 20, 2019; 1 page.
GenPept Accession No. YP_004846745 (Sep. 28, 2012) "response regulator receiver modulated CheB methylesterase [*Pseudogulbenkiania* sp NH8B]" National Center for Biotechnology Information (Ncbi).gov.[online]. Retrieved from: http://www.ncbi.nlm.nih.gov/protein/YP_004846745; retrieved on Feb. 20, 2019; 2 pages.
GenPept Accession No. YP_005027668 (Jun. 25, 2012) "chemotaxis response regulator containing a CheY-like receiver domain and a methylesterase domain [*Dechlorosoma suillum* PS]" National Center for Biotechnology Information (NCBI).gov [online]. Retrieved from: http://www.ncbi.nlm.nih.gov/protein/YP_005027668; retrieved on Feb. 20, 2019; 2 pages.
GenPept Accession No. ZP_03698248 (Nov. 9, 2010) "response regulator receiver modulated CheB methylesterase [*Pseudogulbenkiania ferrooxidans* 2002]" National Center for Biotechnology Information (NCBI).gov [online]. Retrieved from: http://www.ncbi.nlm.nih.gov/protein/ZP_03698248; retrieved on Feb. 20, 2019; 2 pages.
GenPept Accession No. ZP_04590480 (Nov. 14, 2012) "chemotaxis-specific methylesterase [*Pseudomonas syringae* pv. oryzae str. 1_6]" National Center for Biotechnology Information (NCBI).gov [online]. Retrieved from: http://www.ncbi.nlm.nih.gov/protein/ZP_04590480; retrieved on Feb. 20, 2019; 1 page.
GenPept Accession No. ZP_05638023 (Nov. 14, 2012) "chemotaxis-specific methylesterase [*Pseudomonas syringae* pv. tabaci str. ATCC 11528]" National Center for Biotechnology Information (NCBI).gov [online]. Retrieved from: http://www.ncbi.nlm.nih.gov/protein/ZP_05638023; retrieved on Feb. 20, 2019; 1 page.
GenPept Accession No. ZP_06457223 (Nov. 14, 2012) "chemotaxis-specific methylesterase [*Pseudomonas syringae* pv. aesculi str. NCPPB 3681]" National Center for Biotechnology Information (NCBI).gov [online]. Retrieved from: http://www.ncbi.nlm.nih.gov/protein/ZP_06457223; retrieved on Feb. 20, 2019; 1 page.
GenPept Accession No. ZP_06495900 (Nov. 14, 2012) "chemotaxis-specific methylesterase, partial [*Pseudomonas syringae* pv. syringae FF5]" National Center for Biotechnology Information (NCBI).gov [online]. Retrieved from: http://www.ncbi.nlm.nih.gov/protein/ZP_06495900; retrieved on Feb. 20, 2019; 1 page.
GenPept Accession No. ZP_07003572 (Jun. 22, 2010) "Chemotaxis response regulator protein-glutamate methylesterase CheB [*Pseudomonas savastanoi* pv. savastanoi NCPPB 3335]" National Center for Biotechnology Information (NCBI).gov [online]. Retrieved from: http://www.ncbi.nlm.nih.gov/protein/ZP_07003572; retrieved on Feb. 20, 2019; 1 page.
GenPept Accession No. ZP_07251539 (Dec. 10, 2010) "chemotaxis-specific methylesterase [*Pseudomonas syringae* pv. tomato K40]" National Center for Biotechnology Information (NCBI).gov [online]. Retrieved from: http://www.ncbi.nlm.nih.gov/protein/ZP_07251539; retrieved on Feb. 20, 2019; 2 pages.
GenPept Accession No. ZP_07265841 (Dec. 10, 2010) "chemotaxis-specific methylesterase [*Pseudomonas syringae* pv. syringae 642]" National Center for Biotechnology Information (NCBI).gov [online]. Retrieved from: http://www.ncbi.nlm.nih.gov/protein/ZP_07265841; retrieved on Feb. 20, 2019; 2 pages.
GenPept Accession No. ZP_08780698 (Nov. 15, 2011) "response regulator receiver modulated CheB methylesterase [*Methylobacter tundripaludum* SV96]" National Center for Biotechnology Information (NCBI).gov [online]. Retrieved from: http://www.ncbi.nlm.nih.gov/protein/ZP_08780698; retrieved on Feb. 20, 2019; 2 pages.
GenPept Accession No. ZP_10381001 (Jul. 11, 2012) "chemotaxis-specific methylesterase [*Sulfuricella denitrificans* skB26]" National

(56) References Cited

OTHER PUBLICATIONS

Center for Biotechnology Information (NCBI).gov [online]. Retrieved from: http://www.ncbi.nlm.nih.gov/protein/ZP_10381001; retrieved on Feb. 20, 2019; 1 page.

GenPept Accession No. ZP_10442431 (Jul. 11, 2012) "response regulator receiver modulated cheb methylesterase [*Janthinobacterium lividum* PAMC 25724]" National Center for Biotechnology Information (NCBI).gov [online]. Retrieved from: http://www.ncbi.nlm.nih.gov/protein/ZP_10442431; retrieved on Feb. 20, 2019; 2 pages.

GenPept Accession No. ZP_10991552 (Nov. 14, 2012) "chemotaxis-specific protein-glutamate methyltransferase [*Pseudomonas fuscovaginae* UPB0736]" National Center for Biotechnology Information (NCBI).gov [online]. Retrieved from: http://www.ncbi.nlm.nih.gov/protein/ZP_10991552; retrieved on Feb. 20, 2019; 2 pages.

GenPept Accession No. ZP_10995147 (Sep. 13, 2012) "response regulator receiver modulated CheB methylesterase [*Pseudomonas fuscovaginae* UPB0736]" National Center for Biotechnology Information (NCBI).gov [online]. Retrieved from: http://www.ncbi.nlm.nih.gov/protein/ZP_10995147; retrieved on Feb. 20, 2019; 2 pages.

Biocca, S. (2011) "Intrabody Expression in Mammalian Cells" in *Antibody Expression and Production. Cell Engineering*, vol. 7. Mohamed Al-Rubeai (Ed.) New York: Springer Science+Business Media; pp. 179-195.

* cited by examiner

Lane1: Xanthomonas TALEN transfected sample
Lane2: Ralstonia TALEN transfected sample
Lane3: WT sample
Lane4: DNA Ladder

SEQUENCE LISTING

<160> NUMBER OF SEQ ID NOS: 237

<210> SEQ ID NO 1
<211> LENGTH: 35
<212> TYPE: PRT
<213> ORGANISM: Artificial Sequence
<220> FEATURE:
<223> OTHER INFORMATION: Ralstonia DNA-binding peptide 1
<220> FEATURE:
<221> NAME/KEY: MISC_FEATURE
<222> LOCATION: (12)..(12)
<223> OTHER INFORMATION: Xaa = A, N, H, R or G
<220> FEATURE:
<221> NAME/KEY: MISC_FEATURE
<222> LOCATION: (13)..(13)
<223> OTHER INFORMATION: Xaa = I, N, H, K, Y, T, D, S, or P

<400> SEQUENCE: 1

```
Leu Ser Thr Glu Gln Val Val Ala Ile Ala Ser Xaa Xaa Gly Gly Lys
1               5                   10                  15

Gln Ala Leu Glu Ala Val Lys Ala Gln Leu Leu Val Leu Arg Ala Ala
            20                  25                  30

Pro Tyr Glu
```

35

<210> SEQ ID NO 2
<211> LENGTH: 35
<212> TYPE: PRT
<213> ORGANISM: Artificial Sequence
<220> FEATURE:
<223> OTHER INFORMATION: Ralstonia DNA-binding peptide 2

<400> SEQUENCE: 2

Leu Ser Thr Glu Gln Val Val Ala Ile Ala Ser Ser Ile Gly Gly Lys
1 5 10 15

Gln Ala Leu Glu Ala Val Lys Ala Gln Leu Leu Val Leu Arg Ala Ala
20 25 30

Pro Tyr Glu
35

<210> SEQ ID NO 3
<211> LENGTH: 35
<212> TYPE: PRT
<213> ORGANISM: Artificial Sequence
<220> FEATURE:
<223> OTHER INFORMATION: Ralstonia DNA-binding peptide 3

<400> SEQUENCE: 3

Leu Ser Thr Glu Gln Val Val Ala Ile Ala Ser Ser Asn Gly Gly Lys
1 5 10 15

Gln Ala Leu Glu Ala Val Lys Ala Gln Leu Leu Val Leu Arg Ala Ala
20 25 30

Pro Tyr Glu
35

<210> SEQ ID NO 4
<211> LENGTH: 35
<212> TYPE: PRT
<213> ORGANISM: Artificial Sequence
<220> FEATURE:
<223> OTHER INFORMATION: Ralstonia DNA-binding peptide 4

<400> SEQUENCE: 4

Leu Ser Thr Glu Gln Val Val Ala Ile Ala Ser Ser His Gly Gly Lys
1 5 10 15

Gln Ala Leu Glu Ala Val Lys Ala Gln Leu Leu Val Leu Arg Ala Ala
20 25 30

Pro Tyr Glu
35

<210> SEQ ID NO 5
<211> LENGTH: 35
<212> TYPE: PRT
<213> ORGANISM: Artificial Sequence
<220> FEATURE:
<223> OTHER INFORMATION: Ralstonia DNA-binding peptide 5

<400> SEQUENCE: 5

Leu Ser Thr Glu Gln Val Val Ala Ile Ala Ser Asn Pro Gly Gly Lys
1 5 10 15

Gln Ala Leu Glu Ala Val Lys Ala Gln Leu Leu Val Leu Arg Ala Ala
20 25 30

Pro Tyr Glu
35

<210> SEQ ID NO 6
<211> LENGTH: 35
<212> TYPE: PRT
<213> ORGANISM: Artificial Sequence
<220> FEATURE:
<223> OTHER INFORMATION: Ralstonia DNA-binding peptide 6

<400> SEQUENCE: 6

```
Leu Ser Thr Glu Gln Val Val Ala Ile Ala Ser Asn His Gly Gly Lys
1               5                   10                  15

Gln Ala Leu Glu Ala Val Lys Ala Gln Leu Leu Val Leu Arg Ala Ala
            20                  25                  30

Pro Tyr Glu
        35
```

<210> SEQ ID NO 7
<211> LENGTH: 35
<212> TYPE: PRT
<213> ORGANISM: Artificial Sequence
<220> FEATURE:
<223> OTHER INFORMATION: Ralstonia DNA-binding peptide 7

<400> SEQUENCE: 7

```
Leu Ser Thr Glu Gln Val Val Ala Ile Ala Ser Asn Thr Gly Gly Lys
1               5                   10                  15

Gln Ala Leu Glu Ala Val Lys Ala Gln Leu Leu Val Leu Arg Ala Ala
            20                  25                  30

Pro Tyr Glu
        35
```

<210> SEQ ID NO 8
<211> LENGTH: 35
<212> TYPE: PRT
<213> ORGANISM: Artificial Sequence
<220> FEATURE:
<223> OTHER INFORMATION: Ralstonia DNA-binding peptide 8

<400> SEQUENCE: 8

```
Leu Ser Thr Glu Gln Val Val Ala Ile Ala Ser Asn Lys Gly Gly Lys
1               5                   10                  15

Gln Ala Leu Glu Ala Val Lys Ala Gln Leu Leu Val Leu Arg Ala Ala
            20                  25                  30

Pro Tyr Glu
        35
```

<210> SEQ ID NO 9
<211> LENGTH: 35
<212> TYPE: PRT
<213> ORGANISM: Artificial Sequence
<220> FEATURE:
<223> OTHER INFORMATION: Ralstonia DNA-binding peptide 9

<400> SEQUENCE: 9

```
Leu Ser Thr Glu Gln Val Val Ala Ile Ala Ser Asn Pro Gly Gly Lys
1               5                   10                  15

Gln Ala Leu Glu Ala Val Lys Ala Gln Leu Leu Val Leu Arg Ala Ala
            20                  25                  30

Pro Tyr Glu
        35
```

<210> SEQ ID NO 10
<211> LENGTH: 35
<212> TYPE: PRT

```
<213> ORGANISM: Artificial Sequence
<220> FEATURE:
<223> OTHER INFORMATION: Ralstonia DNA-binding peptide 10

<400> SEQUENCE: 10

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Val Leu Arg Ala Ala
            20                  25                  30

Pro Tyr Glu
        35


<210> SEQ ID NO 11
<211> LENGTH: 35
<212> TYPE: PRT
<213> ORGANISM: Artificial Sequence
<220> FEATURE:
<223> OTHER INFORMATION: Ralstonia DNA-binding peptide 11

<400> SEQUENCE: 11

Leu Ser Thr Glu Gln Val Val Ala Ile Ala Ser Asn Asp Gly Gly Lys
1               5                   10                  15

Gln Ala Leu Glu Ala Val Lys Ala Gln Leu Leu Val Leu Arg Ala Ala
            20                  25                  30

Pro Tyr Glu
        35


<210> SEQ ID NO 12
<211> LENGTH: 35
<212> TYPE: PRT
<213> ORGANISM: Artificial Sequence
<220> FEATURE:
<223> OTHER INFORMATION: Ralstonia DNA-binding peptide 12

<400> SEQUENCE: 12

Leu Ser Thr Glu Gln Val Val Ala Ile Ala Ser Asn Gly Gly Gly Lys
1               5                   10                  15

Gln Ala Leu Glu Ala Val Lys Ala Gln Leu Leu Val Leu Arg Ala Ala
            20                  25                  30

Pro Tyr Glu
        35


<210> SEQ ID NO 13
<211> LENGTH: 35
<212> TYPE: PRT
<213> ORGANISM: Artificial Sequence
<220> FEATURE:
<223> OTHER INFORMATION: Ralstonia DNA-binding peptide 13

<400> SEQUENCE: 13

Leu Ser Thr Glu Gln Val Val Ala Ile Ala Ser His Asn Gly Gly Lys
1               5                   10                  15

Gln Ala Leu Glu Ala Val Lys Ala Gln Leu Leu Val Leu Arg Ala Ala
            20                  25                  30

Pro Tyr Glu
        35


<210> SEQ ID NO 14
<211> LENGTH: 35
<212> TYPE: PRT
<213> ORGANISM: Artificial Sequence
<220> FEATURE:
<223> OTHER INFORMATION: Ralstonia DNA-binding peptide 14
```

<400> SEQUENCE: 14

```
Leu Ser Thr Glu Gln Val Val Ala Ile Ala Ser His Tyr Gly Gly Lys
1               5                   10                  15

Gln Ala Leu Glu Ala Val Lys Ala Gln Leu Leu Val Leu Arg Ala Ala
            20                  25                  30

Pro Tyr Glu
        35
```

<210> SEQ ID NO 15
<211> LENGTH: 35
<212> TYPE: PRT
<213> ORGANISM: Artificial Sequence
<220> FEATURE:
<223> OTHER INFORMATION: Ralstonia DNA-binding peptide 15

<400> SEQUENCE: 15

```
Leu Ser Thr Glu Gln Val Val Ala Ile Ala Ser His Asp Gly Gly Lys
1               5                   10                  15

Gln Ala Leu Glu Ala Val Lys Ala Gln Leu Leu Val Leu Arg Ala Ala
            20                  25                  30

Pro Tyr Glu
        35
```

<210> SEQ ID NO 16
<211> LENGTH: 35
<212> TYPE: PRT
<213> ORGANISM: Artificial Sequence
<220> FEATURE:
<223> OTHER INFORMATION: Ralstonia DNA-binding peptide 16

<400> SEQUENCE: 16

```
Leu Ser Thr Glu Gln Val Val Ala Ile Ala Ser His His Gly Gly Lys
1               5                   10                  15

Gln Ala Leu Glu Ala Val Lys Ala Gln Leu Leu Val Leu Arg Ala Ala
            20                  25                  30

Pro Tyr Glu
        35
```

<210> SEQ ID NO 17
<211> LENGTH: 35
<212> TYPE: PRT
<213> ORGANISM: Artificial Sequence
<220> FEATURE:
<223> OTHER INFORMATION: Ralstonia DNA-binding peptide 17

<400> SEQUENCE: 17

```
Leu Ser Thr Glu Gln Val Val Ala Ile Ala Ser Arg Asn Gly Gly Lys
1               5                   10                  15

Gln Ala Leu Glu Ala Val Lys Ala Gln Leu Leu Val Leu Arg Ala Ala
            20                  25                  30

Pro Tyr Glu
        35
```

<210> SEQ ID NO 18
<211> LENGTH: 35
<212> TYPE: PRT
<213> ORGANISM: Artificial Sequence
<220> FEATURE:
<223> OTHER INFORMATION: Ralstonia DNA-binding peptide 18

<400> SEQUENCE: 18

```
Leu Ser Thr Glu Gln Val Val Ala Ile Ala Ser Arg Ser Gly Gly Lys
1               5                   10                  15

Gln Ala Leu Glu Ala Val Lys Ala Gln Leu Leu Val Leu Arg Ala Ala
            20                  25                  30

Pro Tyr Glu
        35


<210> SEQ ID NO 19
<211> LENGTH: 35
<212> TYPE: PRT
<213> ORGANISM: Artificial Sequence
<220> FEATURE:
<223> OTHER INFORMATION: Ralstonia DNA-binding peptide 19

<400> SEQUENCE: 19

Leu Ser Thr Glu Gln Val Val Ala Ile Ala Ser Gly Ser Gly Gly Lys
1               5                   10                  15

Gln Ala Leu Glu Ala Val Lys Ala Gln Leu Leu Val Leu Arg Ala Ala
            20                  25                  30

Pro Tyr Glu
        35


<210> SEQ ID NO 20
<211> LENGTH: 24
<212> TYPE: DNA
<213> ORGANISM: Artificial Sequence
<220> FEATURE:
<223> OTHER INFORMATION: oJS2581 primer

<400> SEQUENCE: 20

tctagagaag acaagaacct gacc                                              24


<210> SEQ ID NO 21
<211> LENGTH: 24
<212> TYPE: DNA
<213> ORGANISM: Artificial Sequence
<220> FEATURE:
<223> OTHER INFORMATION: oJS2582 primer

<400> SEQUENCE: 21

ggatccggtc tcttaaggcc gtgg                                              24


<210> SEQ ID NO 22
<211> LENGTH: 28
<212> TYPE: DNA
<213> ORGANISM: Artificial Sequence
<220> FEATURE:
<223> OTHER INFORMATION: oSQT34 primer

<400> SEQUENCE: 22

gacggtggct gtcaaatacc aagatatg                                          28


<210> SEQ ID NO 23
<211> LENGTH: 30
<212> TYPE: DNA
<213> ORGANISM: Artificial Sequence
<220> FEATURE:
<223> OTHER INFORMATION: oSQT35 primer

<400> SEQUENCE: 23

tctcctccag ttcacttttg actagttggg                                        30


<210> SEQ ID NO 24
<211> LENGTH: 20
```

<212> TYPE: DNA
<213> ORGANISM: Artificial Sequence
<220> FEATURE:
<223> OTHER INFORMATION: oSQT1 primer

<400> SEQUENCE: 24
agtaacagcg gtagaggcag 20

<210> SEQ ID NO 25
<211> LENGTH: 25
<212> TYPE: DNA
<213> ORGANISM: Artificial Sequence
<220> FEATURE:
<223> OTHER INFORMATION: oJS2980 primer

<400> SEQUENCE: 25
ttaattcaat atattcatga ggcac 25

<210> SEQ ID NO 26
<211> LENGTH: 146
<212> TYPE: DNA
<213> ORGANISM: Artificial Sequence
<220> FEATURE:
<223> OTHER INFORMATION: DNA-binding peptide insert 1

<400> SEQUENCE: 26
atgcatctag agaagacaac tgagcaccga gcaggtggtg gccatcgcca gcaacaaggg 60
cggcaagcag gccctggagg ccgtgaaggc ccacctgctg gacctgctgg gcgcccccta 120
cgagctgaag agaccggatc ccgggc 146

<210> SEQ ID NO 27
<211> LENGTH: 146
<212> TYPE: DNA
<213> ORGANISM: Artificial Sequence
<220> FEATURE:
<223> OTHER INFORMATION: DNA-binding peptide insert 2

<400> SEQUENCE: 27
atgcatctag agaagacaac tgagcaccga gcaggtggtg gccatcgcca gcaacaacgg 60
cggcaagcag gccctggagg ccgtgaaggc ccagctgctg gagctgaggg ccgcccccta 120
cgagctgaag agaccggatc ccgggc 146

<210> SEQ ID NO 28
<211> LENGTH: 146
<212> TYPE: DNA
<213> ORGANISM: Artificial Sequence
<220> FEATURE:
<223> OTHER INFORMATION: DNA-binding peptide insert 3

<400> SEQUENCE: 28
atgcatctag agaagacaac tgagcaccga gcaggtggtg gccatcgcca gcaacggcgg 60
cggcaagcag gccctggagg gcatcggcga gcagctgctg aagctgagga ccgcccccta 120
cgagctgaag agaccggatc ccgggc 146

<210> SEQ ID NO 29
<211> LENGTH: 146
<212> TYPE: DNA
<213> ORGANISM: Artificial Sequence
<220> FEATURE:
<223> OTHER INFORMATION: DNA-binding peptide insert 4

<400> SEQUENCE: 29

```
atgcatctag agaagacaac tgagcaccga gcaggtggtg gccatcgcca gccacgacgg     60

cggcaagccc gccctggagg ccgtgtgggc caagctgccc gtgctgaggg gcgtgcccta    120

cgagctgaag agaccggatc ccgggc                                         146


<210> SEQ ID NO 30
<211> LENGTH: 146
<212> TYPE: DNA
<213> ORGANISM: Artificial Sequence
<220> FEATURE:
<223> OTHER INFORMATION: DNA-binding peptide insert 5

<400> SEQUENCE: 30

atgcatctag agaagacaac tgagcaccga gcaggtggtg accatcgcca gcagcatcgg     60

cggcaagcag gccctggagg ccgtgaaggt gcagctgccc gtgctgaggg ccgcccccta    120

cgagctgaag agaccggatc ccgggc                                         146


<210> SEQ ID NO 31
<211> LENGTH: 34
<212> TYPE: PRT
<213> ORGANISM: Artificial Sequence
<220> FEATURE:
<223> OTHER INFORMATION: DNA-binding fragment 1

<400> SEQUENCE: 31

Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly


<210> SEQ ID NO 32
<211> LENGTH: 34
<212> TYPE: PRT
<213> ORGANISM: Artificial Sequence
<220> FEATURE:
<223> OTHER INFORMATION: DNA-binding fragment 2

<400> SEQUENCE: 32

Leu Thr Pro Glu Gln Val Val Ala Ile Ala Asn Asn Asn Gly Gly Lys
1               5                   10                  15

Gln Ala Leu Glu Thr Val Gln Arg Leu Leu Pro Val Leu Cys Gln Ala
            20                  25                  30

His Gly


<210> SEQ ID NO 33
<211> LENGTH: 34
<212> TYPE: PRT
<213> ORGANISM: Artificial Sequence
<220> FEATURE:
<223> OTHER INFORMATION: DNA-binding fragment 3

<400> SEQUENCE: 33

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly


<210> SEQ ID NO 34
<211> LENGTH: 34
```

<212> TYPE: PRT
<213> ORGANISM: Artificial Sequence
<220> FEATURE:
<223> OTHER INFORMATION: DNA-binding fragment 4

<400> SEQUENCE: 34

```
Leu Thr Pro Ala Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly
```

<210> SEQ ID NO 35
<211> LENGTH: 29
<212> TYPE: PRT
<213> ORGANISM: Pseudomonas mendocina DLHK

<400> SEQUENCE: 35

```
Thr Thr Asp Arg Val Val Ala Leu Gly Thr Ser Thr Gly Gly Thr Gln
1               5                   10                  15

Ala Leu Glu Val Val Leu Arg Gln Leu Pro Val Asp Cys
            20                  25
```

<210> SEQ ID NO 36
<211> LENGTH: 30
<212> TYPE: PRT
<213> ORGANISM: Gallionella capsiferriformans ES-2

<400> SEQUENCE: 36

```
Met Thr Ser Glu Gln Ile Val Ala Ile Gly Thr Ser Thr Gly Gly Thr
1               5                   10                  15

Gln Ala Leu Glu Ala Val Leu Thr Ala Leu Pro Arg Val Cys
            20                  25                  30
```

<210> SEQ ID NO 37
<211> LENGTH: 29
<212> TYPE: PRT
<213> ORGANISM: Methylobacter tundripaludum SV96

<400> SEQUENCE: 37

```
Thr Thr Asp Arg Val Val Ala Ile Gly Thr Ser Thr Gly Gly Thr Gln
1               5                   10                  15

Ala Leu Glu Val Val Leu Thr Ala Leu Pro Arg Val Cys
            20                  25
```

<210> SEQ ID NO 38
<211> LENGTH: 29
<212> TYPE: PRT
<213> ORGANISM: Pseudogulbenkiania sp. NH8B

<400> SEQUENCE: 38

```
Thr Thr Glu Arg Ile Val Ala Ile Gly Thr Ser Thr Gly Gly Thr Gln
1               5                   10                  15

Ala Leu Glu Thr Val Leu His Arg Leu Pro Ala Thr Cys
            20                  25
```

<210> SEQ ID NO 39
<211> LENGTH: 29
<212> TYPE: PRT
<213> ORGANISM: Dechlorosoma suillum PS

<400> SEQUENCE: 39

```
Thr Thr Asp Lys Ile Ile Ala Ile Gly Thr Ser Thr Gly Gly Thr Gln
1               5                   10                  15

Ala Leu Glu Ala Val Leu Thr Lys Leu Pro Ala Val Cys
            20                  25


<210> SEQ ID NO 40
<211> LENGTH: 29
<212> TYPE: PRT
<213> ORGANISM: Pseudomonas fuscovaginae UPB0736

<400> SEQUENCE: 40

Thr Thr Glu Arg Ile Val Ala Ile Gly Thr Ser Thr Gly Gly Thr Gln
1               5                   10                  15

Ala Leu Glu Thr Val Leu Thr Ala Leu Pro Arg Val Cys
            20                  25


<210> SEQ ID NO 41
<211> LENGTH: 29
<212> TYPE: PRT
<213> ORGANISM: Artificial Sequence
<220> FEATURE:
<223> OTHER INFORMATION: DNA-binding fragment 11

<400> SEQUENCE: 41

Thr Thr Glu Arg Val Val Ala Leu Gly Thr Ser Thr Gly Gly Thr Gln
1               5                   10                  15

Ala Leu Glu Val Val Leu Arg Thr Leu Pro Arg Val Cys
            20                  25


<210> SEQ ID NO 42
<211> LENGTH: 29
<212> TYPE: PRT
<213> ORGANISM: Artificial Sequence
<220> FEATURE:
<223> OTHER INFORMATION: DNA-binding fragment 12

<400> SEQUENCE: 42

Thr Thr Asp Gln Leu Ile Ala Ile Gly Thr Ser Thr Gly Gly Thr Gln
1               5                   10                  15

Ala Leu Glu Ala Ile Leu Thr Lys Leu Pro Ala Thr Cys
            20                  25


<210> SEQ ID NO 43
<211> LENGTH: 29
<212> TYPE: PRT
<213> ORGANISM: Artificial Sequence
<220> FEATURE:
<223> OTHER INFORMATION: DNA-binding fragment 13

<400> SEQUENCE: 43

Thr Thr Asp Gln Leu Ile Ala Ile Gly Thr Ser Thr Gly Gly Thr Gln
1               5                   10                  15

Ala Leu Glu Ala Ile Leu Thr Lys Leu Pro Ala Thr Cys
            20                  25


<210> SEQ ID NO 44
<211> LENGTH: 29
<212> TYPE: PRT
<213> ORGANISM: Pseudogulbenkiania ferrooxidans 2002

<400> SEQUENCE: 44

Thr Thr Glu Arg Ile Val Ala Ile Gly Thr Ser Thr Gly Gly Thr Gln
1               5                   10                  15
```

```
Ala Leu Glu Thr Val Leu Pro Arg Leu Pro Ala Thr Cys
            20                  25
```

<210> SEQ ID NO 45
<211> LENGTH: 29
<212> TYPE: PRT
<213> ORGANISM: Janthinobacterium lividum PAMC 25724

<400> SEQUENCE: 45

```
Thr Ser Asp Lys Val Val Ala Ile Gly Ala Ser Thr Gly Gly Thr Gln
1               5                   10                  15

Ala Leu Glu Leu Leu Leu Thr Gly Leu Pro Ala Val Cys
            20                  25
```

<210> SEQ ID NO 46
<211> LENGTH: 29
<212> TYPE: PRT
<213> ORGANISM: Burkholderia rhizoxinica HKI 454

<400> SEQUENCE: 46

```
Phe Ser Gln Ala Asp Ile Val Arg Ile Ala Asp Asn Ile Gly Gly Ala
1               5                   10                  15

Gln Ala Leu Lys Ala Val Leu Glu His Gly Pro Thr Leu
            20                  25
```

<210> SEQ ID NO 47
<211> LENGTH: 28
<212> TYPE: PRT
<213> ORGANISM: Artificial Sequence
<220> FEATURE:
<223> OTHER INFORMATION: DNA-binding fragment 17

<400> SEQUENCE: 47

```
Ala Asp Ile Val Lys Ile Ala Ser Asn Gly Gly Gly Ala Gln Ala Leu
1               5                   10                  15

Glu Ala Val Ala Met His Gly Ser Thr Leu Cys Glu
            20                  25
```

<210> SEQ ID NO 48
<211> LENGTH: 28
<212> TYPE: PRT
<213> ORGANISM: Burkholderia rhizoxinica HKI 454

<400> SEQUENCE: 48

```
Ala Asp Ile Val Lys Ile Ala Gly Asn Gly Gly Gly Ala Arg Ala Leu
1               5                   10                  15

Lys Ala Val Val Met His Gly Pro Thr Leu Cys Glu
            20                  25
```

<210> SEQ ID NO 49
<211> LENGTH: 29
<212> TYPE: PRT
<213> ORGANISM: Pseudomonas fuscovaginae UPB0736

<400> SEQUENCE: 49

```
Thr Thr Asp Arg Val Val Ala Leu Gly Cys Ser Thr Gly Gly Thr Gln
1               5                   10                  15

Ala Leu Glu Phe Ile Leu Arg Gln Leu Pro Arg Asp Cys
            20                  25
```

<210> SEQ ID NO 50
<211> LENGTH: 24
<212> TYPE: PRT

<213> ORGANISM: Pseudomonas syringae Cit 7

<400> SEQUENCE: 50

```
Ala Leu Ala Ala Ala Val Gly Gly Lys Gly Ala Leu Glu Val Pro Ala
1               5                   10                  15

Asn Leu Ile Pro Ala Asn Cys Glu
            20
```

<210> SEQ ID NO 51
<211> LENGTH: 23
<212> TYPE: PRT
<213> ORGANISM: Burkholderia sp. CCGE1003

<400> SEQUENCE: 51

```
Arg Ile Val Ala Ile Gly Thr Ser Thr Gly Gly Thr Gln Ala Leu Glu
1               5                   10                  15

Val Val Leu Thr Ala Leu Pro
            20
```

<210> SEQ ID NO 52
<211> LENGTH: 34
<212> TYPE: PRT
<213> ORGANISM: Artificial Sequence
<220> FEATURE:
<223> OTHER INFORMATION: DNA-binding fragment 22

<400> SEQUENCE: 52

```
Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly
```

<210> SEQ ID NO 53
<211> LENGTH: 34
<212> TYPE: PRT
<213> ORGANISM: Artificial Sequence
<220> FEATURE:
<223> OTHER INFORMATION: DNA-binding fragment 23

<400> SEQUENCE: 53

```
Leu Thr Pro Ala Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly
```

<210> SEQ ID NO 54
<211> LENGTH: 34
<212> TYPE: PRT
<213> ORGANISM: Artificial Sequence
<220> FEATURE:
<223> OTHER INFORMATION: DNA-binding fragment 24

<400> SEQUENCE: 54

```
Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly
```

<210> SEQ ID NO 55
<211> LENGTH: 34
<212> TYPE: PRT
<213> ORGANISM: Artificial Sequence
<220> FEATURE:
<223> OTHER INFORMATION: DNA-binding fragment 25

<400> SEQUENCE: 55

```
Leu Thr Pro Glu Gln Val Val Ala Ile Ala Asn Asn Asn Gly Gly Lys
1               5                   10                  15

Gln Ala Leu Glu Thr Val Gln Arg Leu Leu Pro Val Leu Cys Gln Ala
            20                  25                  30

His Gly
```

<210> SEQ ID NO 56
<211> LENGTH: 29
<212> TYPE: PRT
<213> ORGANISM: Pseudomonas mendocina DLHK

<400> SEQUENCE: 56

```
Thr Thr Asp Arg Val Val Ala Leu Gly Thr Ser Thr Gly Gly Thr Gln
1               5                   10                  15

Ala Leu Glu Val Val Leu Arg Gln Leu Pro Val Asp Cys
            20                  25
```

<210> SEQ ID NO 57
<211> LENGTH: 29
<212> TYPE: PRT
<213> ORGANISM: Pseudomonas fuscovaginae UPB0736

<400> SEQUENCE: 57

```
Thr Thr Asp Arg Val Val Ala Leu Gly Cys Ser Thr Gly Gly Thr Gln
1               5                   10                  15

Ala Leu Glu Phe Ile Leu Arg Gln Leu Pro Arg Asp Cys
            20                  25
```

<210> SEQ ID NO 58
<211> LENGTH: 29
<212> TYPE: PRT
<213> ORGANISM: Leptothrix cholodnii SP-6

<400> SEQUENCE: 58

```
Thr Thr Glu Arg Val Val Ala Leu Gly Thr Ser Thr Gly Gly Thr Gln
1               5                   10                  15

Ala Leu Glu Val Val Leu Arg Thr Leu Pro Arg Val Cys
            20                  25
```

<210> SEQ ID NO 59
<211> LENGTH: 29
<212> TYPE: PRT
<213> ORGANISM: Artificial Sequence
<220> FEATURE:
<223> OTHER INFORMATION: DNA-binding fragment 29

<400> SEQUENCE: 59

```
Thr Thr Asp Arg Val Val Ala Ile Gly Thr Ser Thr Gly Gly Thr Gln
1               5                   10                  15

Ala Leu Glu Val Val Leu Thr Ala Leu Pro Arg Val Cys
            20                  25
```

<210> SEQ ID NO 60
<211> LENGTH: 29
<212> TYPE: PRT

<213> ORGANISM: Artificial Sequence
<220> FEATURE:
<223> OTHER INFORMATION: DNA-binding fragment 30

<400> SEQUENCE: 60

Thr Thr Glu Arg Ile Val Ala Ile Gly Thr Ser Thr Gly Gly Thr Gln
1 5 10 15

Ala Leu Glu Thr Val Leu Pro Arg Leu Pro Ala Thr Cys
20 25

<210> SEQ ID NO 61
<211> LENGTH: 29
<212> TYPE: PRT
<213> ORGANISM: Dechlorosoma suillum PS

<400> SEQUENCE: 61

Thr Thr Asp Lys Ile Ile Ala Ile Gly Thr Ser Thr Gly Gly Thr Gln
1 5 10 15

Ala Leu Glu Ala Val Leu Thr Lys Leu Pro Ala Val Cys
20 25

<210> SEQ ID NO 62
<211> LENGTH: 29
<212> TYPE: PRT
<213> ORGANISM: uncultured bacterium

<400> SEQUENCE: 62

Thr Thr Asp Gln Leu Ile Ala Ile Gly Thr Ser Thr Gly Gly Thr Gln
1 5 10 15

Ala Leu Glu Ala Ile Leu Thr Lys Leu Pro Ala Thr Cys
20 25

<210> SEQ ID NO 63
<211> LENGTH: 29
<212> TYPE: PRT
<213> ORGANISM: Janthinobacterium lividum PAMC 25724

<400> SEQUENCE: 63

Thr Ser Asp Lys Val Val Ala Ile Gly Ala Ser Thr Gly Gly Thr Gln
1 5 10 15

Ala Leu Glu Leu Leu Leu Thr Gly Leu Pro Ala Val Cys
20 25

<210> SEQ ID NO 64
<211> LENGTH: 28
<212> TYPE: PRT
<213> ORGANISM: Burkholderia rhizoxinica HKI 454

<400> SEQUENCE: 64

Ala Asp Ile Val Lys Ile Ala Ser Asn Gly Gly Gly Ala Gln Ala Leu
1 5 10 15

Glu Ala Val Ala Met His Gly Ser Thr Leu Cys Glu
20 25

<210> SEQ ID NO 65
<211> LENGTH: 28
<212> TYPE: PRT
<213> ORGANISM: Burkholderia rhizoxinica HKI 454

<400> SEQUENCE: 65

Ala Asp Ile Val Lys Ile Ala Gly Asn Gly Gly Gly Ala Arg Ala Leu
1 5 10 15

Lys Ala Val Val Met His Gly Pro Thr Leu Cys Glu
            20                  25

<210> SEQ ID NO 66
<211> LENGTH: 29
<212> TYPE: PRT
<213> ORGANISM: Burkholderia rhizoxinica HKI 454

<400> SEQUENCE: 66

Phe Ser Gln Ala Asp Ile Val Arg Ile Ala Asp Asn Ile Gly Gly Ala
1               5                   10                  15

Gln Ala Leu Lys Ala Val Leu Glu His Gly Pro Thr Leu
            20                  25

<210> SEQ ID NO 67
<211> LENGTH: 24
<212> TYPE: PRT
<213> ORGANISM: Pseudomonas syringae Cit 7

<400> SEQUENCE: 67

Ala Leu Ala Ala Ala Val Gly Gly Lys Gly Ala Leu Glu Val Pro Ala
1               5                   10                  15

Asn Leu Ile Pro Ala Asn Cys Glu
            20

<210> SEQ ID NO 68
<211> LENGTH: 229
<212> TYPE: DNA
<213> ORGANISM: Artificial Sequence
<220> FEATURE:
<223> OTHER INFORMATION: Sleeping Beauty 5' Inverted Tandem Repeat

<400> SEQUENCE: 68
cagttgaagt cggaagttta catacactta agttggagtc attaaaactc gtttttcaac     60
tactccacaa atttcttgtt aacaaacaat agttttggca agtcagttag gacatctact    120
ttgtgcatga cacaagtcat ttttccaaca attgtttaca gacagattat ttcacttata    180
attcactgta tcacaattcc agtgggtcag aagtttacat acactaagt                229

<210> SEQ ID NO 69
<211> LENGTH: 229
<212> TYPE: DNA
<213> ORGANISM: Artificial Sequence
<220> FEATURE:
<223> OTHER INFORMATION: Sleeping Beauty 3' Inverted Tandem Repeat

<400> SEQUENCE: 69
attgagtgta tgtaaacttc tgacccactg ggaatgtgat gaaagaaata aaagctgaaa     60
tgaatcattc tctctactat tattctgata tttcacattc ttaaaataaa gtggtgatcc    120
taactgacct aagacaggga atttttacta ggattaaatg tcaggaattg tgaaaaagtg    180
agtttaaatg tatttggcta aggtgtatgt aaacttccga cttcaactg                229

<210> SEQ ID NO 70
<211> LENGTH: 309
<212> TYPE: DNA
<213> ORGANISM: Artificial Sequence
<220> FEATURE:
<223> OTHER INFORMATION: piggyBac 5' Inverted Tandem Repeat

<400> SEQUENCE: 70
ccctagaaag atagtctgcg taaaattgac gcatgcattc ttgaaatatt gctctctctt     60

```
tctaaatagc gcgaatccgt cgctgtgcat ttaggacatc tcagtcgccg cttggagctc    120

ccgtgaggcg tgcttgtcaa tgcggtaagt gtcactgatt ttgaactata acgaccgcgt    180

gagtcaaaat gacgcatgat tatcttttac gtgactttta agatttaact catacgataa    240

ttatattgtt atttcatgtt ctacttacgt gataacttat tatatatata ttttcttgtt    300

atagatatc                                                            309


<210> SEQ ID NO 71
<211> LENGTH: 238
<212> TYPE: DNA
<213> ORGANISM: Artificial Sequence
<220> FEATURE:
<223> OTHER INFORMATION: piggyBac 3' Inverted Tandem Repeat

<400> SEQUENCE: 71

taaaagtttt gttactttat agaagaaatt ttgagttttt gttttttttt aataaataaa     60

taaacataaa taaattgttt gttgaattta ttattagtat gtaagtgtaa atataataaa    120

acttaatatc tattcaaatt aataaataaa cctcgatata cagaccgata aaacacatgc    180

gtcaatttta cgcatgatta tctttaacgt acgtcacaat atgattatct ttctaggg      238


<210> SEQ ID NO 72
<211> LENGTH: 35
<212> TYPE: PRT
<213> ORGANISM: Artificial Sequence
<220> FEATURE:
<223> OTHER INFORMATION: Ralstonia DNA-binding peptide 20

<400> SEQUENCE: 72

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35


<210> SEQ ID NO 73
<211> LENGTH: 35
<212> TYPE: PRT
<213> ORGANISM: Artificial Sequence
<220> FEATURE:
<223> OTHER INFORMATION: Ralstonia DNA-binding peptide 21

<400> SEQUENCE: 73

Leu Ser Thr Glu Gln Val Val Ala Val Ala Ser Asn Lys Gly Gly Lys
1               5                   10                  15

Gln Ala Leu Ala Ala Val Glu Ala Gln Leu Leu Arg Leu Arg Ala Ala
            20                  25                  30

Pro Tyr Glu
        35


<210> SEQ ID NO 74
<211> LENGTH: 35
<212> TYPE: PRT
<213> ORGANISM: Artificial Sequence
<220> FEATURE:
<223> OTHER INFORMATION: Ralstonia DNA-binding peptide 22

<400> SEQUENCE: 74

Leu Asn Thr Glu Gln Val Val Ala Val Ala Ser Asn Lys Gly Gly Lys
1               5                   10                  15
```

```
Gln Ala Leu Glu Ala Val Gly Ala Gln Leu Leu Ala Leu Arg Ala Val
            20                  25                  30

Pro Tyr Ala
        35


<210> SEQ ID NO 75
<211> LENGTH: 35
<212> TYPE: PRT
<213> ORGANISM: Artificial Sequence
<220> FEATURE:
<223> OTHER INFORMATION: Ralstonia DNA-binding peptide 24

<400> SEQUENCE: 75

Leu Ser Thr Glu Gln Val Val Ala Val Ala Ser Asn Lys Gly Gly Lys
1               5                   10                  15

Gln Val Leu Glu Ala Val Gly Ala Gln Leu Leu Ala Leu Arg Ala Val
            20                  25                  30

Pro Tyr Glu
        35


<210> SEQ ID NO 76
<211> LENGTH: 35
<212> TYPE: PRT
<213> ORGANISM: Artificial Sequence
<220> FEATURE:
<223> OTHER INFORMATION: Ralstonia DNA-binding peptide 24

<400> SEQUENCE: 76

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35


<210> SEQ ID NO 77
<211> LENGTH: 35
<212> TYPE: PRT
<213> ORGANISM: Artificial Sequence
<220> FEATURE:
<223> OTHER INFORMATION: Ralstonia DNA-binding peptide 25

<400> SEQUENCE: 77

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35


<210> SEQ ID NO 78
<211> LENGTH: 35
<212> TYPE: PRT
<213> ORGANISM: Artificial Sequence
<220> FEATURE:
<223> OTHER INFORMATION: Ralstonia DNA-binding peptide 26

<400> SEQUENCE: 78

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30
```

```
Pro Tyr Val
        35


<210> SEQ ID NO 79
<211> LENGTH: 35
<212> TYPE: PRT
<213> ORGANISM: Artificial Sequence
<220> FEATURE:
<223> OTHER INFORMATION: Ralstonia DNA-binding peptide 27

<400> SEQUENCE: 79

Leu Ser Thr Glu Gln Val Val Ala Ile Ala Ser Asn Lys Gly Gly Lys
1               5                   10                  15

Gln Ala Leu Glu Ala Val Lys Ala Gln Leu Leu Glu Leu Arg Gly Ala
            20                  25                  30

Pro Tyr Ala
        35


<210> SEQ ID NO 80
<211> LENGTH: 35
<212> TYPE: PRT
<213> ORGANISM: Artificial Sequence
<220> FEATURE:
<223> OTHER INFORMATION: Ralstonia DNA-binding peptide 28

<400> SEQUENCE: 80

Leu Ser Thr Glu Gln Val Val Ala Val Ala Ser Asn Lys Gly Gly Lys
1               5                   10                  15

Gln Ala Leu Ala Ala Val Glu Ala Gln Leu Leu Arg Leu Arg Ala Ala
            20                  25                  30

Pro Tyr Glu
        35


<210> SEQ ID NO 81
<211> LENGTH: 35
<212> TYPE: PRT
<213> ORGANISM: Artificial Sequence
<220> FEATURE:
<223> OTHER INFORMATION: Ralstonia DNA-binding peptide 29

<400> SEQUENCE: 81

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35


<210> SEQ ID NO 82
<211> LENGTH: 35
<212> TYPE: PRT
<213> ORGANISM: Artificial Sequence
<220> FEATURE:
<223> OTHER INFORMATION: Ralstonia DNA-binding peptide 30

<400> SEQUENCE: 82

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35
```

<210> SEQ ID NO 83
<211> LENGTH: 35
<212> TYPE: PRT
<213> ORGANISM: Artificial Sequence
<220> FEATURE:
<223> OTHER INFORMATION: Ralstonia DNA-binding peptide 31

<400> SEQUENCE: 83

```
Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Asp Leu Arg Gly Ala
            20                  25                  30

Pro Tyr Ala
        35
```

<210> SEQ ID NO 84
<211> LENGTH: 35
<212> TYPE: PRT
<213> ORGANISM: Artificial Sequence
<220> FEATURE:
<223> OTHER INFORMATION: Ralstonia DNA-binding peptide 32

<400> SEQUENCE: 84

```
Leu Ser Thr Glu Gln Val Val Ala Ile Ala Ser Asn Asn Gly Gly Lys
1               5                   10                  15

Gln Ala Leu Glu Ala Val Lys Ala Gln Leu Pro Val Leu Arg Arg Ala
            20                  25                  30

Pro Tyr Gly
        35
```

<210> SEQ ID NO 85
<211> LENGTH: 35
<212> TYPE: PRT
<213> ORGANISM: Artificial Sequence
<220> FEATURE:
<223> OTHER INFORMATION: Ralstonia DNA-binding peptide 33

<400> SEQUENCE: 85

```
Leu Ser Pro Glu Gln Val Val Ala Ile Ala Ser Asn Asn Gly Gly Lys
1               5                   10                  15

Pro Ala Leu Glu Ala Val Lys Ala Gln Leu Leu Glu Leu Arg Ala Ala
            20                  25                  30

Pro Tyr Glu
        35
```

<210> SEQ ID NO 86
<211> LENGTH: 35
<212> TYPE: PRT
<213> ORGANISM: Artificial Sequence
<220> FEATURE:
<223> OTHER INFORMATION: Ralstonia DNA-binding peptide 34

<400> SEQUENCE: 86

```
Leu Ser Pro Glu Gln Val Val Ala Ile Ala Ser Asn Asn Gly Gly Lys
1               5                   10                  15

Pro Ala Leu Glu Ala Val Lys Ala Leu Leu Leu Ala Leu Arg Ala Ala
            20                  25                  30

Pro Tyr Glu
        35
```

<210> SEQ ID NO 87
<211> LENGTH: 35

<212> TYPE: PRT
<213> ORGANISM: Artificial Sequence
<220> FEATURE:
<223> OTHER INFORMATION: Ralstonia DNA-binding peptide 35

<400> SEQUENCE: 87

Leu Ser Thr Glu Gln Val Val Ala Ile Ala Ser Asn Asn Gly Gly Lys
1 5 10 15

Pro Ala Leu Glu Ala Val Lys Ala Leu Leu Leu Glu Leu Arg Ala Ala
20 25 30

Pro Tyr Glu
35

<210> SEQ ID NO 88
<211> LENGTH: 35
<212> TYPE: PRT
<213> ORGANISM: Artificial Sequence
<220> FEATURE:
<223> OTHER INFORMATION: Ralstonia DNA-binding peptide 36

<400> SEQUENCE: 88

Leu Ser Thr Glu Gln Val Val Ala Ile Ala Ser Asn Asn Gly Gly Lys
1 5 10 15

Gln Ala Leu Glu Ala Val Lys Thr Gln Leu Leu Ala Leu Arg Thr Ala
20 25 30

Pro Tyr Glu
35

<210> SEQ ID NO 89
<211> LENGTH: 35
<212> TYPE: PRT
<213> ORGANISM: Artificial Sequence
<220> FEATURE:
<223> OTHER INFORMATION: Ralstonia DNA-binding peptide 37

<400> SEQUENCE: 89

Leu Ser Thr Glu Gln Val Val Ala Ile Ala Ser Asn Asn Gly Gly Lys
1 5 10 15

Gln Ala Leu Glu Ala Val Lys Ala Gln Leu Pro Ala Leu Arg Ala Ala
20 25 30

Pro Tyr Glu
35

<210> SEQ ID NO 90
<211> LENGTH: 35
<212> TYPE: PRT
<213> ORGANISM: Artificial Sequence
<220> FEATURE:
<223> OTHER INFORMATION: Ralstonia DNA-binding peptide 38

<400> SEQUENCE: 90

Leu Ser Thr Glu Gln Val Val Ala Ile Ala Ser Asn Asn Gly Gly Lys
1 5 10 15

Gln Ala Leu Glu Ala Val Lys Ala Gln Leu Leu Val Leu Arg Ala Ala
20 25 30

Pro Tyr Gly
35

<210> SEQ ID NO 91
<211> LENGTH: 35
<212> TYPE: PRT
<213> ORGANISM: Artificial Sequence
<220> FEATURE:

<223> OTHER INFORMATION: Ralstonia DNA-binding peptide 39

<400> SEQUENCE: 91

```
Leu Ser Thr Ala Gln Val Val Ala Ile Ala Ala Asn Asn Gly Gly Lys
1               5                   10                  15

Gln Ala Leu Glu Ala Val Arg Ala Leu Leu Pro Val Leu Arg Val Ala
            20                  25                  30

Pro Tyr Glu
        35
```

<210> SEQ ID NO 92
<211> LENGTH: 35
<212> TYPE: PRT
<213> ORGANISM: Artificial Sequence
<220> FEATURE:
<223> OTHER INFORMATION: Ralstonia DNA-binding peptide 40

<400> SEQUENCE: 92

```
Leu Ser Pro Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
        35
```

<210> SEQ ID NO 93
<211> LENGTH: 35
<212> TYPE: PRT
<213> ORGANISM: Artificial Sequence
<220> FEATURE:
<223> OTHER INFORMATION: Ralstonia DNA-binding peptide 41

<400> SEQUENCE: 93

```
Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
        35
```

<210> SEQ ID NO 94
<211> LENGTH: 35
<212> TYPE: PRT
<213> ORGANISM: Artificial Sequence
<220> FEATURE:
<223> OTHER INFORMATION: Ralstonia DNA-binding peptide 42

<400> SEQUENCE: 94

```
Leu Ser Pro Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
        35
```

<210> SEQ ID NO 95
<211> LENGTH: 35
<212> TYPE: PRT
<213> ORGANISM: Artificial Sequence
<220> FEATURE:
<223> OTHER INFORMATION: Ralstonia DNA-binding peptide 43

<400> SEQUENCE: 95

```
Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
        35


<210> SEQ ID NO 96
<211> LENGTH: 35
<212> TYPE: PRT
<213> ORGANISM: Artificial Sequence
<220> FEATURE:
<223> OTHER INFORMATION: Ralstonia DNA-binding peptide 44

<400> SEQUENCE: 96

Leu Ser Pro Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
        35


<210> SEQ ID NO 97
<211> LENGTH: 35
<212> TYPE: PRT
<213> ORGANISM: Artificial Sequence
<220> FEATURE:
<223> OTHER INFORMATION: Ralstonia DNA-binding peptide 45

<400> SEQUENCE: 97

Leu Ser Thr Glu Gln Val Val Val Ile Ala Ser Asn Asn Gly Gly Lys
1               5                   10                  15

Gln Ala Leu Glu Ala Val Lys Ala Gln Leu Leu Ala Leu Arg Ala Ala
            20                  25                  30

Pro Tyr Glu
        35


<210> SEQ ID NO 98
<211> LENGTH: 35
<212> TYPE: PRT
<213> ORGANISM: Artificial Sequence
<220> FEATURE:
<223> OTHER INFORMATION: Ralstonia DNA-binding peptide 46

<400> SEQUENCE: 98

Leu Ser Thr Glu Gln Val Val Ala Ile Ala Ser Asn Asn Gly Gly Lys
1               5                   10                  15

Gln Ala Leu Glu Ala Val Lys Ala Leu Leu Leu Glu Leu Arg Ala Ala
            20                  25                  30

Pro Tyr Glu
        35


<210> SEQ ID NO 99
<211> LENGTH: 35
<212> TYPE: PRT
<213> ORGANISM: Artificial Sequence
<220> FEATURE:
<223> OTHER INFORMATION: Ralstonia DNA-binding peptide 47

<400> SEQUENCE: 99

Leu Ser Thr Glu Gln Val Val Ala Ile Ala Ser Asn Asn Gly Gly Lys
1               5                   10                  15
```

```
Gln Ala Leu Glu Ala Val Lys Thr Gln Leu Leu Ala Leu Arg Thr Ala
            20                  25                  30

Pro Tyr Glu
        35


<210> SEQ ID NO 100
<211> LENGTH: 35
<212> TYPE: PRT
<213> ORGANISM: Artificial Sequence
<220> FEATURE:
<223> OTHER INFORMATION: Ralstonia DNA-binding peptide 48

<400> SEQUENCE: 100

Leu Ser Thr Glu Gln Val Val Ala Ile Ala Ser Asn Asn Gly Gly Lys
1               5                   10                  15

Gln Ala Leu Glu Ala Val Lys Ala Gln Leu Pro Ala Leu Arg Ala Ala
            20                  25                  30

Pro Tyr Glu
        35


<210> SEQ ID NO 101
<211> LENGTH: 35
<212> TYPE: PRT
<213> ORGANISM: Artificial Sequence
<220> FEATURE:
<223> OTHER INFORMATION: Ralstonia DNA-binding peptide 49

<400> SEQUENCE: 101

Leu Ser Pro Glu Gln Val Val Ala Ile Ala Ser Asn Asn Gly Gly Lys
1               5                   10                  15

Gln Ala Leu Glu Ala Val Arg Ala Leu Leu Pro Val Leu Arg Val Ala
            20                  25                  30

Pro Tyr Glu
        35


<210> SEQ ID NO 102
<211> LENGTH: 35
<212> TYPE: PRT
<213> ORGANISM: Artificial Sequence
<220> FEATURE:
<223> OTHER INFORMATION: Ralstonia DNA-binding peptide 50

<400> SEQUENCE: 102

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35


<210> SEQ ID NO 103
<211> LENGTH: 35
<212> TYPE: PRT
<213> ORGANISM: Artificial Sequence
<220> FEATURE:
<223> OTHER INFORMATION: Ralstonia DNA-binding peptide 51

<400> SEQUENCE: 103

Leu Ser Thr Glu Gln Val Val Ala Ile Ala Ser Asn Gly Gly Gly Lys
1               5                   10                  15

Gln Ala Leu Glu Gly Ile Gly Lys Gln Leu Gln Glu Leu Arg Ala Ala
            20                  25                  30
```

```
Pro His Gly
        35


<210> SEQ ID NO 104
<211> LENGTH: 35
<212> TYPE: PRT
<213> ORGANISM: Artificial Sequence
<220> FEATURE:
<223> OTHER INFORMATION: Ralstonia DNA-binding peptide 52

<400> SEQUENCE: 104

Leu Ser Thr Gly Gln Val Val Ala Ile Ala Ser Asn Gly Gly Gly Arg
1               5                   10                  15

Gln Ala Leu Glu Ala Val Arg Glu Gln Leu Leu Ala Leu Arg Ala Val
            20                  25                  30

Pro Tyr Glu
        35


<210> SEQ ID NO 105
<211> LENGTH: 35
<212> TYPE: PRT
<213> ORGANISM: Artificial Sequence
<220> FEATURE:
<223> OTHER INFORMATION: Ralstonia DNA-binding peptide 53

<400> SEQUENCE: 105

Leu Ser Thr Gly Gln Val Val Ala Ile Ala Ser Asn Gly Gly Gly Arg
1               5                   10                  15

Gln Ala Leu Glu Ala Val Arg Glu Gln Leu Leu Ala Leu Arg Ala Val
            20                  25                  30

Pro Tyr Glu
        35


<210> SEQ ID NO 106
<211> LENGTH: 35
<212> TYPE: PRT
<213> ORGANISM: Artificial Sequence
<220> FEATURE:
<223> OTHER INFORMATION: Ralstonia DNA-binding peptide 54

<400> SEQUENCE: 106

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35


<210> SEQ ID NO 107
<211> LENGTH: 35
<212> TYPE: PRT
<213> ORGANISM: Artificial Sequence
<220> FEATURE:
<223> OTHER INFORMATION: Ralstonia DNA-binding peptide 55

<400> SEQUENCE: 107

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35
```

<210> SEQ ID NO 108
<211> LENGTH: 35
<212> TYPE: PRT
<213> ORGANISM: Artificial Sequence
<220> FEATURE:
<223> OTHER INFORMATION: Ralstonia DNA-binding peptide 56

<400> SEQUENCE: 108

```
Leu Ser Thr Ala Gln Val Val Ala Ile Ala Ser Asn Gly Gly Gly Lys
1               5                   10                  15

Gln Ala Leu Glu Gly Ile Gly Glu Gln Leu Arg Lys Leu Arg Thr Ala
            20                  25                  30

Pro Tyr Gly
        35
```

<210> SEQ ID NO 109
<211> LENGTH: 35
<212> TYPE: PRT
<213> ORGANISM: Artificial Sequence
<220> FEATURE:
<223> OTHER INFORMATION: Ralstonia DNA-binding peptide 57

<400> SEQUENCE: 109

```
Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35
```

<210> SEQ ID NO 110
<211> LENGTH: 35
<212> TYPE: PRT
<213> ORGANISM: Artificial Sequence
<220> FEATURE:
<223> OTHER INFORMATION: Ralstonia DNA-binding peptide 58

<400> SEQUENCE: 110

```
Leu Ser Thr Glu Gln Val Val Ala Ile Ala Ser Asn Gly Gly Gly Lys
1               5                   10                  15

Gln Ala Leu Glu Gly Ile Gly Lys Gln Leu Gln Glu Leu Arg Ala Ala
            20                  25                  30

Pro His Gly
        35
```

<210> SEQ ID NO 111
<211> LENGTH: 35
<212> TYPE: PRT
<213> ORGANISM: Artificial Sequence
<220> FEATURE:
<223> OTHER INFORMATION: Ralstonia DNA-binding peptide 59

<400> SEQUENCE: 111

```
Leu Asn Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Glu
        35
```

<210> SEQ ID NO 112

<211> LENGTH: 35
<212> TYPE: PRT
<213> ORGANISM: Artificial Sequence
<220> FEATURE:
<223> OTHER INFORMATION: Ralstonia DNA-binding peptide 60

<400> SEQUENCE: 112

Leu Asn Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Glu
        35

<210> SEQ ID NO 113
<211> LENGTH: 35
<212> TYPE: PRT
<213> ORGANISM: Artificial Sequence
<220> FEATURE:
<223> OTHER INFORMATION: Ralstonia DNA-binding peptide 61

<400> SEQUENCE: 113

Leu Asn Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35

<210> SEQ ID NO 114
<211> LENGTH: 35
<212> TYPE: PRT
<213> ORGANISM: Artificial Sequence
<220> FEATURE:
<223> OTHER INFORMATION: Ralstonia DNA-binding peptide 62

<400> SEQUENCE: 114

Leu Ser Thr Glu Gln Val Val Ala Ile Ala Ser His Asp Gly Gly Lys
1               5                   10                  15

Gln Ala Leu Glu Ala Val Gly Ala Gln Leu Val Ala Leu Arg Ala Ala
            20                  25                  30

Pro Tyr Ala
        35

<210> SEQ ID NO 115
<211> LENGTH: 35
<212> TYPE: PRT
<213> ORGANISM: Artificial Sequence
<220> FEATURE:
<223> OTHER INFORMATION: Ralstonia DNA-binding peptide 63

<400> SEQUENCE: 115

Leu Ser Thr Ala Gln Val Val Ala Ile Ala Ser His Asp Gly Gly Asn
1               5                   10                  15

Gln Ala Leu Glu Ala Val Gly Thr Gln Leu Val Ala Leu Arg Ala Ala
            20                  25                  30

Pro Tyr Ala
        35

<210> SEQ ID NO 116
<211> LENGTH: 35
<212> TYPE: PRT
<213> ORGANISM: Artificial Sequence

```
<220> FEATURE:
<223> OTHER INFORMATION: Ralstonia DNA-binding peptide 64

<400> SEQUENCE: 116

Leu Ser Thr Glu Gln Val Val Ala Ile Ala Ser His Asp Gly Gly Lys
1               5                   10                  15

Gln Ala Leu Glu Ala Val Gly Ala Gln Leu Val Ala Leu Arg Ala Ala
            20                  25                  30

Pro Tyr Ala
        35


<210> SEQ ID NO 117
<211> LENGTH: 35
<212> TYPE: PRT
<213> ORGANISM: Artificial Sequence
<220> FEATURE:
<223> OTHER INFORMATION: Ralstonia DNA-binding peptide 65

<400> SEQUENCE: 117

Leu Asn Thr Ala Gln Ile Val Ala Ile Ala Ser His Asp Gly Gly Lys
1               5                   10                  15

Pro Ala Leu Glu Ala Val Trp Ala Lys Leu Pro Val Leu Arg Gly Ala
            20                  25                  30

Pro Tyr Ala
        35


<210> SEQ ID NO 118
<211> LENGTH: 35
<212> TYPE: PRT
<213> ORGANISM: Artificial Sequence
<220> FEATURE:
<223> OTHER INFORMATION: Ralstonia DNA-binding peptide 66

<400> SEQUENCE: 118

Leu Ser Thr Ala Gln Val Val Ala Val Ala Ser His Asp Gly Gly Lys
1               5                   10                  15

Pro Ala Leu Glu Ala Val Arg Lys Gln Leu Pro Val Leu Arg Gly Val
            20                  25                  30

Pro His Gln
        35


<210> SEQ ID NO 119
<211> LENGTH: 35
<212> TYPE: PRT
<213> ORGANISM: Artificial Sequence
<220> FEATURE:
<223> OTHER INFORMATION: Ralstonia DNA-binding peptide 67

<400> SEQUENCE: 119

Leu Ser Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Ala
            20                  25                  30

Pro Tyr Ala
        35


<210> SEQ ID NO 120
<211> LENGTH: 35
<212> TYPE: PRT
<213> ORGANISM: Artificial Sequence
<220> FEATURE:
<223> OTHER INFORMATION: Ralstonia DNA-binding peptide 68
```

<400> SEQUENCE: 120

Leu Asn Thr Ala Gln Val Val Ala Ile Ala Ser His Asp Gly Gly Lys
1 5 10 15

Pro Ala Leu Glu Ala Val Trp Ala Lys Leu Pro Val Leu Arg Gly Val
20 25 30

Pro Tyr Glu
35

<210> SEQ ID NO 121
<211> LENGTH: 35
<212> TYPE: PRT
<213> ORGANISM: Artificial Sequence
<220> FEATURE:
<223> OTHER INFORMATION: Ralstonia DNA-binding peptide 69

<400> SEQUENCE: 121

Leu Asn Thr Ala Gln Val Val Ala Ile Ala Ser His Asp Gly Gly Lys
1 5 10 15

Pro Ala Leu Glu Ala Val Trp Ala Lys Leu Pro Val Leu Arg Gly Val
20 25 30

Pro Tyr Ala
35

<210> SEQ ID NO 122
<211> LENGTH: 35
<212> TYPE: PRT
<213> ORGANISM: Artificial Sequence
<220> FEATURE:
<223> OTHER INFORMATION: Ralstonia DNA-binding peptide 70

<400> SEQUENCE: 122

Leu Ser Thr Ala Gln Val Val Ala Ile Ala Ser His Asp Gly Gly Lys
1 5 10 15

Gln Ala Leu Glu Ala Val Gly Ala Gln Leu Val Glu Leu Arg Ala Ala
20 25 30

Pro Tyr Ala
35

<210> SEQ ID NO 123
<211> LENGTH: 35
<212> TYPE: PRT
<213> ORGANISM: Artificial Sequence
<220> FEATURE:
<223> OTHER INFORMATION: Ralstonia DNA-binding peptide 71

<400> SEQUENCE: 123

Leu Ser Thr Glu Gln Val Val Ala Ile Ala Ser His Asp Gly Gly Lys
1 5 10 15

Gln Ala Leu Glu Ala Val Gly Ala Gln Leu Val Ala Leu Arg Ala Ala
20 25 30

Pro Tyr Ala
35

<210> SEQ ID NO 124
<211> LENGTH: 35
<212> TYPE: PRT
<213> ORGANISM: Artificial Sequence
<220> FEATURE:
<223> OTHER INFORMATION: Ralstonia DNA-binding peptide 72

<400> SEQUENCE: 124

Leu Asn Thr Ala Gln Val Val Ala Ile Ala Ser His Asp Gly Gly Lys

```
1               5                   10                  15

Pro Ala Leu Glu Ala Val Arg Ala Lys Leu Pro Val Leu Arg Gly Val
            20                  25                  30

Pro Tyr Ala
        35


<210> SEQ ID NO 125
<211> LENGTH: 35
<212> TYPE: PRT
<213> ORGANISM: Artificial Sequence
<220> FEATURE:
<223> OTHER INFORMATION: Ralstonia DNA-binding peptide 73

<400> SEQUENCE: 125

Leu Thr Pro Gln Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35


<210> SEQ ID NO 126
<211> LENGTH: 35
<212> TYPE: PRT
<213> ORGANISM: Artificial Sequence
<220> FEATURE:
<223> OTHER INFORMATION: Ralstonia DNA-binding peptide 74

<400> SEQUENCE: 126

Leu Thr Pro Gln Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35


<210> SEQ ID NO 127
<211> LENGTH: 35
<212> TYPE: PRT
<213> ORGANISM: Artificial Sequence
<220> FEATURE:
<223> OTHER INFORMATION: Ralstonia DNA-binding peptide 75

<400> SEQUENCE: 127

Leu Ser Thr Ala Gln Val Ala Thr Ile Ala Ser Ser Ile Gly Gly Arg
1               5                   10                  15

Gln Ala Leu Glu Ala Val Lys Val Gln Leu Pro Val Leu Arg Ala Ala
            20                  25                  30

Pro Tyr Gly
        35


<210> SEQ ID NO 128
<211> LENGTH: 35
<212> TYPE: PRT
<213> ORGANISM: Artificial Sequence
<220> FEATURE:
<223> OTHER INFORMATION: Ralstonia DNA-binding peptide 76

<400> SEQUENCE: 128

Leu Ser Thr Glu Gln Val Val Val Ile Ala Asn Ser Ile Gly Gly Lys
1               5                   10                  15

Gln Ala Leu Glu Ala Val Lys Val Gln Leu Pro Val Leu Arg Ala Ala
```

```
            20                  25                  30

Pro Tyr Glu
        35


<210> SEQ ID NO 129
<211> LENGTH: 35
<212> TYPE: PRT
<213> ORGANISM: Artificial Sequence
<220> FEATURE:
<223> OTHER INFORMATION: Ralstonia DNA-binding peptide 77

<400> SEQUENCE: 129

Leu Ser Thr Glu Gln Val Val Val Ile Ala Asn Ser Ile Gly Gly Lys
1               5                   10                  15

Gln Ala Leu Glu Ala Val Lys Val Gln Leu Pro Val Leu Arg Ala Ala
            20                  25                  30

Pro Tyr Glu
        35


<210> SEQ ID NO 130
<211> LENGTH: 35
<212> TYPE: PRT
<213> ORGANISM: Artificial Sequence
<220> FEATURE:
<223> OTHER INFORMATION: Ralstonia DNA-binding peptide 78

<400> SEQUENCE: 130

Leu Ser Thr Ala Gln Val Ala Thr Ile Ala Ser Ser Ile Gly Gly Arg
1               5                   10                  15

Gln Ala Leu Glu Ala Val Lys Val Gln Leu Pro Val Leu Arg Ala Ala
            20                  25                  30

Pro Tyr Gly
        35


<210> SEQ ID NO 131
<211> LENGTH: 35
<212> TYPE: PRT
<213> ORGANISM: Artificial Sequence
<220> FEATURE:
<223> OTHER INFORMATION: Ralstonia DNA-binding peptide 79

<400> SEQUENCE: 131

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35


<210> SEQ ID NO 132
<211> LENGTH: 35
<212> TYPE: PRT
<213> ORGANISM: Artificial Sequence
<220> FEATURE:
<223> OTHER INFORMATION: Ralstonia DNA-binding peptide 80

<400> SEQUENCE: 132

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
```

```
        35


<210> SEQ ID NO 133
<211> LENGTH: 35
<212> TYPE: PRT
<213> ORGANISM: Artificial Sequence
<220> FEATURE:
<223> OTHER INFORMATION: Ralstonia DNA-binding peptide 81

<400> SEQUENCE: 133

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35


<210> SEQ ID NO 134
<211> LENGTH: 35
<212> TYPE: PRT
<213> ORGANISM: Artificial Sequence
<220> FEATURE:
<223> OTHER INFORMATION: Ralstonia DNA-binding peptide 82

<400> SEQUENCE: 134

Leu Ser Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35


<210> SEQ ID NO 135
<211> LENGTH: 35
<212> TYPE: PRT
<213> ORGANISM: Artificial Sequence
<220> FEATURE:
<223> OTHER INFORMATION: Ralstonia DNA-binding peptide 83

<400> SEQUENCE: 135

Leu Ser Thr Glu Gln Val Val Thr Ile Ala Ser Ser Ile Gly Gly Lys
1               5                   10                  15

Gln Ala Leu Glu Ala Val Lys Val Gln Leu Pro Val Leu Arg Ala Ala
            20                  25                  30

Pro Tyr Glu
        35


<210> SEQ ID NO 136
<211> LENGTH: 29
<212> TYPE: PRT
<213> ORGANISM: Pseudomonas syringae pv. pisi str. 1704B

<400> SEQUENCE: 136

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 137
<211> LENGTH: 30
<212> TYPE: PRT
<213> ORGANISM: Gallionella capsiferriformans ES-2
```

```
<400> SEQUENCE: 137

Met Thr Ser Glu Gln Ile Val Ala Ile Gly Thr Ser Thr Gly Gly Thr
1               5                   10                  15

Gln Ala Leu Glu Ala Val Leu Thr Ala Leu Pro Arg Val Cys
            20                  25                  30


<210> SEQ ID NO 138
<211> LENGTH: 29
<212> TYPE: PRT
<213> ORGANISM: Pseudomonas fuscovaginae UPB0736

<400> SEQUENCE: 138

Thr Thr Glu Arg Ile Val Ala Ile Gly Thr Ser Thr Gly Gly Thr Gln
1               5                   10                  15

Ala Leu Glu Thr Val Leu Thr Ala Leu Pro Arg Val Cys
            20                  25


<210> SEQ ID NO 139
<211> LENGTH: 23
<212> TYPE: PRT
<213> ORGANISM: Artificial Sequence
<220> FEATURE:
<223> OTHER INFORMATION: DNA-binding fragment 41

<400> SEQUENCE: 139

Arg Ile Val Ala Ile Gly Thr Ser Thr Gly Gly Thr Gln Ala Leu Glu
1               5                   10                  15

Val Val Leu Thr Ala Leu Pro
            20


<210> SEQ ID NO 140
<211> LENGTH: 29
<212> TYPE: PRT
<213> ORGANISM: Artificial Sequence
<220> FEATURE:
<223> OTHER INFORMATION: DNA-binding fragment 42

<400> SEQUENCE: 140

Thr Thr Glu Arg Ile Val Ala Ile Gly Thr Ser Thr Gly Gly Thr Gln
1               5                   10                  15

Ala Leu Glu Thr Val Leu His Arg Leu Pro Ala Thr Cys
            20                  25


<210> SEQ ID NO 141
<211> LENGTH: 52
<212> TYPE: DNA
<213> ORGANISM: Artificial Sequence
<220> FEATURE:
<223> OTHER INFORMATION: Bmpr2 Target site

<400> SEQUENCE: 141

ttgatagtcg ccttatgttt tggatacaga atgttgacag gtaaacgaaa ta             52


<210> SEQ ID NO 142
<211> LENGTH: 16
<212> TYPE: DNA
<213> ORGANISM: Artificial Sequence
<220> FEATURE:
<223> OTHER INFORMATION: Forward RTN

<400> SEQUENCE: 142

tgatagtcgc cttatg                                                     16
```

```
<210> SEQ ID NO 143
<211> LENGTH: 16
<212> TYPE: DNA
<213> ORGANISM: Artificial Sequence
<220> FEATURE:
<223> OTHER INFORMATION: Reverse RTN

<400> SEQUENCE: 143

atttggttta cctgtc                                                    16


<210> SEQ ID NO 144
<211> LENGTH: 560
<212> TYPE: PRT
<213> ORGANISM: Artificial Sequence
<220> FEATURE:
<223> OTHER INFORMATION: Bmpr2 FWD RTN EBE

<400> SEQUENCE: 144

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly Leu Ser Thr Glu Gln Val Val Ala Ile Ala Ser Asn Lys
        35                  40                  45

Gly Gly Lys Gln Ala Leu Glu Ala Val Lys Ala His Leu Leu Asp Leu
    50                  55                  60

Leu Gly Ala Pro Tyr Val Leu Ser Thr Glu Gln Val Val Ala Ile Ala
65                  70                  75                  80

Ser Asn Asn Gly Gly Lys Gln Ala Leu Glu Ala Val Lys Ala Gln Leu
                85                  90                  95

Leu Glu Leu Arg Ala Ala Pro Tyr Glu Leu Ser Thr Ala Gln Val Val
            100                 105                 110

Ala Ile Ala Ser Asn Gly Gly Gly Lys Gln Ala Leu Glu Gly Ile Gly
        115                 120                 125

Glu Gln Leu Leu Lys Leu Arg Thr Ala Pro Tyr Gly Leu Ser Thr Glu
    130                 135                 140

Gln Val Val Ala Ile Ala Ser Asn Asn Gly Gly Lys Gln Ala Leu Glu
145                 150                 155                 160

Ala Val Lys Ala Gln Leu Leu Glu Leu Arg Ala Ala Pro Tyr Glu Leu
                165                 170                 175

Ser Thr Glu Gln Val Val Ala Ile Ala Ser Asn Lys Gly Gly Lys Gln
            180                 185                 190

Ala Leu Glu Ala Val Lys Ala His Leu Leu Asp Leu Leu Gly Ala Pro
        195                 200                 205

Tyr Val Leu Ser Thr Ala Gln Val Val Ala Ile Ala Ser Asn Gly Gly
    210                 215                 220

Gly Lys Gln Ala Leu Glu Gly Ile Gly Glu Gln Leu Leu Lys Leu Arg
225                 230                 235                 240

Thr Ala Pro Tyr Gly Leu Ser Thr Ala Gln Val Val Ala Ile Ala Ser
                245                 250                 255

His Asp Gly Gly Lys Pro Ala Leu Glu Ala Val Trp Ala Lys Leu Pro
            260                 265                 270

Val Leu Arg Gly Val Pro Tyr Ala Leu Ser Thr Glu Gln Val Val Ala
        275                 280                 285

Ile Ala Ser Asn Lys Gly Gly Lys Gln Ala Leu Glu Ala Val Lys Ala
    290                 295                 300

His Leu Leu Asp Leu Leu Gly Ala Pro Tyr Val Leu Ser Thr Ala Gln
```

```
305                 310                 315                 320

Val Val Ala Ile Ala Ser His Asp Gly Gly Lys Pro Ala Leu Glu Ala
                325                 330                 335

Val Trp Ala Lys Leu Pro Val Leu Arg Gly Val Pro Tyr Ala Leu Ser
            340                 345                 350

Thr Ala Gln Val Val Ala Ile Ala Ser His Asp Gly Gly Lys Pro Ala
        355                 360                 365

Leu Glu Ala Val Trp Ala Lys Leu Pro Val Leu Arg Gly Val Pro Tyr
    370                 375                 380

Ala Leu Ser Thr Ala Gln Val Val Ala Ile Ala Ser Asn Gly Gly Gly
385                 390                 395                 400

Lys Gln Ala Leu Glu Gly Ile Gly Glu Gln Leu Leu Lys Leu Arg Thr
                405                 410                 415

Ala Pro Tyr Gly Leu Ser Thr Ala Gln Val Val Ala Ile Ala Ser Asn
            420                 425                 430

Gly Gly Gly Lys Gln Ala Leu Glu Gly Ile Gly Glu Gln Leu Leu Lys
        435                 440                 445

Leu Arg Thr Ala Pro Tyr Gly Leu Ser Thr Glu Gln Val Val Ala Ile
    450                 455                 460

Ala Ser Asn Asn Gly Gly Lys Gln Ala Leu Glu Ala Val Lys Ala Gln
465                 470                 475                 480

Leu Leu Glu Leu Arg Ala Ala Pro Tyr Glu Leu Ser Thr Ala Gln Val
                485                 490                 495

Val Ala Ile Ala Ser Asn Gly Gly Gly Lys Gln Ala Leu Glu Gly Ile
            500                 505                 510

Gly Glu Gln Leu Leu Lys Leu Arg Thr Ala Pro Tyr Gly Leu Ser Thr
        515                 520                 525

Glu Gln Val Val Ala Ile Ala Ser Asn Lys Gly Gly Lys Gln Ala Leu
    530                 535                 540

Glu Ala Val Lys Ala His Leu Leu Asp Leu Leu Gly Ala Pro Tyr Val
545                 550                 555                 560
```

<210> SEQ ID NO 145
<211> LENGTH: 8106
<212> TYPE: DNA
<213> ORGANISM: Artificial Sequence
<220> FEATURE:
<223> OTHER INFORMATION: Bmpr2 FWD RTN

<400> SEQUENCE: 145

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660
```

```
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
accatggact acaaagacca tgacggtgat tataaagatc atgacatcga ttacaaggat    960
gacgatgaca agatggcccc caagaagaag aggaaggtgg gcattcaccg cggggtacct   1020
atggtggact tgaggacact cggttattcg caacagcaac aggagaaaat caagcctaag   1080
gtcaggagca ccgtcgcgca acaccacgag gcgcttgtgg ggcatggctt cactcatgcg   1140
catattgtcg cgctttcaca gcaccctgcg gcgcttggga cggtggctgt caaataccaa   1200
gatatgattg cggccctgcc cgaagccacg cacgaggcaa ttgtaggggt cggtaaacag   1260
tggtcgggag cgcgagcact tgaggcgctg ctgactgtgg cgggtgagct tagggggcct   1320
ccgctccagc tcgacaccgg gcagctgctg aagatcgcga agagaggggg agtaacagcg   1380
gtagaggcag tgcacgcctg gcgcaatgcg ctcaccgggg ccccttgaa cctgagcacc    1440
gcccaggtgg tggccatcgc cagcaacggc ggcggcaagc aggccctgga gggcatcggc   1500
gagcagctgc tgaagctgag gaccgccccc tacggcctga gcaccgagca ggtggtggcc   1560
atcgccagca acaagggcgg caagcaggcc ctggaggccg tgaaggccca cctgctggac   1620
ctgctgggcg cccccctacgt gctgagcacc gagcaggtgg tggccatcgc cagcaacaac   1680
ggcggcaagc aggccctgga ggccgtgaag gcccagctgc tggagctgag ggccgccccc   1740
tacgagctga gcaccgccca ggtggtggcc atcgccagca acggcggcgg caagcaggcc   1800
ctggagggca tcggcgagca gctgctgaag ctgaggaccg cccccctacgg cctgagcacc  1860
gagcaggtgg tggccatcgc cagcaacaac ggcggcaagc aggccctgga ggccgtgaag   1920
gcccagctgc tggagctgag ggccgccccc tacgagctga gcaccgagca ggtggtggcc   1980
atcgccagca acaagggcgg caagcaggcc ctggaggccg tgaaggccca cctgctggac   2040
ctgctgggcg cccccctacgt gctgagcacc gcccaggtgg tggccatcgc cagcaacggc  2100
ggcggcaagc aggccctgga gggcatcggc gagcagctgc tgaagctgag gaccgccccc   2160
tacggcctga gcaccgccca ggtggtggcc atcgccagcc acgacggcgg caagcccgcc   2220
ctggaggccg tgtgggccaa gctgcccgtg ctgaggggcg tgccctacgc cctgagcacc   2280
gagcaggtgg tggccatcgc cagcaacaag ggcggcaagc aggccctgga ggccgtgaag   2340
gcccacctgc tggacctgct gggcgccccc tacgtgctga gcaccgccca ggtggtggcc   2400
atcgccagcc acgacggcgg caagcccgcc ctggaggccg tgtgggccaa gctgcccgtg   2460
ctgaggggcg tgccctacgc cctgagcacc gcccaggtgg tggccatcgc cagccacgac   2520
ggcggcaagc ccgccctgga ggccgtgtgg gccaagctgc ccgtgctgag gggcgtgccc   2580
tacgccctga gcaccgccca ggtggtggcc atcgccagca acggcggcgg caagcaggcc   2640
ctggagggca tcggcgagca gctgctgaag ctgaggaccg cccccctacgg cctgagcacc  2700
gcccaggtgg tggccatcgc cagcaacggc ggcggcaagc aggccctgga gggcatcggc   2760
gagcagctgc tgaagctgag gaccgccccc tacggcctga gcaccgagca ggtggtggcc   2820
atcgccagca acaacggcgg caagcaggcc ctggaggccg tgaaggccca gctgctggag   2880
ctgagggccg cccccctacga gctgagcacc gcccaggtgg tggccatcgc cagcaacggc  2940
ggcggcaagc aggccctgga gggcatcggc gagcagctgc tgaagctgag gaccgccccc   3000
tacggcctga gcaccgagca ggtggtggcc atcgccagca acaagggcgg caagcaggcc   3060
```

```
ctggaggccg tgaaggccca cctgctggac ctgctgggcg ccccctacgt gctgagcacc   3120
gcccaggtgg tggccatcgc cagcaacggc ggaggacggc cagccttgga gtccatcgta   3180
gcccaattgt ccaggcccga tcccgcgttg gctgcgttaa cgaatgacca tctggtggcg   3240
ttggcatgtc ttggtggacg acccgcgctc gatgcagtca aaaagggtct gcctcatgct   3300
cccgcattga tcaaaagaac caaccggcgg attcccgaga gaacttccca tcgagtcgcg   3360
ggatcccaac tagtcaaaag tgaactggag gagaagaaat ctgaacttcg tcataaattg   3420
aaatatgtgc ctcatgaata tattgaatta attgaaattg ccagaaattc cactcaggat   3480
agaattcttg aaatgaaggt aatggaattt tttatgaaag tttatggata tagaggtaaa   3540
catttgggtg gatcaaggaa accggacgga gcaatttata ctgtcggatc tcctattgat   3600
tacggtgtga tcgtggatac taaagcttat agcggaggtt ataatctgcc aattggccaa   3660
gcagatgaaa tgcaacgata tgtcgaagaa aatcaaacac gaaacaaaca tatcaaccct   3720
aatgaatggt ggaaagtcta tccatcttct gtaacggaat ttaagttttt atttgtgagt   3780
ggtcacttta aaggaaacta caaagctcag cttacacgat taaatcatat cactaattgt   3840
aatggagctg ttcttagtgt agaagagctt ttaattggtg gagaaatgat taaagccggc   3900
acattaacct tagaggaagt cagacggaaa tttaataacg gcgagataaa cttttaaggg   3960
cccttcgaag gtaagcctat ccctaaccct ctcctcggtc tcgattctac gcgtaccggt   4020
catcatcacc atcaccattg agtttaaacc cgctgatcag cctcgactgt gccttctagt   4080
tgccagccat ctgttgtttg cccctccccc gtgccttcct tgaccctgga aggtgccact   4140
cccactgtcc tttcctaata aaatgaggaa attgcatcgc attgtctgag taggtgtcat   4200
tctattctgg ggggtggggt ggggcaggac agcaaggggg aggattggga agacaatagc   4260
aggcatgctg gggatgcggt gggctctatg gcttctgagg cggaaagaac cagctggggc   4320
tctagggggt atccccacgc gccctgtagc ggcgcattaa gcgcggcggg tgtggtggtt   4380
acgcgcagcg tgaccgctac acttgccagc gccctagcgc ccgctccttt cgctttcttc   4440
ccttcctttc tcgccacgtt cgccggcttt ccccgtcaag ctctaaatcg ggcatccct   4500
ttagggttcc gatttagtgc tttacggcac ctcgacccca aaaaacttga ttagggtgat   4560
ggttcacgta gtgggccatc gccctgatag acggtttttc gccctttgac gttggagtcc   4620
acgttcttta atagtggact cttgttccaa actggaacaa cactcaaccc tatctcggtc   4680
tattcttttg atttataagg gattttgggg atttcggcct attggttaaa aaatgagctg   4740
atttaacaaa aatttaacgc gaattaattc tgtggaatgt gtgtcagtta gggtgtggaa   4800
agtccccagg ctccccaggc aggcagaagt atgcaaagca tgcatctcaa ttagtcagca   4860
accaggtgtg gaaagtcccc aggctcccca gcaggcagaa gtatgcaaag catgcatctc   4920
aattagtcag caaccatagt cccgccccta actccgccca tcccgcccct aactccgccc   4980
agttccgccc attctccgcc ccatggctga ctaatttttt ttatttatgc agaggccgag   5040
gccgcctctg cctctgagct attccagaag tagtgaggag gcttttttgg aggcctaggc   5100
ttttgcaaaa agctcccggg agcttgtata tccattttcg gatctgatca gcacgtgttg   5160
acaattaatc atcggcatag tatatcggca tagtataata cgacaaggtg aggaactaaa   5220
ccatggccaa gcctttgtct caagaagaat ccaccctcat tgaaagagca acggctacaa   5280
tcaacagcat ccccatctct gaagactaca gcgtcgccag cgcagctctc tctagcgacg   5340
gccgcatctt cactggtgtc aatgtatatc attttactgg gggaccttgt gcagaactcg   5400
```

```
tggtgctggg cactgctgct gctgcggcag ctggcaacct gacttgtatc gtcgcgatcg   5460
gaaatgagaa caggggcatc ttgagcccct gcggacggtg tcgacaggtg cttctcgatc   5520
tgcatcctgg gatcaaagcg atagtgaagg acagtgatgg acagccgacg gcagttggga   5580
ttcgtgaatt gctgccctct ggttatgtgt gggagggcta agcacttcgt ggccgaggag   5640
caggactgac acgtgctacg agatttcgat tccaccgccg ccttctatga aaggttgggc   5700
ttcggaatcg ttttccggga cgccggctgg atgatcctcc agcgcgggga tctcatgctg   5760
gagttcttcg cccaccccaa cttgtttatt gcagcttata atggttacaa ataaagcaat   5820
agcatcacaa atttcacaaa taaagcattt ttttcactgc attctagttg tggtttgtcc   5880
aaactcatca atgtatctta tcatgtctgt ataccgtcga cctctagcta gagcttggcg   5940
taatcatggt catagctgtt tcctgtgtga aattgttatc cgctcacaat tccacacaac   6000
atacgagccg gaagcataaa gtgtaaagcc tggggtgcct aatgagtgag ctaactcaca   6060
ttaattgcgt tgcgctcact gcccgctttc cagtcgggaa acctgtcgtg ccagctgcat   6120
taatgaatcg gccaacgcgc ggggagaggc ggtttgcgta ttgggcgctc ttccgcttcc   6180
tcgctcactg actcgctgcg ctcggtcgtt cggctgcggc gagcggtatc agctcactca   6240
aaggcggtaa tacggttatc cacagaatca ggggataacg caggaaagaa catgtgagca   6300
aaaggccagc aaaaggccag gaaccgtaaa aaggccgcgt tgctggcgtt tttccatagg   6360
ctccgccccc ctgacgagca tcacaaaaat cgacgctcaa gtcagaggtg gcgaaacccg   6420
acaggactat aaagatacca ggcgtttccc cctggaagct ccctcgtgcg ctctcctgtt   6480
ccgaccctgc cgcttaccgg atacctgtcc gcctttctcc cttcgggaag cgtggcgctt   6540
tctcaatgct cacgctgtag gtatctcagt tcggtgtagg tcgttcgctc caagctgggc   6600
tgtgtgcacg aaccccccgt tcagcccgac cgctgcgcct tatccggtaa ctatcgtctt   6660
gagtccaacc cggtaagaca cgacttatcg ccactggcag cagccactgg taacaggatt   6720
agcagagcga ggtatgtagg cggtgctaca gagttcttga agtggtggcc taactacggc   6780
tacactagaa ggacagtatt tggtatctgc gctctgctga agccagttac cttcggaaaa   6840
agagttggta gctcttgatc cggcaaacaa accaccgctg gtagcggtgg tttttttgtt   6900
tgcaagcagc agattacgcg cagaaaaaaa ggatctcaag aagatccttt gatcttttct   6960
acggggtctg acgctcagtg gaacgaaaac tcacgttaag ggattttggt catgagatta   7020
tcaaaaagga tcttcaccta gatcctttta aattaaaaat gaagttttaa atcaatctaa   7080
agtatatatg agtaaacttg gtctgacagt taccaatgct taatcagtga ggcacctatc   7140
tcagcgatct gtctatttcg ttcatccata gttgcctgac tccccgtcgt gtagataact   7200
acgatacggg agggcttacc atctggcccc agtgctgcaa tgataccgcg agacccacgc   7260
tcaccggctc cagatttatc agcaataaac cagccagccg gaagggccga gcgcagaagt   7320
ggtcctgcaa ctttatccgc ctccatccag tctattaatt gttgccggga agctagagta   7380
agtagttcgc cagttaatag tttgcgcaac gttgttgcca ttgctacagg catcgtggtg   7440
tcacgctcgt cgtttggtat ggcttcattc agctccggtt cccaacgatc aaggcgagtt   7500
acatgatccc ccatgttgtg caaaaaagcg gttagctcct tcggtcctcc gatcgttgtc   7560
agaagtaagt tggccgcagt gttatcactc atggttatgg cagcactgca taattctctt   7620
actgtcatgc catccgtaag atgcttttct gtgactggtg agtactcaac caagtcattc   7680
tgagaatagt gtatgcggcg accgagttgc tcttgcccgg cgtcaatacg ggataatacc   7740
gcgccacata gcagaacttt aaaagtgctc atcattggaa aacgttcttc ggggcgaaaa   7800
```

```
ctctcaagga tcttaccgct gttgagatcc agttcgatgt aacccactcg tgcacccaac   7860

tgatcttcag catcttttac tttcaccagc gtttctgggt gagcaaaaac aggaaggcaa   7920

aatgccgcaa aaaagggaat aagggcgaca cggaaatgtt gaatactcat actcttcctt   7980

tttcaatatt attgaagcat ttatcagggt tattgtctca tgagcggata catatttgaa   8040

tgtatttaga aaaataaaca aataggggtt ccgcgcacat ttccccgaaa agtgccacct   8100

gacgtc                                                              8106
```

<210> SEQ ID NO 146
<211> LENGTH: 560
<212> TYPE: PRT
<213> ORGANISM: Artificial Sequence
<220> FEATURE:
<223> OTHER INFORMATION: Bmpr2 REV RTN EBE

<400> SEQUENCE: 146

```
Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu Leu Ser Thr Ala Gln Val Val Ala Ile Ala Ser Asn Gly
        35                  40                  45

Gly Gly Lys Gln Ala Leu Glu Gly Ile Gly Glu Gln Leu Leu Lys Leu
    50                  55                  60

Arg Thr Ala Pro Tyr Gly Leu Ser Thr Ala Gln Val Val Ala Ile Ala
65                  70                  75                  80

Ser Asn Gly Gly Gly Lys Gln Ala Leu Glu Gly Ile Gly Glu Gln Leu
                85                  90                  95

Leu Lys Leu Arg Thr Ala Pro Tyr Gly Leu Ser Thr Ala Gln Val Val
            100                 105                 110

Ala Ile Ala Ser Asn Gly Gly Gly Lys Gln Ala Leu Glu Gly Ile Gly
        115                 120                 125

Glu Gln Leu Leu Lys Leu Arg Thr Ala Pro Tyr Gly Leu Ser Thr Ala
    130                 135                 140

Gln Val Val Ala Ile Ala Ser His Asp Gly Gly Lys Pro Ala Leu Glu
145                 150                 155                 160

Ala Val Trp Ala Lys Leu Pro Val Leu Arg Gly Val Pro Tyr Ala Leu
                165                 170                 175

Ser Thr Glu Gln Val Val Ala Ile Ala Ser Asn Lys Gly Gly Lys Gln
            180                 185                 190

Ala Leu Glu Ala Val Lys Ala His Leu Leu Asp Leu Leu Gly Ala Pro
        195                 200                 205

Tyr Val Leu Ser Thr Ala Gln Val Val Ala Ile Ala Ser Asn Gly Gly
    210                 215                 220

Gly Lys Gln Ala Leu Glu Gly Ile Gly Glu Gln Leu Leu Lys Leu Arg
225                 230                 235                 240

Thr Ala Pro Tyr Gly Leu Ser Thr Ala Gln Val Val Ala Ile Ala Ser
                245                 250                 255

Asn Gly Gly Gly Lys Gln Ala Leu Glu Gly Ile Gly Glu Gln Leu Leu
            260                 265                 270

Lys Leu Arg Thr Ala Pro Tyr Gly Leu Ser Thr Ala Gln Val Val Ala
        275                 280                 285

Ile Ala Ser Asn Gly Gly Gly Lys Gln Ala Leu Glu Gly Ile Gly Glu
    290                 295                 300
```

```
Gln Leu Leu Lys Leu Arg Thr Ala Pro Tyr Gly Leu Ser Thr Glu Gln
305                 310                 315                 320

Val Val Ala Ile Ala Ser Asn Asn Gly Gly Lys Gln Ala Leu Glu Ala
                325                 330                 335

Val Lys Ala Gln Leu Leu Glu Leu Arg Ala Ala Pro Tyr Glu Leu Ser
            340                 345                 350

Thr Ala Gln Val Val Ala Ile Ala Ser His Asp Gly Gly Lys Pro Ala
        355                 360                 365

Leu Glu Ala Val Trp Ala Lys Leu Pro Val Leu Arg Gly Val Pro Tyr
    370                 375                 380

Ala Leu Ser Thr Ala Gln Val Val Ala Ile Ala Ser His Asp Gly Gly
385                 390                 395                 400

Lys Pro Ala Leu Glu Ala Val Trp Ala Lys Leu Pro Val Leu Arg Gly
                405                 410                 415

Val Pro Tyr Ala Leu Ser Thr Ala Gln Val Val Ala Ile Ala Ser Asn
            420                 425                 430

Gly Gly Gly Lys Gln Ala Leu Glu Gly Ile Gly Glu Gln Leu Leu Lys
        435                 440                 445

Leu Arg Thr Ala Pro Tyr Gly Leu Ser Thr Glu Gln Val Val Ala Ile
    450                 455                 460

Ala Ser Asn Lys Gly Gly Lys Gln Ala Leu Glu Ala Val Lys Ala His
465                 470                 475                 480

Leu Leu Asp Leu Leu Gly Ala Pro Tyr Val Leu Ser Thr Ala Gln Val
                485                 490                 495

Val Ala Ile Ala Ser Asn Gly Gly Gly Lys Gln Ala Leu Glu Gly Ile
            500                 505                 510

Gly Glu Gln Leu Leu Lys Leu Arg Thr Ala Pro Tyr Gly Leu Ser Thr
        515                 520                 525

Ala Gln Val Val Ala Ile Ala Ser His Asp Gly Gly Lys Pro Ala Leu
    530                 535                 540

Glu Ala Val Trp Ala Lys Leu Pro Val Leu Arg Gly Val Pro Tyr Ala
545                 550                 555                 560
```

<210> SEQ ID NO 147
<211> LENGTH: 8102
<212> TYPE: DNA
<213> ORGANISM: Artificial Sequence
<220> FEATURE:
<223> OTHER INFORMATION: Bmpr2 REV RTN

<400> SEQUENCE: 147

```
gacggatcgg gagatctccc gatcccctat ggtcgactct cagtacaatc tgctctgatg      60

ccgcatagtt aagccagtat ctgctccctg cttgtgtgtt ggaggtcgct gagtagtgcg     120

cgagcaaaat ttaagctaca acaaggcaag gcttgaccga caattgcatg aagaatctgc     180

ttagggttag gcgttttgcg ctgcttcgcg atgtacgggc cagatatacg cgttgacatt     240

gattattgac tagttattaa tagtaatcaa ttacggggtc attagttcat agcccatata     300

tggagttccg cgttacataa cttacggtaa atggcccgcc tggctgaccg cccaacgacc     360

cccgcccatt gacgtcaata atgacgtatg ttcccatagt aacgccaata gggactttcc     420

attgacgtca atgggtggag tatttacggt aaactgccca cttggcagta catcaagtgt     480

atcatatgcc aagtacgccc cctattgacg tcaatgacgg taaatggccc gcctggcatt     540

atgcccagta catgacctta tgggactttc ctacttggca gtacatctac gtattagtca     600
```

-continued

```
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
accatggact acaaagacca tgacggtgat tataaagatc atgacatcga ttacaaggat    960
gacgatgaca agatggcccc caagaagaag aggaaggtgg gcattcaccg cggggtacct   1020
atggtggact tgaggacact cggttattcg caacagcaac aggagaaaat caagcctaag   1080
gtcaggagca ccgtcgcgca acaccacgag gcgcttgtgg ggcatggctt cactcatgcg   1140
catattgtcg cgctttcaca gcaccctgcg gcgcttggga cggtggctgt caaataccaa   1200
gatatgattg cggccctgcc cgaagccacg cacgaggcaa ttgtaggggt cggtaaacag   1260
tggtcgggag cgcgagcact tgaggcgctg ctgactgtgg cgggtgagct tagggggcct   1320
ccgctccagc tcgacaccgg gcagctgctg aagatcgcga agagaggggg agtaacagcg   1380
gtagaggcag tgcacgcctg gcgcaatgcg ctcaccgggg ccccccttctg agcaccgagc   1440
aggtggtggc catcgccagc aacaacggcg gcaagcaggc cctggaggcc gtgaaggccc   1500
agctgctgga gctgagggcc gccccctacg agctgagcac cgcccaggtg gtggccatcg   1560
ccagcaacgg cggcggcaag caggccctgg agggcatcgg cgagcagctg ctgaagctga   1620
ggaccgcccc ctacggcctg agcaccgccc aggtggtggc catcgccagc aacggcggcg   1680
gcaagcaggc cctggagggc atcggcgagc agctgctgaa gctgaggacc gcccccctacg   1740
gcctgagcac cgcccaggtg gtggccatcg ccagcaacgg cggcggcaag caggccctgg   1800
agggcatcgg cgagcagctg ctgaagctga ggaccgcccc ctacggcctg agcaccgccc   1860
aggtggtggc catcgccagc cacgacggcg gcaagcccgc cctggaggcc gtgtgggcca   1920
agctgcccgt gctgaggggc gtgccctacg ccctgagcac cgagcaggtg gtggccatcg   1980
ccagcaacaa gggcggcaag caggccctgg aggccgtgaa ggcccacctg ctggacctgc   2040
tgggcgcccc ctacgtgctg agcaccgccc aggtggtggc catcgccagc aacggcggcg   2100
gcaagcaggc cctggagggc atcggcgagc agctgctgaa gctgaggacc gcccccctacg   2160
gcctgagcac cgcccaggtg gtggccatcg ccagcaacgg cggcggcaag caggccctgg   2220
agggcatcgg cgagcagctg ctgaagctga ggaccgcccc ctacggcctg agcaccgccc   2280
aggtggtggc catcgccagc aacggcggcg gcaagcaggc cctggagggc atcggcgagc   2340
agctgctgaa gctgaggacc gcccccctacg gcctgagcac cgagcaggtg gtggccatcg   2400
ccagcaacaa cggcggcaag caggccctgg aggccgtgaa ggcccagctg ctggagctga   2460
gggccgcccc ctacgagctg agcaccgccc aggtggtggc catcgccagc cacgacggcg   2520
gcaagcccgc cctggaggcc gtgtgggcca agctgcccgt gctgaggggc gtgccctacg   2580
ccctgagcac cgcccaggtg gtggccatcg ccagccacga cggcggcaag cccgccctgg   2640
aggccgtgtg ggccaagctg cccgtgctga ggggcgtgcc ctacgccctg agcaccgccc   2700
aggtggtggc catcgccagc aacggcggcg gcaagcaggc cctggagggc atcggcgagc   2760
agctgctgaa gctgaggacc gcccccctacg gcctgagcac cgagcaggtg gtggccatcg   2820
ccagcaacaa gggcggcaag caggccctgg aggccgtgaa ggcccacctg ctggacctgc   2880
tgggcgcccc ctacgtgctg agcaccgccc aggtggtggc catcgccagc aacggcggcg   2940
gcaagcaggc cctggagggc atcggcgagc agctgctgaa gctgaggacc gcccccctacg   3000
```

```
gcctgagcac cgcccaggtg gtggccatcg ccagccacga cggcggcaag cccgccctgg   3060
aggccgtgtg ggccaagctg cccgtgctga ggggcgtgcc ctacgccctg agcaccgagc   3120
aggtggtgac catcgccagc agcatcggag gacggccagc cttggagtcc atcgtagccc   3180
aattgtccag gcccgatccc gcgttggctg cgttaacgaa tgaccatctg gtggcgttgg   3240
catgtcttgg tggacgaccc gcgctcgatg cagtcaaaaa gggtctgcct catgctcccg   3300
cattgatcaa aagaaccaac cggcggattc ccgagagaac ttcccatcga gtcgcgggat   3360
cccaactagt caaaagtgaa ctggaggaga agaaatctga acttcgtcat aaattgaaat   3420
atgtgcctca tgaatatatt gaattaattg aaattgccag aaattccact caggatagaa   3480
ttcttgaaat gaaggtaatg gaattttta tgaaagttta tggatataga ggtaaacatt   3540
tgggtggatc aaggaaaccg gacggagcaa tttatactgt cggatctcct attgattacg   3600
gtgtgatcgt ggatactaaa gcttatagcg gaggttataa tctgccaatt ggccaagcag   3660
atgaaatgca acgatatgtc gaagaaaatc aaacacgaaa caaacatatc aaccctaatg   3720
aatggtggaa agtctatcca tcttctgtaa cggaatttaa gtttttattt gtgagtggtc   3780
actttaaagg aaactacaaa gctcagctta cacgattaaa tcatatcact aattgtaatg   3840
gagctgttct tagtgtagaa gagcttttaa ttggtggaga aatgattaaa gccggcacat   3900
taaccttaga ggaagtcaga cggaaattta ataacggcga gataaacttt taagggccct   3960
tcgaaggtaa gcctatccct aaccctctcc tcggtctcga ttctacgcgt accggtcatc   4020
atcaccatca ccattgagtt taaacccgct gatcagcctc gactgtgcct tctagttgcc   4080
agccatctgt tgtttgcccc tcccccgtgc cttccttgac cctggaaggt gccactccca   4140
ctgtcctttc ctaataaaat gaggaaattg catcgcattg tctgagtagg tgtcattcta   4200
ttctgggggg tggggtgggg caggacagca agggggagga ttgggaagac aatagcaggc   4260
atgctgggga tgcggtgggc tctatggctt ctgaggcgga aagaaccagc tggggctcta   4320
gggggtatcc ccacgcgccc tgtagcggcg cattaagcgc ggcgggtgtg gtggttacgc   4380
gcagcgtgac cgctacactt gccagcgccc tagcgcccgc tcctttcgct ttcttccctt   4440
cctttctcgc cacgttcgcc ggctttcccc gtcaagctct aaatcggggc atccctttag   4500
ggttccgatt tagtgcttta cggcacctcg accccaaaaa acttgattag ggtgatggtt   4560
cacgtagtgg gccatcgccc tgatagacgg tttttcgccc tttgacgttg gagtccacgt   4620
tctttaatag tggactcttg ttccaaactg gaacaacact caaccctatc tcggtctatt   4680
cttttgattt ataagggatt ttggggattt cggcctattg gttaaaaaat gagctgattt   4740
aacaaaaatt taacgcgaat taattctgtg gaatgtgtgt cagttagggt gtggaaagtc   4800
cccaggctcc ccaggcaggc agaagtatgc aaagcatgca tctcaattag tcagcaacca   4860
ggtgtggaaa gtccccaggc tccccagcag gcagaagtat gcaaagcatg catctcaatt   4920
agtcagcaac catagtcccg cccctaactc cgcccatccc gcccctaact ccgcccagtt   4980
ccgcccattc tccgccccat ggctgactaa ttttttttat ttatgcagag gccgaggccg   5040
cctctgcctc tgagctattc cagaagtagt gaggaggctt ttttggaggc ctaggctttt   5100
gcaaaaagct cccgggagct tgtatatcca ttttcggatc tgatcagcac gtgttgacaa   5160
ttaatcatcg gcatagtata tcggcatagt ataatacgac aaggtgagga actaaaccat   5220
ggccaagcct ttgtctcaag aagaatccac cctcattgaa agagcaacgg ctacaatcaa   5280
cagcatcccc atctctgaag actacagcgt cgccagcgca gctctctcta gcgacggccg   5340
```

-continued

```
catcttcact ggtgtcaatg tatatcattt tactgggggga ccttgtgcag aactcgtggt   5400
gctgggcact gctgctgctg cggcagctgg caacctgact tgtatcgtcg cgatcggaaa   5460
tgagaacagg ggcatcttga gcccctgcgg acggtgtcga caggtgcttc tcgatctgca   5520
tcctgggatc aaagcgatag tgaaggacag tgatggacag ccgacggcag ttgggattcg   5580
tgaattgctg ccctctggtt atgtgtggga gggctaagca cttcgtggcc gaggagcagg   5640
actgacacgt gctacgagat ttcgattcca ccgccgcctt ctatgaaagg ttgggcttcg   5700
gaatcgtttt ccgggacgcc ggctggatga tcctccagcg cggggatctc atgctggagt   5760
tcttcgccca ccccaacttg tttattgcag cttataatgg ttacaaataa agcaatagca   5820
tcacaaattt cacaaataaa gcattttttt cactgcattc tagttgtggt ttgtccaaac   5880
tcatcaatgt atcttatcat gtctgtatac cgtcgacctc tagctagagc ttggcgtaat   5940
catggtcata gctgtttcct gtgtgaaatt gttatccgct cacaattcca cacaacatac   6000
gagccggaag cataaagtgt aaagcctggg gtgcctaatg agtgagctaa ctcacattaa   6060
ttgcgttgcg ctcactgccc gctttccagt cgggaaacct gtcgtgccag ctgcattaat   6120
gaatcggcca acgcgcgggg agaggcggtt tgcgtattgg gcgctcttcc gcttcctcgc   6180
tcactgactc gctgcgctcg gtcgttcggc tgcggcgagc ggtatcagct cactcaaagg   6240
cggtaatacg gttatccaca gaatcagggg ataacgcagg aaagaacatg tgagcaaaag   6300
gccagcaaaa ggccaggaac cgtaaaaagg ccgcgttgct ggcgtttttc cataggctcc   6360
gcccccctga cgagcatcac aaaaatcgac gctcaagtca gaggtggcga aacccgacag   6420
gactataaag ataccaggcg tttccccctg gaagctccct cgtgcgctct cctgttccga   6480
ccctgccgct taccggatac ctgtccgcct ttctcccttc gggaagcgtg gcgctttctc   6540
aatgctcacg ctgtaggtat ctcagttcgg tgtaggtcgt tcgctccaag ctgggctgtg   6600
tgcacgaacc ccccgttcag cccgaccgct gcgccttatc cggtaactat cgtcttgagt   6660
ccaacccggt aagacacgac ttatcgccac tggcagcagc cactggtaac aggattagca   6720
gagcgaggta tgtaggcggt gctacagagt tcttgaagtg gtggcctaac tacggctaca   6780
ctagaaggac agtatttggt atctgcgctc tgctgaagcc agttaccttc ggaaaaagag   6840
ttggtagctc ttgatccggc aaacaaacca ccgctggtag cggtggtttt tttgtttgca   6900
agcagcagat tacgcgcaga aaaaaaggat ctcaagaaga tcctttgatc ttttctacgg   6960
ggtctgacgc tcagtggaac gaaaactcac gttaagggat tttggtcatg agattatcaa   7020
aaaggatctt cacctagatc cttttaaatt aaaaatgaag ttttaaatca atctaaagta   7080
tatatgagta aacttggtct gacagttacc aatgcttaat cagtgaggca cctatctcag   7140
cgatctgtct atttcgttca tccatagttg cctgactccc cgtcgtgtag ataactacga   7200
tacgggaggg cttaccatct ggccccagtg ctgcaatgat accgcgagac ccacgctcac   7260
cggctccaga tttatcagca ataaaccagc cagccggaag ggccgagcgc agaagtggtc   7320
ctgcaacttt atccgcctcc atccagtcta ttaattgttg ccgggaagct agagtaagta   7380
gttcgccagt taatagtttg cgcaacgttg ttgccattgc tacaggcatc gtggtgtcac   7440
gctcgtcgtt tggtatggct tcattcagct ccggttccca acgatcaagg cgagttacat   7500
gatcccccat gttgtgcaaa aaagcggtta gctccttcgg tcctccgatc gttgtcagaa   7560
gtaagttggc cgcagtgtta tcactcatgg ttatggcagc actgcataat tctcttactg   7620
tcatgccatc cgtaagatgc ttttctgtga ctggtgagta ctcaaccaag tcattctgag   7680
aatagtgtat gcggcgaccg agttgctctt gcccggcgtc aatacgggat aataccgcgc   7740
```

```
cacatagcag aactttaaaa gtgctcatca ttggaaaacg ttcttcgggg cgaaaactct   7800

caaggatctt accgctgttg agatccagtt cgatgtaacc cactcgtgca cccaactgat   7860

cttcagcatc ttttactttc accagcgttt ctgggtgagc aaaaacagga aggcaaaatg   7920

ccgcaaaaaa gggaataagg gcgacacgga aatgttgaat actcatactc ttcctttttc   7980

aatattattg aagcatttat cagggttatt gtctcatgag cggatacata tttgaatgta   8040

tttagaaaaa taaacaaata ggggttccgc gcacatttcc ccgaaaagtg ccacctgacg   8100

tc                                                                  8102
```

<210> SEQ ID NO 148
<211> LENGTH: 2706
<212> TYPE: DNA
<213> ORGANISM: Artificial Sequence
<220> FEATURE:
<223> OTHER INFORMATION: XTN sub-array backbone

<400> SEQUENCE: 148

```
ggatcccggg cccgtcgact gcagaggcct gcatgcaagc ttggcgtaat catggtcata     60

gctgtttcct gtgtgaaatt gttatccgct cacaattcca cacaacatac gagccggaag    120

cataaagtgt aaagcctggg gtgcctaatg agtgagctaa ctcacattaa ttgcgttgcg    180

ctcactgccc gctttccagt cgggaaacct gtcgtgccag ctgcattaat gaatcggcca    240

acgcgcgggg agaggcggtt tgcgtattgg gcgctcttcc gcttcctcgc tcactgactc    300

gctgcgctcg gtcgttcggc tgcggcgagc ggtatcagct cactcaaagg cggtaatacg    360

gttatccaca gaatcagggg ataacgcagg aaagaacatg tgagcaaaag gccagcaaaa    420

ggccaggaac cgtaaaaagg ccgcgttgct ggcgtttttc cataggctcc gcccccctga    480

cgagcatcac aaaaatcgac gctcaagtca gaggtggcga aacccgacag gactataaag    540

ataccaggcg tttccccctg gaagctccct cgtgcgctct cctgttccga ccctgccgct    600

taccggatac ctgtccgcct ttctcccttc gggaagcgtg gcgctttctc atagctcacg    660

ctgtaggtat ctcagttcgg tgtaggtcgt tcgctccaag ctgggctgtg tgcacgaacc    720

ccccgttcag cccgaccgct gcgccttatc cggtaactat cgtcttgagt ccaacccggt    780

aagacacgac ttatcgccac tggcagcagc cactggtaac aggattagca gagcgaggta    840

tgtaggcggt gctacagagt tcttgaagtg gtggcctaac tacggctaca ctagaagaac    900

agtatttggt atctgcgctc tgctgaagcc agttaccttc ggaaaaagag ttggtagctc    960

ttgatccggc aaacaaacca ccgctggtag cggtggtttt tttgtttgca agcagcagat   1020

tacgcgcaga aaaaaaggat ctcaagaaga tcctttgatc ttttctacgg ggtctgacgc   1080

tcagtggaac gaaaactcac gttaagggat tttggtcatg agattatcaa aaaggatctt   1140

cacctagatc cttttaaatt aaaaatgaag ttttaaatca atctaaagta tatatgagta   1200

aacttggtct gacagttacc aatgcttaat cagtgaggca cctatctcag cgatctgtct   1260

atttcgttca tccatagttg cctgactccc cgtcgtgtag ataactacga tacgggaggg   1320

cttaccatct ggccccagtg ctgcaatgat accgcgagag ccacgctcac cggctccaga   1380

tttatcagca ataaaccagc cagccggaag ggccgagcgc agaagtggtc ctgcaacttt   1440

atccgcctcc atccagtcta ttaattgttg ccgggaagct agagtaagta gttcgccagt   1500

taatagtttg cgcaacgttg ttgccattgc tacaggcatc gtggtgtcac gctcgtcgtt   1560

tggtatggct tcattcagct ccggttccca acgatcaagg cgagttacat gatcccccat   1620
```

```
gttgtgcaaa aaagcggtta gctccttcgg tcctccgatc gttgtcagaa gtaagttggc   1680
cgcagtgtta tcactcatgg ttatggcagc actgcataat tctcttactg tcatgccatc   1740
cgtaagatgc ttttctgtga ctggtgagta ctcaaccaag tcattctgag aatagtgtat   1800
gcggcgaccg agttgctctt gcccggcgtc aatacgggat aataccgcgc cacatagcag   1860
aactttaaaa gtgctcatca ttggaaaacg ttcttcgggg cgaaaactct caaggatctt   1920
accgctgttg agatccagtt cgatgtaacc cactcgtgca cccaactgat cttcagcatc   1980
ttttactttc accagcgttt ctgggtgagc aaaaacagga aggcaaaatg ccgcaaaaaa   2040
gggaataagg gcgacacgga aatgttgaat actcatactc ttcctttttc aatattattg   2100
aagcatttat cagggttatt gtctcatgag cggatacata tttgaatgta tttagaaaaa   2160
taaacaaata ggggttccgc gcacatttcc ccgaaaagtg ccacctgacg tctaagaaac   2220
cattattatc atgacattaa cctataaaaa taggcgtatc acgaggccct ttcgtctcgc   2280
gcgtttcggt gatgacggtg aaaacctctg acacatgcag ctcccggaga cggtcacagc   2340
ttgtctgtaa gcggatgccg ggagcagaca agcccgtcag ggcgcgtcag cgggtgttgg   2400
cgggtgtcgg ggctggctta actatgcggc atcagagcag attgtactga gagtgcacca   2460
tatgcggtgt gaaataccgc acagatgcgt aaggagaaaa taccgcatca ggcgccattc   2520
gccattcagg ctgcgcaact gttgggaagg gcgatcggtg cgggcctctt cgctattacg   2580
ccagctggcg aaagggggat gtgctgcaag gcgattaagt tgggtaacgc cagggttttc   2640
ccagtcacga cgttgtaaaa cgacggccag tgaattcgag ctcggtacct cgcgaatgca   2700
tctaga                                                              2706
```

<210> SEQ ID NO 149
<211> LENGTH: 6426
<212> TYPE: DNA
<213> ORGANISM: Artificial Sequence
<220> FEATURE:
<223> OTHER INFORMATION: XTN-bb
<220> FEATURE:
<221> NAME/KEY: misc_feature
<222> LOCATION: (31)..(39)
<223> OTHER INFORMATION: n is a, c, g, or t

<400> SEQUENCE: 149

```
ctgacacccg aacaggtggt cgccattgct nnnnnnnnng gaggacggcc agccttggag     60
tccatcgtag cccaattgtc caggcccgat cccgcgttgg ctgcgttaac gaatgaccat    120
ctggtggcgt tggcatgtct tggtggacga cccgcgctcg atgcagtcaa aaagggtctg    180
cctcatgctc ccgcattgat caaaagaacc aaccggcgga ttcccgagag aacttcccat    240
cgagtcgcgg gatcccaact agtcaaaagt gaactggagg agaagaaatc tgaacttcgt    300
cataaattga aatatgtgcc tcatgaatat attgaattaa ttgaaattgc cagaaattcc    360
actcaggata gaattcttga aatgaaggta atggaatttt ttatgaaagt ttatggatat    420
agaggtaaac atttgggtgg atcaaggaaa ccggacggag caatttatac tgtcggatct    480
cctattgatt acggtgtgat cgtggatact aaagcttata gcggaggtta taatctgcca    540
attggccaag cagatgaaat gcaacgatat gtcgaagaaa atcaaacacg aaacaaacat    600
atcaacccta atgaatggtg gaaagtctat ccatcttctg taacggaatt taagttttta    660
tttgtgagtg gtcactttaa aggaaactac aaagctcagc ttacacgatt aaatcatatc    720
actaattgta atggagctgt tcttagtgta gaagagcttt taattggtgg agaaatgatt    780
aaagccggca cattaacctt agaggaagtc agacggaaat ttaataacgg cgagataaac    840
```

```
ttttaagggc ccttcgaagg taagcctatc cctaaccctc tcctcggtct cgattctacg    900
cgtaccggtc atcatcacca tcaccattga gtttaaaccc gctgatcagc ctcgactgtg    960
ccttctagtt gccagccatc tgttgtttgc ccctcccccg tgccttcctt gaccctggaa   1020
ggtgccactc ccactgtcct ttcctaataa aatgaggaaa ttgcatcgca ttgtctgagt   1080
aggtgtcatt ctattctggg gggtggggtg gggcaggaca gcaaggggga ggattgggaa   1140
gacaatagca ggcatgctgg ggatgcggtg ggctctatgg cttctgaggc ggaaagaacc   1200
agctggggct ctagggggta tccccacgcg ccctgtagcg gcgcattaag cgcggcgggt   1260
gtggtggtta cgcgcagcgt gaccgctaca cttgccagcg ccctagcgcc cgctcctttc   1320
gctttcttcc cttcctttct cgccacgttc gccggctttc cccgtcaagc tctaaatcgg   1380
ggcatccctt tagggttccg atttagtgct ttacggcacc tcgaccccaa aaaacttgat   1440
tagggtgatg gttcacgtag tgggccatcg ccctgataga cggtttttcg ccctttgacg   1500
ttggagtcca cgttctttaa tagtggactc ttgttccaaa ctggaacaac actcaaccct   1560
atctcggtct attcttttga tttataaggg attttgggga tttcggccta ttggttaaaa   1620
aatgagctga tttaacaaaa atttaacgcg aattaattct gtggaatgtg tgtcagttag   1680
ggtgtggaaa gtccccaggc tccccaggca ggcagaagta tgcaaagcat gcatctcaat   1740
tagtcagcaa ccaggtgtgg aaagtcccca ggctccccag caggcagaag tatgcaaagc   1800
atgcatctca attagtcagc aaccatagtc ccgcccctaa ctccgcccat cccgccccta   1860
actccgccca gttccgccca ttctccgccc catggctgac taattttttt tatttatgca   1920
gaggccgagg ccgcctctgc ctctgagcta ttccagaagt agtgaggagg cttttttgga   1980
ggcctaggct tttgcaaaaa gctcccggga gcttgtatat ccattttcgg atctgatcag   2040
cacgtgttga caattaatca tcggcatagt atatcggcat agtataatac gacaaggtga   2100
ggaactaaac catggccaag cctttgtctc aagaagaatc caccctcatt gaaagagcaa   2160
cggctacaat caacagcatc cccatctctg aagactacag cgtcgccagc gcagctctct   2220
ctagcgacgg ccgcatcttc actggtgtca atgtatatca ttttactggg ggaccttgtg   2280
cagaactcgt ggtgctgggc actgctgctg ctgcggcagc tggcaacctg acttgtatcg   2340
tcgcgatcgg aaatgagaac aggggcatct tgagcccctg cggacggtgt cgacaggtgc   2400
ttctcgatct gcatcctggg atcaaagcga tagtgaagga cagtgatgga cagccgacgg   2460
cagttgggat tcgtgaattg ctgccctctg gttatgtgtg ggagggctaa gcacttcgtg   2520
gccgaggagc aggactgaca cgtgctacga gatttcgatt ccaccgccgc cttctatgaa   2580
aggttgggct tcggaatcgt tttccgggac gccggctgga tgatcctcca gcgcggggat   2640
ctcatgctgg agttcttcgc ccaccccaac ttgtttattg cagcttataa tggttacaaa   2700
taaagcaata gcatcacaaa tttcacaaat aaagcatttt tttcactgca ttctagttgt   2760
ggtttgtcca aactcatcaa tgtatcttat catgtctgta taccgtcgac ctctagctag   2820
agcttggcgt aatcatggtc atagctgttt cctgtgtgaa attgttatcc gctcacaatt   2880
ccacacaaca tacgagccgg aagcataaag tgtaaagcct ggggtgccta atgagtgagc   2940
taactcacat taattgcgtt gcgctcactg cccgctttcc agtcgggaaa cctgtcgtgc   3000
cagctgcatt aatgaatcgg ccaacgcgcg gggagaggcg gtttgcgtat tgggcgctct   3060
tccgcttcct cgctcactga ctcgctgcgc tcggtcgttc ggctgcggcg agcggtatca   3120
gctcactcaa aggcggtaat acggttatcc acagaatcag gggataacgc aggaaagaac   3180
```

-continued

```
atgtgagcaa aaggccagca aaaggccagg aaccgtaaaa aggccgcgtt gctggcgttt   3240
ttccataggc tccgcccccc tgacgagcat cacaaaaatc gacgctcaag tcagaggtgg   3300
cgaaacccga caggactata aagataccag gcgtttcccc ctggaagctc cctcgtgcgc   3360
tctcctgttc cgaccctgcc gcttaccgga tacctgtccg cctttctccc ttcgggaagc   3420
gtggcgcttt ctcaatgctc acgctgtagg tatctcagtt cggtgtaggt cgttcgctcc   3480
aagctgggct gtgtgcacga accccccgtt cagcccgacc gctgcgcctt atccggtaac   3540
tatcgtcttg agtccaaccc ggtaagacac gacttatcgc cactggcagc agccactggt   3600
aacaggatta gcagagcgag gtatgtaggc ggtgctacag agttcttgaa gtggtggcct   3660
aactacggct acactagaag gacagtattt ggtatctgcg ctctgctgaa gccagttacc   3720
ttcggaaaaa gagttggtag ctcttgatcc ggcaaacaaa ccaccgctgg tagcggtggt   3780
tttttgttt gcaagcagca gattacgcgc agaaaaaaag gatctcaaga agatcctttg   3840
atcttttcta cggggtctga cgctcagtgg aacgaaaact cacgttaagg gattttggtc   3900
atgagattat caaaaaggat cttcacctag atccttttaa attaaaaatg aagttttaaa   3960
tcaatctaaa gtatatatga gtaaacttgg tctgacagtt accaatgctt aatcagtgag   4020
gcacctatct cagcgatctg tctatttcgt tcatccatag ttgcctgact ccccgtcgtg   4080
tagataacta cgatacggga gggcttacca tctggcccca gtgctgcaat gataccgcga   4140
gacccacgct caccggctcc agatttatca gcaataaacc agccagccgg aagggccgag   4200
cgcagaagtg gtcctgcaac tttatccgcc tccatccagt ctattaattg ttgccgggaa   4260
gctagagtaa gtagttcgcc agttaatagt ttgcgcaacg ttgttgccat tgctacaggc   4320
atcgtggtgt cacgctcgtc gtttggtatg gcttcattca gctccggttc ccaacgatca   4380
aggcgagtta catgatcccc catgttgtgc aaaaaagcgg ttagctcctt cggtcctccg   4440
atcgttgtca gaagtaagtt ggccgcagtg ttatcactca tggttatggc agcactgcat   4500
aattctctta ctgtcatgcc atccgtaaga tgcttttctg tgactggtga gtactcaacc   4560
aagtcattct gagaatagtg tatgcggcga ccgagttgct cttgcccggc gtcaatacgg   4620
gataataccg cgccacatag cagaacttta aaagtgctca tcattggaaa acgttcttcg   4680
gggcgaaaac tctcaaggat cttaccgctg ttgagatcca gttcgatgta acccactcgt   4740
gcacccaact gatcttcagc atcttttact ttcaccagcg tttctgggtg agcaaaaaca   4800
ggaaggcaaa atgccgcaaa aaagggaata agggcgacac ggaaatgttg aatactcata   4860
ctcttccttt ttcaatatta ttgaagcatt tatcagggtt attgtctcat gagcggatac   4920
atatttgaat gtatttagaa aaataaacaa ataggggttc cgcgcacatt tccccgaaaa   4980
gtgccacctg acgtcgacgg atcgggagat ctcccgatcc cctatggtcg actctcagta   5040
caatctgctc tgatgccgca tagttaagcc agtatctgct ccctgcttgt gtgttggagg   5100
tcgctgagta gtgcgcgagc aaaatttaag ctacaacaag gcaaggcttg accgacaatt   5160
gcatgaagaa tctgcttagg gttaggcgtt ttgcgctgct tcgcgatgta cgggccagat   5220
atacgcgttg acattgatta ttgactagtt attaatagta atcaattacg gggtcattag   5280
ttcatagccc atatatggag ttccgcgtta cataacttac ggtaaatggc ccgcctggct   5340
gaccgcccaa cgacccccgc ccattgacgt caataatgac gtatgttccc atagtaacgc   5400
caatagggac tttccattga cgtcaatggg tggagtattt acggtaaact gcccacttgg   5460
cagtacatca agtgtatcat atgccaagta cgccccctat tgacgtcaat gacggtaaat   5520
ggcccgcctg gcattatgcc cagtacatga ccttatggga ctttcctact tggcagtaca   5580
```

```
tctacgtatt agtcatcgct attaccatgg tgatgcggtt ttggcagtac atcaatgggc   5640

gtggatagcg gtttgactca cggggatttc caagtctcca ccccattgac gtcaatggga   5700

gtttgttttg gcaccaaaat caacgggact ttccaaaatg tcgtaacaac tccgccccat   5760

tgacgcaaat gggcggtagg cgtgtacggt gggaggtcta tataagcaga gctctctggc   5820

taactagaga acccactgct tactggctta tcgaaattaa tacgactcac tatagggaga   5880

cccaagctgg ctagcaccat ggactacaaa gaccatgacg gtgattataa agatcatgac   5940

atcgattaca aggatgacga tgacaagatg gcccccaaga agaagaggaa ggtgggcatt   6000

caccgcgggg tacctatggt ggacttgagg acactcggtt attcgcaaca gcaacaggag   6060

aaaatcaagc ctaaggtcag gagcaccgtc gcgcaacacc acgaggcgct tgtggggcat   6120

ggcttcactc atgcgcatat tgtcgcgctt tcacagcacc ctgcggcgct tgggacggtg   6180

gctgtcaaat accaagatat gattgcggcc ctgcccgaag ccacgcacga ggcaattgta   6240

ggggtcggta aacagtggtc gggagcgcga gcacttgagg cgctgctgac tgtggcgggt   6300

gagcttaggg ggcctccgct ccagctcgac accgggcagc tgctgaagat cgcgaagaga   6360

gggggagtaa cagcggtaga ggcagtgcac gcctggcgca atgcgctcac cggggccccc   6420

ttgaac                                                               6426
```

<210> SEQ ID NO 150
<211> LENGTH: 6426
<212> TYPE: DNA
<213> ORGANISM: Artificial Sequence
<220> FEATURE:
<223> OTHER INFORMATION: XTN-bbA

<400> SEQUENCE: 150

```
ctgacacccg aacaggtggt cgccattgct tctaacatcg gaggacggcc agccttggag     60

tccatcgtag cccaattgtc caggcccgat cccgcgttgg ctgcgttaac gaatgaccat    120

ctggtggcgt tggcatgtct tggtggacga cccgcgctcg atgcagtcaa aaagggtctg    180

cctcatgctc ccgcattgat caaaagaacc aaccggcgga ttcccgagag aacttcccat    240

cgagtcgcgg gatcccaact agtcaaaagt gaactggagg agaagaaatc tgaacttcgt    300

cataaattga aatatgtgcc tcatgaatat attgaattaa ttgaaattgc cagaaattcc    360

actcaggata gaattcttga aatgaaggta atggaatttt ttatgaaagt ttatggatat    420

agaggtaaac atttgggtgg atcaaggaaa ccggacggag caatttatac tgtcggatct    480

cctattgatt acggtgtgat cgtggatact aaagcttata gcggaggtta taatctgcca    540

attggccaag cagatgaaat gcaacgatat gtcgaagaaa atcaaacacg aaacaaacat    600

atcaacccta atgaatggtg gaaagtctat ccatcttctg taacggaatt taagttttta    660

tttgtgagtg gtcactttaa aggaaactac aaagctcagc ttacacgatt aaatcatatc    720

actaattgta atggagctgt tcttagtgta gaagagcttt taattggtgg agaaatgatt    780

aaagccggca cattaacctt agaggaagtc agacggaaat ttaataacgg cgagataaac    840

ttttaagggc ccttcgaagg taagcctatc cctaaccctc tcctcggtct cgattctacg    900

cgtaccggtc atcatcacca tcaccattga gtttaaaccc gctgatcagc ctcgactgtg    960

ccttctagtt gccagccatc tgttgtttgc ccctcccccg tgccttcctt gaccctggaa   1020

ggtgccactc ccactgtcct ttcctaataa aatgaggaaa ttgcatcgca ttgtctgagt   1080

aggtgtcatt ctattctggg gggtggggtg gggcaggaca gcaaggggga ggattgggaa   1140
```

```
gacaatagca ggcatgctgg ggatgcggtg ggctctatgg cttctgaggc ggaaagaacc   1200
agctggggct ctagggggta tccccacgcg ccctgtagcg gcgcattaag cgcggcgggt   1260
gtggtggtta cgcgcagcgt gaccgctaca cttgccagcg ccctagcgcc cgctcctttc   1320
gctttcttcc cttcctttct cgccacgttc gccggctttc cccgtcaagc tctaaatcgg   1380
ggcatccctt tagggttccg atttagtgct ttacggcacc tcgaccccaa aaaacttgat   1440
tagggtgatg gttcacgtag tgggccatcg ccctgataga cggtttttcg ccctttgacg   1500
ttggagtcca cgttctttaa tagtggactc ttgttccaaa ctggaacaac actcaaccct   1560
atctcggtct attcttttga tttataaggg attttgggga tttcggccta ttggttaaaa   1620
aatgagctga tttaacaaaa atttaacgcg aattaattct gtggaatgtg tgtcagttag   1680
ggtgtggaaa gtccccaggc tccccaggca ggcagaagta tgcaaagcat gcatctcaat   1740
tagtcagcaa ccaggtgtgg aaagtcccca ggctccccag caggcagaag tatgcaaagc   1800
atgcatctca attagtcagc aaccatagtc ccgcccctaa ctccgcccat cccgccccta   1860
actccgccca gttccgccca ttctccgccc catggctgac taattttttt tatttatgca   1920
gaggccgagg ccgcctctgc ctctgagcta ttccagaagt agtgaggagg cttttttgga   1980
ggcctaggct tttgcaaaaa gctcccggga gcttgtatat ccattttcgg atctgatcag   2040
cacgtgttga caattaatca tcggcatagt atatcggcat agtataatac gacaaggtga   2100
ggaactaaac catggccaag cctttgtctc aagaagaatc caccctcatt gaaagagcaa   2160
cggctacaat caacagcatc cccatctctg aagactacag cgtcgccagc gcagctctct   2220
ctagcgacgg ccgcatcttc actggtgtca atgtatatca ttttactggg ggaccttgtg   2280
cagaactcgt ggtgctgggc actgctgctg ctgcggcagc tggcaacctg acttgtatcg   2340
tcgcgatcgg aaatgagaac aggggcatct tgagcccctg cggacggtgt cgacaggtgc   2400
ttctcgatct gcatcctggg atcaaagcga tagtgaagga cagtgatgga cagccgacgg   2460
cagttgggat tcgtgaattg ctgccctctg gttatgtgtg ggagggctaa gcacttcgtg   2520
gccgaggagc aggactgaca cgtgctacga gatttcgatt ccaccgccgc cttctatgaa   2580
aggttgggct tcggaatcgt tttccgggac gccggctgga tgatcctcca gcgcggggat   2640
ctcatgctgg agttcttcgc ccaccccaac ttgtttattg cagcttataa tggttacaaa   2700
taaagcaata gcatcacaaa tttcacaaat aaagcatttt tttcactgca ttctagttgt   2760
ggtttgtcca aactcatcaa tgtatcttat catgtctgta taccgtcgac ctctagctag   2820
agcttggcgt aatcatggtc atagctgttt cctgtgtgaa attgttatcc gctcacaatt   2880
ccacacaaca tacgagccgg aagcataaag tgtaaagcct ggggtgccta atgagtgagc   2940
taactcacat taattgcgtt gcgctcactg cccgctttcc agtcgggaaa cctgtcgtgc   3000
cagctgcatt aatgaatcgg ccaacgcgcg gggagaggcg gtttgcgtat tgggcgctct   3060
tccgcttcct cgctcactga ctcgctgcgc tcggtcgttc ggctgcggcg agcggtatca   3120
gctcactcaa aggcggtaat acggttatcc acagaatcag gggataacgc aggaaagaac   3180
atgtgagcaa aaggccagca aaaggccagg aaccgtaaaa aggccgcgtt gctggcgttt   3240
ttccataggc tccgcccccc tgacgagcat cacaaaaatc gacgctcaag tcagaggtgg   3300
cgaaacccga caggactata aagataccag gcgtttcccc ctggaagctc cctcgtgcgc   3360
tctcctgttc cgaccctgcc gcttaccgga tacctgtccg cctttctccc ttcgggaagc   3420
gtggcgcttt ctcaatgctc acgctgtagg tatctcagtt cggtgtaggt cgttcgctcc   3480
aagctgggct gtgtgcacga accccccgtt cagcccgacc gctgcgcctt atccggtaac   3540
```

```
tatcgtcttg agtccaaccc ggtaagacac gacttatcgc cactggcagc agccactggt   3600
aacaggatta gcagagcgag gtatgtaggc ggtgctacag agttcttgaa gtggtggcct   3660
aactacggct acactagaag gacagtattt ggtatctgcg ctctgctgaa gccagttacc   3720
ttcggaaaaa gagttggtag ctcttgatcc ggcaaacaaa ccaccgctgg tagcggtggt   3780
tttttgttt gcaagcagca gattacgcgc agaaaaaaag gatctcaaga agatcctttg    3840
atcttttcta cggggtctga cgctcagtgg aacgaaaact cacgttaagg gattttggtc   3900
atgagattat caaaaaggat cttcacctag atccttttaa attaaaaatg aagttttaaa   3960
tcaatctaaa gtatatatga gtaaacttgg tctgacagtt accaatgctt aatcagtgag   4020
gcacctatct cagcgatctg tctatttcgt tcatccatag ttgcctgact ccccgtcgtg   4080
tagataacta cgatacggga gggcttacca tctggcccca gtgctgcaat gataccgcga   4140
gacccacgct caccggctcc agatttatca gcaataaacc agccagccgg aagggccgag   4200
cgcagaagtg gtcctgcaac tttatccgcc tccatccagt ctattaattg ttgccgggaa   4260
gctagagtaa gtagttcgcc agttaatagt ttgcgcaacg ttgttgccat tgctacaggc   4320
atcgtggtgt cacgctcgtc gtttggtatg gcttcattca gctccggttc ccaacgatca   4380
aggcgagtta catgatcccc catgttgtgc aaaaaagcgg ttagctcctt cggtcctccg   4440
atcgttgtca gaagtaagtt ggccgcagtg ttatcactca tggttatggc agcactgcat   4500
aattctctta ctgtcatgcc atccgtaaga tgcttttctg tgactggtga gtactcaacc   4560
aagtcattct gagaatagtg tatgcggcga ccgagttgct cttgcccggc gtcaatacgg   4620
gataataccg cgccacatag cagaacttta aaagtgctca tcattggaaa acgttcttcg   4680
gggcgaaaac tctcaaggat cttaccgctg ttgagatcca gttcgatgta acccactcgt   4740
gcacccaact gatcttcagc atcttttact ttcaccagcg tttctgggtg agcaaaaaca   4800
ggaaggcaaa atgccgcaaa aaagggaata agggcgacac ggaaatgttg aatactcata   4860
ctcttccttt ttcaatatta ttgaagcatt tatcagggtt attgtctcat gagcggatac   4920
atatttgaat gtatttagaa aaataaacaa ataggggttc cgcgcacatt tccccgaaaa   4980
gtgccacctg acgtcgacgg atcgggagat ctcccgatcc cctatggtcg actctcagta   5040
caatctgctc tgatgccgca tagttaagcc agtatctgct ccctgcttgt gtgttggagg   5100
tcgctgagta gtgcgcgagc aaaatttaag ctacaacaag gcaaggcttg accgacaatt   5160
gcatgaagaa tctgcttagg gttaggcgtt ttgcgctgct tcgcgatgta cgggccagat   5220
atacgcgttg acattgatta ttgactagtt attaatagta atcaattacg gggtcattag   5280
ttcatagccc atatatggag ttccgcgtta cataacttac ggtaaatggc ccgcctggct   5340
gaccgcccaa cgacccccgc ccattgacgt caataatgac gtatgttccc atagtaacgc   5400
caatagggac tttccattga cgtcaatggg tggagtattt acggtaaact gcccacttgg   5460
cagtacatca agtgtatcat atgccaagta cgccccctat tgacgtcaat gacggtaaat   5520
ggcccgcctg gcattatgcc cagtacatga ccttatggga ctttcctact tggcagtaca   5580
tctacgtatt agtcatcgct attaccatgg tgatgcggtt ttggcagtac atcaatgggc   5640
gtggatagcg gtttgactca cggggatttc caagtctcca ccccattgac gtcaatggga   5700
gtttgttttg gcaccaaaat caacgggact ttccaaaatg tcgtaacaac tccgccccat   5760
tgacgcaaat gggcggtagg cgtgtacggt gggaggtcta tataagcaga gctctctggc   5820
taactagaga acccactgct tactggctta tcgaaattaa tacgactcac tatagggaga   5880
```

```
cccaagctgg ctagcaccat ggactacaaa gaccatgacg gtgattataa agatcatgac   5940

atcgattaca aggatgacga tgacaagatg gccccccaaga agaagaggaa ggtgggcatt   6000

caccgcgggg tacctatggt ggacttgagg acactcggtt attcgcaaca gcaacaggag   6060

aaaatcaagc ctaaggtcag gagcaccgtc gcgcaacacc acgaggcgct tgtggggcat   6120

ggcttcactc atgcgcatat tgtcgcgctt tcacagcacc ctgcggcgct tgggacggtg   6180

gctgtcaaat accaagatat gattgcggcc ctgcccgaag ccacgcacga ggcaattgta   6240

ggggtcggta aacagtggtc gggagcgcga gcacttgagg cgctgctgac tgtggcgggt   6300

gagcttaggg ggcctccgct ccagctcgac accgggcagc tgctgaagat cgcgaagaga   6360

gggggagtaa cagcggtaga ggcagtgcac gcctggcgca atgcgctcac cggggccccc   6420

ttgaac                                                                6426
```

<210> SEQ ID NO 151
<211> LENGTH: 6426
<212> TYPE: DNA
<213> ORGANISM: Artificial Sequence
<220> FEATURE:
<223> OTHER INFORMATION: XTN-bbC

<400> SEQUENCE: 151

```
ctgacacccg aacaggtggt cgccattgct tcccacgacg gaggacggcc agccttggag     60

tccatcgtag cccaattgtc caggcccgat cccgcgttgg ctgcgttaac gaatgaccat    120

ctggtggcgt tggcatgtct tggtggacga cccgcgctcg atgcagtcaa aaagggtctg    180

cctcatgctc ccgcattgat caaaagaacc aaccggcgga ttcccgagag aacttcccat    240

cgagtcgcgg gatcccaact agtcaaaagt gaactggagg agaagaaatc tgaacttcgt    300

cataaattga aatatgtgcc tcatgaatat attgaattaa ttgaaattgc cagaaattcc    360

actcaggata gaattcttga aatgaaggta atggaatttt ttatgaaagt ttatggatat    420

agaggtaaac atttgggtgg atcaaggaaa ccggacggag caatttatac tgtcggatct    480

cctattgatt acggtgtgat cgtggatact aaagcttata gcggaggtta taatctgcca    540

attggccaag cagatgaaat gcaacgatat gtcgaagaaa atcaaacacg aaacaaacat    600

atcaacccta atgaatggtg gaaagtctat ccatcttctg taacggaatt taagtttttta    660

tttgtgagtg gtcactttaa aggaaactac aaagctcagc ttacacgatt aaatcatatc    720

actaattgta atggagctgt tcttagtgta gaagagcttt taattggtgg agaaatgatt    780

aaagccggca cattaacctt agaggaagtc agacggaaat ttaataacgg cgagataaac    840

ttttaagggc ccttcgaagg taagcctatc cctaaccctc tcctcggtct cgattctacg    900

cgtaccggtc atcatcacca tcaccattga gtttaaaccc gctgatcagc ctcgactgtg    960

ccttctagtt gccagccatc tgttgtttgc ccctcccccg tgccttcctt gaccctggaa   1020

ggtgccactc ccactgtcct ttcctaataa aatgaggaaa ttgcatcgca ttgtctgagt   1080

aggtgtcatt ctattctggg gggtggggtg gggcaggaca gcaaggggga ggattgggaa   1140

gacaatagca ggcatgctgg ggatgcggtg ggctctatgg cttctgaggc ggaaagaacc   1200

agctggggct ctagggggta tccccacgcg ccctgtagcg gcgcattaag cgcggcgggt   1260

gtggtggtta cgcgcagcgt gaccgctaca cttgccagcg ccctagcgcc cgctcctttc   1320

gctttcttcc cttcctttct cgccacgttc gccggctttc cccgtcaagc tctaaatcgg   1380

ggcatccctt tagggttccg atttagtgct ttacggcacc tcgaccccaa aaaacttgat   1440

tagggtgatg gttcacgtag tgggccatcg ccctgataga cggtttttcg ccctttgacg   1500
```

```
ttggagtcca cgttctttaa tagtggactc ttgttccaaa ctggaacaac actcaaccct   1560
atctcggtct attcttttga tttataaggg attttgggga tttcggccta ttggttaaaa   1620
aatgagctga tttaacaaaa atttaacgcg aattaattct gtggaatgtg tgtcagttag   1680
ggtgtggaaa gtccccaggc tccccaggca ggcagaagta tgcaaagcat gcatctcaat   1740
tagtcagcaa ccaggtgtgg aaagtcccca ggctccccag caggcagaag tatgcaaagc   1800
atgcatctca attagtcagc aaccatagtc ccgcccctaa ctccgcccat cccgccccta   1860
actccgccca gttccgccca ttctccgccc catggctgac taattttttt tatttatgca   1920
gaggccgagg ccgcctctgc ctctgagcta ttccagaagt agtgaggagg cttttttgga   1980
ggcctaggct tttgcaaaaa gctcccggga gcttgtatat ccattttcgg atctgatcag   2040
cacgtgttga caattaatca tcggcatagt atatcggcat agtataatac gacaaggtga   2100
ggaactaaac catggccaag cctttgtctc aagaagaatc caccctcatt gaaagagcaa   2160
cggctacaat caacagcatc cccatctctg aagactacag cgtcgccagc gcagctctct   2220
ctagcgacgg ccgcatcttc actggtgtca atgtatatca ttttactggg ggaccttgtg   2280
cagaactcgt ggtgctgggc actgctgctg ctgcggcagc tggcaacctg acttgtatcg   2340
tcgcgatcgg aaatgagaac aggggcatct tgagcccctg cggacggtgt cgacaggtgc   2400
ttctcgatct gcatcctggg atcaaagcga tagtgaagga cagtgatgga cagccgacgg   2460
cagttgggat tcgtgaattg ctgccctctg gttatgtgtg ggagggctaa gcacttcgtg   2520
gccgaggagc aggactgaca cgtgctacga gatttcgatt ccaccgccgc cttctatgaa   2580
aggttgggct tcggaatcgt tttccgggac gccggctgga tgatcctcca gcgcggggat   2640
ctcatgctgg agttcttcgc ccaccccaac ttgtttattg cagcttataa tggttacaaa   2700
taaagcaata gcatcacaaa tttcacaaat aaagcatttt tttcactgca ttctagttgt   2760
ggtttgtcca aactcatcaa tgtatcttat catgtctgta taccgtcgac ctctagctag   2820
agcttggcgt aatcatggtc atagctgttt cctgtgtgaa attgttatcc gctcacaatt   2880
ccacacaaca tacgagccgg aagcataaag tgtaaagcct ggggtgccta atgagtgagc   2940
taactcacat taattgcgtt gcgctcactg cccgctttcc agtcgggaaa cctgtcgtgc   3000
cagctgcatt aatgaatcgg ccaacgcgcg gggagaggcg gtttgcgtat tgggcgctct   3060
tccgcttcct cgctcactga ctcgctgcgc tcggtcgttc ggctgcggcg agcggtatca   3120
gctcactcaa aggcggtaat acggttatcc acagaatcag gggataacgc aggaaagaac   3180
atgtgagcaa aaggccagca aaaggccagg aaccgtaaaa aggccgcgtt gctggcgttt   3240
ttccataggc tccgcccccc tgacgagcat cacaaaaatc gacgctcaag tcagaggtgg   3300
cgaaacccga caggactata aagataccag gcgtttcccc ctggaagctc cctcgtgcgc   3360
tctcctgttc cgaccctgcc gcttaccgga tacctgtccg cctttctccc ttcgggaagc   3420
gtggcgcttt ctcaatgctc acgctgtagg tatctcagtt cggtgtaggt cgttcgctcc   3480
aagctgggct gtgtgcacga accccccgtt cagcccgacc gctgcgcctt atccggtaac   3540
tatcgtcttg agtccaaccc ggtaagacac gacttatcgc cactggcagc agccactggt   3600
aacaggatta gcagagcgag gtatgtaggc ggtgctacag agttcttgaa gtggtggcct   3660
aactacggct acactagaag gacagtattt ggtatctgcg ctctgctgaa gccagttacc   3720
ttcggaaaaa gagttggtag ctcttgatcc ggcaaacaaa ccaccgctgg tagcggtggt   3780
tttttgttt gcaagcagca gattacgcgc agaaaaaaag gatctcaaga agatcctttg   3840
```

```
atcttttcta cggggtctga cgctcagtgg aacgaaaact cacgttaagg gattttggtc   3900
atgagattat caaaaaggat cttcacctag atcctttttaa attaaaaatg aagttttaaa   3960
tcaatctaaa gtatatatga gtaaacttgg tctgacagtt accaatgctt aatcagtgag   4020
gcacctatct cagcgatctg tctatttcgt tcatccatag ttgcctgact ccccgtcgtg   4080
tagataacta cgatacggga gggcttacca tctggcccca gtgctgcaat gataccgcga   4140
gacccacgct caccggctcc agatttatca gcaataaacc agccagccgg aagggccgag   4200
cgcagaagtg gtcctgcaac tttatccgcc tccatccagt ctattaattg ttgccgggaa   4260
gctagagtaa gtagttcgcc agttaatagt ttgcgcaacg ttgttgccat tgctacaggc   4320
atcgtggtgt cacgctcgtc gtttggtatg gcttcattca gctccggttc ccaacgatca   4380
aggcgagtta catgatcccc catgttgtgc aaaaaagcgg ttagctcctt cggtcctccg   4440
atcgttgtca gaagtaagtt ggccgcagtg ttatcactca tggttatggc agcactgcat   4500
aattctctta ctgtcatgcc atccgtaaga tgcttttctg tgactggtga gtactcaacc   4560
aagtcattct gagaatagtg tatgcggcga ccgagttgct cttgcccggc gtcaatacgg   4620
gataataccg cgccacatag cagaacttta aaagtgctca tcattggaaa acgttcttcg   4680
gggcgaaaac tctcaaggat cttaccgctg ttgagatcca gttcgatgta acccactcgt   4740
gcacccaact gatcttcagc atcttttact ttcaccagcg tttctgggtg agcaaaaaca   4800
ggaaggcaaa atgccgcaaa aaagggaata agggcgacac ggaaatgttg aatactcata   4860
ctcttccttt ttcaatatta ttgaagcatt tatcagggtt attgtctcat gagcggatac   4920
atatttgaat gtatttagaa aaataaacaa ataggggttc cgcgcacatt tccccgaaaa   4980
gtgccacctg acgtcgacgg atcgggagat ctcccgatcc cctatggtcg actctcagta   5040
caatctgctc tgatgccgca tagttaagcc agtatctgct ccctgcttgt gtgttggagg   5100
tcgctgagta gtgcgcgagc aaaatttaag ctacaacaag gcaaggcttg accgacaatt   5160
gcatgaagaa tctgcttagg gttaggcgtt ttgcgctgct tcgcgatgta cgggccagat   5220
atacgcgttg acattgatta ttgactagtt attaatagta atcaattacg gggtcattag   5280
ttcatagccc atatatggag ttccgcgtta cataacttac ggtaaatggc ccgcctggct   5340
gaccgcccaa cgacccccgc ccattgacgt caataatgac gtatgttccc atagtaacgc   5400
caatagggac tttccattga cgtcaatggg tggagtattt acggtaaact gcccacttgg   5460
cagtacatca agtgtatcat atgccaagta cgccccctat tgacgtcaat gacggtaaat   5520
ggcccgcctg gcattatgcc cagtacatga ccttatggga ctttcctact tggcagtaca   5580
tctacgtatt agtcatcgct attaccatgg tgatgcggtt ttggcagtac atcaatgggc   5640
gtggatagcg gtttgactca cggggatttc caagtctcca ccccattgac gtcaatggga   5700
gtttgttttg gcaccaaaat caacgggact ttccaaaatg tcgtaacaac tccgccccat   5760
tgacgcaaat gggcggtagg cgtgtacggt gggaggtcta tataagcaga gctctctggc   5820
taactagaga acccactgct tactggctta tcgaaattaa tacgactcac tatagggaga   5880
cccaagctgg ctagcaccat ggactacaaa gaccatgacg gtgattataa agatcatgac   5940
atcgattaca aggatgacga tgacaagatg gcccccaaga agaagaggaa ggtgggcatt   6000
caccgcgggg tacctatggt ggacttgagg acactcggtt attcgcaaca gcaacaggag   6060
aaaatcaagc ctaaggtcag gagcaccgtc gcgcaacacc acgaggcgct tgtggggcat   6120
ggcttcactc atgcgcatat tgtcgcgctt tcacagcacc ctgcggcgct tgggacggtg   6180
gctgtcaaat accaagatat gattgcggcc ctgcccgaag ccacgcacga ggcaattgta   6240
```

```
ggggtcggta aacagtggtc gggagcgcga gcacttgagg cgctgctgac tgtggcgggt   6300

gagcttaggg ggcctccgct ccagctcgac accgggcagc tgctgaagat cgcgaagaga   6360

gggggagtaa cagcggtaga ggcagtgcac gcctggcgca atgcgctcac cggggccccc   6420

ttgaac                                                              6426
```

<210> SEQ ID NO 152
<211> LENGTH: 6426
<212> TYPE: DNA
<213> ORGANISM: Artificial Sequence
<220> FEATURE:
<223> OTHER INFORMATION: XTN-bbG

<400> SEQUENCE: 152

```
ctgacacccg aacaggtggt cgccattgct aataataacg gaggacggcc agccttggag     60

tccatcgtag cccaattgtc caggcccgat cccgcgttgg ctgcgttaac gaatgaccat    120

ctggtggcgt tggcatgtct tggtggacga cccgcgctcg atgcagtcaa aaagggtctg    180

cctcatgctc ccgcattgat caaaagaacc aaccggcgga ttcccgagag aacttcccat    240

cgagtcgcgg gatcccaact agtcaaaagt gaactggagg agaagaaatc tgaacttcgt    300

cataaattga aatatgtgcc tcatgaatat attgaattaa ttgaaattgc cagaaattcc    360

actcaggata gaattcttga aatgaaggta atggaatttt ttatgaaagt ttatggatat    420

agaggtaaac atttgggtgg atcaaggaaa ccggacggag caatttatac tgtcggatct    480

cctattgatt acggtgtgat cgtggatact aaagcttata gcggaggtta taatctgcca    540

attggccaag cagatgaaat gcaacgatat gtcgaagaaa atcaaacacg aaacaaacat    600

atcaacccta atgaatggtg gaaagtctat ccatcttctg taacggaatt taagttttta    660

tttgtgagtg gtcactttaa aggaaactac aaagctcagc ttacacgatt aaatcatatc    720

actaattgta atggagctgt tcttagtgta gaagagcttt taattggtgg agaaatgatt    780

aaagccggca cattaacctt agaggaagtc agacggaaat ttaataacgg cgagataaac    840

ttttaagggc ccttcgaagg taagcctatc cctaaccctc tcctcggtct cgattctacg    900

cgtaccggtc atcatcacca tcaccattga gtttaaaccc gctgatcagc ctcgactgtg    960

ccttctagtt gccagccatc tgttgtttgc ccctcccccg tgccttcctt gaccctggaa   1020

ggtgccactc ccactgtcct ttcctaataa aatgaggaaa ttgcatcgca ttgtctgagt   1080

aggtgtcatt ctattctggg gggtggggtg gggcaggaca gcaaggggga ggattgggaa   1140

gacaatagca ggcatgctgg ggatgcggtg ggctctatgg cttctgaggc ggaaagaacc   1200

agctggggct ctagggggta tccccacgcg ccctgtagcg gcgcattaag cgcggcgggt   1260

gtggtggtta cgcgcagcgt gaccgctaca cttgccagcg ccctagcgcc cgctcctttc   1320

gctttcttcc cttcctttct cgccacgttc gccggctttc cccgtcaagc tctaaatcgg   1380

ggcatccctt tagggttccg atttagtgct ttacggcacc tcgaccccaa aaaacttgat   1440

tagggtgatg gttcacgtag tgggccatcg ccctgataga cggtttttcg ccctttgacg   1500

ttggagtcca cgttctttaa tagtggactc ttgttccaaa ctggaacaac actcaaccct   1560

atctcggtct attcttttga tttataaggg attttgggga tttcggccta ttggttaaaa   1620

aatgagctga tttaacaaaa atttaacgcg aattaattct gtggaatgtg tgtcagttag   1680

ggtgtggaaa gtccccaggc tccccaggca ggcagaagta tgcaaagcat gcatctcaat   1740

tagtcagcaa ccaggtgtgg aaagtcccca ggctccccag caggcagaag tatgcaaagc   1800
```

-continued

```
atgcatctca attagtcagc aaccatagtc ccgcccctaa ctccgcccat cccgccccta   1860
actccgccca gttccgccca ttctccgccc catggctgac taattttttt tatttatgca   1920
gaggccgagg ccgcctctgc ctctgagcta ttccagaagt agtgaggagg cttttttgga   1980
ggcctaggct tttgcaaaaa gctcccggga gcttgtatat ccattttcgg atctgatcag   2040
cacgtgttga caattaatca tcggcatagt atatcggcat agtataatac gacaaggtga   2100
ggaactaaac catggccaag cctttgtctc aagaagaatc caccctcatt gaaagagcaa   2160
cggctacaat caacagcatc cccatctctg aagactacag cgtcgccagc gcagctctct   2220
ctagcgacgg ccgcatcttc actggtgtca atgtatatca ttttactggg ggaccttgtg   2280
cagaactcgt ggtgctgggc actgctgctg ctgcggcagc tggcaacctg acttgtatcg   2340
tcgcgatcgg aaatgagaac aggggcatct tgagcccctg cggacggtgt cgacaggtgc   2400
ttctcgatct gcatcctggg atcaaagcga tagtgaagga cagtgatgga cagccgacgg   2460
cagttgggat tcgtgaattg ctgccctctg gttatgtgtg ggagggctaa gcacttcgtg   2520
gccgaggagc aggactgaca cgtgctacga gatttcgatt ccaccgccgc cttctatgaa   2580
aggttgggct tcggaatcgt tttccgggac gccggctgga tgatcctcca gcgcggggat   2640
ctcatgctgg agttcttcgc ccaccccaac ttgtttattg cagcttataa tggttacaaa   2700
taaagcaata gcatcacaaa tttcacaaat aaagcatttt tttcactgca ttctagttgt   2760
ggtttgtcca aactcatcaa tgtatcttat catgtctgta taccgtcgac ctctagctag   2820
agcttggcgt aatcatggtc atagctgttt cctgtgtgaa attgttatcc gctcacaatt   2880
ccacacaaca tacgagccgg aagcataaag tgtaaagcct ggggtgccta atgagtgagc   2940
taactcacat taattgcgtt gcgctcactg cccgctttcc agtcgggaaa cctgtcgtgc   3000
cagctgcatt aatgaatcgg ccaacgcgcg gggagaggcg gtttgcgtat tgggcgctct   3060
tccgcttcct cgctcactga ctcgctgcgc tcggtcgttc ggctgcggcg agcggtatca   3120
gctcactcaa aggcggtaat acggttatcc acagaatcag gggataacgc aggaaagaac   3180
atgtgagcaa aaggccagca aaaggccagg aaccgtaaaa aggccgcgtt gctggcgttt   3240
ttccataggc tccgcccccc tgacgagcat cacaaaaatc gacgctcaag tcagaggtgg   3300
cgaaacccga caggactata aagataccag gcgtttcccc ctggaagctc cctcgtgcgc   3360
tctcctgttc cgaccctgcc gcttaccgga tacctgtccg cctttctccc ttcgggaagc   3420
gtggcgcttt ctcaatgctc acgctgtagg tatctcagtt cggtgtaggt cgttcgctcc   3480
aagctgggct gtgtgcacga accccccgtt cagcccgacc gctgcgcctt atccggtaac   3540
tatcgtcttg agtccaaccc ggtaagacac gacttatcgc cactggcagc agccactggt   3600
aacaggatta gcagagcgag gtatgtaggc ggtgctacag agttcttgaa gtggtggcct   3660
aactacggct acactagaag gacagtattt ggtatctgcg ctctgctgaa gccagttacc   3720
ttcggaaaaa gagttggtag ctcttgatcc ggcaaacaaa ccaccgctgg tagcggtggt   3780
ttttttgttt gcaagcagca gattacgcgc agaaaaaaag gatctcaaga agatcctttg   3840
atcttttcta cggggtctga cgctcagtgg aacgaaaact cacgttaagg gattttggtc   3900
atgagattat caaaaaggat cttcacctag atccttttaa attaaaaatg aagttttaaa   3960
tcaatctaaa gtatatatga gtaaacttgg tctgacagtt accaatgctt aatcagtgag   4020
gcacctatct cagcgatctg tctatttcgt tcatccatag ttgcctgact ccccgtcgtg   4080
tagataacta cgatacggga gggcttacca tctggcccca gtgctgcaat gataccgcga   4140
gacccacgct caccggctcc agatttatca gcaataaacc agccagccgg aagggccgag   4200
```

```
cgcagaagtg gtcctgcaac tttatccgcc tccatccagt ctattaattg ttgccgggaa   4260
gctagagtaa gtagttcgcc agttaatagt ttgcgcaacg ttgttgccat tgctacaggc   4320
atcgtggtgt cacgctcgtc gtttggtatg gcttcattca gctccggttc ccaacgatca   4380
aggcgagtta catgatcccc catgttgtgc aaaaaagcgg ttagctcctt cggtcctccg   4440
atcgttgtca gaagtaagtt ggccgcagtg ttatcactca tggttatggc agcactgcat   4500
aattctctta ctgtcatgcc atccgtaaga tgcttttctg tgactggtga gtactcaacc   4560
aagtcattct gagaatagtg tatgcggcga ccgagttgct cttgcccggc gtcaatacgg   4620
gataataccg cgccacatag cagaacttta aaagtgctca tcattggaaa acgttcttcg   4680
gggcgaaaac tctcaaggat cttaccgctg ttgagatcca gttcgatgta acccactcgt   4740
gcacccaact gatcttcagc atcttttact ttcaccagcg tttctgggtg agcaaaaaca   4800
ggaaggcaaa atgccgcaaa aaagggaata agggcgacac ggaaatgttg aatactcata   4860
ctcttccttt ttcaatatta ttgaagcatt tatcagggtt attgtctcat gagcggatac   4920
atatttgaat gtatttagaa aaataaacaa ataggggttc cgcgcacatt tccccgaaaa   4980
gtgccacctg acgtcgacgg atcgggagat ctcccgatcc cctatggtcg actctcagta   5040
caatctgctc tgatgccgca tagttaagcc agtatctgct ccctgcttgt gtgttggagg   5100
tcgctgagta gtgcgcgagc aaaatttaag ctacaacaag gcaaggcttg accgacaatt   5160
gcatgaagaa tctgcttagg gttaggcgtt ttgcgctgct tcgcgatgta cgggccagat   5220
atacgcgttg acattgatta ttgactagtt attaatagta atcaattacg gggtcattag   5280
ttcatagccc atatatggag ttccgcgtta cataacttac ggtaaatggc ccgcctggct   5340
gaccgcccaa cgacccccgc ccattgacgt caataatgac gtatgttccc atagtaacgc   5400
caatagggac tttccattga cgtcaatggg tggagtattt acggtaaact gcccacttgg   5460
cagtacatca agtgtatcat atgccaagta cgccccctat tgacgtcaat gacggtaaat   5520
ggcccgcctg gcattatgcc cagtacatga ccttatggga ctttcctact tggcagtaca   5580
tctacgtatt agtcatcgct attaccatgg tgatgcggtt ttggcagtac atcaatgggc   5640
gtggatagcg gtttgactca cggggatttc caagtctcca ccccattgac gtcaatggga   5700
gtttgttttg gcaccaaaat caacgggact ttccaaaatg tcgtaacaac tccgccccat   5760
tgacgcaaat gggcggtagg cgtgtacggt gggaggtcta tataagcaga gctctctggc   5820
taactagaga acccactgct tactggctta tcgaaattaa tacgactcac tatagggaga   5880
cccaagctgg ctagcaccat ggactacaaa gaccatgacg gtgattataa agatcatgac   5940
atcgattaca aggatgacga tgacaagatg gccccaaga agaagaggaa ggtgggcatt   6000
caccgcgggg tacctatggt ggacttgagg acactcggtt attcgcaaca gcaacaggag   6060
aaaatcaagc ctaaggtcag gagcaccgtc gcgcaacacc acgaggcgct tgtggggcat   6120
ggcttcactc atgcgcatat tgtcgcgctt tcacagcacc ctgcggcgct tgggacggtg   6180
gctgtcaaat accaagatat gattgcggcc ctgcccgaag ccacgcacga ggcaattgta   6240
ggggtcggta aacagtggtc gggagcgcga gcacttgagg cgctgctgac tgtggcgggt   6300
gagcttaggg ggcctccgct ccagctcgac accgggcagc tgctgaagat cgcgaagaga   6360
gggggagtaa cagcggtaga ggcagtgcac gcctggcgca atgcgctcac cggggccccc   6420
ttgaac                                                              6426
```

<210> SEQ ID NO 153

<211> LENGTH: 6426
<212> TYPE: DNA
<213> ORGANISM: Artificial Sequence
<220> FEATURE:
<223> OTHER INFORMATION: XTN-bbT

<400> SEQUENCE: 153
ctgacacccg aacaggtggt cgccattgct tctaatgggg gaggacggcc agccttggag 60
tccatcgtag cccaattgtc caggcccgat cccgcgttgg ctgcgttaac gaatgaccat 120
ctggtggcgt tggcatgtct tggtggacga cccgcgctcg atgcagtcaa aaagggtctg 180
cctcatgctc ccgcattgat caaaagaacc aaccggcgga ttcccgagag aacttcccat 240
cgagtcgcgg gatcccaact agtcaaaagt gaactggagg agaagaaatc tgaacttcgt 300
cataaattga aatatgtgcc tcatgaatat attgaattaa ttgaaattgc cagaaattcc 360
actcaggata gaattcttga aatgaaggta atggaatttt ttatgaaagt ttatggatat 420
agaggtaaac atttgggtgg atcaaggaaa ccggacggag caatttatac tgtcggatct 480
cctattgatt acggtgtgat cgtggatact aaagcttata gcggaggtta taatctgcca 540
attggccaag cagatgaaat gcaacgatat gtcgaagaaa atcaaacacg aaacaaacat 600
atcaacccta atgaatggtg gaaagtctat ccatcttctg taacggaatt taagttttta 660
tttgtgagtg gtcactttaa aggaaactac aaagctcagc ttacacgatt aaatcatatc 720
actaattgta atggagctgt tcttagtgta gaagagcttt taattggtgg agaaatgatt 780
aaagccggca cattaacctt agaggaagtc agacggaaat ttaataacgg cgagataaac 840
ttttaagggc ccttcgaagg taagcctatc cctaaccctc tcctcggtct cgattctacg 900
cgtaccggtc atcatcacca tcaccattga gtttaaaccc gctgatcagc ctcgactgtg 960
ccttctagtt gccagccatc tgttgtttgc ccctcccccg tgccttcctt gaccctggaa 1020
ggtgccactc ccactgtcct ttcctaataa aatgaggaaa ttgcatcgca ttgtctgagt 1080
aggtgtcatt ctattctggg gggtggggtg gggcaggaca gcaaggggga ggattgggaa 1140
gacaatagca ggcatgctgg ggatgcggtg ggctctatgg cttctgaggc ggaaagaacc 1200
agctggggct ctagggggta tccccacgcg ccctgtagcg gcgcattaag cgcggcgggt 1260
gtggtggtta cgcgcagcgt gaccgctaca cttgccagcg ccctagcgcc cgctcctttc 1320
gctttcttcc cttcctttct cgccacgttc gccggctttc cccgtcaagc tctaaatcgg 1380
ggcatccctt tagggttccg atttagtgct ttacggcacc tcgaccccaa aaaacttgat 1440
tagggtgatg gttcacgtag tgggccatcg ccctgataga cggtttttcg ccctttgacg 1500
ttggagtcca cgttctttaa tagtggactc ttgttccaaa ctggaacaac actcaaccct 1560
atctcggtct attcttttga tttataaggg attttgggga tttcggccta ttggttaaaa 1620
aatgagctga tttaacaaaa atttaacgcg aattaattct gtggaatgtg tgtcagttag 1680
ggtgtggaaa gtccccaggc tccccaggca ggcagaagta tgcaaagcat gcatctcaat 1740
tagtcagcaa ccaggtgtgg aaagtcccca ggctccccag caggcagaag tatgcaaagc 1800
atgcatctca attagtcagc aaccatagtc ccgcccctaa ctccgcccat cccgccccta 1860
actccgccca gttccgccca ttctccgccc catggctgac taattttttt tatttatgca 1920
gaggccgagg ccgcctctgc ctctgagcta ttccagaagt agtgaggagg cttttttgga 1980
ggcctaggct tttgcaaaaa gctcccggga gcttgtatat ccattttcgg atctgatcag 2040
cacgtgttga caattaatca tcggcatagt atatcggcat agtataatac gacaaggtga 2100
ggaactaaac catggccaag cctttgtctc aagaagaatc caccctcatt gaaagagcaa 2160

```
cggctacaat caacagcatc cccatctctg aagactacag cgtcgccagc gcagctctct   2220
ctagcgacgg ccgcatcttc actggtgtca atgtatatca ttttactggg ggaccttgtg   2280
cagaactcgt ggtgctgggc actgctgctg ctgcggcagc tggcaacctg acttgtatcg   2340
tcgcgatcgg aaatgagaac aggggcatct tgagcccctg cggacggtgt cgacaggtgc   2400
ttctcgatct gcatcctggg atcaaagcga tagtgaagga cagtgatgga cagccgacgg   2460
cagttgggat tcgtgaattg ctgccctctg gttatgtgtg ggagggctaa gcacttcgtg   2520
gccgaggagc aggactgaca cgtgctacga gatttcgatt ccaccgccgc cttctatgaa   2580
aggttgggct tcggaatcgt tttccgggac gccggctgga tgatcctcca gcgcggggat   2640
ctcatgctgg agttcttcgc ccaccccaac ttgtttattg cagcttataa tggttacaaa   2700
taaagcaata gcatcacaaa tttcacaaat aaagcatttt tttcactgca ttctagttgt   2760
ggtttgtcca aactcatcaa tgtatcttat catgtctgta taccgtcgac ctctagctag   2820
agcttggcgt aatcatggtc atagctgttt cctgtgtgaa attgttatcc gctcacaatt   2880
ccacacaaca tacgagccgg aagcataaag tgtaaagcct ggggtgccta atgagtgagc   2940
taactcacat taattgcgtt gcgctcactg cccgctttcc agtcgggaaa cctgtcgtgc   3000
cagctgcatt aatgaatcgg ccaacgcgcg gggagaggcg gtttgcgtat tgggcgctct   3060
tccgcttcct cgctcactga ctcgctgcgc tcggtcgttc ggctgcggcg agcggtatca   3120
gctcactcaa aggcggtaat acggttatcc acagaatcag gggataacgc aggaaagaac   3180
atgtgagcaa aaggccagca aaaggccagg aaccgtaaaa aggccgcgtt gctggcgttt   3240
ttccataggc tccgcccccc tgacgagcat cacaaaaatc gacgctcaag tcagaggtgg   3300
cgaaacccga caggactata aagataccag gcgtttcccc ctggaagctc cctcgtgcgc   3360
tctcctgttc cgaccctgcc gcttaccgga tacctgtccg cctttctccc ttcgggaagc   3420
gtggcgcttt ctcaatgctc acgctgtagg tatctcagtt cggtgtaggt cgttcgctcc   3480
aagctgggct gtgtgcacga accccccgtt cagcccgacc gctgcgcctt atccggtaac   3540
tatcgtcttg agtccaaccc ggtaagacac gacttatcgc cactggcagc agccactggt   3600
aacaggatta gcagagcgag gtatgtaggc ggtgctacag agttcttgaa gtggtggcct   3660
aactacggct acactagaag gacagtattt ggtatctgcg ctctgctgaa gccagttacc   3720
ttcggaaaaa gagttggtag ctcttgatcc ggcaaacaaa ccaccgctgg tagcggtggt   3780
ttttttgttt gcaagcagca gattacgcgc agaaaaaaag gatctcaaga agatcctttg   3840
atcttttcta cggggtctga cgctcagtgg aacgaaaact cacgttaagg gattttggtc   3900
atgagattat caaaaaggat cttcacctag atccttttaa attaaaaatg aagttttaaa   3960
tcaatctaaa gtatatatga gtaaacttgg tctgacagtt accaatgctt aatcagtgag   4020
gcacctatct cagcgatctg tctatttcgt tcatccatag ttgcctgact ccccgtcgtg   4080
tagataacta cgatacggga gggcttacca tctggcccca gtgctgcaat gataccgcga   4140
gacccacgct caccggctcc agatttatca gcaataaacc agccagccgg aagggccgag   4200
cgcagaagtg gtcctgcaac tttatccgcc tccatccagt ctattaattg ttgccgggaa   4260
gctagagtaa gtagttcgcc agttaatagt ttgcgcaacg ttgttgccat tgctacaggc   4320
atcgtggtgt cacgctcgtc gtttggtatg gcttcattca gctccggttc ccaacgatca   4380
aggcgagtta catgatcccc catgttgtgc aaaaaagcgg ttagctcctt cggtcctccg   4440
atcgttgtca gaagtaagtt ggccgcagtg ttatcactca tggttatggc agcactgcat   4500
```

```
aattctctta ctgtcatgcc atccgtaaga tgcttttctg tgactggtga gtactcaacc   4560

aagtcattct gagaatagtg tatgcggcga ccgagttgct cttgcccggc gtcaatacgg   4620

gataataccg cgccacatag cagaacttta aaagtgctca tcattggaaa acgttcttcg   4680

gggcgaaaac tctcaaggat cttaccgctg ttgagatcca gttcgatgta acccactcgt   4740

gcacccaact gatcttcagc atcttttact ttcaccagcg tttctgggtg agcaaaaaca   4800

ggaaggcaaa atgccgcaaa aaagggaata agggcgacac ggaaatgttg aatactcata   4860

ctcttccttt ttcaatatta ttgaagcatt tatcagggtt attgtctcat gagcggatac   4920

atatttgaat gtatttagaa aaataaacaa ataggggttc cgcgcacatt tccccgaaaa   4980

gtgccacctg acgtcgacgg atcgggagat ctcccgatcc cctatggtcg actctcagta   5040

caatctgctc tgatgccgca tagttaagcc agtatctgct ccctgcttgt gtgttggagg   5100

tcgctgagta gtgcgcgagc aaaatttaag ctacaacaag gcaaggcttg accgacaatt   5160

gcatgaagaa tctgcttagg gttaggcgtt ttgcgctgct tcgcgatgta cgggccagat   5220

atacgcgttg acattgatta ttgactagtt attaatagta atcaattacg gggtcattag   5280

ttcatagccc atatatggag ttccgcgtta cataacttac ggtaaatggc ccgcctggct   5340

gaccgcccaa cgacccccgc ccattgacgt caataatgac gtatgttccc atagtaacgc   5400

caatagggac tttccattga cgtcaatggg tggagtattt acggtaaact gcccacttgg   5460

cagtacatca agtgtatcat atgccaagta cgccccctat tgacgtcaat gacggtaaat   5520

ggcccgcctg gcattatgcc cagtacatga ccttatggga ctttcctact tggcagtaca   5580

tctacgtatt agtcatcgct attaccatgg tgatgcggtt ttggcagtac atcaatgggc   5640

gtggatagcg gtttgactca cggggatttc caagtctcca ccccattgac gtcaatggga   5700

gtttgttttg gcaccaaaat caacgggact ttccaaaatg tcgtaacaac tccgccccat   5760

tgacgcaaat gggcggtagg cgtgtacggt gggaggtcta tataagcaga gctctctggc   5820

taactagaga acccactgct tactggctta tcgaaattaa tacgactcac tatagggaga   5880

cccaagctgg ctagcaccat ggactacaaa gaccatgacg gtgattataa agatcatgac   5940

atcgattaca aggatgacga tgacaagatg gcccccaaga agaagaggaa ggtgggcatt   6000

caccgcgggg tacctatggt ggacttgagg acactcggtt attcgcaaca gcaacaggag   6060

aaaatcaagc ctaaggtcag gagcaccgtc gcgcaacacc acgaggcgct tgtggggcat   6120

ggcttcactc atgcgcatat tgtcgcgctt tcacagcacc ctgcggcgct tgggacggtg   6180

gctgtcaaat accaagatat gattgcggcc ctgcccgaag ccacgcacga ggcaattgta   6240

ggggtcggta aacagtggtc gggagcgcga gcacttgagg cgctgctgac tgtggcgggt   6300

gagcttaggg ggcctccgct ccagctcgac accgggcagc tgctgaagat cgcgaagaga   6360

gggggagtaa cagcggtaga ggcagtgcac gcctggcgca atgcgctcac cggggccccc   6420

ttgaac                                                               6426
```

<210> SEQ ID NO 154
<211> LENGTH: 128
<212> TYPE: DNA
<213> ORGANISM: Artificial Sequence
<220> FEATURE:
<223> OTHER INFORMATION: gXTN-1C

<400> SEQUENCE: 154

```
tctagaggtc tcattgaccc cagaccaggt agtcgcaatc gcgtcacatg acgggggaaa     60

gcaagccctg gaaaccgtgc aaaggttgtt gccggtcctt tgtcaagacc acggcagaga    120
```

```
ccggatcc                                                            128


<210> SEQ ID NO 155
<211> LENGTH: 131
<212> TYPE: DNA
<213> ORGANISM: Artificial Sequence
<220> FEATURE:
<223> OTHER INFORMATION: gXTN-2C

<400> SEQUENCE: 155

tctagaggtc tcacggcctg actcccgatc aagttgtagc gattgcgtcg catgacggag     60

ggaaacaagc attggagact gtccaacggc tccttcccgt gttgtgtcaa gcccacggag    120

agaccggatc c                                                         131


<210> SEQ ID NO 156
<211> LENGTH: 131
<212> TYPE: DNA
<213> ORGANISM: Artificial Sequence
<220> FEATURE:
<223> OTHER INFORMATION: gXTN-3C

<400> SEQUENCE: 156

tctagaggtc tcaacggttt gacgcctgca caagtggtcg ccatcgccag ccatgatggc     60

ggtaagcagg cgctggaaac agtacagcgc ctgctgcctg tactgtgcca ggatcatgag    120

agaccggatc c                                                         131


<210> SEQ ID NO 157
<211> LENGTH: 131
<212> TYPE: DNA
<213> ORGANISM: Artificial Sequence
<220> FEATURE:
<223> OTHER INFORMATION: gXTN-4C

<400> SEQUENCE: 157

tctagaggtc tcacatggac tgaccccaga ccaggtagtc gcaatcgcgt cacatgacgg     60

gggaaagcaa gccctggaaa ccgtgcaaag gttgttgccg gtcctttgtc aagaccacag    120

agaccggatc c                                                         131


<210> SEQ ID NO 158
<211> LENGTH: 131
<212> TYPE: DNA
<213> ORGANISM: Artificial Sequence
<220> FEATURE:
<223> OTHER INFORMATION: gXTN-5C

<400> SEQUENCE: 158

tctagaggtc tcaccacggc ctgaccccag accaggtagt cgcaatcgcg tcacatgacg     60

ggggaaagca agccctggaa accgtgcaaa ggttgttgcc ggtcctttgt caagaccaag    120

agaccggatc c                                                         131


<210> SEQ ID NO 159
<211> LENGTH: 131
<212> TYPE: DNA
<213> ORGANISM: Artificial Sequence
<220> FEATURE:
<223> OTHER INFORMATION: gXTN-6C

<400> SEQUENCE: 159

tctagaggtc tcaaccacgg cctgactccc gatcaagttg tagcgattgc gtcgcatgac     60
```

```
ggagggaaac aagcattgga gactgtccaa cggctccttc ccgtgttgtg tcaagcccag    120

agaccggatc c                                                          131


<210> SEQ ID NO 160
<211> LENGTH: 131
<212> TYPE: DNA
<213> ORGANISM: Artificial Sequence
<220> FEATURE:
<223> OTHER INFORMATION: gXTN-7C

<400> SEQUENCE: 160

tctagaggtc tcagcccacg gtttgacgcc tgcacaagtg gtcgccatcg ccagccatga     60

tggcggtaag caggcgctgg aaacagtaca gcgcctgctg cctgtactgt gccaggatag    120

agaccggatc c                                                          131


<210> SEQ ID NO 161
<211> LENGTH: 131
<212> TYPE: DNA
<213> ORGANISM: Artificial Sequence
<220> FEATURE:
<223> OTHER INFORMATION: gXTN-8C

<400> SEQUENCE: 161

tctagaggtc tcaggatcat ggactgaccc cagaccaggt agtcgcaatc gcgtcacatg     60

acgggggaaa gcaagccctg gaaaccgtgc aaaggttgtt gccggtcctt tgtcaagaag    120

agaccggatc c                                                          131


<210> SEQ ID NO 162
<211> LENGTH: 131
<212> TYPE: DNA
<213> ORGANISM: Artificial Sequence
<220> FEATURE:
<223> OTHER INFORMATION: gXTN-9C

<400> SEQUENCE: 162

tctagaggtc tcaaagacca cggcctgacc ccagaccagg tagtcgcaat cgcgtcacat     60

gacgggggaa agcaagccct ggaaaccgtg caaaggttgt tgccggtcct ttgtcaagag    120

agaccggatc c                                                          131


<210> SEQ ID NO 163
<211> LENGTH: 140
<212> TYPE: DNA
<213> ORGANISM: Artificial Sequence
<220> FEATURE:
<223> OTHER INFORMATION: gXTN-10C

<400> SEQUENCE: 163

tctagaggtc tcacaagacc acggcctgac tcccgatcaa gttgtagcga ttgcgtcgca     60

tgacggaggg aaacaagcat tggagactgt ccaacggctc cttcccgtgt tgtgtcaagc    120

ccatggaaga gaccggatcc                                                 140


<210> SEQ ID NO 164
<211> LENGTH: 128
<212> TYPE: DNA
<213> ORGANISM: Artificial Sequence
<220> FEATURE:
<223> OTHER INFORMATION: gXTN-1T

<400> SEQUENCE: 164

tctagaggtc tcattgaccc cagaccaggt agtcgcaatc gcgtcaaacg gagggggaaa     60
```

gcaagccctg gaaaccgtgc aaaggttgtt gccggtcctt tgtcaagacc acggcagaga 120
ccggatcc 128

<210> SEQ ID NO 165
<211> LENGTH: 131
<212> TYPE: DNA
<213> ORGANISM: Artificial Sequence
<220> FEATURE:
<223> OTHER INFORMATION: gXTN-2T

<400> SEQUENCE: 165
tctagaggtc tcacggcctg actcccgatc aagttgtagc gattgcgtcg aacggtggag 60
ggaaacaagc attggagact gtccaacggc tccttcccgt gttgtgtcaa gcccacggag 120
agaccggatc c 131

<210> SEQ ID NO 166
<211> LENGTH: 131
<212> TYPE: DNA
<213> ORGANISM: Artificial Sequence
<220> FEATURE:
<223> OTHER INFORMATION: gXTN-3T

<400> SEQUENCE: 166
tctagaggtc tcaacggttt gacgcctgca caagtggtcg ccatcgcctc gaatggcggc 60
ggtaagcagg cgctggaaac agtacagcgc ctgctgcctg tactgtgcca ggatcatgag 120
agaccggatc c 131

<210> SEQ ID NO 167
<211> LENGTH: 131
<212> TYPE: DNA
<213> ORGANISM: Artificial Sequence
<220> FEATURE:
<223> OTHER INFORMATION: gXTN-4T

<400> SEQUENCE: 167
tctagaggtc tcacatggac tgaccccaga ccaggtagtc gcaatcgcgt caaacggagg 60
gggaaagcaa gccctggaaa ccgtgcaaag gttgttgccg gtcctttgtc aagaccacag 120
agaccggatc c 131

<210> SEQ ID NO 168
<211> LENGTH: 131
<212> TYPE: DNA
<213> ORGANISM: Artificial Sequence
<220> FEATURE:
<223> OTHER INFORMATION: gXTN-5T

<400> SEQUENCE: 168
tctagaggtc tcaccacggc ctgaccccag accaggtagt cgcaatcgcg tcaaacggag 60
ggggaaagca agccctggaa accgtgcaaa ggttgttgcc ggtcctttgt caagaccaag 120
agaccggatc c 131

<210> SEQ ID NO 169
<211> LENGTH: 131
<212> TYPE: DNA
<213> ORGANISM: Artificial Sequence
<220> FEATURE:
<223> OTHER INFORMATION: gXTN-6T

<400> SEQUENCE: 169
tctagaggtc tcaaccacgg cctgactccc gatcaagttg tagcgattgc gtcgaacggt 60
ggagggaaac aagcattgga gactgtccaa cggctccttc ccgtgttgtg tcaagcccag 120
agaccggatc c 131

<210> SEQ ID NO 170
<211> LENGTH: 131
<212> TYPE: DNA
<213> ORGANISM: Artificial Sequence
<220> FEATURE:
<223> OTHER INFORMATION: gXTN-7T

<400> SEQUENCE: 170
tctagaggtc tcagcccacg gtttgacgcc tgcacaagtg gtcgccatcg ccagcaatgg 60
cggcggtaag caggcgctgg aaacagtaca gcgcctgctg cctgtactgt gccaggatag 120
agaccggatc c 131

<210> SEQ ID NO 171
<211> LENGTH: 131
<212> TYPE: DNA
<213> ORGANISM: Artificial Sequence
<220> FEATURE:
<223> OTHER INFORMATION: gXTN-8T

<400> SEQUENCE: 171
tctagaggtc tcaggatcat ggactgaccc cagaccaggt agtcgcaatc gcgtcaaacg 60
gagggggaaa gcaagccctg gaaaccgtgc aaaggttgtt gccggtcctt tgtcaagaag 120
agaccggatc c 131

<210> SEQ ID NO 172
<211> LENGTH: 131
<212> TYPE: DNA
<213> ORGANISM: Artificial Sequence
<220> FEATURE:
<223> OTHER INFORMATION: gXTN-9T

<400> SEQUENCE: 172
tctagaggtc tcaaagacca cggcctgacc ccagaccagg tagtcgcaat cgcgtcaaac 60
ggagggggaa agcaagccct ggaaaccgtg caaaggttgt tgccggtcct ttgtcaagag 120
agaccggatc c 131

<210> SEQ ID NO 173
<211> LENGTH: 140
<212> TYPE: DNA
<213> ORGANISM: Artificial Sequence
<220> FEATURE:
<223> OTHER INFORMATION: gXTN-10T

<400> SEQUENCE: 173
tctagaggtc tcacaagacc acggcctgac tcccgatcaa gttgtagcga ttgcgtccaa 60
cggtggaggg aaacaagcat tggagactgt ccaacggctc cttcccgtgt tgtgtcaagc 120
ccatggaaga gaccggatcc 140

<210> SEQ ID NO 174
<211> LENGTH: 128
<212> TYPE: DNA
<213> ORGANISM: Artificial Sequence
<220> FEATURE:
<223> OTHER INFORMATION: gXTN-1A

<400> SEQUENCE: 174
tctagaggtc tcattgaccc cagaccaggt agtcgcaatc gcgtcaaaca ttgggggaaa 60
gcaagccctg gaaaccgtgc aaaggttgtt gccggtcctt tgtcaagacc acggcagaga 120
ccggatcc 128

<210> SEQ ID NO 175
<211> LENGTH: 131
<212> TYPE: DNA
<213> ORGANISM: Artificial Sequence
<220> FEATURE:
<223> OTHER INFORMATION: gXTN-2A

<400> SEQUENCE: 175
tctagaggtc tcacggcctg actcccgatc aagttgtagc gattgcgtcg aacattggag 60
ggaaacaagc attggagact gtccaacggc tccttcccgt gttgtgtcaa gcccacggag 120
agaccggatc c 131

<210> SEQ ID NO 176
<211> LENGTH: 131
<212> TYPE: DNA
<213> ORGANISM: Artificial Sequence
<220> FEATURE:
<223> OTHER INFORMATION: gXTN-3A

<400> SEQUENCE: 176
tctagaggtc tcaacggttt gacgcctgca caagtggtcg ccatcgccag caatattggc 60
ggtaagcagg cgctggaaac agtacagcgc ctgctgcctg tactgtgcca ggatcatgag 120
agaccggatc c 131

<210> SEQ ID NO 177
<211> LENGTH: 131
<212> TYPE: DNA
<213> ORGANISM: Artificial Sequence
<220> FEATURE:
<223> OTHER INFORMATION: gXTN-4A

<400> SEQUENCE: 177
tctagaggtc tcacatggac tgaccccaga ccaggtagtc gcaatcgcgt caaacattgg 60
gggaaagcaa gccctggaaa ccgtgcaaag gttgttgccg gtcctttgtc aagaccacag 120
agaccggatc c 131

<210> SEQ ID NO 178
<211> LENGTH: 131
<212> TYPE: DNA
<213> ORGANISM: Artificial Sequence
<220> FEATURE:
<223> OTHER INFORMATION: gXTN-5A

<400> SEQUENCE: 178
tctagaggtc tcaccacggc ctgaccccag accaggtagt cgcaatcgcg tcgaacattg 60
ggggaaagca agccctggaa accgtgcaaa ggttgttgcc ggtcctttgt caagaccaag 120
agaccggatc c 131

<210> SEQ ID NO 179
<211> LENGTH: 131
<212> TYPE: DNA
<213> ORGANISM: Artificial Sequence
<220> FEATURE:
<223> OTHER INFORMATION: gXTN-6A

<400> SEQUENCE: 179
tctagaggtc tcaaccatgg cctgactccc gatcaagttg tagcgattgc gtcgaacatt 60
ggagggaaac aagcattgga gactgtccaa cggctccttc ccgtgttgtg tcaagcccag 120
agaccggatc c 131

<210> SEQ ID NO 180
<211> LENGTH: 131
<212> TYPE: DNA
<213> ORGANISM: Artificial Sequence
<220> FEATURE:
<223> OTHER INFORMATION: gXTN-7A

<400> SEQUENCE: 180
tctagaggtc tcagcccacg gtttgacgcc tgcacaagtg gtcgccatcg cctccaatat 60
tggcggtaag caggcgctgg aaacagtaca gcgcctgctg cctgtactgt gccaggatag 120
agaccggatc c 131

<210> SEQ ID NO 181
<211> LENGTH: 131
<212> TYPE: DNA
<213> ORGANISM: Artificial Sequence
<220> FEATURE:
<223> OTHER INFORMATION: gXTN-8A

<400> SEQUENCE: 181
tctagaggtc tcaggatcat ggactgaccc cagaccaggt agtcgcaatc gcgtcgaaca 60
ttgggggaaa gcaagccctg gaaaccgtgc aaaggttgtt gccggtcctt tgtcaagaag 120
agaccggatc c 131

<210> SEQ ID NO 182
<211> LENGTH: 131
<212> TYPE: DNA
<213> ORGANISM: Artificial Sequence
<220> FEATURE:
<223> OTHER INFORMATION: gXTN-9A

<400> SEQUENCE: 182
tctagaggtc tcaaagacca cggcctgacc ccagaccagg tagtcgcaat cgcgtcgaac 60
attgggggaa agcaagccct ggaaaccgtg caaaggttgt tgccggtcct ttgtcaagag 120
agaccggatc c 131

<210> SEQ ID NO 183
<211> LENGTH: 140
<212> TYPE: DNA
<213> ORGANISM: Artificial Sequence
<220> FEATURE:
<223> OTHER INFORMATION: gXTN-10A

<400> SEQUENCE: 183
tctagaggtc tcacaagacc acggcctgac tcccgatcaa gttgtagcga ttgcgtcgaa 60
cattggaggg aaacaagcat tggagactgt ccaacggctc cttcccgtgt tgtgtcaagc 120
ccatggaaga gaccggatcc 140

<210> SEQ ID NO 184
<211> LENGTH: 128
<212> TYPE: DNA
<213> ORGANISM: Artificial Sequence
<220> FEATURE:
<223> OTHER INFORMATION: gXTN-1G

<400> SEQUENCE: 184
tctagaggtc tcattgaccc cagaccaggt agtcgcaatc gcgaacaata atgggggaaa 60
gcaagccctg gaaaccgtgc aaaggttgtt gccggtcctt tgtcaagacc acggcagaga 120
ccggatcc 128

<210> SEQ ID NO 185
<211> LENGTH: 131
<212> TYPE: DNA
<213> ORGANISM: Artificial Sequence
<220> FEATURE:
<223> OTHER INFORMATION: gXTN-2G

<400> SEQUENCE: 185
tctagaggtc tcacggcctg actcccgatc aagttgtagc gattgcgaat aacaatggag 60
ggaaacaagc attggagact gtccaacggc tccttcccgt gttgtgtcaa gcccacggag 120
agaccggatc c 131

<210> SEQ ID NO 186
<211> LENGTH: 131
<212> TYPE: DNA
<213> ORGANISM: Artificial Sequence
<220> FEATURE:
<223> OTHER INFORMATION: gXTN-3G

<400> SEQUENCE: 186
tctagaggtc tcaacggttt gacgcctgca caagtggtcg ccatcgccaa caacaacggc 60
ggtaagcagg cgctggaaac agtacagcgc ctgctgcctg tactgtgcca ggatcatgag 120
agaccggatc c 131

<210> SEQ ID NO 187
<211> LENGTH: 131
<212> TYPE: DNA
<213> ORGANISM: Artificial Sequence
<220> FEATURE:
<223> OTHER INFORMATION: gXTN-4G

<400> SEQUENCE: 187
tctagaggtc tcacatggac tgaccccaga ccaggtagtc gcaatcgcga acaataatgg 60
gggaaagcaa gccctggaaa ccgtgcaaag gttgttgccg gtcctttgtc aagaccacag 120
agaccggatc c 131

<210> SEQ ID NO 188
<211> LENGTH: 131
<212> TYPE: DNA
<213> ORGANISM: Artificial Sequence
<220> FEATURE:
<223> OTHER INFORMATION: gXTN-5G

<400> SEQUENCE: 188
tctagaggtc tcaccacggc ctgaccccag accaggtagt cgcaatcgcg aacaataatg 60
ggggaaagca agccctggaa accgtgcaaa ggttgttgcc ggtcctttgt caagaccaag 120
agaccggatc c 131

<210> SEQ ID NO 189
<211> LENGTH: 131
<212> TYPE: DNA
<213> ORGANISM: Artificial Sequence
<220> FEATURE:

<223> OTHER INFORMATION: gXTN-6G

<400> SEQUENCE: 189
tctagaggtc tcaaccatgg cctgactccc gatcaagttg tagcgattgc gaataacaat 60
ggagggaaac aagcattgga gactgtccaa cggctccttc ccgtgttgtg tcaagcccag 120
agaccggatc c 131

<210> SEQ ID NO 190
<211> LENGTH: 131
<212> TYPE: DNA
<213> ORGANISM: Artificial Sequence
<220> FEATURE:
<223> OTHER INFORMATION: gXTN-7G

<400> SEQUENCE: 190
tctagaggtc tcagcccacg gtttgacgcc tgcacaagtg gtcgccatcg ccaacaacaa 60
cggcggtaag caggcgctgg aaacagtaca gcgcctgctg cctgtactgt gccaggatag 120
agaccggatc c 131

<210> SEQ ID NO 191
<211> LENGTH: 131
<212> TYPE: DNA
<213> ORGANISM: Artificial Sequence
<220> FEATURE:
<223> OTHER INFORMATION: gXTN-8G

<400> SEQUENCE: 191
tctagaggtc tcaggatcat ggactgaccc cagaccaggt agtcgcaatc gcgaacaata 60
atgggggaaa gcaagccctg gaaaccgtgc aaaggttgtt gccggtcctt tgtcaagaag 120
agaccggatc c 131

<210> SEQ ID NO 192
<211> LENGTH: 131
<212> TYPE: DNA
<213> ORGANISM: Artificial Sequence
<220> FEATURE:
<223> OTHER INFORMATION: gXTN-9G

<400> SEQUENCE: 192
tctagaggtc tcaaagacca cggcctgacc ccagaccagg tagtcgcaat cgcgaacaat 60
aatgggggaa agcaagccct ggaaaccgtg caaaggttgt tgccggtcct ttgtcaagag 120
agaccggatc c 131

<210> SEQ ID NO 193
<211> LENGTH: 140
<212> TYPE: DNA
<213> ORGANISM: Artificial Sequence
<220> FEATURE:
<223> OTHER INFORMATION: gXTN-10G

<400> SEQUENCE: 193
tctagaggtc tcacaagacc acggcctgac tcccgatcaa gttgtagcga ttgcgaataa 60
caatggaggg aaacaagcat tggagactgt ccaacggctc cttcccgtgt tgtgtcaagc 120
ccatggaaga gaccggatcc 140

<210> SEQ ID NO 194
<211> LENGTH: 81
<212> TYPE: DNA
<213> ORGANISM: Artificial Sequence
<220> FEATURE:
<223> OTHER INFORMATION: pFUS-X

<400> SEQUENCE: 194
cctgcaggtc gaccgtctca gaacttgaag agaccgtacg tgatcgtggt ctcatggatt 60
gaagagacgg gtaccgagct c 81

<210> SEQ ID NO 195
<211> LENGTH: 77
<212> TYPE: DNA
<213> ORGANISM: Artificial Sequence
<220> FEATURE:
<223> OTHER INFORMATION: pFUS-Z1

<400> SEQUENCE: 195
cctgcaggtc gaccgtctca ttgaagagac cgtactggat cgtggtctca cggcctgaag 60
agacgggtac cgagctc 77

<210> SEQ ID NO 196
<211> LENGTH: 78
<212> TYPE: DNA
<213> ORGANISM: Artificial Sequence
<220> FEATURE:
<223> OTHER INFORMATION: pFUS-Z2

<400> SEQUENCE: 196
cctgcaggtc gaccgtctca ttgaagagac cgtactggat cgtggtctca acggtctgaa 60
gagacgggta ccgagctc 78

<210> SEQ ID NO 197
<211> LENGTH: 79
<212> TYPE: DNA
<213> ORGANISM: Artificial Sequence
<220> FEATURE:
<223> OTHER INFORMATION: pFUS-Z3

<400> SEQUENCE: 197
cctgcaggtc gaccgtctca ttgaagagac cgtactggat cgtggtctca catggactga 60
agagacgggt accgagctc 79

<210> SEQ ID NO 198
<211> LENGTH: 80
<212> TYPE: DNA
<213> ORGANISM: Artificial Sequence
<220> FEATURE:
<223> OTHER INFORMATION: pFUS-Z4

<400> SEQUENCE: 198
cctgcaggtc gaccgtctca ttgaagagac cgtactggat cgtggtctca ccacggcctg 60
aagagacggg taccgagctc 80

<210> SEQ ID NO 199
<211> LENGTH: 81
<212> TYPE: DNA
<213> ORGANISM: Artificial Sequence
<220> FEATURE:
<223> OTHER INFORMATION: pFUS-Z5

<400> SEQUENCE: 199
cctgcaggtc gaccgtctca ttgaagagac cgtactggat cgtggtctca accacggcct 60
gaagagacgg gtaccgagct c 81

```
<210> SEQ ID NO 200
<211> LENGTH: 82
<212> TYPE: DNA
<213> ORGANISM: Artificial Sequence
<220> FEATURE:
<223> OTHER INFORMATION: pFUS-Z6

<400> SEQUENCE: 200

cctgcaggtc gaccgtctca ttgaagagac cgtactggat cgtggtctca gcccacggtc     60

tgaagagacg ggtaccgagc tc                                              82


<210> SEQ ID NO 201
<211> LENGTH: 83
<212> TYPE: DNA
<213> ORGANISM: Artificial Sequence
<220> FEATURE:
<223> OTHER INFORMATION: pFUS-Z7

<400> SEQUENCE: 201

cctgcaggtc gaccgtctca ttgaagagac cgtactggat cgtggtctca ggatcatgga     60

ctgaagagac gggtaccgag ctc                                             83


<210> SEQ ID NO 202
<211> LENGTH: 84
<212> TYPE: DNA
<213> ORGANISM: Artificial Sequence
<220> FEATURE:
<223> OTHER INFORMATION: pFUS-Z8

<400> SEQUENCE: 202

cctgcaggtc gaccgtctca ttgaagagac cgtactggat cgtggtctca aagaccacgg     60

cctgaagaga cgggtaccga gctc                                            84


<210> SEQ ID NO 203
<211> LENGTH: 85
<212> TYPE: DNA
<213> ORGANISM: Artificial Sequence
<220> FEATURE:
<223> OTHER INFORMATION: pFUS-Z9

<400> SEQUENCE: 203

cctgcaggtc gaccgtctca ttgaagagac cgtactggat cgtggtctca caagaccacg     60

gcctgaagag acgggtaccg agctc                                           85


<210> SEQ ID NO 204
<211> LENGTH: 77
<212> TYPE: DNA
<213> ORGANISM: Artificial Sequence
<220> FEATURE:
<223> OTHER INFORMATION: pFUS-Z10

<400> SEQUENCE: 204

cctgcaggtc gaccgtctca ttgaagagac cgtactggat cgtggtctca tggactgaag     60

agacgggtac cgagctc                                                    77


<210> SEQ ID NO 205
<211> LENGTH: 34
<212> TYPE: PRT
<213> ORGANISM: Artificial Sequence
<220> FEATURE:
<223> OTHER INFORMATION: Methylesterases and Methyltransferases 34aa
      Consensus EBE
```

<400> SEQUENCE: 205

Gln Thr Thr Glu Arg Ile Val Ala Ile Gly Thr Asn Asn Gly Gly Thr
1 5 10 15

Gln Ala Leu Glu Ala Val Leu Thr Ala Leu Pro Arg Val Cys Pro Gly
20 25 30

Met Val

<210> SEQ ID NO 206
<211> LENGTH: 102
<212> TYPE: DNA
<213> ORGANISM: Artificial Sequence
<220> FEATURE:
<223> OTHER INFORMATION: Backtranseq of 34aa QTTERIVAIGT SH GGTQALEAVLTALPRVCPGMV

<400> SEQUENCE: 206
cagaccaccg agaggatcgt ggccatcggc accagccacg gcggcaccca ggccctggag 60
gccgtgctga ccgccctgcc cagggtgtgc cccggcatgg tg 102

<210> SEQ ID NO 207
<211> LENGTH: 3123
<212> TYPE: DNA
<213> ORGANISM: Artificial Sequence
<220> FEATURE:
<223> OTHER INFORMATION: Methylesterase EBE

<400> SEQUENCE: 207
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
accatggact acaaagacca tgacggtgat tataaagatc atgacatcga ttacaaggat 960
gacgatgaca agatggcccc caagaagaag aggaaggtgg gcattcaccg cggggtacct 1020
atggtggact tgaggacact cggttattcg caacagcaac aggagaaaat caagcctaag 1080
gtcaggagca ccgtcgcgca acaccacgag gcgcttgtgg ggcatggctt cactcatgcg 1140
catattgtcg cgctttcaca gcaccctgcg gcgcttggga cggtggctgt caaataccaa 1200
gatatgattg cggccctgcc cgaagccacg cacgaggcaa ttgtaggggt cggtaaacag 1260
tggtcgggag cgcgagcact tgaggcgctg ctgactgtgg cgggtgagct tagggggcct 1320

```
ccgctccagc tcgacaccgg gcagctgctg aagatcgcga agagaggggg agtaacagcg   1380

gtagaggcag tgcacgcctg gcgcaatgcg ctcaccgggg cccccttgaa ccagaccacc   1440

gagaggatcg tggccatcgg caccagccac ggcggcaccc aggccctgga ggccgtgctg   1500

accgccctgc ccagggtgtg ccccggcatg gtgcagacca ccgagaggat cgtggccatc   1560

ggcaccagcc acggcggcac ccaggccctg gaggccgtgc tgaccgccct gcccagggtg   1620

tgccccggca tggtgcagac caccgagagg atcgtggcca tcggcaccag ccacggcggc   1680

acccaggccc tggaggccgt gctgaccgcc ctgcccaggg tgtgccccgg catggtgcag   1740

accaccgaga ggatcgtggc catcggcacc agccacggcg gcacccaggc cctggaggcc   1800

gtgctgaccg ccctgcccag ggtgtgcccc ggcatggtgc agaccaccga gaggatcgtg   1860

gccatcggca ccagccacgg cggcacccag gccctggagg ccgtgctgac cgccctgccc   1920

agggtgtgcc ccggcatggt gcagaccacc gagaggatcg tggccatcgg caccagccac   1980

ggcggcaccc aggccctgga ggccgtgctg accgccctgc ccagggtgtg ccccggcatg   2040

gtgcagacca ccgagaggat cgtggccatc ggcaccagcc acggcggcac ccaggccctg   2100

gaggccgtgc tgaccgccct gcccagggtg tgccccggca tggtgcagac caccgagagg   2160

atcgtggcca tcggcaccag ccacggcggc acccaggccc tggaggccgt gctgaccgcc   2220

ctgcccaggg tgtgccccgg catggtgcag accaccgaga ggatcgtggc catcggcacc   2280

agccacggcg gcacccaggc cctggaggcc gtgctgaccg ccctgcccag ggtgtgcccc   2340

ggcatggtgc agaccaccga gaggatcgtg gccatcggca ccagccacgg cggcacccag   2400

gccctggagg ccgtgctgac cgccctgccc agggtgtgcc ccggcatggt gcagaccacc   2460

gagaggatcg tggccatcgg caccagccac ggcggcaccc aggccctgga ggccgtgctg   2520

accgccctgc ccagggtgtg ccccggcatg gtgcagacca ccgagaggat cgtggccatc   2580

ggcaccagcc acggcggcac ccaggccctg gaggccgtgc tgaccgccct gcccagggtg   2640

tgccccggca tggtgcagac caccgagagg atcgtggcca tcggcaccag ccacggcggc   2700

acccaggccc tggaggccgt gctgaccgcc ctgcccaggg tgtgccccgg catggtgcag   2760

accaccgaga ggatcgtggc catcggcacc agccacggcg gcacccaggc cctggaggcc   2820

gtgctgaccg ccctgcccag ggtgtgcccc ggcatggtgc tgacacccga acaggtggtc   2880

gccattgcta ataataacgg aggacggcca gccttggagt ccatcgtagc ccaattgtcc   2940

aggcccgatc ccgcgttggc tgcgttaacg aatgaccatc tggtggcgtt ggcatgtctt   3000

ggtggacgac ccgcgctcga tgcagtcaaa aagggtctgc ctcatgctcc cgcattgatc   3060

aaaagaacca accggcggat tcccgagaga acttcccatc gagtcgcggg atcccaacta   3120

gtc                                                                  3123
```

<210> SEQ ID NO 208
<211> LENGTH: 17
<212> TYPE: DNA
<213> ORGANISM: Artificial Sequence
<220> FEATURE:
<223> OTHER INFORMATION: TALEN monomer with 17 RVD array

<400> SEQUENCE: 208

```
tgatagtcgc cttatgt                                                    17
```

<210> SEQ ID NO 209
<211> LENGTH: 34
<212> TYPE: PRT
<213> ORGANISM: Artificial Sequence

```
<220> FEATURE:
<223> OTHER INFORMATION: consensus sequence Xaa is Ala or Asp
<220> FEATURE:
<221> NAME/KEY: X
<222> LOCATION: (32)..(32)
<223> OTHER INFORMATION: Xaa is Ala or Asp

<400> SEQUENCE: 209

Leu Thr Thr Glu Arg Ile Val Ala Ile Gly Thr Ser Thr Gly Gly Thr
1               5                   10                  15

Gln Ala Leu Glu Ala Val Leu Thr Ala Leu Pro Arg Val Cys Gln Xaa
            20                  25                  30

Gly His


<210> SEQ ID NO 210
<211> LENGTH: 20
<212> TYPE: DNA
<213> ORGANISM: Artificial Sequence
<220> FEATURE:
<223> OTHER INFORMATION: PCR primer

<400> SEQUENCE: 210

attgggctac gatggactcc                                                   20


<210> SEQ ID NO 211
<211> LENGTH: 11
<212> TYPE: PRT
<213> ORGANISM: Artificial Sequence
<220> FEATURE:
<223> OTHER INFORMATION: consensus EBE fragment

<400> SEQUENCE: 211

Gln Thr Thr Glu Arg Ile Val Ala Ile Gly Thr
1               5                   10


<210> SEQ ID NO 212
<211> LENGTH: 21
<212> TYPE: PRT
<213> ORGANISM: Artificial Sequence
<220> FEATURE:
<223> OTHER INFORMATION: consensus EBE fragment

<400> SEQUENCE: 212

Gly Gly Thr Gln Ala Leu Glu Ala Val Leu Thr Ala Leu Pro Arg Val
1               5                   10                  15

Cys Pro Gly Met Val
            20


<210> SEQ ID NO 213
<211> LENGTH: 29
<212> TYPE: PRT
<213> ORGANISM: Pseudomonas mendocina ymp

<400> SEQUENCE: 213

Thr Thr Asp Arg Val Val Ala Leu Gly Thr Ser Thr Gly Gly Thr Gln
1               5                   10                  15

Ala Leu Glu Val Val Leu Arg Gln Leu Pro Val Asp Cys
            20                  25


<210> SEQ ID NO 214
<211> LENGTH: 29
<212> TYPE: PRT
<213> ORGANISM: Pseudomonas syringae pv. syringae FF5

<400> SEQUENCE: 214
```

```
Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 215
<211> LENGTH: 29
<212> TYPE: PRT
<213> ORGANISM: Sulfuricella denitrificans skB26

<400> SEQUENCE: 215

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 216
<211> LENGTH: 29
<212> TYPE: PRT
<213> ORGANISM: Pseudomonas syringae pv. pisi str. 1704B

<400> SEQUENCE: 216

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 217
<211> LENGTH: 29
<212> TYPE: PRT
<213> ORGANISM: Pseudomonas syringae pv. syringae FF5

<400> SEQUENCE: 217

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 218
<211> LENGTH: 29
<212> TYPE: PRT
<213> ORGANISM: Pseudomonas syringae pv. maculicola str. ES4326

<400> SEQUENCE: 218

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 219
<211> LENGTH: 29
<212> TYPE: PRT
<213> ORGANISM: Pseudomonas amygdali pv. morsprunorum str. M302280

<400> SEQUENCE: 219

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 220
```

```
<211> LENGTH: 29
<212> TYPE: PRT
<213> ORGANISM: Pseudomonas syringae pv. japonica str. M301072

<400> SEQUENCE: 220

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 221
<211> LENGTH: 29
<212> TYPE: PRT
<213> ORGANISM: Pseudomonas syringae pv. actinidiae str. M302091

<400> SEQUENCE: 221

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 222
<211> LENGTH: 29
<212> TYPE: PRT
<213> ORGANISM: Pseudomonas savastanoi pv. savastanoi NCPPB 3335

<400> SEQUENCE: 222

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 223
<211> LENGTH: 29
<212> TYPE: PRT
<213> ORGANISM: Pseudomonas syringae pv. aesculi str. NCPPB 3681

<400> SEQUENCE: 223

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 224
<211> LENGTH: 29
<212> TYPE: PRT
<213> ORGANISM: Pseudomonas syringae pv. oryzae str. 1_6

<400> SEQUENCE: 224

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 225
<211> LENGTH: 29
<212> TYPE: PRT
<213> ORGANISM: Pseudomonas syringae pv. tomato K40

<400> SEQUENCE: 225

Thr Thr Glu Arg Ile Val Ala Ile Gly Thr Ser Thr Gly Gly Thr Gln
1               5                   10                  15
```

```
Ala Leu Glu Ala Val Leu Thr Ala Leu Pro Arg Val Cys
            20                  25


<210> SEQ ID NO 226
<211> LENGTH: 29
<212> TYPE: PRT
<213> ORGANISM: Pseudomonas syringae pv. tomato str. DC3000

<400> SEQUENCE: 226

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 227
<211> LENGTH: 29
<212> TYPE: PRT
<213> ORGANISM: Pseudomonas syringae pv. aptata str. DSM 50252

<400> SEQUENCE: 227

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 228
<211> LENGTH: 29
<212> TYPE: PRT
<213> ORGANISM: Pseudomonas savastanoi pv. glycinea str. race 4

<400> SEQUENCE: 228

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 229
<211> LENGTH: 29
<212> TYPE: PRT
<213> ORGANISM: Pseudomonas syringae Cit 7

<400> SEQUENCE: 229

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 230
<211> LENGTH: 29
<212> TYPE: PRT
<213> ORGANISM: Pseudomonas syringae pv. syringae B728a

<400> SEQUENCE: 230

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25


<210> SEQ ID NO 231
<211> LENGTH: 29
<212> TYPE: PRT
<213> ORGANISM: Pseudomonas amygdali pv. mori str. 301020
```

<400> SEQUENCE: 231

Thr Thr Glu Arg Ile Val Ala Ile Gly Thr Ser Thr Gly Gly Thr Gln
1 5 10 15

Ala Leu Glu Ala Val Leu Thr Ala Leu Pro Arg Val Cys
20 25

<210> SEQ ID NO 232
<211> LENGTH: 29
<212> TYPE: PRT
<213> ORGANISM: Pseudomonas syringae pv. tabaci str. ATCC 11528

<400> SEQUENCE: 232

Thr Thr Glu Arg Ile Val Ala Ile Gly Thr Ser Thr Gly Gly Thr Gln
1 5 10 15

Ala Leu Glu Ala Val Leu Thr Ala Leu Pro Arg Val Cys
20 25

<210> SEQ ID NO 233
<211> LENGTH: 29
<212> TYPE: PRT
<213> ORGANISM: Pseudomonas syringae pv. aceris str. M302273

<400> SEQUENCE: 233

Thr Thr Glu Arg Ile Val Ala Ile Gly Thr Ser Thr Gly Gly Thr Gln
1 5 10 15

Ala Leu Glu Ala Val Leu Thr Ala Leu Pro Arg Val Cys
20 25

<210> SEQ ID NO 234
<211> LENGTH: 29
<212> TYPE: PRT
<213> ORGANISM: Pseudomonas savastanoi pv. glycinea str. B076

<400> SEQUENCE: 234

Thr Thr Glu Arg Ile Val Ala Ile Gly Thr Ser Thr Gly Gly Thr Gln
1 5 10 15

Ala Leu Glu Ala Val Leu Thr Ala Leu Pro Arg Val Cys
20 25

<210> SEQ ID NO 235
<211> LENGTH: 29
<212> TYPE: PRT
<213> ORGANISM: Pseudomonas syringae pv. syringae 642

<400> SEQUENCE: 235

Thr Thr Glu Arg Ile Val Ala Ile Gly Thr Ser Thr Gly Gly Thr Gln
1 5 10 15

Ala Leu Glu Ala Val Leu Thr Ala Leu Pro Arg Val Cys
20 25

<210> SEQ ID NO 236
<211> LENGTH: 29
<212> TYPE: PRT
<213> ORGANISM: Pseudomonas syringae pv. phaseolicola 1448A

<400> SEQUENCE: 236

Thr Thr Glu Arg Ile Val Ala Ile Gly Thr Ser Thr Gly Gly Thr Gln
1 5 10 15

Ala Leu Glu Ala Val Leu Thr Ala Leu Pro Arg Val Cys
20 25

-continued

```
<210> SEQ ID NO 237
<211> LENGTH: 28
<212> TYPE: PRT
<213> ORGANISM: Burkholderia rhizoxinica HKI 454

<400> SEQUENCE: 237

Ala Asp Ile Val Lys Ile Ala Ser Asn Gly Gly Gly Ala Gln Ala Leu
1               5                   10                  15

Glu Ala Val Ala Met His Gly Ser Thr Leu Cys Glu
            20                  25
```

SITE-SPECIFIC ENZYMES AND METHODS OF USE

CROSS-REFERENCE TO RELATED APPLICATIONS

This application claims priority to and is a United States National Stage filing under 35 U.S.C. § 371 of International PCT Application Serial No. PCT/US2013/070636, filed Nov. 18, 2013, which claims priority to U.S. Provisional Application Nos. 61/727,652, filed Nov. 16, 2012, and 61/802,066, filed Mar. 15, 2013, each of which is incorporated herein by reference in its entirety.

INCORPORATION BY REFERENCE OF SEQUENCE LISTING

The contents of the text file named "POTH-006-N01US_SeqListingR.txt", which was created on Mar. 19, 2019 and is 161 kilobytes in size, are hereby incorporated by reference herein in their entirety.

FIELD OF THE INVENTION

The present invention is directed, in part, to *Ralstonia* proteins, nucleic acids encoding the same, compositions comprising the same, kits comprising the same, as well as methods of using the same.

BACKGROUND OF THE INVENTION

Transcription factors with programmable DNA binding domains offer one potential approach toward creating an exogenous biological circuit in an endogenous system and creating designer proteins that bind to pre-determined DNA sequences or individual nucleic acids. Transcriptional activator-like (TAL) proteins have been recently demonstrated to have modular and predictable DNA binding domains, thereby allowing for the de novo creation of synthetic transcription factors that bind to DNA sequences of interest and, if desirable, allow a second domain present on the protein or polypeptide to perform an activity related to DNA. TAL proteins have been derived from the organism *Xanthomonas*. Provided herein, however, are *Ralstonia* proteins or polypeptides that function in a fashion similar to TAL proteins derived from *Xanthomonas*. The invention relates to polypeptides derived from *Ralstonia* amino acid sequences or amino acid sequences related thereto, nucleic acids encoding the same, compositions comprising the same, kits comprising the same, non-human transgenic animals comprising the same, and methods of using the same.

SUMMARY OF THE INVENTION

The present invention is based in part on the fact that the repeat variable diresidues (RVDs) of *Ralstonia* effectors correspond to the nucleotides in their target sites in a direct, linear fashion, one RVD to one nucleotide, with some degeneracy and no apparent context dependence. This finding represents a mechanism for protein-DNA recognition that enables target site prediction for new target-specific *Ralstonia* effectors. As described herein, these proteins may be useful in research and biotechnology as part of a larger targeted chimeric protein with accessory activities related to nucleic acids such as nuclease activity. For instance, in some embodiments, the polypeptide or pronucleases that can facilitate homologous recombination in genome engineering (e.g., to add or enhance traits useful for bio fuels or biorenewables in plants or bacteria, or animal genomes). These proteins also may be useful as, for example, transcription factors, and especially for therapeutic applications requiring a very high level of specificity such as therapeutics against pathogens (e.g., viruses) as non limiting examples. In some embodiments, the polypeptide or proteins of the invention comprise at least a first domain and a second domain, wherein the first domain comprises at least one coding sequence for a nucleic acid recognition element and the second domain comprises at least one coding sequence for a nucleic acid effector element.

The present invention provides proteins comprising at least 80%, 85%, 90%, 95%, 96%, 97%, 98%, or 99% sequence identity to SEQ ID NO: 1: LSTEQVVAIASX1X2GGKQALEAVKAQLLVLRAAPYE (SEQ ID NO: 1); wherein $X_1$=naturally occurring or non naturally amino acid.

$X_2$=naturally occurring or non naturally amino acid.

In some embodiments, the polypeptide of the present invention comprises at least 80%, 85%, 90%, 95%, 96%, 97%, 98%, or 99% sequence identity to SEQ ID NO: 1: LSTEQVVAIASX1X2GGKQALEAVKAQLLVLRAAPYE; wherein, in any combination, $X_1$ and $X_2$ are independently variable, and $X_1$=A, N, H, R or G; and $X_2$=I, N, H, K, Y, T, D, S, or P.

In some embodiments, the polypeptide of the present invention comprises at least 80%, 85%, 90%, 95%, 96%, 97%, 98%, or 99% sequence identity to SEQ ID NO: 1: LSTEQVVAIASX1X2GGKQALEAVKAQLLVLRAAPYE (SEQ ID NO: 1);

wherein $X_1$=S and $X_2$=I.

In some embodiments, the polypeptide of the present invention comprises at least 80%, 85%, 90%, 95%, 96%, 97%, 98%, or 99% sequence identity to SEQ ID NO:1: LSTEQVVAIASX1X2GGKQALEAVKAQLLVLRAAPYE (SEQ ID NO: 1);

wherein $X_1$=S and $X_2$=N.

In some embodiments, the polypeptide of the present invention comprises at least 80%, 85%, 90%, 95%, 96%, 97%, 98%, or 99% sequence identity to LSTEQVVAIASSIGGKQALEAVKAQLLVLRAAPYE (SEQ ID NO:2).

In some embodiments, the polypeptide of the present invention comprises at least 80%, 85%, 90%, 95%, 96%, 97%, 98%, or 99% sequence identity to LSTEQVVAIASSNGGKQALEAVKAQLLVLRAAPYE (SEQ ID NO:3).

In some embodiments, the polypeptide of the present invention comprises at least 80%, 85%, 90%, 95%, 96%, 97%, 98%, or 99% sequence identity to LSTEQVVAIASSHGGKQALEAVKAQLLVLRAAPYE (SEQ ID NO:4).

In some embodiments, the polypeptide of the present invention comprises at least 80%, 85%, 90%, 95%, 96%, 97%, 98%, or 99% sequence identity to LSTEQVVAIASNPGGKQALEAVKAQLLVLRAAPYE (SEQ ID NO:5).

In some embodiments, the polypeptide of the present invention comprises at least 80%, 85%, 90%, 95%, 96%, 97%, 98%, or 99% sequence identity to LSTEQVVAIASNHGGKQALEAVKAQLLVLRAAPYE (SEQ ID NO:6).

In some embodiments, the polypeptide of the present invention comprises at least 80%, 85%, 90%, 95%, 96%, 97%, 98%, or 99% sequence identity to LSTEQVVAIASNTGGKQALEAVKAQLLVLRAAPYE (SEQ ID NO:7).

In some embodiments, the polypeptide of the present invention comprises at least 80%, 85%, 90%, 95%, 96%, 97%, 98%, or 99% sequence identity to LSTEQVVAIASNKGGKQALEAVKAQLLVLRAAPYE (SEQ ID NO:8).

In some embodiments, the polypeptide of the present invention comprises at least 80%, 85%, 90%, 95%, 96%, 97%, 98%, or 99% sequence identity to LSTEQVVAIASNPGGKQALEAVKAQLLVLRAAPYE (SEQ ID NO:9).

In some embodiments, the polypeptide of the present invention comprises at least 80%, 85%, 90%, 95%, 96%, 97%, 98%, or 99% sequence identity to LSTEQVVAIASNNGGKQALEAVKAQLLVLRAAPYE (SEQ ID NO:10).

In some embodiments, the polypeptide of the present invention comprises at least 80%, 85%, 90%, 95%, 96%, 97%, 98%, or 99% sequence identity to LSTEQVVAIASNDGGKQALEAVKAQLLVLRAAPYE (SEQ ID NO: 11).

In some embodiments, the polypeptide of the present invention comprises at least 80%, 85%, 90%, 95%, 96%, 97%, 98%, or 99% sequence identity to LSTEQVVAIASNGGGKQALEAVKAQLLVLRAAPYE (SEQ ID NO: 12).

In some embodiments, the polypeptide of the present invention comprises at least 80%, 85%, 90%, 95%, 96%, 97%, 98%, or 99% sequence identity to LSTEQVVAIASHNGGKQALEAVKAQLLVLRAAPYE (SEQ ID NO:13).

In some embodiments, the polypeptide of the present invention comprises at least 80%, 85%, 90%, 95%, 96%, 97%, 98%, or 99% sequence identity to LSTEQVVAIASHYGGKQALEAVKAQLLVLRAAPYE (SEQ ID NO: 14).

In some embodiments, the polypeptide of the present invention comprises at least 80%, 85%, 90%, 95%, 96%, 97%, 98%, or 99% sequence identity to LSTEQVVAIASHDGGKQALEAVKAQLLVLRAAPYE (SEQ ID NO:15).

In some embodiments, the polypeptide of the present invention comprises at least 80%, 85%, 90%, 95%, 96%, 97%, 98%, or 99% sequence identity to LSTEQVVAIASHHGGKQALEAVKAQLLVLRAAPYE (SEQ ID NO:16).

In some embodiments, the polypeptide of the present invention comprises at least 80%, 85%, 90%, 95%, 96%, 97%, 98%, or 99% sequence identity to LSTEQVVAIASRNGGKQALEAVKAQLLVLRAAPYE (SEQ ID NO:17).

In some embodiments, the polypeptide of the present invention comprises at least 80%, 85%, 90%, 95%, 96%, 97%, 98%, or 99% sequence identity to LSTEQVVAIASRSGGKQALEAVKAQLLVLRAAPYE (SEQ ID NO:18).

In some embodiments, the polypeptide of the present invention comprises at least 80%, 85%, 90%, 95%, 96%, 97%, 98%, or 99% sequence identity to LSTEQVVAIASGSGGKQALEAVKAQLLVLRAAPYE (SEQ ID NO:19).

In some embodiments, the polypeptide or proteins of the invention comprise at least a first domain and a second domain, wherein the first domain comprises at least one a nucleic acid recognition element and wherein the second domain comprises at least one nucleic acid effector element.

The present invention relates to nucleic acid sequences that encode any protein or polypeptide described herein.

The present invention relates to compositions that comprise any one or a plurality of nucleic acid sequences that encode any protein or polypeptide described herein. The present invention relates to compositions that comprises any one or a plurality of amino acid sequences described herein.

In some embodiments, the polypeptide of the present invention comprises SEQ ID NO: 1. In some embodiments, the polypeptide of the present invention consists essentially of SEQ ID NO: 1. In some embodiments, the polypeptide of the present invention consists of SEQ ID NO: 1. In some embodiments, the polypeptide of the present invention comprises SEQ ID NO: 1, wherein $X_1X_2$ bind to a single nucleic acid. In some embodiments, the polypeptide of the present invention comprises SEQ ID NO: 1, wherein $X_1X_2$ bind to at least one nucleic acid. In some embodiments, the polypeptide of the present invention consists essentially of SEQ ID NO: 1, wherein $X_1X_2$ bind to a nucleic acid. In some embodiments, the polypeptide of the present invention consists of SEQ ID NO: 1, wherein $X_1X_2$ bind to a nucleic acid.

In some embodiments, the polypeptide of the present invention comprises one or more of any combination of a polypeptide sequences with at least 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO:12, SEQ ID NO:13, SEQ ID NO:14, SEQ ID NO:15, SEQ ID NO:16, SEQ ID NO:17, SEQ ID NO: 18, SEQ ID NO: 19, SEQ ID NO:20.

In some embodiments, the polypeptide of the present invention comprises one or more of any combination of a polypeptide sequences with at least 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO: 12, SEQ ID NO: 13, SEQ ID NO 14, SEQ ID NO: 15, SEQ ID NO: 16, SEQ ID NO:17, SEQ ID NO:18, SEQ ID NO:19, SEQ ID NO:20, wherein the 12th and 13th amino acid of at least one of the polypeptide sequences binds at least one nucleic acid.

In some embodiments, the polypeptide of the present invention comprises one or a plurality of any combination of a polypeptide sequences with 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO:12, SEQ ID NO:13, SEQ ID NO:14, SEQ ID NO:15, SEQ ID NO:16, SEQ ID NO 17, SEQ ID NO: 18, and SEQ ID NO: 19.

In some embodiments, the polypeptide of the present invention comprises a first domain and a second domain, wherein the first domain is a nucleic acid recognition domain that comprises one or a plurality of any combination of a polypeptide sequences with 80%, 85%, 90%, 91%, 92%, 93%, 94%, 95%, 96%, 97%, 98%, or 99% sequence identity to the polypeptides chosen from: SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID N: 12, SEQ ID NO: 13, SEQ ID NO: 14, SEQ ID NO: 15, SEQ ID NO: 16, SEQ ID NO:17, SEQ ID NO:18, and SEQ ID NO: 19.

In some embodiments, the polypeptide of the present invention comprises a first domain and a second domain, wherein the first domain is a nucleic acid recognition domain that comprises one or a plurality of any combination of a polypeptide sequences with 80%, 85%, 90%, 91%, 92%, 93%, 94%, 95%, 96%, 97%, 98%, or 99% sequence identity to the polypeptides chosen from: SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO:12, SEQ ID NO: 13, SEQ ID NO: 14, SEQ ID NO: 15, SEQ ID NO:16, SEQ ID NO:17, SEQ ID NO:18, and SEQ ID NO:19; wherein the 12th and 13th amino acid of at least one polypeptide sequence bind a nucleic acid.

In some embodiments, the polypeptide comprises at least 80% sequence identity to SEQ ID NO: 1. In some embodiments, the polypeptide comprises at least 90% sequence identity to SEQ ID NO: 1. In some embodiments, the polypeptide comprises at least 91% sequence identity to SEQ ID NO 1. In some embodiments, the polypeptide comprises at least 92% sequence identity to SEQ ID NO: 1. In some embodiments, the polypeptide comprises at least 93% sequence identity to SEQ ID NO. In some embodiments, the polypeptide comprises at least 94% sequence identity to SEQ ID NO: 1. In some embodiments, the polypeptide comprises at least 95% sequence identity to SEQ ID NO: 1. In some embodiments, the polypeptide comprises at least 96% sequence identity to SEQ ID NO: 1. In some embodiments, the polypeptide comprises at least 97% sequence identity to SEQ ID NO:1. In some embodiments, the polypeptide comprises at least 98% sequence identity to SEQ ID NO: 1. In some embodiments, the polypeptide comprises at least 99% sequence identity to SEQ ID NO:1.

In some embodiments, the protein comprises at least 80% sequence identity to SEQ ID NO: 1, and comprises more than one of the amino acid substitutions in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19. In some embodiments, the protein comprises at least 90% sequence identity to SEQ ID NO: 1, and comprises more than one of the amino acid substitutions in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO:15, SEQ ID NO: 16, SEQ ID NO: 17, SEQ ID NO: 18, or SEQ ID NO: 19. In some embodiments, the protein comprises at least 95% sequence identity to SEQ ID NO:1, and comprises more than one of the amino acid substitutions in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO:13, SEQ ID NO:14, SEQ ID NO:15, SEQ ID NO:16, SEQ ID NO:17, SEQ ID NO:18, or SEQ ID NO: 19. In some embodiments, the protein comprises at least 99% sequence identity to SEQ ID NO:1, and comprises more than one of the amino acid substitutions in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO: 18, or SEQ ID NO: 19.

In some embodiments, the protein or polypeptide comprises at least 80%, 85%, 90%, 91%, 92%, 93%, 94%, 95%, 96%, 97%, 98%, or 99% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO 14, SEQ ID NO: 15, SEQ ID NO: 16, SEQ ID NO: 17, SEQ ID NO:18, or SEQ ID NO:19. In some embodiments, the protein or polypeptide comprises at least one, two, three, or four polypeptide sequences selected from polypeptides comprising at least 80%, 85%, 90%, 91%, 92%, 93%, 94%, 95%, 96%, 97%, 98%, or 99% sequence identity to SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO: 17, SEQ ID NO:18, or SEQ ID NO:19.

The present invention also provides nucleic acids encoding any of the proteins described above. In some embodiments, the nucleic acid comprises nucleic acid sequences that encode at least 2, 3, 4, 5 or more polypeptides chosen from polypeptides comprising at least 80%, 85%, 90%, 91%, 92%, 93%, 94%, 95%, 96%, 97%, 98%, or 99% sequence identity to SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO: 18, or SEQ ID NO: 19.

The present invention also provides vectors comprising any of the nucleic acid sequences described above encoding any of the proteins described above. In some embodiments, the vector is a plasmid. In some embodiments, the vector is a retrovirus. In some embodiments, the retrovirus comprises long terminal repeats, a psi packaging signal, a cloning site, and a sequence encoding a selectable marker.

The present invention also provides cells comprising any of the nucleic acids or vectors described herein. In some embodiments, the cell is a sperm or an egg.

The present invention also provides kits comprising: a vector comprising a nucleic acid encoding any of the proteins described herein.

The present invention also provides non-human, transgenic animals comprising a nucleic acid molecule encoding any of the proteins described herein.

The present invention also provides methods of modifying genetic material of a cell or at least one cell of a multicellular or unicellular organism, the method comprising administering directly to the cell or at least one cell of a multicellular or unicellular organism any one or more of nucleic acids described herein or any polypeptide described herein. In some embodiments, the protein is administered as a nucleic acid encoding the protein. In some embodiments, nucleic acid encoding the protein is administered with a second nucleic acid sequence that encodes an effector. In some embodiments, the multicellular or unicellular organism is a vertebrate. In some embodiments, the vertebrate animal is a mammal. In some embodiments, the vertebrate animal is a non-human mammal. In some embodiments, the administering is administering systemically.

The present invention also provides methods of generating a non-human, transgenic animal comprising a germline mutation comprising: introducing a vector comprising a nucleotide sequence encoding any of the proteins described herein into a cell of the non-human, transgenic animal.

The present invention also provides methods of mutagenizing the germ line of a non-human, transgenic animal comprising: introducing a nucleic acid molecule encoding any of the proteins described herein into a cell under conditions sufficient to generate a transgenic animal.

DETAILED DESCRIPTION OF EMBODIMENTS

Figure 1:
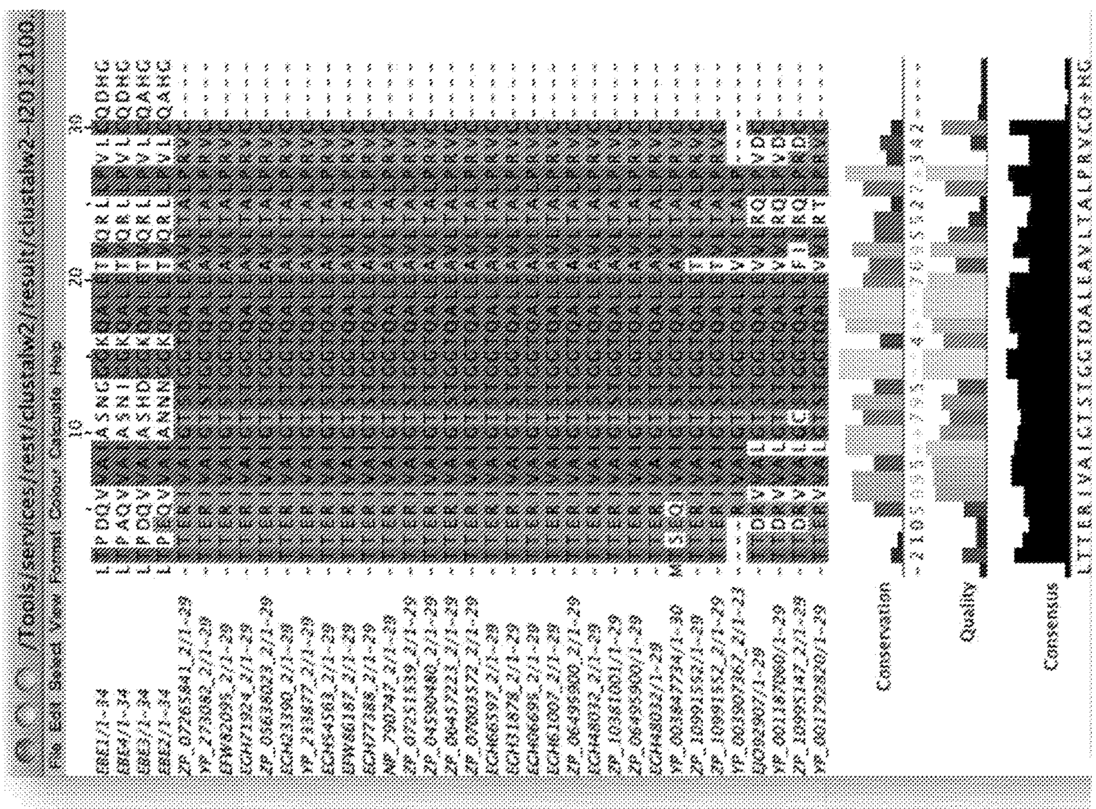
FIG. 1 depicts a consensus sequence of a DNA-binding protein from Xanthamonas aligned via BLAST to methyltransferase sequences from bacterial strains. Based upon sequence alignment, DNA binding function of the sequences is predicted. The sequences in the alignment have the following SEQ ID NOs, in order from top to bottom: SEQ ID NO: 31, SEQ ID NO: 34, SEQ ID NO: 33, SEQ ID NO: 32, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 136, SEQ ID NO: 137, SEQ ID NO: 138, SEQ ID NO: 138, SEQ ID NO: 139, SEQ ID NO: 56, SEQ ID NO: 56, SEQ ID NO: 57, SEQ ID NO: 58. The consensus sequence at the bottom reads LTTERIVAIGT-STGGTQALEAVLTALPRVCQXHG (SEQ ID NO: 209), wherein X is either an aspartic acid (D) or an alanine (A).

In some embodiments, the polypeptide or proteins of the invention comprise at least a first domain and a second domain, wherein the first domain comprises at least one coding sequence for a nucleic acid recognition element and wherein the second domain comprises at least one coding sequence for a nucleic acid effector element. In some embodiments, the polypeptide or proteins of the invention comprise at least a first domain wherein the first domain comprises at least one coding sequence for a nucleic acid recognition element derived from a amino acid sequence derived from *Ralstonia* or a variant thereof. In some embodiments, the polypeptide or proteins of the invention comprise at least a first domain wherein the first domain comprises at least one coding sequence for a nucleic acid recognition element derived from an amino acid sequence derived from *Ralstonia*.

The term “RTN” refers to a polypeptide or proteins of the invention that comprise at least a first domain wherein the first domain comprises at least one coding sequence for a nucleic acid recognition element derived from an amino acid sequence derived from *Ralstonia*. In some embodiments, the term “RTN” refers to a polypeptide or proteins of the invention that comprise at least a first domain and a second domain, wherein the first domain comprises at least one coding sequence for a nucleic acid recognition element derived from an amino acid sequence derived from *Ralstonia* and the second domain comprises a amino acid that is an effector protein. In some embodiments, the term “RTN” refers to a polypeptide or proteins of the invention that comprise at least a first domain and a second domain, wherein the first domain comprises at least one coding sequence for a nucleic acid recognition element derived from an amino acid sequence derived from *Ralstonia* and the second domain comprises a amino acid that is a nuclease. RTN DNA binding specificity depends on the number and order of repeat domains in the DNA binding domain. Repeats are generally composed of from about 30 to about 40 amino acids. In some embodiments, the repeat domains comprise from about 32 to about 38 amino acids. In some embodiments, nucleotide binding specificity is determined by the 12 and 13 amino acids of each repeat domain. In some embodiments, the repeat domains comprise from about 33 to about 37 amino acids. In some embodiments, the repeat domains comprise from about 34 to about 35 amino acids. In some embodiments, the repeat domains comprise from about 33 to about 36 amino acids. In some embodiments, the repeat domains comprise from about 33 to about 35 amino acids. In some embodiments, the repeat domains consist of 34 to 35 amino acids. In some embodiments, the repeat domains consist of 33 to 35 amino acids. In some embodiments, the repeat domains consist of 34 to 36 amino acids.

“Nucleic acid” or “oligonucleotide” or “polynucleotide” as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions. Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. In some embodiments, is synthesized, comprises non-natural amino acid modifications. Nucleic acids can be obtained by chemical synthesis methods or by recombinant methods.

“Operably linked” as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

“Promoter” as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter, “Substantially complementary” as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

As used herein "variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157: 105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of +2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity, as is understood in the art. Substitutions can be performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Vector

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

The present invention provides polypeptide, proteins and nucleic acid sequences that encode any of the polypeptides or proteins of the claimed invention. In some embodiments, the protein comprises at least 75% sequence identity to SEQ ID NO: 1. In some embodiments, the protein comprises at least 75% sequence identity to SEQ ID NO: 1 and comprises a nucleic acid binding domain at the 12th and 13th amino acids of SEQ ID NO: 1. In some embodiments, the proteins or polypeptides of the present invention comprise at least one RVD sequence selected from the following: SI, SN, SH, NP, NH, NT, NK, NN, ND, HN, HY, HD, HH, RN, RS, and GS. In some embodiments, the proteins or polypeptides of the present invention comprise at least one or a plurality of RVD sequences in any combination selected from the following: SI, SN, SH, NP, NH, NT, NK, NN, ND, HN, HY, HD, HH, RN, RS, NG and GS; wherein SI, SN, SH, NP, and NH bind any nucleic acid base; wherein NT, NK, and NN bind adenine; wherein ND, HN, HY, HD, and HH bind adenine and/or guanine; wherein NG binds thymine; wherein RN, RS, and GS bind guanine. In some embodiments, the proteins or polypeptides of the present invention comprise at least one or a plurality of RVD sequences in any combination selected from the following: SI, SN, SH, NP, NH, NT, NK, NN, ND, HN, HY, HD, HH, RN, RS, NG and GS; wherein SI, SN, SH, NP, and NH bind any nucleic acid base; wherein NK binds guanine, and NN binds adenine or guanine; wherein ND, HN, HY, HD, and HH bind cytosine; wherein NG binds thymine; wherein RN, RS, and GS bind guanine. In some embodiments, the proteins or polypeptides of the present invention comprise at least one or a plurality of RVD sequences in any combination selected from the following: SI, SN, SH, NP, NH, NT, NK, NN, ND, HN, HY, HD, HH, RN, RS, NG and GS; wherein SI binds adenine; SN binds guanine and/or adenine, SH, NP, and NH bind any nucleic acid base; wherein NK binds guanine; and NN binds adenine and/or guanine; wherein ND binds cytosine, HN binds guanine, HY, HD, and HH bind cytosine; wherein NG binds thymine; wherein RN binds guanine and/or adenine; wherein RS and GS binds guanine. In some embodiments, the the proteins or polypeptides of the present invention comprise at least one or a plurality of RVD sequences in any combination wherein at least one of the RVD sequences is NP, ND, or HN; and wherein NP binds cytosine, adenine, and guanine; wherein ND binds cytosine; and wherein HN binds adenine and/or guanine.

In some embodiments, the protein comprises at least 75% sequence identity to SEQ ID NO: 1, and comprises a conservative amino acid substitution in at least one of the following amino acid positions in SEQ ID NO:1: position 12 and position 13. In some embodiments, the protein comprises at least 80% sequence identity to SEQ ID NO: 1, and comprises a conservative amino acid substitution in at least one of the following amino acid positions in SEQ ID NO:1: position 12 and position 13. In some embodiments, the protein comprises at least 85% sequence identity to SEQ ID NO: 1, and comprises a conservative amino acid substitution in at least one of the following amino acid positions in SEQ ID NO: 1: position 12 and position 13. In some embodiments, the protein comprises at least 90% sequence identity to SEQ ID NO: 1, and comprises a conservative amino acid substitution in at least one of the following amino acid positions in SEQ ID NO:1: position 12 and position 13. In some embodiments, the protein comprises at least 91% sequence identity to SEQ ID NO: 1, and comprises a conservative amino acid substitution in at least one of the following amino acid positions in SEQ ID NO:1: position 12 and position 13. In some embodiments, the protein comprises at least 92% sequence identity to SEQ ID NO:1, and comprises a conservative amino acid substitution in at least one of the following amino acid positions in SEQ ID NO:1: position 12 and position 13. In some embodiments, the protein comprises at least 93% sequence identity to SEQ ID NO: 1, and comprises a conservative amino acid substitution in at least one of the following amino acid positions in SEQ ID NO: 1: position 12 and position 13. In some embodiments, the protein comprises at least 94% sequence identity to SEQ ID NO: 1, and comprises a conservative amino acid substitution in at least one of the following amino acid positions in SEQ ID NO:1: position 12 and position 13. In some embodiments, the protein comprises at least 95% sequence identity to SEQ ID NO: 1, and comprises a conservative amino acid substitution in at least one of the following amino acid positions in SEQ ID NO:1: position 12 and position 13. In some embodiments, the protein comprises at least 96% sequence identity to SEQ ID NO: 1, and comprises a conservative amino acid substitution in at least one of the following amino acid positions in SEQ ID NO:1: position 12 and position 13. In some embodiments, the protein comprises at least 97% sequence identity to SEQ ID NO: 1, and comprises a conservative amino acid substitution in at least one of the following amino acid positions in SEQ ID NO: 1: position 12 and position 13. In some embodiments, the protein comprises at least 98% sequence identity to SEQ ID NO: 1, and comprises a conservative amino acid substitution in at least one of the following amino acid positions in SEQ ID NO:1: position 12 and position 13. In some embodiments, the protein comprises at least 99% sequence identity to SEQ ID NO: 1, and comprises a conservative amino acid substitution in at least one of the following amino acid positions in SEQ ID NO:1: position 12 and position 13.

In some embodiments, the protein comprises at least 75% sequence identity to SEQ ID NO:1.

In some embodiments, the protein (as nucleic acid, as nucleic acid in a vector, or as purified recombinant protein) comprises at least 80% sequence identity to SEQ ID NO:2, and comprises at least one of the aforementioned amino acid substitutions in SEQ ID NO:2. In some embodiments, the protein (as nucleic acid, as nucleic acid in a vector, or as purified recombinant protein) comprises at least 85% sequence identity to SEQ ID NO:2, and comprises at least one of the aforementioned amino acid substitutions in SEQ ID NO:2. In some embodiments, the protein (as nucleic acid, as nucleic acid in a vector, or as purified recombinant protein) comprises at least 90% sequence identity to SEQ ID NO:2, and comprises at least one of the aforementioned amino acid substitutions in SEQ ID NO:2. In some embodiments, the protein (as nucleic acid, as nucleic acid in a vector, or as purified recombinant protein) comprises at least 95% sequence identity to SEQ ID NO:2, and comprises at least one of the aforementioned amino acid substitutions in SEQ ID NO:2. In some embodiments, the protein (as nucleic acid, as nucleic acid in a vector, or as purified recombinant protein) comprises at least 99% sequence identity to SEQ ID NO:2, and comprises at least one of the aforementioned amino acid substitutions in SEQ ID NO:2.

In some embodiments, the protein (encoded by a nucleic acid or as nucleic acid in a vector, or as purified recombinant protein) comprises at least 80% sequence identity to SEQ ID NO:3, and comprises at least one of the aforementioned amino acid substitutions in SEQ ID NO:3. In some embodiments, the protein (encoded by a nucleic acid or as nucleic acid in a vector, or as purified recombinant protein) comprises at least 85% sequence identity to SEQ ID NO:3, and comprises at least one of the aforementioned amino acid substitutions in SEQ ID NO:3. In some embodiments, the protein (encoded by a nucleic acid or as nucleic acid in a vector, or as purified recombinant protein) comprises at least 90% sequence identity to SEQ ID NO:3, and comprises at least one of the aforementioned amino acid substitutions in SEQ ID NO:3. In some embodiments, the protein (encoded by a nucleic acid or as nucleic acid in a vector, or as purified recombinant protein) comprises at least 95% sequence identity to SEQ ID NO:3, and comprises at least one of the aforementioned amino acid substitutions in SEQ ID NO:3. In some embodiments, the protein (encoded by a nucleic acid or as nucleic acid in a vector, or as purified recombinant protein) comprises at least 99% sequence identity to SEQ ID NO:3, and comprises at least one of the aforementioned amino acid substitutions in SEQ ID NO:3.

In some embodiments, the protein (encoded by a nucleic acid or as nucleic acid in a vector, or as purified recombinant protein) comprises at least 75% sequence identity to any of SEQ ID NO:4, SEQ ID NO:5, SEQ ID NO:6, SEQ ID NO:7, SEQ ID NO:8, SEQ ID NO:9, SEQ ID NO: 10, SEQ ID NO 11, SEQ ID NO: 12, SEQ ID NO: 13, SEQ ID NO 14, SEQ ID NO:15, SEQ ID NO: 16, SEQ ID NO: 17, SEQ ID NO: 18, SEQ ID NO: 19, and comprises more than one of the aforementioned amino acid substitutions in SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO:16, SEQ ID NO:17, SEQ ID NO:18, SEQ ID NO:19. In some embodiments, the protein (encoded by a nucleic acid or as nucleic acid in a vector, or as purified recombinant protein) comprises at least 80% sequence identity to SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO:12, SEQ ID NO:13, SEQ ID NO:14, SEQ ID NO:15, SEQ ID NO:16, SEQ ID NO:17, SEQ ID NO: 18, SEQ ID NO: 19, and comprises more than one of the aforementioned amino acid substitutions in SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO:13, SEQ ID NO:14, SEQ ID NO:15, SEQ ID NO:16, SEQ ID NO:17, SEQ ID NO:18, SEQ ID NO: 19. In some embodiments, the protein (as nucleic acid, as nucleic acid in a vector, or as purified recombinant protein) comprises at least 85% sequence identity to SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO 13, SEQ ID NO: 14, SEQ ID NO: 15, SEQ ID NO:16, SEQ ID NO:17, SEQ ID NO:18, SEQ ID NO:19, and comprises more than one of the aforementioned amino acid substitutions in any one or more of: SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO:16, SEQ ID NO:17, SEQ ID NO:18, SEQ ID NO:19. In some embodiments, the protein (as nucleic acid, as nucleic acid in a vector, or as purified recombinant protein) comprises at least 90% sequence identity to any one or more of, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO:12, SEQ ID NO:13, SEQ ID NO:14, SEQ ID NO:15, SEQ ID NO:16, SEQ ID NO:17, SEQ ID NO: 18, SEQ ID NO: 19, and comprises more than one of the aforementioned amino acid substitutions in any one or more of, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19. In some embodiments, the protein (as nucleic acid, as nucleic acid in a vector, or as purified recombinant protein) comprises at least 95% sequence identity to SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and comprises more than one of the aforementioned amino acid substitutions in any one or more of SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO:15, SEQ ID NO:16, SEQ ID NO:17, SEQ ID NO:18, SEQ ID NO:19. In some embodiments, the protein (as nucleic acid, as nucleic acid in a vector, or as purified recombinant protein) comprises at least 99% sequence identity to any one or more of SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO:16, SEQ ID NO:17, SEQ ID NO:18, SEQ ID NO:19, and comprises more than one of the aforementioned amino acid substitutions in any one or more of SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO:16, SEQ ID NO:17, SEQ ID NO:18, SEQ ID NO:19.

As used herein, "sequence identity" is determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). "Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used herein, "conservative" amino acid substitutions may be defined as set out in Tables A, B, or C below. In some embodiments, fusion polypeptides and/or nucleic acids encoding such fusion polypeptides include conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A.

TABLE A

| Conservative Substitutions I | |
|---|---|
| Side Chain Characteristics | Amino Acid |
| Aliphatic | |
| Non-polar | GAPILVF |
| Polar-uncharged | CSTMNQ |
| Polar-charged | DEKR |
| Aromatic | HFWY |
| Other | NQDE |

Alternately, conservative amino acids can be grouped as described in Lehninger, (Biochemistry, Second Edition; Worth Publishers, Inc. N.Y., N.Y. (1975), pp. 71-77) as set forth in Table B.

TABLE B

| Conservative Substitutions II | |
|---|---|
| Side Chain Characteristic | Amino Acid |
| Non-polar (hydrophobic) | |
| Aliphatic: | ALIVP |
| Aromatic: | FWY |
| Sulfur-containing: | M |
| Borderline: | GY |
| Uncharged-polar | |
| Hydroxyl: | STY |
| Amides: | NQ |
| Sulfhydryl: | C |
| Borderline: | GY |
| Positively Charged (Basic): | KRH |
| Negatively Charged (Acidic): | DE |

Alternately, exemplary conservative substitutions are set out in Table C.

TABLE C

| Conservative Substitutions III | |
|---|---|
| Original Residue | Exemplary Substitution |
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |

TABLE C-continued

| Conservative Substitutions III | |
|---|---|
| Original Residue | Exemplary Substitution |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides described herein are intended to include polypeptides bearing one or more insertions, deletions, or substitutions, or any combination thereof, of amino acid residues as well as modifications other than insertions, deletions, or substitutions of amino acid residues. In some embodiments, the polypeptides or nucleic acids disclosed herein contain one or more conservative substitution. In some embodiments, the polypeptides or nucleic acids disclosed herein contain more than one conservative substitution.

As used herein, "more than one" of the aforementioned amino acid substitutions means 2, 3, 4, 5, 6, 7, 8, 9, 10, 11, 12, 13, 14, 15, 16, 17, 18, 19, or 20 or more of the recited amino acid substitutions. In some embodiments, "more than one" means 2, 3, 4, or 5 of the recited amino acid substitutions. In some embodiments, "more than one" means 2, 3, or 4 of the recited amino acid substitutions. In some embodiments, "more than one" means 2 or 3 of the recited amino acid substitutions. In some embodiments, "more than one" means 2 of the recited amino acid substitutions.

As used herein, "endogenous" refers to nucleic acid or protein sequence naturally associated with a target gene or a host cell into which it is introduced.

As used herein, "exogenous" refers to nucleic acid or protein sequence not naturally associated with a target gene or a host cell into which it is introduced, including non-naturally occurring multiple copies of a naturally occurring nucleic acid, e.g., DNA sequence, or naturally occurring nucleic acid sequence located in a non-naturally occurring genome location.

As used herein, "genetically modified plant (or transgenic plant)" refers to a plant which comprises within its genome an exogenous polynucleotide. Generally, and preferably, the exogenous polynucleotide is stably integrated within the genome such that the polynucleotide is passed on to successive generations. The exogenous polynucleotide may be integrated into the genome alone or as part of a recombinant expression cassette. "Transgenic" is used herein to include any cell, cell line, callus, tissue, plant part or plant, the genotype of which has been altered by the presence of exogenous nucleic acid including those trans genies initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "modifying" as used herein is intended to mean that the sequence is considered modified simply by the binding of the polypeptide. It is not intended to suggest that the sequence of nucleotides is changed, although such changes (and others) could ensue following binding of the polypeptide to the nucleic acid of interest. In some embodiments, the nucleic acid sequence is DNA. Modification of the nucleic acid of interest (in the sense of binding thereto by a polypeptide modified to contain modular repeat units) could be detected in any of a number of methods (e.g. gel mobility shift assays, use of labelled polypeptides—labels could include radioactive, fluorescent, enzyme or biotin/streptavidin labels). Modification of the nucleic acid sequence of interest (and detection thereof) may be all that is required (e.g. in diagnosis of disease). Desirably, however, further processing of the sample is performed. Conveniently the polypeptide (and nucleic acid sequences specifically bound thereto) is separated from the rest of the sample. Advantageously the polypeptide-DNA complex is bound to a solid phase support, to facilitate such separation. For example, the polypeptide may be present in an acrylamide or agarose gel matrix or, more preferably, is immobilised on the surface of a membrane or in the wells of a microtitre plate.

In some embodiments, the fusion proteins of the invention comprise at least two domains, wherein the first domain is a *Ralstonia* DNA binding element and the second domain is a methylase.

The DNA sequences of the invention can be provided in expression cassettes for expression in any prokaryotic or eukaryotic cell and/or organism of interest including, but not limited to, bacteria, fungi, algae, plants, and animals. The cassette will include 5' and 3' regulatory sequences operably linked to a DNA sequence of the invention. "Operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the DNA sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), a DNA sequence of the invention, and a transcriptional and translational termination region (i.e., termination region) functional in plants or other organism or non-human host cell. The regulatory regions (i.e., promoters, transcriptional regulatory regions, and translational termination regions) and/or the DNA sequence of the invention may be native/analogous to the host cell or to each other. Alternatively, the regulatory regions and/or DNA sequence of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked DNA sequence of interest, may be native with the host, or may be derived from another source (i.e., foreign or heterologous) to the promoter, the DNA sequence of interest, the plant host, or any combination thereof. Convenient termination regions for use in plants are available from the Ti-plasmid of *A. tumefaciens*, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballas et al. (1989) Nucleic Acids Res. 17:7891-7903; and Joshi et al. (1987) Nucleic Acids Res. 15:9627-9639.

Where appropriate, the polynucleotides may be optimized for increased expression in a transformed organism. That is, the polynucleotides can be synthesized using codons preferred by the host for improved expression. See, for example, Campbell and Gown (1990) Plant Physiol. 92: 1-11 for a discussion of host-preferred codon usage. Methods are available in the art for synthesizing host-preferred gene, particularly plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Tabling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed DNA sequences and proteins encoded thereby are also encompassed by the present invention. By "fragment" is intended a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the invention.

In some embodiments, the protein comprises SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, and/or SEQ ID NO:19. In some embodiments any one of the polypeptide sequences SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and/or SEQ ID NO:19 is repeated at least once. In some embodiments, the polypeptide does not comprise any of the sequences in Table 1. In some embodiments, the polypeptide comprises a single sequence in Table 1 but does not comprise at least one or more of the alternative sequences in Table 1. In some embodiments, the alternative sequence comprises SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, or SEQ ID NO: 19.

The present invention also provides nucleic acids encoding any one of the polypeptide proteins described herein. Thus, the present invention provides nucleic acids encoding a protein that comprises at least 75% (or 80%, 85%, 90%, 95%, or 99%) sequence identity to SEQ ID NO:1.

In some embodiments, the nucleic acid encodes a protein that comprises at least 75% (or 80%, 85%, 90%, 95%, or 99%) sequence identity to SEQ ID NO:1, where $X_1X_2$ are any combination of naturally occurring to non-naturally occurring amino acids.

Given the redundancy in the genetic code, one skilled in the art could generate numerous nucleotide sequences that encode any particular protein. All such nucleotides sequences are contemplated herein.

The present invention also provides vectors comprising any of the aforementioned nucleic acids. Thus, the present invention provides vectors comprising a nucleic acid that encodes a protein that comprises at least 75% (or 80%, 85%, 90%, 95%, or 99%) sequence identity to SEQ ID NO: 1. The present invention provides vectors comprising a nucleic acid that encodes at least one protein that comprises at least 75% (or 80%, 85%, 90%, 95%, or 99%) sequence identity to SEQ ID NO: 1, and comprises at least one RVD sequence at its $12^{th}$ and $13^{th}$ amino acids of SEQ ID NO: 1 selected from the following: SI, SN, SH, NP, NH, NT, NK, NN, ND, HN, HY, HD, HH, RN, RS, and GS. In some embodiments, the proteins or polypeptides of the present invention comprise at least one or a plurality of RVD sequences in any combination selected from the following: SI, SN, SH, NP, NH, NT, NK, NN, ND, HN, HY, HD, HH, RN, RS, NG and GS; wherein SI, SN, SH, NP, and NH bind any nucleic acid base; wherein NT, NK, and NN bind adenine; wherein ND, HN, HY, HD, and HH bind adenine and/or guanine; wherein NG binds thymine; wherein RN, RS, and GS bind guanine. In some embodiments, NK binds to guanine, NG binds to thymine, NN binds to guanine or adenine, and or/HD binds cytosine. In some embodiments SI binds adenine, SN binds guanine or adenine, ND binds cytosine, HN binds guanine, and/or RN binds guanine or adenine.

In some embodiments, the polypeptide comprises at least a first and a second domain, wherein the first domain comprises at least one polypeptide monomer that comprises a single RVD sequence described above. In some embodiments, the first domain comprises 1, 2, 3, 4, 5, 6, 7, 8, 9, 10, 11, 12, 13, 14 15, 16, 17, 18, 19, or 20 or more monomers, wherein each monomer comprises a single nucleic acid binding domain consisting of two amino acids, or RVD. In some embodiments of the invention, the first domain comprises at least two monomers wherein each monomer is separated by a spacer of at least 1, 2, 3, 4, 5, 6, 7, 8, 9, 10, 11, 12, 13, 14, 15, 16, 17, 18, 19, or 20 or more amino acids.

In some embodiments, the second domain comprises another function complementary to the nucleic acid binding conferred by the presence first domain. In some embodiments, the second domain is a nuclease or functional fragment of a nuclease. In some embodiments, the second domain is an endonuclease or functional fragment of an endonuclease. In some embodiments, the second domain is a nickase or functional fragment of a nickase. In some embodiments, the second domain is a repressor or functional fragment of a repressor. In some embodiments, the second domain is a transcriptional activator or functional fragment of a transcriptional activator.

In some embodiments, the vector comprises a nucleic acid that comprises a sequence that encodes one or more of each polypeptide described herein. In some embodiments, the vector comprises a nucleic acid that comprises a sequence that encodes one or more of each polypeptides chosen from: SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

In some embodiments, the vector is a plasmid. In other embodiments, the vector is a retrovirus. In some embodiments, the vector is a linear DNA molecule. In some embodiments, the retrovirus comprises long terminal repeats, a psi packaging signal, a cloning site, and a sequence encoding a selectable marker. In some embodiments, the vector is a viral vector, such as pLXIN (Clontech).

The present invention also provides cells or organisms comprising any of the aforementioned nucleic acids. Thus, the present invention provides cells or organisms comprising a nucleic acid that encodes a protein that comprises at least 75% (or 80%, 85%, 90%, 95%, or 99%) sequence identity to SEQ ID NO: 1. The present invention provides cells or organisms comprising a nucleic acid that encodes a protein that comprises at least 75% (or 80%, 85%, 90%, 95%, or 99%) sequence identity to any one or more of the following polypeptides in any combination: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO:15, SEQ ID NO:16, SEQ ID NO 17, SEQ ID NO:18, or SEQ ID NO:19. The present invention provides cells or organisms comprising a nucleic acid that encodes a protein that comprises at least 75% (or 80%, 85%, 90%, 95%, or 99%) sequence identity to any one or more of the following polypeptides in any combination: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19; and comprises at least one mutation at at least one of the RVD domains at position 12 and 13 of any of SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO 10, SEQ ID NO: 11, SEQ ID NO: 12, SEQ ID NO:13, SEQ ID NO:14, SEQ ID NO:15, SEQ ID NO:16, SEQ ID NO:17, SEQ ID NO:18, or SEQ ID NO:19. The present invention provides cells or organisms comprising a nucleic acid mutated by contact with a protein that comprises at least 75% (or 80%, 85%, 90%, 95%, or 99%) sequence identity to any one or more of the following polypeptides in any combination: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO: 12, SEQ ID NO: 13, SEQ ID NO: 14, SEQ ID NO: 15, SEQ ID NO:16, SEQ ID NO:17, SEQ ID NO:18, or SEQ ID NO:19; and comprises at least one mutation at at least one of the RVD domains at position 12 and 13 of any of SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

In some embodiments, the cells or organisms comprise a nucleic acid that encodes a protein that comprises a nucleic acid sequence with at least 75% (or 80%, 85%, 90%, 95%, or 99%) sequence identity to SEQ ID NO: 1. In some embodiments, the polypeptide or protein of the claimed invention comprises multiple repeat domains, wherein at least one repeat domain comprises a nucleic acid sequence with at least 75% (or 80%, 85%, 90%, 95%, or 99%) sequence identity to SEQ ID NO:1-19 or a variant thereof that has 75% (or 80%, 85%, 90%, 95%, or 99% sequence identity to SEQ ID NO: 1-19.

In some embodiments, the cell comprises any of the aforementioned vectors or nucleic acid sequences.

In one aspect of the invention, the polypeptides of the invention comprise monomer subunits, wherein at least one monomer subunit comprises at least one amino acid sequence derived from *Ralstonia* that comprises a nucleotide recognition element. In some embodiments, the polypeptides of the invention comprise monomer subunits, wherein at least one monomer subunit comprises at least one amino acid sequence derived from *Ralstonia* that comprises a nucleotide recognition element that comprises at least 75% (or 80%, 85%, 90%, 95%, 96%, 97%, 98% or 99%) sequence identity to any one or more of the following polypeptides: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO: 12, SEQ ID NO: 13, SEQ ID NO: 14, SEQ ID NO: 15, SEQ ID NO:16, SEQ ID NO:17, SEQ ID NO:18, or SEQ ID NO:19. In some embodiments, the polypeptides of the invention comprise monomer subunits, wherein at least one monomer subunit comprises at least one amino acid sequence derived from *Ralstonia* that comprises a nucleotide recognition element that consist of at least 75% (or 80%, 85%, 90%, 95%, 96%, 97%, 98% or 99%) sequence identity to any one or more of the following polypeptides: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19. In some embodiments, nucleic acid molecules of the present invention comprise a nucleic acid sequence that encodes one or more monomer subunits, wherein the one or more monomer subunits, when encoded, comprise two or more, three of more, four or more, five or more, six or more, seven or more, eight or more, nine or more, ten or more, eleven or more, or twelve or more sequential monomers, each monomer comprising at least one amino acid sequence derived from *Ralstonia* that comprises a nucleotide recognition element. In some embodiments, nucleic acid molecules of the present invention comprise a nucleic acid sequence that encodes one or more monomer subunits, wherein the one or more monomer subunits, when encoded, comprise two or more, three of more, four or more, five or more, six or more, seven or more, eight or more, nine or more, ten or more, eleven or more, or twelve or more sequential monomers, each monomer comprising at least one amino acid sequence derived from *Ralstonia* that comprises a nucleotide recognition element consisting of at least 75% (or 80%, 85%, 90%, 95%, 96%, 97%, 98% or 99%) sequence identity to any one or more of the following polypeptides: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO: 12, SEQ ID NO: 13, SEQ ID NO:14, SEQ ID NO:15, SEQ ID NO:16, SEQ ID NO:17, SEQ ID NO:18, or SEQ ID NO: 19 or any variant or analog thereof. In some embodiments, the protein comprises one or more nucleic acid sequences that encode one or more polypeptide sequences comprising a nucleic acid recognition element derived from *Ralstonia* and one or more nucleic acid sequences that encode one or more polypeptide sequences comprising a nucleic acid recognition element derived from *Xanthamonus*. In some embodiments, the fusion protein comprises successive, independently variable monomer subunits that are DNA recognition elements, wherein at least one or more of the monomer subunits are derived from a *Ralstonia* sequence disclosed herein. In some embodiments, the invention relates to a fusion protein comprising successive, independently variable monomer subunits that are DNA recognition elements, wherein at least one or more of the monomer subunits are derived from a *Ralstonia* sequence disclosed in Table 1. In some embodiments, the invention relates to a fusion protein comprising successive, monomer subunits that are DNA recognition elements, wherein the fusion protein comprises a combination of successive polypeptides chosen from at least one of the following polypeptide sequences: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO: 12, SEQ ID NO: 13, SEQ ID NO:14, SEQ ID NO:15, SEQ ID NO:16, SEQ ID NO:17, SEQ ID NO:18, or SEQ ID NO: 19 or any variant or analog thereof. In some embodiments, the invention relates to a fusion protein comprising successive, monomer subunits that are DNA recognition elements, wherein the fusion protein comprises a combination of successive polypeptides chosen from at least one of the following polypeptide sequences: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19 or any variant or analog thereof, wherein each monomer binds one nucleotide of a DNA target sequence. In some embodiments, the invention relates to a fusion protein comprising successive, monomer subunits that are DNA recognition elements, wherein the fusion protein comprises a combination of successive polypeptides chosen from at least one of the following polypeptide sequences: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO:15, SEQ ID NO:16, SEQ ID NO:17, SEQ ID NO:18, or SEQ ID NO:19 or any variant or analog thereof that is at least 70%, 75%, 80%, 85%, 90%, 95%, 96%, 97%, 98% or 99% percent homologous thereof, wherein each monomer binds one nucleotide of a DNA target sequence in the presence of a nucleic acid sequence. In some embodiments, the invention relates to a fusion protein comprising successive, monomer subunits that are DNA recognition elements, wherein the fusion protein comprises a combination of successive polypeptides chosen from at least one of the following polypeptide sequences: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19 or any variant or analog thereof that is at least 70%, 75%, 80%, 85%, 90%, 95%, 96%, 97%, 98% or 99% percent homologous thereof, wherein each monomer binds one nucleotide of a DNA target sequence in the presence of a nucleic acid sequence, wherein the fusion protein further comprises at least one polypeptide sequence that is an effector protein/polypeptide. In some embodiments, the fusion protein comprises a first domain that binds a DNA target sequence and a second domain that has an effector function. In some embodiments, the invention relates to a fusion protein comprising successive, monomer subunits that are DNA recognition elements, wherein the fusion protein comprises a combination of successive polypeptides chosen from at least one of the following polypeptide sequences: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO:13, SEQ ID NO:14, SEQ ID NO:15, SEQ ID NO:16, SEQ ID NO:17, SEQ ID NO:18, or SEQ ID NO:19 or any variant or analog thereof that is at least 70%, 75%, 80%, 85%, 90%, 95%, 96%, 97%, 98% or 99% percent homologous thereof, wherein each monomer binds one nucleotide of a DNA target sequence in the presence of a nucleic acid sequence, wherein the fusion protein further comprises at least one polypeptide sequence that is an effector protein/polypeptide. In some embodiments, the fusion protein comprises a first domain that binds a DNA target sequence and a second domain that has a nuclease function. In some embodiments, the invention relates to a fusion protein comprising successive, monomer subunits that are DNA recognition elements, wherein the fusion protein comprises a combination of successive polypeptides chosen from at least one of the following polypeptide sequences: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO: 13, SEQ ID NO: 14, SEQ ID NO: 15, SEQ ID NO:16, SEQ ID NO:17, SEQ ID NO:18, or SEQ ID NO:19 or any variant or analog thereof that is at least 70%, 75%, 80%, 85%, 90%, 95%, 96%, 97%, 98% or 99% percent homologous thereof, wherein each monomer binds one nucleotide of a DNA target sequence in the presence of a nucleic acid sequence, wherein the fusion protein further comprises at least one polypeptide sequence that is an effector protein/polypeptide. In some embodiments, the fusion protein comprises a first domain that binds a DNA target sequence and a second domain that has a nickase or ligase function. In some embodiments, the fusion protein comprises a first domain that binds a DNA target sequence and a second domain that has a nuclease function. In some embodiments, the invention relates to a fusion protein comprising successive, monomer subunits that are DNA recognition elements, wherein the fusion protein comprises any combination of successive polypeptides chosen from at least one of the following polypeptide sequences: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO:15, SEQ ID NO:16, SEQ ID NO:17, SEQ ID NO:18, or SEQ ID NO:19 or any variant or analog thereof that is at least 70%, 75%, 80%, 85%, 90%, 95%, 96%, 97%, 98% or 99% percent homologous thereof, wherein each monomer binds one nucleotide of a DNA target sequence in the presence of a nucleic acid sequence, and wherein the fusion protein further comprises at least one polypeptide sequence that is an effector protein/polypeptide.

In some embodiments, the invention relates to a fusion protein comprising successive, monomer subunits that are DNA recognition elements, wherein the fusion protein comprises any combination of successive polypeptides chosen from at least one of the following polypeptide sequences: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO: 12, SEQ ID NO: 13, SEQ ID NO: 14, SEQ ID NO: 15, SEQ ID NO:16, SEQ ID NO:17, SEQ ID NO:18, or SEQ ID NO:19 or any variant or analog thereof that is at least 70%, 75%, 80%, 85%, 90%, 95%, 96%, 97%, 98% or 99% percent homologous thereof, wherein each monomer binds one nucleotide of a DNA target sequence in the presence of a nucleic acid sequence, and wherein the fusion protein further comprises at least one polypeptide sequence that is an effector protein/polypeptide and further comprises at least one polypeptide sequence that has any disclosed effector protein function. In some embodiments, the invention relates to a fusion protein comprising successive, monomer subunits that are DNA recognition elements, wherein the fusion protein comprises any combination of successive polypeptides chosen from at least one of the following polypeptide sequences: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO: 12, SEQ ID NO: 13, SEQ ID NO: 14, SEQ ID NO: 15, SEQ ID NO:16, SEQ ID NO:17, SEQ ID NO:18, or SEQ ID NO:19 or any variant or analog thereof that is at least 70%, 75%, 80%, 85%, 90%, 95%, 96%, 97%, 98% or 99% percent homologous thereof, wherein each monomer binds one nucleotide of a DNA target sequence in the presence of a nucleic acid sequence, and wherein the fusion protein further comprises at least two polypeptide sequences that comprise an effector protein/polypeptide function or that are effector proteins or variants thereof. In some embodiments, the invention relates to a fusion protein comprising successive, monomer subunits that are DNA recognition elements, wherein the fusion protein comprises any combination of successive polypeptides chosen from at least one of the following polypeptide sequences: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19 or any variant or analog thereof that is at least 70%, 75%, 80%, 85%, 90%, 95%, 96%, 97%, 98% or 99% percent homologous thereof, wherein each monomer binds one nucleotide of a DNA target sequence in the presence of a nucleic acid sequence, and wherein the fusion protein further comprises at least three or more polypeptide sequences that comprise an effector/protein function. In some embodiments, the invention relates to a fusion protein comprising successive, monomer subunits that are DNA recognition elements, wherein the fusion protein comprises any combination of successive polypeptides chosen from at least one of the following polypeptide sequences: SEQ ID NO: 1, SEQ ID NO: 2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19 or any variant or analog thereof that is at least 70%, 75%, 80%, 85%, 90%, 95%, 96%, 97%, 98% or 99% percent homologous thereof, wherein each monomer binds one nucleotide of a DNA target sequence in the presence of a nucleic acid sequence, and wherein the fusion protein further comprises at least four or more polypeptide sequences that comprise effector protein/polypeptide.

Nucleic acids or proteins of the present invention can be constructed by a modular approach by preassembling monomer units and/or repeat units in target vectors that can subsequently be assembled into a final destination vector. In one aspect of the invention, the polypeptides of the invention comprise repeat monomers of the present invention and can be constructed by a modular approach by preassembling repeat units in target vectors that can subsequently be assembled into a final destination vector. The invention provides the polypeptide produced this method as well as nucleic acid sequences encoding the polypeptides and host organisms and cells comprising such DNA sequences.

Techniques to specifically modify DNA sequences in order to obtain a specified codon for a specific amino acid are known in the art. Methods for mutagenesis and polynucleotide alterations have been widely described. See, for example, Kunkel (1985) Proc. Nat!. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. All these publications are herein incorporated by reference.

The following examples provide methods for constructing new repeat units and testing the specific binding activities of artificially constructed repeat units specifically recognizing base pairs in a target DNA sequence. The number of repeat units to be used in a repeat domain can be ascertained by one skilled in the art by routine experimentation. Generally, at least 1.5 repeat units are considered as a minimum, although typically at least about 8 repeat units will be used. The repeat units do not have to be complete repeat units, as repeat units of half the size can be used. Moreover, the methods and polypeptides disclosed herein do depend on repeat domains with a particular number of repeat units. Thus, a polypeptide of the invention can comprise, for example, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 46, 46.5, 47, 47.5, 48, 48.5, 49, 49.5, 50, 50.5 or more repeat units.

In the present invention, polypeptides can be designed which comprise a repeat domain with repeat units wherein in the repeat units hypervariable regions are included which determine recognition of a base pair in a target DNA sequence. In one embodiment of the invention, each repeat unit includes a hypervariable region which determine recognition of one base pair in a target DNA sequence. In a further embodiment, 1 or 2 repeat units in a repeat domain are included which do not specifically recognize a base pair in a target DNA sequence. Considering the recognition code found by the inventors, a modular arrangement of repeat units is feasible wherein each repeat unit is responsible for the specific recognition of one base pair in a target DNA sequence. Consequently, a sequence of repeat units corresponds to a sequence of base pairs in a target DNA sequence so that 1 repeat unit matches to one base pair.

The present invention provides a method for selectively recognizing a base pair in a target DNA sequence by a polypeptide wherein said polypeptide comprises at least one repeat domain comprising repeat units wherein in said repeat units each comprise at least one RVD region which determines recognition of a base pair or nucleotide in said target DNA sequence. More specifically, the inventors have determined those amino acids in a DNA-binding polypeptide responsible for selective recognition of base pairs in a target DNA sequence. With elucidation of the recognition code, a general principle for recognizing specific base pairs in a target DNA sequence by selected amino acids in a polypeptide has been determined. The inventors have found that distinct types of monomers that are part of a repeat unit array (or polymer) of varying amino acid length have the capacity to recognize one defined/specific base pair. Within each repeat unit forming a repeat domain, a RVD region is responsible for the specific recognition of a base pair in a target DNA sequence.

Thus, the present invention provides not only a method for selectively recognizing a base pair in a target DNA sequence by a polypeptide comprising at least one repeat domain comprising repeat units but also methods wherein target DNA sequences can be generated which are selectively recognized by repeat domains in a polypeptide. These polypeptides are useful for molecular biology tools in order to clone, mutagenize or otherwise alter an isolated nucleic acid sequence or other in vivo sequence in a laboratory. This provides an efficient means of selective mutagenesis.

The invention also provides for a method for constructing and/or making polypeptides that recognize specific DNA sequences. These polypeptides of the invention comprise repeat monomers of the present invention and can be constructed by a modular approach by preassembling repeat units in target vectors that can subsequently be assembled into a final destination vector. In some embodiments, the DNA constructs are codon optimized to recombinantly produce and/or secrete the polypeptides disclosed herein. Any recombinant system in the art can be used to produce the recombinant protein. Examples include baculovirus cells, other eukaryotic cells such as mammalian cells, or bacterial cells.

Provided that a target DNA sequence is known and to which recognition by a protein is desired, the person skilled in the art is able to specifically construct a modular series of repeat units, including specific recognition amino acid sequences, and assemble these repeat units into a polypeptide in the appropriate order to enable recognition of and binding to the desired target DNA sequence. Any polypeptide can be modified by being combined with a modular repeat unit DNA-binding domain of the present invention. Such examples include polypeptides that are transcription activator and repressor proteins, resistance-mediating proteins, nucleases, topoisomerases, ligases, integrases, recombinases, resolvases, methylases, acetylases, demethylases, deacetylases, and any other polypeptide capable of modifying DNA, RNA, or proteins.

The modular repeat unit DNA-binding domain of the present invention can be combined with cell compartment localisation signals such as nuclear localisation signals, to function at any other regulatory regions, including but not limited to, transcriptional regulatory regions and translational termination regions.

In a further embodiment of the invention, these modularly designed repeat units are combined with an endonuclease domain capable of cleaving DNA when brought into proximity with DNA as a result of binding by the repeat domain. Such endonucleo lytic breaks are known to stimulate the rate of homologous recombination in eukaryotes, including fungi, plants, and animals. The ability to simulate homologous recombination at a specific site as a result of a site-specific endonucleolytic break allows the recovery of transformed cells that have integrated a DNA sequence of interest at the specific site, at a much higher frequency than is possible without having made the site-specific break. In addition, endonucleolytic breaks such as those caused by polypeptides formed from a repeat domain and an endonuclease domain are sometimes repaired by the cellular DNA metabolic machinery in a way that alters the sequence at the site of the break, for instance by causing a short insertion or deletion at the site of the break compared to the unaltered sequence. These sequence alterations can cause inactivation of the function of a gene or protein, for instance by altering a protein-coding sequence to make a non-functional protein, modifying a splice site so that a gene transcript is not properly cleaved, making a non-functional transcript, changing the promoter sequence of a gene so that it can no longer by appropriately transcribed, etc.

Breaking DNA using site specific endonucleases can increase the rate of homologous recombination in the region of the breakage. In some embodiments, the Fok I (*Flavobacterium okeanokoites*) endonuclease may be utilized in an effector to induce DNA breaks. The Fok I endonuclease domain functions independently of the DNA binding domain and cuts a double stranded DNA typically as a dimer (Li et al. (1992) Proc. Natl. Acad. Sci. U.S.A 89 (10):4275-4279, and Kim et al. (1996) Proc. Natl. Acad. Sci. U.S.A 93 (3): 1156-1160; the disclosures of which are incorporated herein by reference in their entireties). A single-chain FokI dimer has also been developed and could also be utilized (Mino et al. (2009) J. Biotechnol. 140: 156-161). An effector could be constructed that contains a repeat domain for recognition of a desired target DNA sequence as well as a FokI endonuclease domain to induce DNA breakage at or near the target DNA sequence similar to previous work done employing zinc finger nucleases (Townsend et al. (2009) Nature 459:442-445; Shukla et al. (2009) Nature 459, 437-441, all of which are herein incorporated by reference in their entireties). Utilization of such effectors could enable the generation of targeted changes in genomes which include additions, deletions and other modifications, analogous to those uses reported for zinc finger nucleases as per Bibikova et al. (2003) Science 300, 764; Urnov et al. (2005) Nature 435, 646; Wright et al. (2005) The Plant Journal 44:693-705; and U.S. Pat. Nos. 7,163,824 and 7,001,768, all of which are herein incorporated by reference in their entireties.

The FokI endonuclease domain can be cloned by PCR from the genomic DNA of the marine bacteria *Flavobacterium okeanokoites* (ATCC) prepared by standard methods. The sequence of the FokI endonuclease is available on Pubmed (Ace. No. M28828 and Acc. No J04623, the disclosures of which are incorporated herein by reference in their entireties). The I-Sce I endonuclease from the yeast *Saccharomyces cerevisiae* has been used to produce DNA breaks that increase the rate of homologous recombination. I-Sce I is an endonuclease encoded by a mitochondrial intron which has an 18 bp recognition sequence, and therefore a very low frequency of recognition sites within a given DNA, even within large genomes (Thierry et al. (1991) Nucleic Acids Res. 19 (1): 189-190; the disclosure of which is incorporated herein by reference in its entirety). The infrequency of cleavage sites recognized by I-SceI makes it suitable to use for enhancing homologous recombination. Additional description regarding the use of I-Sce I to induce said DNA breaks can be found in U.S. Pat. Appl. 20090305402, which is incorporated herein by reference in its entirety.

The recognition site for I-Sce I has been introduced into a range of different systems. Subsequent cutting of this site with I-Sce I increases homologous recombination at the position where the site has been introduced. Enhanced frequencies of homologous recombination have been obtained with I-Sce I sites introduced into the extra-chromosomal DNA in *Xenopus* oocytes, the mouse genome, and the genomic DNA of the tobacco plant *Nicotiana plumbaginifolia*. See, for example, Segal et al. (1995) Proc. Natl. Acad. Sci. U.S.A. 92 (3):806-810; Choulika et al. (1995) Mol. Cell Biol. 15 (4): 1968-1973; and Puchta et al. (1993) Nucleic Acids Res. 21 (22):5034-5040; the disclosures of which are incorporated herein by reference in their entireties. It will be appreciated that any other endonuclease domain that works with heterologous DNA binding domains can be utilized in an effector and that the I-Sce I endonuclease is one such non-limiting example. The limitation of the use of endonucleases that have a DNA recognition and binding domain such as I-Sce I is that the recognition site has to be introduced by standard methods of homologous recombination at the desired location prior to the use of said endonuclease to enhance homologous recombination at that site, if such site is not already present in the desired location. Methods have been reported that enable the design and synthesis of novel endonucleases, such as by modifying known endonucleases or making chimeric versions of one or more such endonucleases, that recognize novel target DNA sequences, thus paving the way for generation of such engineered endonuclease domains to cleave endogenous target DNA sequences of interest (Chevalier et al. (2002) Molecular Cell 10:895-905; WO2007/060495; WO2009/095793; Fajardo-Sanchez et al. (2008) Nucleic Acids Res. 36:2163-2173, both of which are incorporated by reference in their entireties). As such, it could be envisioned that such endonuclease domains could be similarly engineered so as to render the DNA-binding activity non-functional but leaving the DNA cleaving function active and to utilize said similarly engineered endonuclease cleavage domain in an effector to induce DNA breaks similar to the use of FokI above. In such applications, target DNA sequence recognition would preferably be provided by the repeat domain of the effector but DNA cleavage would be accomplished by the engineered endonuclease domain.

As mentioned above, an effector includes a repeat domain with specific recognition for a desired specific target sequence. In preferred embodiments, the effector specifically binds to an endogenous chromosomal DNA sequence. The specific nucleic acid sequence or more preferably specific endogenous chromosomal sequence can be any sequence in a nucleic acid region where it is desired to enhance homologous recombination. For example, the nucleic acid region may be a region which contains a gene in which it is desired to introduce a mutation, such as a point mutation or deletion, or a region into which it is desired to introduce a gene conferring a desired phenotype.

Further embodiments relate to methods of generating a modified plant in which a desired addition has been introduced. The methods can include obtaining a plant cell that includes an endogenous target DNA sequence into which it is desired to introduce a modification; generating a double-stranded cut within the endogenous target DNA sequence with an effector that includes a repeat domain that binds to an endogenous target DNA sequence and an endonuclease domain; introducing an exogenous nucleic acid that includes a sequence homologous to at least a portion of the endogenous target DNA into the plant cell under conditions which permit homologous recombination to occur between the exogenous nucleic acid and the endogenous target DNA sequence; and generating a plant from the plant cell in which homologous recombination has occurred. Other embodiments relate to genetically modified cells and plants made according to the method described above and herein. It should be noted that the target DNA sequence could be artificial or naturally occurring. It will be appreciated that such methods could be used in any organism (such non-limiting organisms to include animals, humans, fungi, oomycetes bacteria and viruses) using techniques and methods known in the art and utilized for such purposes in such organisms.

In a further embodiment of the invention, these modularly designed repeat domains are combined with one or more domains responsible for the modulation or control of the expression of a gene, for instance of plant genes, animal genes, fungal genes, oomycete genes, viral genes, or human genes. Methods for modulating gene expression by generating DNA-binding polypeptides containing zinc finger domains is known in the art (U.S. Pat. Nos. 7,285,416, 7,521,241, 7,361,635, 7,273,923, 7,262,054, 7,220,719, 7,070,934, 7,013,219, 6,979,539, 6,933, 113, 6,824,978, each of which is hereby herein incorporated by reference in its entirety). For instance, these effectors of the *Ralstonia*-like family are modified in order to bind to specific target DNA sequences. Such polypeptides might for instance be transcription activators or repressor proteins of transcription which are modified by the method of the present invention to specifically bind to genetic control regions in a promoter of or other regulatory region for a gene of interest in order to activate, repress or otherwise modulate transcription of said gene.

In a still further embodiment of the invention, the target DNA sequences are modified in order to be specifically recognized by a naturally occurring repeat domain or by a modified repeat domain. As one example, the target DNA sequences for members of the *Ralstonia*-like family can be inserted into promoters to generate novel controllable promoters that can be induced by the corresponding effector. Secondary inducible systems can be constructed using a trans-activator and a target gene, wherein the trans-activator is a polypeptide wherein said polypeptide comprises at least a repeat domain comprising repeat units of the present invention that bind to said target gene and induce expression. The trans-activator and the target gene can be introduced into one cell line but may also be present in different cell lines and later be introgressed. In a further embodiment, disease-resistant plants can be constructed by inserting the target DNA sequence of a repeat domain containing polypeptide of the present invention in front of a gene which after expression leads to a defense reaction of the plant by activating a resistance-mediating gene.

In a further embodiment, custom DNA-binding polypeptides can be constructed by rearranging repeat unit types thus allowing the generation of repeat domains with novel target DNA binding specificity. Individual repeat units are nearly identical at the DNA level which precludes classical cloning strategies. The present invention provides a quick and inexpensive strategy to assemble custom polypeptides with repeat domains of the present invention. To improve cloning versatility such polypeptides, a two-step assembly method was designed. This method was used to assemble polypeptides with novel repeat types to study their target DNA recognition and binding specificity.

Summarily, any DNA sequence can be modified to enable binding by a repeat domain containing polypeptide of the present invention by introducing base pairs into any DNA region or specific regions of a gene or a genetic control element to specifically target a polypeptide having a repeat domain comprised of repeat units that will bind said modified DNA sequence in order to facilitate specific recognition and binding to each other.

In some embodiments, polypeptides can be synthetically manufactured using known amino acid chemistries familiar to one of ordinary skill in organic chemistry synthesis. Such procedures include both solution and solid phase procedures, e.g., using either Boc and Fmoc methodologies. The compounds of the invention may be synthesized using solid phase synthesis techniques. Fmoc-N-Protected β-amino acids can be used to synthesize poly-α/β-peptides by conventional manual solid-phase synthesis procedures under standard conditions on any number of solid supports, including ortho-chloro-trityl chloride resin. Esterification of Fmoc-β-amino acids with the ortho-chloro-trityl resin can be performed according to the method of Barlos et. al., Tetrahedron Lett, 1989, 30, 3943. The resin (150 mg, 1.05 mmol Cl) is swelled in 2 ml $CH_2Cl_2$ for 10 min. A solution of the Fmoc-protected β-amino acid in $CH_2Cl_2$ and $iPr_2EtN$ are then added successively and the suspension is mixed under argon for 4 h. Subsequently, the resin is filtered and washed with $CH_2Cl_2$/MeOH/$iPr_2EtN$ (17:2:1, 3×3 min), $CH_2Cl_2$ (3×3 min), DMF (2×3 min), $CH_2Cl_2$ (3×3 min), and MeOH (2×3 min). The substitution of the resin is determined on a 3 mg sample by measuring the absorbance of the dibenzofulvene adduct at 300 nm. The Fmoc group is removed using 20% piperidine in DMF (4 ml, 2×20 min) under Ar bubbling. The resin is then filtered and washed with DMF (6×3 min). For each coupling step, a solution of the β-amino acid (3 equiv.), BOP (3 equiv.) and HOBT (3 equiv.) in DMF (2 ml) and $iPr_2EtN$ (9 eq) are added successively to the resin and the suspension is mixed for 1 h under Ar. Monitoring of the coupling reaction is performed with 2,4,6-trinitrobenzenesulfonic acid (TNBS) (W. S. Hancock and J. E. Battersby, Anal. Biochem. (1976), 71, 260). In the case of a positive TNBS test (indicating incomplete coupling), the suspension is allowed to react for a further 1 h. The resin is then filtered and washed with DMF (3×3 min) prior to the following Fmoc deprotection step. After the removal of the last Fmoc protecting group, the resin is washed with DMF (6×3 min), $CH_2Cl_2$ (3×3 min), $Et_2O$ (3×3 min) and dried under vacuum for 3 h. Finally the peptides are cleaved from the resin using 2% TFA in $CH_2Cl_2$ (2 ml, 5×15 min) under Ar. The solvent is removed and the oily residues are triturated in ether to give the crude polypeptides. The compounds are further purified by HPLC.

The invention also provides a method for targeted modulation of gene expression by constructing modular repeat units specific for a target DNA sequence of interest, modifying a polypeptide by the addition of said repeat monomers so as to enable said polypeptide to now recognize the target DNA, introducing or expressing said modified polypeptide in a prokaryotic or eurkaryotic cell so as to enable said modified polypeptide to recognize the target DNA sequence, and modulation of the expression of said target gene in said cell as a result of such recognition.

The invention also provides a method for directed modification of a target DNA sequence by the construction of a polypeptide including at least a repeat domain of the present invention that recognizes said target DNA sequence and that said polypeptide also contains a functional domain capable of modifying the target DNA (such as via site specific recombination, restriction or integration of donor target sequences) thereby enabling targeted DNA modifications in complex genomes.

The invention further provides for the production of modified polypeptides including at least a repeat domain comprising repeat units wherein a hypervariable region within each of the repeat units determines selective recognition of a base pair in a target DNA sequence. In a further embodiment of the invention, DNA is provided which encodes for a polypeptide containing a repeat domain as described above.

In another embodiment of the invention, DNA is provided which is modified to include one or more base pairs located in a target DNA sequence so that each of the said base pairs can be specifically recognized by a polypeptide including a repeat domain having corresponding repeat units, each repeat unit comprising a hypervariable region which determines recognition of the corresponding base pair in said DNA.

In a still another embodiment of the invention, uses of those polypeptides and DNAs are provided. Additionally provided are plants, plant parts, seeds, plant cells and other non-human host cells transformed with the isolated nucleic acid molecules of the present invention and the proteins or polypeptides encoded by the coding sequences of the present invention. Still further, the polypeptides and DNA described herein can be introduced into animal and human cells as well as cells of other organisms like fungi or plants.

In summary, the invention focuses on a method for selectively recognizing base pairs in a target DNA sequence by a polypeptide wherein said polypeptide comprises at least a repeat domain comprising repeat units wherein each repeat unit contains a hypervariable region which determines recognition of a base pair in said target DNA sequence wherein consecutive repeat units correspond to consecutive base pairs in said target DNA sequence. In some embodiments, the invention relates to a human cell comprising any one or combination of proteins or nucleic acid sequences disclosed herein. In some embodiments, the invention relates to cells such as a human cell comprising a mutation, heterologous gene, variant or other genetic modification caused by introduction of one or more nucleic acids or polypeptides disclosed herein. In some embodiments, the invention relates to cells such as a non-human animal cell comprising a mutation, heterologous gene, variant or other genetic modification caused by introduction of one or more nucleic acids or polypeptides disclosed herein. In some embodiments, the invention relates to cells such as an insect cell comprising a mutation, heterologous gene, variant or other genetic modification caused by introduction of one or more nucleic acids or polypeptides disclosed herein. In some embodiments, the invention relates to cells such as a plant cell comprising a mutation, heterologous gene, variant or other genetic modification caused by introduction of one or more nucleic acids or polypeptides disclosed herein. In some embodiments, the invention relates to cells such as a fish cell comprising a mutation, heterologous gene, variant or other genetic modification caused by introduction of one or more nucleic acids or polypeptides disclosed herein. In some embodiments, the invention relates to cells such as a mammalian cell comprising a mutation, heterologous gene, variant or other genetic modification caused by introduction of one or more nucleic acids or polypeptides disclosed herein. In some embodiments, the invention relates to cells such as a eukaryotic cell comprising a mutation, heterologous gene, variant or other genetic modification caused by introduction of one or more nucleic acids or polypeptides disclosed herein.

In another aspect, a method of modulating expression of a target gene in a cell is provided. The cell may be preferably a plant cell, a human cell, animal cell, fungal cell or any other living cell. The cells contain a polypeptide wherein said polypeptide comprises at least a repeat domain comprising repeat units, and these repeat units contain a hypervariable region and each repeat unit is responsible for the recognition of 1 base pair in said target DNA sequence. Said polypeptide is introduced either as DNA encoding for the polypeptide or the polypeptide is introduced per se into the cell by methods known in the art. Regardless of how introduced, the polypeptide should include at least one repeat domain that specifically recognizes and preferably binds to a target DNA sequence of base pairs and modulates the expression of a target gene. In a preferred embodiment, all repeat units contain a hypervariable region which determines recognition of base pairs in a target DNA sequence.

Examples of peptide sequences which can be linked to an polpeptide or RTN of the present invention, for facilitating uptake of effectors into cells, include, but are not limited to: an 11 amino acid peptide of the tat protein of HIV; a 20 residue peptide sequence which corresponds to amino acids 84 103 of the p 16 protein (see Fahraeus et al. (1996) Current Biology 6:84); the third helix of the 60-amino acid long homeodomain of Antennapedia (Derossi et al. (1994) J. Biol. Chem. 269: 10444); the h region of a signal peptide such as the Kaposi fibroblast growth factor (K-FGF) h region; or the VP22 translocation domain from HSV (Elliot & O'Hare (1997) Cell 88:223 233). Other suitable chemical moieties that provide enhanced cellular uptake may also be chemically linked to effectors. As described herein, effectors can be designed to recognize any suitable target site, for regulation of expression of any endogenous gene of choice. Examples of endogenous genes suitable for regulation include VEGF, CCR5, ER.alpha., Her2/Neu, Tat, Rev, HBV C, S, X, and P, LDL-R, PEPCK, CYP7, Fibrinogen, ApoB, Apo E, Apo(a), renin, NF-.kappa.B, I-.kappa.B, TNF-.alpha., FAS ligand, amyloid precursor protein, atrial naturetic factor, ob-leptin, ucp-1, IL-1, IL-2, IL-3, IL-4, IL-5, IL-6, IL-12, G-CSF, GM-CSF, Epo, PDGF, PAF, p53, Rb, fetal hemoglobin, dystrophin, eutrophin, GDNF, NGF, IGF-1, VEGF receptors fit and flk, topoisomerase, telomerase, bcl-2, cyclins, angiostatin, IGF, ICAM-1, STATS, c-myc, c-myb, TH, PTI-1, polygalacturonase, EPSP synthase, FAD2-1, delta-12 desaturase, delta-9 desaturase, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, viral genes, protozoal genes, fungal genes, and bacterial genes. In general, suitable genes to be regulated include cytokines, lymphokines, growth factors, mitogenic factors, chemotactic factors, onto-active factors, receptors, potassium channels, G-proteins, signal transduction molecules, disease resistance genes, and other disease-related genes.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al. (1993) J. Biol. Chem. 268:3334 3341; Perelle et al. (1993) Infect. Immun. 61:5147 5156 (1993); Stenmark et al. (1991) J. Cell Biol. 1 13: 1025 1032 (1991); Donnelly et al. (1993) Proc. Natl. Acad. Sci. USA 90:3530 3534; Carbonetti et al. (1995) Abstr. Annu. Meet. Am. Soc. Microbiol. 95:295; Sebo et al. (1995) Infect. Immun. 63:3851 3857; Klimpel et al. (1992) Proc. Natl. Acad. Sci. USA 89: 10277 10281; and Novak et al. (1992) J. Biol. Chem. 267: 17186 17193).

Effectors can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, in this case an effector. The liposome fuses with the plasma membrane, thereby releasing the effector into the cytosol. Alternatively, the liposome is phagocytosed or taken up by the cell in a transport vesicle. Once in the endosome or phagosome, the liposome either degrades or fuses with the membrane of the transport vesicle and releases its contents.

The invention particularly relates to the field of plant and agricultural technology. In one aspect, the present invention is directed to a method to modulate the expression of a target gene in plant cells, which method comprises providing plant cells with a polypeptide modified according to the invention, said polypeptide being capable of specifically recognizing a target nucleotide sequence, or a complementary strand thereof, within a target gene, and allowing said polypeptide to recognize and particularly bind to said target nucleotide sequence, whereby the expression of said target gene in said plant cells is modulated.

The polypeptide can be provided to the plant cells via any suitable methods known in the art. For example, the protein can be exogenously added to the plant cells and the plant cells are maintained under conditions such that the polypeptide is introduced into the plant cell, binds to the target nucleotide sequence and regulates the expression of the target gene in the plant cells. Alternatively, a nucleotide sequence, e.g., DNA or RNA, encoding the polypeptide can be expressed in the plant cells and the plant cells are maintained under conditions such that the expressed polypeptide binds to the target nucleotide sequence and regulates the expression of the target gene in the plant cells.

A preferred method to modulate the expression of a target gene in plant cells comprises the following steps: a) providing plant cells with an expression system for a polypeptide modified according to the invention, said polypeptide being capable of specifically recognizing, and preferably binding, to a target nucleotide sequence, or a complementary strand thereof, within an expression control element of a target gene, preferably a promoter; and b) culturing said plant cells under conditions wherein said polypeptide is produced and binds to said target nucleotide sequence, whereby expression of said target gene in said plant cells is modulated.

Any target nucleotide sequence can be modulated by the present method. For example, the target nucleotide sequence can be endogenous or exogenous to the target gene. In an embodiment of the invention the target nucleotide sequence can be present in a living cell or present in vitro. In a specific embodiment, the target nucleotide sequence is endogenous to the plant. The target nucleotide sequence can be located in any suitable place in relation to the target gene. For example, the target nucleotide sequence can be upstream or downstream of the coding region of the target gene. Alternatively, the target nucleotide sequence is within the coding region of the target gene. Preferably, the target nucleotide sequence is a promoter of a gene.

Any target gene can be modulated by the present method. For example, the target gene can encode a product that affects biosynthesis, modification, cellular trafficking, metabolism and degradation of a peptide, a protein, an oligonucleotide, a nucleic acid, a vitamin, an oligosaccharide, a carbohydrate, a lipid, or a small molecule. Furthermore, effectors can be used to engineer plants for traits such as increased disease resistance, modification of structural and storage polysaccharides, flavors, proteins, and fatty acids, fruit ripening, yield, color, nutritional characteristics, improved storage capability, and the like.

Therefore, the invention provides a method of altering the expression of a gene of interest in a target cell, comprising: determining (if necessary) at least part of the DNA sequence of the structural region and/or a regulatory region of the gene of interest; designing a polypeptide including the repeat units modified in accordance with the invention to recognize specific base pairs on the DNA of known sequence, and causing said modified polypeptide to be present in the target cell, (preferably in the nucleus thereof). (It will be apparent that the DNA sequence need not be determined if it is already known.) The present invention also provides kits comprising: (1) any of the aforementioned vectors or (2) any of the aforementioned proteins or polypeptides. The present invention also provides kits comprising: (1) any of the aforementioned vectors or (2) any of the aforementioned proteins or polypeptides; and (3) any of the aforementioned cells (either modified or not modified) disclosed herein.

In another embodiments, the invention relates to kits that are used to produce site specific-mutations in stem cells, which can be used to generate genetically modified organisms. The kits typically include one or more site-specific genetic engineering technology, such as RTNs. The kit may also contain one or more sets of stem cells or embryonic cells for site-specific modification. The stem cells may include, but is not limited to spermatogonial stem cells (SSCs), as well as media and conditions necessary for growing SSCs. The kits may include exogenous sequences for site-specific genomic introduction, such as but not limited to reporter genes or selectable markers. The kits may include instructions for (i) introducing the RTNs into the stem cells (ii) identifying stem cells which have been site specifically modified (iii) growing site-specifically modified stem cells in media or conditions necessary and to numbers required for stem cells to produce genetically modified organisms (iv) using the grown stem cells to produce a genetically modified organism (v) identifying which organisms or progeny harbor the site-specific mutation of interest.

In some embodiment, the invention provides a kit which includes a mixed population of different or distinct genetically modified SSCs which may be custom made. The mixed population of genetically modified SSCs may be provided in suitable quantities for direct injection into a sterile male recipient for the production of multiple genetically modified organisms in a single step. The mixed population of separate or distinct genetically modified SSCs may consist of at least two genetically modified SSCs, at least two genetically modified SSCs, at least three genetically modified SSCs, at least four genetically modified SSCs, at least five genetically modified SSCs, at least six genetically modified SSCs, at least seven genetically modified SSCs, at least eight genetically modified SSCs, at least nine genetically modified SSCs, at least ten genetically modified SSCs, at least twenty genetically modified SSCs, at least thirty genetically modified SSCs, at least forty genetically modified SSCs, at least fifty genetically modified SSCs, at least one hundred genetically modified SSCs, at least one thousand genetically modified SSCs, at least ten thousand genetically modified SSCs, at least thirty thousand genetically modified SSCs or with genetically modified SSCs which harbor genetic modification within every gene in the organisms genome.

In some embodiment, the invention provides a kit which includes a mixed population of different or distinct genetically modified stem cells or embryonic cells which may be custom made by any of the methods disclosed herein. The mixed population of genetically modified modified stem cells or embryonic cells may be provided in suitable quantities for direct injection into a sterile male recipient for the production of multiple genetically modified organisms in a single step. The mixed population of separate or distinct genetically modified stem cells or embryonic cells may consist of at least two genetically modified stem cells or embryonic cells, at least two genetically modified stem cells or embryonic cells, at least three genetically modified stem cells or embryonic cells, at least four genetically modified stem cells or embryonic cells, at least five genetically modified stem cells or embryonic cells, at least six genetically modified stem cells or embryonic cells, at least seven genetically modified stem cells or embryonic cells, at least eight genetically modified stem cells or embryonic cells, at least nine genetically modified stem cells or embryonic cells, at least ten genetically modified stem cells or embryonic cells, at least twenty genetically modified stem cells or embryonic cells, at least thirty genetically modified stem cells or embryonic cells, at least forty genetically modified stem cells or embryonic cells, at least fifty genetically modified stem cells or embryonic cells, at least one hundred genetically modified stem cells or embryonic cells, at least one thousand genetically modified stem cells or embryonic cells, at least ten thousand genetically modified stem cells or embryonic cells, at least thirty thousand genetically modified stem cells or embryonic cells or with genetically modified stem cells or embryonic cells which harbor genetic modification within every gene in the organisms genome.

In some embodiment, the invention provides a kit which includes one or more sets of stem cells or embryonic cells or SSCs for site-specific modification. The sets of SSCs may be derived from well-characterized organisms having different disease states. The SSCs may contain multiple mutations, which may be derived from genetic modification or naturally or by any method. The kit may include the media and conditions to grow disease state SSCs, as well as the sterile recipient male for the production of genetically modified organisms.

In some embodiment, the invention provides a kit which includes the necessary tools for the derivation of SSC lines from an organism or tissue sample, as well as the necessary tools to genetically modify the derived SSC and produce a genetically modified organism from the derived SSCs. The kit may include cell collection tools such as spermatocytes for harvest, and SSC selection tools such as laminin selection, and SSC propagation and cryopreservation tools as well as SSC validation tools which may include cell surface marker staining. The kit may also include media and conditions for growing the SSCs, tools for genetic modification of the SSCs as well as sterile recipient males for production of genetically modified organisms from the SSCs.

In some embodiment, the invention provides a kit, which includes SSCs which have been generated from induced pluripotent stem (iPS) cells. The iPS cells may be derived from well characterized different genetic backgrounds including disease states as well as regional, strain, ethnic genetic backgrounds. The kit may also include media and conditions for growing the iPSs, tools for genetic modification of the iPSs as well as sterile recipient males for production of genetically modified organisms from the iPSs.

Further methods for transformation and generation of transgenic animals or modified cells appear in PCT Application Serial No. PCT/US2012/03 8465, the contents of which are incorporated by reference in its entirety.

One aspect of the present invention relates to a method for delivering fusion proteins into a target cell wherein the fusion protein comprises an effector protein. Creating a fusion protein of the present invention involves isolating one or more polypeptide components from media and subsequently ligating the free amino terminus of one polypeptide component to the carboxy terminus of a second polypeptide component, in other embodiments, fusion proteins may be made by simple polypeptide synthesis and or expressed through cloning a nucleic acid sequence into an expression vector. In the case of protein purification from cell-based reecmobinant systems that express expression constructs of the present invention, one of ordinary skill in the art can identify compatible secretion signals can readily be determined for any particular type III secretion system that is to be employed if such expression constructs are transformed into bacterial host cells for protein production. By identifying proteins that are normally secreted by the type III secretion system, it is possible to prepare deletion mutants missing various fragments of the full length protein that is normally secreted by the secretion system. Using labeled antibodies raised against epitopes of the various deletion fragments that are expressed (i.e., N-terminal epitopes, C-terminal epitopes, etc.), it is possible to identify deletion mutants that are secreted and those that are not secreted. Thus, protein domains necessary for secretion of the full length protein can be readily identified. Once the protein domains have been identified and sequenced, they can be utilized as secretion signals in fusion proteins of the present invention.

Typically, the secretion signal is an N-terminal domain of a protein that is normally secreted by the particular type III secretion system, for example, a 201 amino acid sequence from the N-terminal domain of the DspE protein of *Erwinia amylovora* (see, e.g., U.S. patent application Ser. No. 09/350,852, filed Jul. 9, 1999, which is hereby incorporated by reference). The 201 amino acid secretion signal of *Erwinia amylovora* DspE is compatible with the hacpin secretion system of *Erwinia amylovora*. Other secretion signals that are compatible with various type III secretion systems have been described in the art and others are continually being identified.

Purified effector protein may be obtained by several methods. The protein or polypeptide is preferably produced in purified form (at least about 80%, 90%, pure) by conventional techniques. Because recombinant host cells express a type III secretion system, the protein or polypeptide is secreted into the growth medium of recombinant host cells. In such cases, to isolate the protein, the recombinant host cells are propagated, the growth medium is centrifuged to separate cellular components from supernatant containing the secreted protein or polypeptide, and the supernatant is removed. The supernatant is then subjected to sequential ammonium sulfate precipitation. The fraction containing the polypeptide or protein is subjected to gel filtration in an appropriately sized dextran or polyacrylamide column to separate the proteins. If necessary, the protein fraction may be further purified by HPLC.

Effector proteins carrying protein transduction domains may also be prepared independently of the type III secretion system by using current state-of-the-art techniques for preparing large amounts of purified proteins from recombinant *E. coli* cells. Such techniques employ strong, inducible promoters and peptide tags, such as His6, for one-step affinity purification of the recombinant protein from *E. coli* cell lysates.

In one embodiment, the target cell is a eucaryote cell. The eucaryote cells include those in tissue culture, such as HeLa cells, or in whole animals, such as those delivered to mouse via intraperitoneal injection (Schwarze et al., "Protein Transduction: Unrestricted Delivery into all Cells?" Trends Cell Biol. 10:290-295 (2000), which is hereby incorporated by reference).

In one aspect of the invention the DNA binding or recognition elements of the present invention may be fused together in a modular fashion to create a string of amino acids that bind to a DNA target sequence of choice. In another aspect of the invention the one or more DNA binding recognition elements may be bound to one or more effector proteins. The effector protein may be produced by a bacterial plant pathogen, animal pathogen, or a rhizosphere bacteria, including, but not limited to enteropathogenic *Escherichia coli, Salmonella typhimurium, Shigella* spp., *Yersinia* spp., *Pseudomonas syringae, Xanthomonas campestris, Ralstonia solanacearum, Erwinia amylovora, Pseudomonas fluorescens*, and *Pseudomonas aeruginosa*. Suitable effector proteins include a hypersensitive response elicitor, an avirulence protein, a hypersensitive response and pathogenicity-dependent outer protein, a virulence protein, and a pathogenicity protein. Examples of effector proteins include HopPsyA AAF71481 (*P. syringae*), HopPtoA AF232006 (*P. syringae*), Tir BAA96815 (*E. coli*), ExoS AAG07228 (*P. aeruginosa*), ExoT AAG03434 (*P. aeruginosa*), ExoY AAG05579 (*P. aeruginosa*), SopE AAC02071 (*S. typhimurium*), SopB AAF21057 (SigA) (*S. typhimurium*), SipA CAA63302 (*S. typhimurium*), SptP AAC44349 (*S. typhimurium*), IpaB A34965 (*Shigella* spp.), IpaA AAA26525 (*Shigella* spp.), IpaD SI 5579 (*Shigella* spp.), YopE SI 4242 (*Yersinia* spp.), YopH AAC69768 (*Yersinia* spp.), YpkA AAC69765 (*Yersinia* spp.), YopJ AAC69766 (YopP) (*Yersinia* spp.), AvrPto AAA25728 (*P. syringae*), AvrBs2 AAD 1 1434 (*X. campestris*), and AvrBs3 CAA34257 (*X. campestris*) (see, e.g., Galan et al., "Type III Secretion Machines: Bacterial Devices for Protein Delivery into Host Cells," Science 284: 1322-1328 (1999), which is hereby incorporated by reference). In one embodiment, the effector protein is heterologous (i.e., not normally present) to the target cell.

In accordance with the purposes of this invention, as embodied and broadly described herein, this invention relates to methods for site-specific genetic engineering using RTNs of stem cells and gametes, including but not limited to pluripotent cells, totipotent cells, somatic stem cells, spermatogonial stem cells (SSCs), embryonic stem (ES) cells, induced pluripotent stem (iPS) cells, embryos, germ cells, primordial germ cells (PGCs), plant tube cells, pollen cells, and spores. Methods for site-specific engineering of stem cells include, but are not limited to using site specific DNA binding and cleaving proteins such as RTNs.

Site-specific engineering of stem cells results in altered function of gene(s) or gene product(s) and genetically modified organisms, and cell or tissue culture models are produced from these engineered stem cells. Modified stem cells and organisms include knockout and knockin cells and organisms.

In another aspect, the invention relates to genetically modified organisms created by site-specific engineering using RTNs including but not limited to mammals, including rats, mice, pigs, rabbits, guinea pigs, dogs, non-human primates, mini-pigs, as well as plants, including but not limited to maize, soybean, rice, potato, wheat, tobacco, tomato, and *Arabidopsis*, as well as the descendants and ancestors of such organisms.

In another embodiment, the invention provides kits that are used to produce site specific-mutations in stem cells, which can be used to generate genetically modified organisms. The kits typically include one or more site-specific genetic engineering technology, such as RTNs. The kit may also comprise one or more sets of stem cells for site-specific modification. In some embodiments of the invention, the stem cells may include, but are not limited to, spermatogonial stem cells (SSCs), as well as media and conditions necessary for growing SSCs. In some embodiments, the kit comprise exogenous sequences for site-specific genomic introduction, such as but not limited to reporter genes or selectable markers. In some embodiments, the kit comprises instructions for (i) introducing the RTNs (or nuleic acid sequence encoding the RTN) into the stem cells (ii) identifying stem cells which have been site specifically modified by the XTN (iii) growing site-specifically modified stem cells in media or conditions necessary and to numbers required for stem cells to produce genetically modified organisms or effect germline transmission in an animal; (iv) using or transplanting the grown stem cells to produce a genetically modified organism; and/or (v) identifying which organisms or progeny comprise the site-specific mutation of interest. In some embodiments of the invention, a composition comprises one or more stem cells or one or more embryos, the one or more stem cells or one or more embryos comprise one or more of the following mutations: (i) a deletion mutation; (ii) a knockout mutation; and/or (iii) an addition of a heterologous nucleic acid sequence; the one or more mutations of (i), (ii), and/or (iii) are site-specific mutations caused by a RTN.

In some embodiments of the invention, the heterologous nucleic acid sequence is chosen from a selectable marker or an orthologous gene. In some embodiments of the invention, the one or more stem cells is chosen from a spermatogonial stem cell (SSC), an embryonic stem cell, or an induced pluripotent stem cell.

In some embodiments of the invention, the one or more stem cells is derived from the germline lineage of an animal or plant. In some embodiments of the invention, the one or more stem cells or the one or more embryos further comprise at least one inverted tandem repeat of a transposon or a variant thereof.

In some embodiments of the invention, the one or more stem cells is a somatic stem cell. In some embodiments of the invention, an organism comprising one or more stem cells, the one or more stem cells comprise one or more of the following mutations: (i) a deletion mutation; (ii) a knockout mutation; and/or (iii) an addition of a heterologous nucleic acid sequence; the one or more mutations of (i), (ii), and/or (iii) are site-specific mutations caused by a RTN. In some embodiments of the invention, the one or more stem cells comprises an SSC.

In the present invention, the effector protein is fused to at least one DNA recognition elements disclosed herein or derivatives or functional analogs thereof to produce a fusion protein.

One aspect of the present invention relates to a method for delivering effector proteins into a target cell. This method involves introducing into the target cell an effector protein fused to a polypeptide including at least one repeat domain or DNA recognition element of the present invention that recognizes said target DNA or derivatives or functional analogs thereof. Another aspect of the present invention relates to a DNA construct including a first DNA molecule encoding an effector protein and a second DNA molecule operatively associated with the first DNA molecule and encoding a polypeptide including at least one repeat domain of the present invention that recognizes said target DNA or derivatives or functional analogs thereof.

The method of the present invention allows efficient delivery of effector proteins into cells, in particular, mammalian cells. This method also allows for delivery of effector proteins for use in pharmaceutical, insecticide, fungicide, herbicide, and other applications. In particular, the present invention will allow the delivery of effector proteins into patients in the form of protein therapy. Therapy with biologically active full-length proteins will allow access to the built-in evolutionary specificity of these proteins for their targets, thereby potentially avoiding the nonspecific effects sometimes seen with small-molecule therapies. Moreover, when used in conjunction with tissue-specific viral vectors, use of the present invention allows the targeted delivery of effector proteins to particular cells with the added benefit of secondary redistribution of the effector protein subsequent to the initial targeting. A precedent for this approach can be found in an experiment wherein the VP22 protein transduction domain was fused to the p53 tumor suppressor protein (Phelan et al, "Intercellular Delivery of Functional p53 by the Herpesvirus Protein VP22," Nat. Biotechnol. 16:440-443 (1998), which is hereby incorporated by reference).

In some embodiments, the invention relates to a composition comprising one or more nucleic acid sequences with an inserted nucleic acid sequence. In some embodiments, the inserted nucleic acid comprises at least one transcriptionally active gene, which is a coding sequence that is capable of being expressed under intracellular conditions, e.g. a coding sequence in combination with any requisite expression regulatory elements that are required for expression in the intracellular environment of the target cell whose genome is modified by binding and subsequent action by any of the polypeptides described herein. The transcriptionally active genes of the nucleic acids can comprise a domain of nucleotides, i.e., an expression module that includes a coding sequence of nucleotides operably linked with requisite transcriptional mediation or regulatory element(s). Requisite transcriptional mediation elements that may be present in the expression module include, but are not limited to, promoters, enhancers, termination and polyadenylation signal elements, splicing signal elements, and the like. In some embodiments of the invention, the one or more stem cells further comprise at least one inverted terminal repeat of a transposon or variant thereof.

In some embodiments, the expression module includes transcription regulatory elements that provide for expression of the gene in a broad host range. A variety of such combinations are known, where specific transcription regulatory elements include, but are not limited to: SV40 elements, transcription regulatory elements derived from the LTR of the Rous sarcoma virus, transcription regulatory elements derived from the LTR of human cytomegalovirus (CMV), hsp70 promoters, and the like.

In some embodiments, at least one transcriptionally active gene or expression module present in the inserted nucleic acid acts as a selectable marker. A variety of different genes have been employed as selectable markers, and the particular gene employed in the vectors described herein as a selectable marker is chosen primarily as a matter of convenience. Known selectable marker genes include, but are not limited to: thymidine kinase gene, dihydrofolate reductase gene, xanthine-guanine phosporibosyl transferase gene, CAD, adenosine deaminase gene, asparagine synthetase gene, numerous antibiotic resistance genes (tetracycline, ampicillin, kanamycin, neomycin, and the like), aminoglycoside phosphotransferase genes, hygromycin B phosphotransferase gene, and genes whose expression provides for the presence of a detectable product, either directly or indirectly, such as, for example, beta-galactosidase, GFP, and the like.

In some embodiments, the nucleic acids of the present invention comprise least one transcriptionally active gene, the portion of the nucleic acid also comprises at least one restriction endonuclease recognized site, e.g. restriction site which serves as a site for insertion of an exogenous nucleic acid. A variety of restriction sites are known in the art and include, but are not limited to: HindIII, PstI, SalI, AccI, HincII, XbaI, BamHI, SmaI, XmaI, KpnI, SacI, EcoRI, and the like. In some embodiments, the vector includes a polylinker, i.e. a closely arranged series or array of sites recognized by a plurality of different restriction enzymes, such as those disclosed herein. In other embodiments, the inserted exogenous nucleic acid could comprise recombinase recognition sites, such as LoxP, FRT, or AttB/AttP sites, which are recognized by the Cre, Flp, and PhiC31 recombinases, respectively.

In another aspect, the present invention relates to a method for generating a nucleic acid encoding a polypeptide specific for binding a selected nucleotide sequence, comprising: (1) linearizing a starter plasmid with PspX1 or nuclease, the starter plasmid comprising a nucleotide sequence that encodes a first monomer comprising a RVD specific for the first nucleotide of the selected nucleotide sequence, wherein the first monomer has a unique PspX1 or nuclease site at its 3' end; (2) ligating into the starter plasmid PspX1 site a DNA module encoding one or more monomers that comprise RVDs specific for the next nucleotide(s) of the selected nucleotide sequence, wherein the DNA module has XhoI sticky ends; and (3) repeating steps (1) and (2) until the nucleic acid encodes a polypeptide capable of binding to the selected nucleotide sequence. The method can further comprise, after the ligating, determining the orientation of the DNA module in the PspX1 site or nuclease site. The method can comprise repeating steps (1) and (2) from one to 30 times.

Where the source of DNA-binding domain is a nucleic acid that encodes the polypeptides of the present invention, the nucleic acid encoding the polypeptide or protein is generally part of an expression module, as described above, where the additional elements provide for expression of the transposase as required.

In some embodiments, multicellular organisms can be made using cells mytogenized by the compositions disclosed herein. In some embodiments, the multicellular or unicellular organism is a plant or animal. In some embodiments, the multicellular or unicellular organism is a vertebrate. In some embodiments, the vertebrate animal is a mammal, such as for example, a rodent (mouse or rat), livestock (pig, horse, cow, etc.), pets (dog or cat), and primates, such as, for example, a human.

The methods described herein can be used in a variety of applications in which it is desired to introduce and stably integrate an exogenous nucleic acid into the genome of a target cell. In vivo methods of integrating exogenous nucleic acid into a target cell are known. The route of administration of the nucleic acid-binding system to the multicellular or unicellular organism depends on several parameters, including: the nature of the vectors that carry the system components, the nature of the delivery vehicle, the nature of the multicellular or unicellular organism, and the like, where a common feature of the mode of administration is that it provides for in vivo delivery of the nucleic acid-binding system components to the target cell(s). In certain embodiments, linear or circularized DNA, such as a plasmid, is employed as the vector for delivery of the nucleic acid-binding system to the target cell. In such embodiments, the plasmid may be administered in an aqueous delivery vehicle, such as a saline solution. Alternatively, an agent that modulates the distribution of the vector in the multicellular or unicellular organism can be employed. For example, where the vectors comprising the subject system components are plasmid vectors, lipid-based such as a liposome, vehicles can be employed, where the lipid-based vehicle may be targeted to a specific cell type for cell or tissue specific delivery of the vector. Alternately, polylysine-based peptides can be employed as carriers, which may or may not be modified with targeting moieties, and the like (Brooks et al., J. Neurosci. Methods, 1998, 80, 137-47; and Muramatsu et al., Int. J. Mol. Med., 1998, 1, 55-62). The system components can also be incorporated onto viral vectors, such as adenovirus-derived vectors, sindbis-virus derived vectors, retrovirus-derived vectors, hybrid vectors, and the like. The above vectors and delivery vehicles are merely representative. Any vector/delivery vehicle combination can be employed, so long as it provides for in vivo administration of the nucleic acid-binding system to the multicellular or unicellular organism and target cell.

The amount of vector nucleic acid comprising the nucleic acid-binding element, and in many embodiments the amount of vector nucleic acid encoding the polypeptide, which is introduced into the cell is sufficient to provide for the desired excision and insertion of the nucleic acid-binding nucleic acid into the target cell genome. As such, the amount of vector nucleic acid introduced should provide for a sufficient amount of DNA-binding activity and a sufficient copy number of the nucleic acid that is desired to be inserted into the target cell. The amount of vector nucleic acid that is introduced into the target cell varies depending on the efficiency of the particular introduction protocol that is employed, such as the particular in vivo administration protocol that is employed.

The particular dosage of each component of the system that is administered to the multicellular or unicellular organism varies depending on the nature of the nucleic acid-binding nucleic acid, e.g. the nature of the expression module and gene, the nature of the vector on which the component elements are present, the nature of the delivery vehicle and the like. Dosages can readily be determined empirically by those of skill in the art. For example, in mice where the nucleic acid-binding system components are present on separate plasmids which are intravenously administered to a mammal in a saline solution vehicle, the amount of nucleic acid-binding plasmid that is administered in many embodiments typically ranges from about 0.5 to 40 μg and is typically about 25 μg, while the amount of nucleic acid-binding system encoding plasmid that is administered typically ranges from about 0.5 to 25 μg and is usually about 1 μg.

The subject methods may be used to bind and effect nucleic acids of various sizes. Generally, the size of DNA that is inserted into a target cell genome using the subject methods ranges from about 0.5 kb to 100.0 kb, usually from about 1.0 kb to about 60.0 kb, or from about 1.0 kb to about 10.0 kb.

The present invention can be used in, for example, germline mutagenesis in a rat, mouse, or other vertebrate; somatic mutagenesis in a rat, mouse, or other vertebrate; transgenesis in a rat, mouse, or other vertebrate; and use in human gene therapy. In each of these, the composition can be delived as DNA, RNA, or protein.

Transformed cells and/or transgenic organisms, such as those containing the DNA inserted into the host cell's DNA, can be selected from untransformed cells and/or transformed organisms if a selectable marker is included as part of the introduced DNA sequences. Selectable markers include, for example, genes that provide antibiotic resistance; genes that modify the physiology of the host, such as for example green fluorescent protein, to produce an altered visible phenotype. Cells and/or organisms containing these genes are capable of surviving in the presence of antibiotic, insecticides or herbicide concentrations that kill untransformed cells/organisms or producing an altered visible phenotype. Using standard techniques known to those familiar with the field, techniques such as, for example, Southern blotting and polymerase chain reaction, DNA can be isolated from transgenic cells and/or organisms to confirm that the introduced DNA has been inserted.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

In other aspects of the invention, the invention relates to viral vectors comprising any one or more than one nucleic acid sequence disclosed herein. The viral vector is optionally selected from the group comprising a retroviral vector, an adenoviral vector, an adeno-associated viral vector, spumaviral, a lentiviral vector and a plasmid or other vector, such as transposons, described in the application. The retroviral vector optionally comprises an oncoretroviral vector. The retroviral vector optionally comprises a lentiviral vector.

The application includes compositions and methods for providing a RTN coding nucleic acid molecule to a subject such that expression of the molecule in the cells provides the biological activity of the polypeptide encoded by the coding nucleic acid molecule to those cells. A coding nucleic acid as used herein means a nucleic acid that comprises nucleotides which specify an RTN amino acid sequence, or a portion thereof, of the corresponding *Ralstonia* amino acid sequence. A coding sequence may comprise a start codon and/or a termination sequence.

In some embodiments, the compositions of the present invention are pharmaceutical compositions. The pharmaceutical compositions of this application used to treat patients having diseases, disorders or abnormal physical states could include an acceptable carrier, auxiliary or excipient.

The pharmaceutical compositions are optionally administered by ex vivo and in vivo methods such as electroporation, DNA microinjection, liposome DNA delivery, and virus vectors that have RNA or DNA genomes including retrovirus vectors, lentivirus vectors, Adenovirus vectors and Adeno-associated virus (AAV) vectors, Semliki Forest Virus. Derivatives or hybrids of these vectors are also useful.

Dosages to be administered depend on patient needs, on the desired effect and on the chosen route of administration.

The expression cassettes are optionally introduced into the cells or their precursors using ex vivo or in vivo delivery vehicles such as liposomes or DNA or RNA virus vectors. They are also optionally introduced into these cells using physical techniques such as microinjection or chemical methods such as coprecipitation. The pharmaceutical compositions are typically prepared by known methods for the preparation of pharmaceutically acceptable compositions which are administered to patients, and such that an effective quantity of the nucleic acid molecule is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA). Any selectable marker gene can be used in the present invention.

On this basis, the pharmaceutical compositions could include an active compound or substance, such as a nucleic acid molecule, in association with one or more pharmaceutically acceptable vehicles or diluents, and contained in buffered solutions with a suitable pH and isoosmotic with the physiological fluids. The methods of combining the expression cassettes with the vehicles or combining them with diluents is well known to those skilled in the art. The composition could include a targeting agent for the transport of the active compound to specified sites within cells. The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as .beta.-galactosidase and fluorescent proteins such as green fluorescent protein (GFP) (Su et al. (2004) Biotechnol Bioeng 85:610-9 and Fetter et al. (2004) Plant Cell 16:215-28), cyan florescent protein (CYP) (Bolte et al. (2004) J. Cell Science 1 17:943-54 and Kato et al. (2002) Plant Physiol 129:913-42), and yellow florescent protein (PhiYFP™ from Evrogen, see, Bolte et al. (2004) J. Cell Science 117:943-54). For additional selectable markers, see generally, Yarranton (1992) Curr. Opin. Biotech. 3:506-511; Christophers on et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Aci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90: 1917-1921; Labow et al. (1990) Mol. Cell. Biol. 10:3343-3356; Zambretti et al. (1992) Proc. Natl Acad. Sci. USA 89:3952-3956; Bairn et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10: 143-162; Degenkolb et al. (1991) Antimicrob. Agents Chemother. 35: 1591-1595; Kleinschnidt et al. (1988) Biochemistry 27: 1094-1 104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference.

Numerous plant transformation vectors and methods for transforming plants are available. See, for example, An, G. et al. (1986) Plant Pysiol, 81:301-305; Fry, J., et al. (1987) Plant Cell Rep. 6:321-325; Block, M. (1988) Theor. Appl Genet. 76:767-774; Hinchee, et al. (1990) Stadler. Genet. Symp. 203212.203-212; Cousins, et al. (1991) Aust. J. Plant Physiol. 18:481-494; Chee, P. P. and Slightom, J. L. (1992) Gene. 118:255-260; Christou, et al. (1992) Trends. Biotechnol. 10:239-246; D'Halluin, et al. (1992) Bio/Technol. 10:309-314; Dhir, et al. (1992) Plant Physiol. 99:81-88; Casas et al. (1993) Proc. Nat. Acad Sci. USA 90: 11212-1 1216; Christou, P. (1993) In Vitro Cell. Dev. Biol.-Plant; 29P: 119-124; Davies, et al. (1993) Plant Cell Rep. 12: 180-183; Dong, J. A. and Mchughen, A. (1993) Plant Sci. 91: 139-148; Franklin, C. I. and Trieu, T. N. (1993) Plant. Physiol. 102: 167; Golovkin, et al. (1993) Plant Sci. 90:41-52; Guo Chin Sci. Bull. 38:2072-2078; Asano, et al. (1994) Plant Cell Rep. 13; Ayeres N. M. and Park, W. D. (1994) Crit. Rev. Plant. Sci. 13:219-239; Barcelo, et al. (1994) Plant. J. 5:583-592; Becker, et al. (1994) Plant. J. 5:299-307; Borkowska et al. (1994) Acta. Physiol Plant. 16:225-230; Christou, P. (1994) Agro. Food. Ind. Hi Tech. 5: 17-27; Eapen et al. (1994) Plant Cell Rep. 13:582-586; Hartman, et al. (1994) Bio-Technology 12: 919923; Ritala, et al. (1994) Plant. Mol. Biol. 24:317-325; and Wan, Y. C. and Lemaux, P. G. (1994) Plant Physiol. 104:3748.

The methods of the invention involve introducing a polynucleotide construct comprising a DNA sequence into a host cell. By "introducing" is intended presenting to the plant the polynucleotide construct in such a manner that the construct gains access to the interior of the host cell. The methods of the invention do not depend on a particular method for introducing a polynucleotide construct into a host cell, only that the polynucleotide construct gains access to the interior of one cell of the host. Methods for introducing polynucleotide constructs into bacteria, plants, fungi and animals are known in the art including, but not limited to, stable transformation methods, transient transformation methods, and virus-mediated methods.

By "stable transformation" is intended that the polynucleotide construct introduced into a plant integrates into the genome of the host and is capable of being inherited by progeny thereof. By "transient transformation" is intended that a polynucleotide construct introduced into the host does not integrate into the genome of the host.

The application includes methods and compositions for providing a coding nucleic acid molecule to the cells of an individual such that expression of the coding nucleic acid molecule in the cells provides the biological activity or phenotype of the polypeptide encoded by the coding nucleic acid molecule. The method also relates to a method for providing an individual having a disease, disorder or abnormal physical state with a biologically active polypeptide by administering a nucleic acid molecule of the present application. The method may be performed ex vivo or in vivo. Gene therapy methods and compositions are demonstrated, for example, in U.S. Pat. Nos. 5,869,040, 5,639,642, 5,928,214, 5,911,983, 5,830,880, 5,910,488, 5,854,019, 5,672,344, 5,645,829, 5,741,486, 5,656,465, 5,547,932, 5,529,774, 5,436, 146, 5,399,346 and 5,670,488, 5,240,846. The amount of polypeptide will vary with the subject's needs. The optimal dosage of vector may be readily determined using empirical techniques, for example by escalating doses (see U.S. Pat. No. 5,910,488 for an example of escalating doses). Vectors containing the nucleic acid molecules of the application are typically administered to mammals, preferably humans, in gene therapy using techniques described below. The polypeptides produced from the nucleic acid molecules are also optionally administered to mammals, preferably humans. The application relates to a method of medical treatment of a mammal in need thereof, preferably a human, by administering to the mammal a vector of the application or a cell containing a vector of the application. A recipient, preferably human, who develops an adverse event, such as graft versus host disease, is typically administered a drug, such as AZT, that is a substrate for the modified tmpk molecules of the application. Diseases, such as blood diseases or neural diseases (neurodegenerative), that are readily treated are described in this application and known in the art (eg. diseases, such as thalassemia or sickle cell anemia that are treated by administering a globin gene as described in Canadian patent application no. 2,246,005). Blood diseases treatable by stem cell transplant include leukemias, myelodysplastic syndromes, stem cell disorders, myeloproliferative disorders, lymphoproliferative disorders phagocyte disorders, inherited metabolic disorders, histiocytic disorders, inherited erythrocyte abnormalities, inherited immune system disorders, inherited platelet abnormalities, plasma cell disorders, malignancies (See also, Medical Professional's Guide to Unrelated Donor Stem Cell Transplants, 4th Edition). Stem cell nerve diseases to be treated by neural stem cell transplantation include diseases resulting in neural cell damage or loss, eg. paralysis, Parkinson's disease, Alzheimer's disease, ALS, multiple sclerosis). The vector of the application is useful as a stem cell marker and to express genes that cause stem cells to differentiate (e.g. growth factor).

Various approaches to gene therapy may be used. The application includes a process for providing a human with a therapeutic polypeptide including: introducing human cells into a human, said human cells having been treated in vitro or ex vivo to insert therein a vector of the application, the human cells expressing in vivo in said human a therapeutically effective amount of said therapeutic polypeptide.

The method also relates to a method for producing a stock of recombinant virus by producing virus suitable for gene therapy comprising modified DNA encoding globin. This method preferably involves transfecting cells permissive for virus replication (the virus containing modified globin) and collecting the virus produced.

Cotransfection (DNA and marker on separate molecules) may be employed (see eg U.S. Pat. Nos. 5,928,914 and 5,817,492). As well, a detection cassette or marker (such as Green Fluorescent Protein marker or a derivative, CD 19 or CD25) may be used within the vector itself (preferably a viral vector).

The methods of the present invention can be used to mutate any eukaryotic stem cell, including, but not limited to, haploid, diploid, triploid, tetraploid, or aneuploid. In one embodiment, the cell is diploid. Stem cells in which the methods of the present invention can be advantageously used include, but are not limited to stem cells such as somatic stem cells, SSCs, ES cells, iPS cells, embryos, or any cell capable of developing into one or more organisms.

In one embodiment, the invention relates to a method to produce a site-specific knockout, knock-in or otherwise genetically modified stem cell. The site-specific mutation is generated using a RTN which cleaves the desired site, followed by NHEJ, resulting in deletion mutations. The site-specific mutation can be produced in spermatogonial stem cells (SSCs) which are used to generate heterozygous or homozygous genetically modified organisms.

In another embodiment, the invention relates to a method to produce a site-specific knockout, knock-in or otherwise genetically modified stem cell. The site-specific mutation is generated using a RTN which cleaves the desired site resulting in deletion mutations. The site specific mutation is produced in embryonic stem (ES) cells, which are used to generate heterozygous or homozygous genetically modified organisms.

In another embodiment, the invention comprises of methods to produce a site-specific knockout, knock-in or otherwise genetically modified stem cell. The site specific mutation is generated using a RTN which cleaves the desired site resulting in deletion mutations. The site-specific mutation is produced in induced pluripotent stem (iPS) cells, which are used to generate heterozygous or homozygous genetically modified organisms.

In another embodiment, the invention comprises of methods to produce a site-specific knockout, knockin or otherwise genetically modified stem cell. The site specific mutation is generated using a RTN which cleaves the desired site resulting in deletion mutations. The site-specific mutation is produced in embryos which are used to generate heterozygous or homozygous genetically modified organisms.

In certain embodiments of the invention, cells can be mutated within the organism or within the native environment as in tissue explants (e.g., in vivo or in situ). Alternatively, tissues or stem cells isolated from the organism using art-known methods and genes can be mutated according to the present methods. The tissues or stem cells are either maintained in culture (e.g., in vitro), or re-implanted into a tissue or organism (e.g., ex vivo).

RTNs comprising effector protein function, such as a nuclease.

In some embodiments, the invention relates to compositions comprising any one of the nucleic acids or polypeptides or fragments thereof described in Example 2.

In some embodiments, the invention relates to compositions comprising any one of the nucleic acids or polypeptides described herein.

In some embodiment of the invention, genetic modification of SSCs using RTNs relates to generating multiple mutations in separate SSCs or SSC lines followed by pooling or combining separate SSCs or SSC lines and injecting into a single recipient male, which relates to generating multiple genetically modified organisms containing one or more mutations is fewer experimental steps and in a shorter timeframe than is possible with other systems. The separate stem cells or stem cell lines may be fifteen or more. In some embodiment of the invention, genetic modification of stem cells using RTNs relates to generating multiple mutations in separate stem cells or stem cell lines followed by pooling or combining separate stem cells or stem cell lines and injecting into a single recipient male, which relates to generating multiple genetically modified organisms containing one or more mutations is fewer experimental steps and in a shorter timeframe than is possible with other systems. The separate stem cells or stem cell lines may be fifteen or more.

In some embodiment of the invention, increasing the number of distinct or separate pools or lines of genetically modified SSCs or modified stem cells or embryonic cells, which may be used to generate a genetically modified organism, does not increase the amount of effort, time, and resources used, as well as does not decrease the efficiency of genetically modified organism production. Multiple separate and distinct genetically modified SSCs may be transplanted into a single sterile recipient. The mixed population of distinct genetically modified cells (SSCs or stem cells), which are derived from separate cell pools from two or more pools to fifteen or more pools mature within the sterile recipient. The sterile recipient is then bred with multiple wild type females which may be two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more. These multiple females produce offspring which have incorporated the desired mutation into their germline.

In some embodiment of the invention, increasing the number distinct or separate pools or lines of genetically modified cells, which may be used to generate a genetically modified organism, does not increase the amount of effort, time, and resources used, as well as does not decrease the efficiency of genetically modified organism production. The sterile recipient rat may be a recipient for multiple rounds of separate or distinct genetically modified cells. The sterile rat may be a recipient of fifteen or more different genetically modified cells and breed with twenty or more wild type females to produce fifteen or more separately genetically modified organisms. Following the first round of breeding, the sterile male may be treated to eliminate the first round of genetically modified cells and become a recipient of another round of fifteen or more separately or distinct genetically modified cells, breed with twenty or more wild type females to produce fifteen or more separate genetically modified organisms. The sterile male may be a recipient of mixed populations of fifteen or more genetically modified cells and breed twenty or more wild type females two times or more, three times or more, four times or more, or five times or more.

In some embodiment of the invention, increasing the number distinct or separate pools or lines of genetically modified cells, which may be used to generate a genetically modified organism, does not increase the amount of effort, time, and resources used, as well as does not decrease the efficiency of genetically modified organism production. Increasing the number of genetically modified cells does not require the effort and resources of other cell systems such as embryonic stem (ES) cells or embryos. Increasing the amount of genetically modified ES cells for genetically modified organism production requires an increase in the number of technical steps such as blastocyst injections, as well as the number of oviduct transfer surgeries. In some embodiments of the invention, the method does not comprise blastocyst injection, oviduct transfer, DNA microinjection reimplantation of injected zygotes, or breeding of chimeric progeny. The cell system may produce fifteen or more separate genetically modified stem cell populations for genetically modified organism production in a single step, while in order to produce fifteen or more separately genetically modified ES cells, fifteen or more separate steps must be performed on all levels of the procedure, which include but are not limited to blastocyst injection, oviduct transfer, zygote production, preparation of DNA, DNA microinjection, reimplantation of injected zygotes or breeding chimeric progeny.

In some embodiment of the invention, genetic modification of SSCs using RTNs relates to generating genetically modified organisms without requiring the steps required in producing genetically modified organisms from alternative stem cells including but not limited to embryonic stem cells, embryo's, induced pluripotent stem (iPS) cells, somatic stem cells. Genetic modification in alternative stem cells includes but is not limited to zygote production, preparation of DNA, DNA microinjection, reimplantation of injected zygotes or breeding chimeric progeny.

In some embodiments, the stem cells of the present invention comprise one or more transposons, one or more inverted terminal repeats (ITRs) of a transposon of variants thereof. In some embodiments, the stem cells of the present invention comprise one or more transposons, one or more inverted terminal repeats (ITRs) of a transposon of variants derived from the sequences of Table 2.

In some embodiments, the present invention comprise one or more transposons, one or more inverted terminal repeats (ITRs) of a transposon wherein the variant sequence inverted tandem repeats are at least 70% homologous to known ITRs and known transposon elements (shown in table 2).

In some embodiments, the present invention comprise one or more transposons, one or more inverted tandem repeats (ITRs) of a transposon wherein the variant sequence inverted tandem repeats are at least 75% homologous to known ITRs and known transposon elements (shown in table 2).

In some embodiments, the present invention comprise one or more transposons, one or more inverted tandem repeats (ITRs) of a transposon wherein the variant sequence inverted terminal repeats are at least 80% homologous to known ITRs and known transposon elements (shown in table 2).

In some embodiments, the present invention comprise one or more transposons, one or more inverted terminal repeats (ITRs) of a transposon wherein the variant sequence inverted tandem repeats are at least 85% homologous to known ITRs and known transposon elements (shown in table 2).

In some embodiments, the present invention comprise one or more transposons, one or more inverted terminal repeats (ITRs) of a transposon wherein the variant sequence inverted tandem repeats are at least 90% homologous to known ITRs and known transposon elements (shown in table 2).

In some embodiments, the present invention comprise one or more transposons, one or more inverted terminal repeats (ITRs) of a transposon wherein the variant sequence inverted tandem repeats are at least 95% homologous to known ITRs and known transposon elements (shown in table 2).

In some embodiments, the present invention comprise one or more transposons, one or more inverted terminal repeats (ITRs) of a transposon wherein the variant sequence inverted tandem repeats are at least 96% homologous to known ITRs and known transposon elements (shown in table 2).

In some embodiments, the present invention comprise one or more transposons, one or more inverted terminal repeats (ITRs) of a transposon wherein the variant sequence inverted tandem repeats are at least 97% homologous to known ITRs and known transposon elements (shown in table 2).

In some embodiments, the present invention comprise one or more transposons, one or more inverted terminal repeats (ITRs) of a transposon wherein the variant sequence inverted tandem repeats are at least 98% homologous to known ITRs and known transposon elements (shown in table 2).

In some embodiments, the present invention comprise one or more transposons, one or more inverted terminal repeats (ITRs) of a transposon wherein the variant sequence inverted tandem repeats are at least 99% homologous to known ITRs and known transposon elements (shown in table 2).

TABLE 2

| Transposon ITRs |
|---|
| Sleeping Beauty<br>5' Inverted Tandem Repeat:<br>CAGTTGAAGTCGGAAGTTTACATACACTTAAGTTGGAGTCATTAAAACT<br>CGTTTTTCAACTACTCCACAAATTTCTTGTTAACAAACAATAGTTTTGG<br>CAAGTCAGTTAGGACATCTACTTTGTGCATGACACAAGTCATTTTTCCA<br>ACAATTGTTTACAGACAGATTATTTCACTTATAATTCACTGTATCACAA<br>TTCCAGTGGGTCAGAAGTTTACATACACTAAGT (SEQ ID NO: 68) |
| 3' Inverted Tandem Repeat:<br>ATTGAGTGTATGTAAACTTCTGACCCACTGGGAATGTGATGAAAGAAAT<br>AAAAGCTGAAATGAATCATTCTCTCTACTATTATTCTGATATTTCACAT<br>TCTTAAAATAAAGTGGTGATCCTAACTGACCTAAGACAGGGAATTTTTA<br>CTAGGATTAAATGTCAGGAATTGTGAAAAAGTGAGTTTAAATGTATTTG<br>GCTAAGGTGTATGTAAACTTCCGACTTCAACTG (SEQ ID NO: 69) |
| piggyBac<br>5' Inverted Tandem Repeat:<br>CCCTAGAAAGATAGTCTGCGTAAAATTGACGCATGCATTCTTGAAATAT<br>TGCTCTCTCTTTCTAAATAGCGCGAATCCGTCGCTGTGCATTTAGGACA<br>TCTCAGTCGCCGCTTGGAGCTCCCGTGAGGCGTGCTTGTCAATGCGGTA<br>AGTGTCACTGATTTTGAACTATAACGACCGCGTGAGTCAAAATGACGCA<br>TGATTATCTTTTACGTGACTTTTAAGATTTAACTCATACGATAATTATA<br>TTGTTATTTCATGTTCTACTTACGTGATAACTTATTATATATATATTTT<br>CTTGTTATAGATATC (SEQ ID NO: 70, minimal sequence is underlined and bold, i.e., first 35 bp) |
| 3' Inverted Tandem Repeat:<br>TAAAAGTTTTGTTACTTTATAGAAGAAATTTTGAGTTTTTGTTTTTTTT<br>TAATAAATAAATAAACATAAATAAATTGTTTGTTGAATTTATTATTAGT<br>ATGTAAGTGTAAATATAATAAAACTTAATATCTATTCAAATTAATAAAT<br>AAACCTCGATATACAGACCGATAAAACACATGCGTCAATTTTACGCATG<br>ATTATCTTTAACGTACGTCACAATATGATTATCTTTCTAGGG<br>(SEQ ID NO: 71, minimal sequence is underlined and bold, i.e., first 35 bp) |

The invention also comprises DNA which encodes for any one of the polypeptides described herein with any number of repeat units disclosed herein.

Any polypeptides of the invention or nucleic acids that encode the polypeptides of the present invention can be used in the methods described in PCT Application No. PCT/IB2010/000154, which is incorporated by reference in its entirety.

In an aspect fo the invention, the invention relates to a composition comprising one or more cells modified by one or more polypeptides disclosed herein. In some embodiments of the invention, the composition of the present invention comprise one or more stem cells. In some embodiments of the invention, the composition of the present invention comprises one or more mammalian stem cells modified by one or more polypeptides disclosed herein. In some embodiments of the invention, the composition of the present invention comprises one or more iPSC cells modified by one or more polypeptides disclosed herein. In some embodiments of the invention, the composition of the present invention comprise one or more human stem cells modified by one or more polypeptides disclosed herein. In some embodiments of the invention, the composition of the present invention comprises one or more spermatogonial stem cells modified by one or more polypeptides disclosed herein. In some embodiments of the invention, the cell is derived from a mammal, in some embodiments, the cell is from a rat or mini pig. In some embodiments of the invention, the mammal is a sterile male rat or sterile male mini pig. In some embodiments of the invention, the rat or mini pig is DAZL deficient or DAZL−/−. In some embodiments of the invention, the invention relates to a colony of genetically modified organisms comprising: at least one organism comprising one or more stem cells, the one or more stem cells comprise one or more of the following mutations: (i) a deletion mutation; (ii) a knockout mutation; and/or (iii) an addition of a heterologous nucleic acid sequence; the one or more mutations of (i), (ii), and/or (iii) are site-specific mutations caused by by one or more polypeptides disclosed herein (one or more RTNs); and (b) progeny of the organism of subpart (a).

In some embodiments of the invention, the cell or transgenic animal, colony or progeny thereof comprises a heterologous nucleic acid sequence that comprises a selectable marker or an orthologous gene. In some embodiments of the invention, the at least one organism and the progeny further comprise at least one inverted terminal repeat of a transposon or variant thereof.

In some embodiments of the invention, the at least one organism and the progeny further comprise a nucleic acid that comprises a a nucleic acid sequence that is at least 70% homologous to any or or combination of: SEQ ID NO: 1 through 19, or any sequence of Table 1, or any variants or functional fragments thereof. In some embodiments of the invention, the invention relates to a method of generating one or more genetically modified organisms comprising: (a) contacting at least one stem cell derived from the germline lineage of an animal or plant by the stem cell with: (i) at least one RTN that mutates a gene of interest; or (ii) at least one expression vector that encodes a RTN that mutates a gene of interest, thereby creating at least one stem cell comprising at least one mutation at a gene of interest; (b) expanding an in vitro culture of the at least one stem cell comprising at least one mutation at a gene of interest; (c) implanting one or more stem cells from the culture of step (b) into an organism.

In some embodiments of the invention, the invention relates to a method of generating one or more genetically modified organisms comprising: (a) contacting at least a first and second set of stem cell derived from the germline lineage of an animal or plant with: (i) at least one RTN that mutates a gene of interest; or (ii) at least one expression vector that encodes a RTN that mutates a gene of interest, thereby creating at least a first and second set of stem cells comprising at least one mutation at a gene of interest; (b) expanding an in vitro culture of the at least one stem cell comprising at least one mutation at a gene of interest; (c) implanting one or more sets of stem cells from the culture of step (b) into an organism. In some embodiments, the method further comprises a third, fourth, fifth, sixth, seventh, eighth, ninth, or ten or more sets of stem cells which have been mutated in a site-specific fashion by a RTN, and, in which case, after expanding each of the third, fourth, fifth, sixth, seventh, eighth, ninth, or ten or more sets of mutated stem cells, each set of transplanted into a single organism. In some embodiments, the single organism that comprises a set of mutated stem cells is a sterile male.

In some embodiments of the invention, the organism is capable of passing at least one mutation at a gene of interest to progeny by germline transmission. In some embodiments of the invention, the genetically modified organism is a mammal. In some embodiments of the invention, the genetically modified organism is a rat or mini pig. In some embodiments of the invention, the genetically modified organism is a sterile male rat or sterile male mini pig.

In some embodiments of the invention, the method further comprises: breeding the organism implanted with the one or more stem cells with another animal to generate one or more progeny that comprise the mutated gene of interest. In some embodiments of the invention, the method further comprises: breeding the organism implanted with the one or more set of stem cells with another animal to generate one or more progeny that comprise the one or more mutated genes of interest that correspond to each of the mutated stem cell lines.

In some embodiments of the invention, the progeny are mammals.

In some embodiments of the invention, a method of breeding a colony of genetically modified organisms comprising:

(a) contacting at least one stem cell derived from the germline lineage of an animal or plant by the stem cell with: (i) at least one RTN that mutates a gene of interest; or (ii) at least one expression vector that encodes a RTN that mutates a gene of interest, thereby creating a stem cell comprising at least one mutation at a gene of interest;

(b) expanding an in vitro culture of the stem cell comprising at least one mutation at a gene of interest;

(c) implanting the at least one stem cell comprising at least one mutation at a gene of interest from the culture of step (b) into a first organism.

(d) breeding the first organism with a second organism of the same species; (e) selecting progeny of the first and second organism that comprise the at least one mutation at a gene of interest; and (f) breeding the progeny to create a colony of organisms that comprise the at least one mutation at a gene of interest.

In some embodiments of the invention, the first and second organisms are mammals.

In some embodiments of the invention, the first and second organisms are rats or mini pigs.

In some embodiments of the invention, the invention relates to a method of manufacturing a first filial generation of genetically modified organisms comprising two or more distinct subsets of organisms, the method comprising:

(a) contacting a first stem cell with: (i) a RTN that mutates a first gene of interest; or (ii) an expression vector that encodes a RTN that mutates a first gene of interest; thereby creating a first stem cell comprising a first mutation;

(b) contacting a second stem cell with a modifying agent, thereby creating a second stem cell comprising a second mutation;

(c) expanding an in vitro culture of each of the first and the second stem cells;

(d) implanting a mixed population of stem cells comprising the first and the second stem cells into an organism;

(e) breeding the organism with another organism of the same species.

In some embodiments of the invention, the first filial generation of genetically modified organisms comprises two or more sets of organisms, each set comprising a distinct mutation of interest derived from a haplotype of distinct stem cells transplanted into a parent of the organism.

In some embodiments of the invention, at least one stem cell of the mixed population is a spermatogonial stem cell of a mammal.

In some embodiments of the invention, the organism is a mammal.

In some embodiments of the invention, a kit comprising:

(a) a RTN or a nucleic acid sequence that encodes a RTN that cleaves a nucleic acid sequence at a gene of interest; and (b) an instruction manual comprising directions; and, optionally In some embodiments of the invention, a kit comprising:

(a) In some embodiments of the invention; and, optionally (b) culture media for the one or more stem cells or one or more embryos.

In some embodiments of the invention, the kit comprises:

(a) an RTN or a nucleic acid sequence that encodes an RTN that cleaves a nucleic acid sequence at a gene of interest; and optionally (b) culture media for the one or more stem cells or one or more embryos.

In some embodiments of the invention, the kit comprises:

(a) an RTN or a nucleic acid sequence that encodes an RTN that cleaves a nucleic acid sequence at a gene of interest; and (b) one or more stem cell lines derived from a germline lineage of animal or plant; and, optionally (c) culture media for the one or more stem cells or one or more embryos; and, optionally (d) an instruction manual that comprises instructions on how to mutate the one or more stem cells with the RTN or a nucleic acid sequence that encodes the RTN that cleaves a nucleic acid sequence at a gene of interest.

TABLE 1

| |
|---|
| (SEQ ID NO: 72)<br>lsteqvvaia snkggkqale avkahlldll gapyv |
| (SEQ ID NO: 73)<br>lsteqvvava snkggkqala aveaqllrlr aapye |
| (SEQ ID NO: 74)<br>lnteqvvava snkggkqale avgaqllalr avpya |
| (SEQ ID NO: 75)<br>lsteqvvava snkggkqvle avgaqllalr avpye |
| (SEQ ID NO: 76)<br>lsteqvvaia snkggkqale avkahlldll gapyv |
| (SEQ ID NO: 77)<br>lsteqvvaia snkggkqale avkahlldll gapyv |
| (SEQ ID NO: 78)<br>lsteqvvaia snkggkqale avkahlldll gapyv |
| (SEQ ID NO: 79)<br>lsteqvvaia snkggkqale avkaqllelr gapya |
| (SEQ ID NO: 80)<br>lsteqvvava snkggkqala aveaqllrlr aapye |
| (SEQ ID NO: 81)<br>lsteqvvaia snkggkqale avkahlldll gapyv |
| (SEQ ID NO: 82)<br>lsteqvvaia snkggkqale avkahlldll gapyv |
| (SEQ ID NO: 83)<br>lsteqvvaia snnggkqale avkaqlldlr gapya |
| (SEQ ID NO: 84)<br>lsteqvvaia snnggkqale avkaqlpvlr rapyg |
| (SEQ ID NO: 85)<br>lspeqvvaia snnggkpale avkaqllelr aapye |
| (SEQ ID NO: 86)<br>lspeqvvaia snnggkpale avkalllalr aapye |
| (SEQ ID NO: 87)<br>lsteqvvaia snnggkpale avkallleLr aapye |

TABLE 1-continued (SEQ ID NO: 88)
lsteqvvaia snnggkqale avktqllalr tapye (SEQ ID NO: 89)
lsteqvvaia snnggkqale avkaqlpalr aapye (SEQ ID NO: 90)
lsleqvvaia snnggkqale avkaqllvlr aapyg (SEQ ID NO: 91)
lstaqvvaia annggkqale avrallpvlr vapye (SEQ ID NO: 92)
lspeqvvaia snnggkqale avkaqllclr aapye (SEQ ID NO: 93)
lsleqvvaia snnggkqale avkaqllclr aapye (SEQ ID NO: 94)
lspeqvvaia snnggkqale avkaqllclr aapye (SEQ ID NO: 95)
lsteqvvaia snnggkqale avkaqllclr aapye (SEQ ID NO: 96)
lspeqvvaia snnggkqale avkaqllclr aapye (SEQ ID NO: 97)
lsteqvvaia snnggkqale avkaqllalr aapye (SEQ ID NO: 98)
lsleqvvaia snnggkqale avkalllelr aapye (SEQ ID NO: 99)
lsteqvvaia snnggkqale avktqllalr tapye (SEQ ID NO: 100)
lsteqvvaia snnggkqale avkaqlpalr aapye (SEQ ID NO: 101)
lspeqvvaia snnggkqale avrallpvlr vapye (SEQ ID NO: 102)
lstaqvvaia sngggkqale gigcqllklr tapyg (SEQ ID NO: 103)
lsteqvvaia sngggkqale gigkqlqclr aaphg (SEQ ID NO: 104)
lstgqvvaia sngggrqale avrcqllalr avpye (SEQ ID NO: 105)
lstgqvvaia sngggrqale avrcqllalr avpye (SEQ ID NO: 106)
lstaqvvaia sngggkqale gigcqllklr tapyg (SEQ ID NO: 107)
lstaqvvaia sngggkqale gigeqllklr tapyg (SEQ ID NO: 108)
lstaqvvaia sngggkqale gigcqlrklr tapyg (SEQ ID NO: 109)
lstaqvvaia sngggkqale gigcqllklr tapyg (SEQ ID NO: 110)
lsteqvvaia sngggkqale gigkqlqclr aaphg (SEQ ID NO: 111)
lntaqvvaia shdggkpale avwaklpvlr gvpye (SEQ ID NO: 112)
lntaqvvaia shdggkpale avwaklpvlr gvpye (SEQ ID NO: 113)
lntaqvvaia shdggkpale avwaklpvlr gvpya (SEQ ID NO: 114)
lstcqvvaia shdggkqale avgaqlvalr aapya (SEQ ID NO: 115)
lstaqvvaia shdggnqale avgtqlvalr aapya (SEQ ID NO: 116)
lsteqvvaia shdggkqale avgaqlvalr aapya (SEQ ID NO: 117)
lntaqivaia shdggkpale avwaklpvlr gapya (SEQ ID NO: 118)
lstaqvvava shdggkpale avrkqlpylr gvphq (SEQ ID NO: 119)
lstaqvvaia shdggkpale avwaklpvlr gapya (SEQ ID NO: 120)
lntaqvvaia shdggkpale avwaklpvlr gvpye (SEQ ID NO: 121)
lntaqvvaia shdggkpale avwaklpvlr gvpya (SEQ ID NO: 122)
lstaqvvaia shdggkqale avgaqlvelr aapya (SEQ ID NO: 123)
lsteqvvaia shdggkqale avgaqlvalr aapya (SEQ ID NO: 124)
lntaqvvaia shdggkpale avraklpvlr gvpya (SEQ ID NO: 125)
ltpqqvvaia shdggkpale avwaklpvlr gvpya (SEQ ID NO: 126)
ltpqqvvaia shdggkpale avwaklpvlr gvpya (SEQ ID NO: 127)
lstaqvatia ssiggrqale avkvqlpylr aapyg (SEQ ID NO: 128)
lsteqvvvia nsiggkqale avkvqlpylr aapye (SEQ ID NO: 129)
lsteqvvvia nsiggkqale avkvqlpylr aapye (SEQ ID NO: 130)
lstaqvatia ssiggrqale avkvqlpylr aapyg Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

EXAMPLES

Example 1: Generating Nucleic Acid Vectors with *Ralstonia* TALs (RTALs) with Functional Analysis Cluster analysis and review of sequence homologies of *Ralstonia* genome revealed the sequence of SEQ ID NO: 1 which is homolgous to known TAL sequences.

Nucleic acid sequences that encode the polypeptides of the claimed invention will be made through molecular biology techniques known to those with ordinary skill in the art. DNA sequences, for instance, will be synthesized with the XbaI and/or Sail restriction sites flanking each nucleic acid sequence that encodes the polyproteins of the present invention. Polymerase chain reaction will be performed to amplify the DNA with certain restriction endonuclease sites. Sequences will be gel-purified, isolated, and reconstituted in water or suitable buffer for ligation reactions. A plasmid that encodes a protein with effector function (such as nuclease function) that comprises requisite regulatory elements will be ligated to one or more of the nucleic acid sequences that encode the following sequences at the plasmid multiple cloning sites:

```
a.
LSTEQVVAIAS NK GGKQALEAVKAHLLDLLGAPYV
(SEQ ID NO: 72)

b.
LSTEQVVAIAS NN GGKQALEAVKAQLLELRAAPYE
(SEQ ID NO: 93)

c.
LSTAQVVAIAS NG GGKQALEGIGEQLLKLRTAPYG
(SEQ ID NO: 102)

d.
LSTAQVVAIAS HD GGKPALEAVWAKLPVLRGVPYA
(SEQ ID NO: 134)

e.
LSTEQVVTIAS SI GGKQALEAVKVQLPVLRAAPYE
(SEQ ID NO: 135)
```

Plasmid sequences will be transformed in suitable bacteria for production of high copy numbers of plasmid. Plasmids containing at least one polypeptide above can be selected using antibiotic selection, isolated and purified from bacterial cells using techniques known to those skilled in the art.

Plasmids will also be built and in-vitro testing of expressed DNA-binding polypeptides will be validated using the methods described in Nature Biotechnology 2012 May; 30(5):460-5. "FLASH assembly of TALENs for high-throughput genome editing." Reyon D, Tsai S Q, Khayter C, Foden J A, Sander J D, Joung J K, which is incorporated by reference in its entirety.

Construction of a Plasmid Archive Encoding Pre-Assembled TALE Repeats

We sought to construct TALE repeat arrays using the same architecture first described by Miller, J. C. et al. "A TALE nuclease architecture for efficient genome editing.", Nat Biotechnol. 2011; 29: 143-148 in which distinct TALE repeat backbones that differ slightly in their amino acid and DNA sequences occur in a repeated pattern. In some embodiments, we designated the first, amino-terminal TALE repeat in an array as the α unit. This is followed by β, γ; and δ units and then an ε unit that is essentially identical to the α unit except for the different positioning of a Type IIS restriction site on the 5' end (required to enable creation of a unique overhang on the α unit needed for cloning). The ε unit is then followed again by repeats of β, γ; δ and ε units. Due to constraints related to creation of a 3' end required for cloning, slightly modified DNA sequences were required for TALE repeat arrays that end with a carboxyterminal γ for ε unit.

Preparation of TALE Repeat-Encoding DNA Fragments for FLASH Assembly

To prepare DNA fragments encoding a units for use in FLASH assembly, we will perform 20 rounds of PCR with each a unit plasmid as a template using primers oJS2581 (5'-Biotin-TCTAGAGAAGACAAGAACCTGACC-3', SEQ ID NO: 20) and oJS2582(5'-GGATCCGGTCTCT-TAAGGCCGTGG-3', SEQ ID NO: 21). The resulting PCR products will be biotinylated on the 5' end. Each a PCR product will then be digested with 40 units of BsaI-HF restriction enzyme to generate 4 bp overhangs, purified using the QIAquick PCR purification kit (QIAGEN) according to manufacturer's instructions except that the final product will be eluted in 50 μl of 0.1×EB.

To prepare DNA fragments encoding polypeptide repeats, we will digest 10 μg of each of these plasmids with 50 units of BsaI restriction enzyme in NEBuffer 2 for 2 hours at 37° C. followed by serial restriction digests performed in NEBuffer 4 at 37° C. using 100 units each of XbaI, BamHI-HF, and SalI-HF enzymes that will be added at 5 minute intervals. The latter set of restriction digestions will be designed to cleave the plasmid backbone to ensure that this larger DNA fragment will not interfere with subsequent ligations performed during the FLASH assembly process. These restriction digest reactions will then be purified using the QIAquick PCR purification kit (QIAGEN) according to manufacturer's instructions except that the final product will be eluted in 180 μl of 0.1×EB.

Automated FLASH Assembly

All steps of FLASH assembly will be performed using a Sciclone G3 liquid-handling workstation (Caliper) or similar device sold by another company in 96-well plates and using a SPRIplate 96-ring magnet (Beckman Coulter Genomics) and a DynaMag-96 Side magnet (Life Technologies). In the first step of FLASH, a biotinylated a unit fragment will be ligated to the first βγδε fragment and then the resulting αβγε fragments will be bound to Dynabeads MyOne Cl streptavidin-coated magnetic beads (Life Technologies) in 2×B&W Buffer. Beads will then be drawn to the side of the well by placing the plate on the magnet and then will be washed with 100 μl B&W buffer with 0.005% Tween 20 (Sigma) and again with 100 μl 0.1 mg/ml bovine serum albumin (BSA) (New England Biolabs). Additional βγδε fragments will be ligated by removing the plate from the magnet, resuspending the beads in solution in each well, digesting the bead-bound fragment with BsaI-HF restriction enzyme, placing the plate on the magnet, washing with 100 μl B&W/Tween20 followed by 100 μl of 0.1 mg/ml BSA, and then ligating the next fragment. This process will be repeated multiple times with additional βγδε units to extend the bead-bound fragment. The last fragment to be ligated is always a β, β γ*, βγδ, or δε* unit to enable cloning of the full-length fragment into expression vectors (note that fragments that end with a δε* unit will always be preceded by ligation of a βγ unit).

The final full-length bead-bound fragment will be digested with 40 units of Bsal-HF restriction enzyme followed by 25 units of BsaI restriction enzyme (New England Biolabs). Digestion with BsaI will release the fragment from the beads and generates a unique 5' overhang for cloning of the fragment. Digestion with Bsal-HF results in creation of a unique 3' overhang for cloning.

Subcloning of TALE Repeat Array-Encoding DNA Fragments into TALEN Expression Vectors We will subclone DNA fragments encoding our FLASH assembled TALE repeat arrays into TALE expression vectors. In some embodiments, there will be 4 or more separate plasmids. In some embodiments, vectors will include a CMV promoter, a translational start codon optimized for mammalian cell expression, a triple FLAG epitope tag, a nuclear localization signal, amino acids 153 to 288 from the TALE 13 protein (as numbered by Miller et al. 6), two unique and closely positioned Type IIS BsmBI restriction sites, a 0.5 TALE repeat domain encoding RVDs, amino acids 715 to 777 from the TALE 13 protein, and the wild-type FokI cleavage domain.

All DNA fragments assembled by FLASH will possess overhangs that enable directional cloning into any of the expression vectors that will be digested with BsmBI. Standard TALEN expression vectors (each possessing a different 0.5 TALE repeat) are available from suppliers such as Addgene and full sequences of these plasmids are freely available on a web page dedicated to these constructs: addgene.org/talengineering/expressionvectors/ for synthetic construction.

To prepare a TALEN expression vector for subcloning, we will digest 5 μg of plasmid DNA with 50 units of BsmBI restriction enzyme (New England Biolabs) in NEBuffer 3 for 8 hours at 55 degrees C. Digested DNA will be purified using 90 μl of Ampure XP beads (Agencourt) according to manufacturer's instructions and will be diluted to a final concentration of 5 ng/l in 1 mM TrisHCl. FLASH-assembled TALE repeat arrays will be ligated into TALEN expression vectors using 400 U of T4 DNA Ligase (New England Biolabs). Ligation products will be transformed into chemically competent XL-1 Blue cells. Typically, six colonies will be picked for each ligation and plasmid DNA will be isolated by an alkaline lysis miniprep procedure. Simultaneously, the same colonies will be screened by PCR using primers oSQT34 (5'-GACGGTGGCTGTCAAATACCAAGATATG-3', SEQ ID NO: 22) and oSQT35 (5'-TCTCCTCCAGTTCACTTTTGACTAGTTGGG-3', SEQ ID NO: 23). PCR products will be analyzed on a QIAxcel capillary electrophoresis system (Qiagen). Miniprep DNA from clones that contain correctly sized PCR products will be sent for DNA sequence confirmation with primers oSQT1 (5'-AGTAACAGCGGTAGAGGCAG-3', SEQ ID NO: 24), oSQT3 (5'-ATTGGGCTACGATGGACTCC-3', SEQ ID NO: 210), and oJS2980 (5'-TTAATTCAATATATTCATGAGGCAC-3', SEQ ID NO: 25); oSQT1 anneals at the 5' end of the TALE repeat array coding sequence and will enable sequencing of the amino-terminal half of the assembled array, oSQT3 anneals at the 3' end of the TALE repeat array coding sequence and enables sequencing of the carboxy-terminal half of the assembled array, and oJS2980 primes within the coding sequence of the FokI domain (downstream of oSQT3) and will enable sequencing and verification of the carboxy-terminal 0.5 TALE repeat domain.

We will screen six colonies for each assembly as described above, followed by six additional colonies if necessary. With this approach, one or more sequence-verified clones for >90% of assembly reactions. These percentages will be derived primarily from experiments designed to construct DNA fragments encoding 16.5 TALE repeats.

EGFP TALEN Activity and Toxicity Assays

EGFP reporter assays will be performed in a clonal U2OS human cell line bearing an integrated construct that constitutively expresses an EGFP-PEST fusion protein. This clonal line will be derived from a polyclonal U2OS EGFP-PEST reporter line. Clonal U2OS EGFP-PEST cells will be cultured in Advanced DMEM (Life Technologies) supplemented with 10% FBS, 2 mM GlutaMax (Life Technologies), penicillin/streptomycin, and 400 μg/ml G418. Cells will be transfected in triplicate with 500 ng of each TALEN plasmid DNA and 50 ng ptdTomato-N1 plasmid DNA using a Lonza 4D-Nucleofector System, Solution SE, and program DN-100 according to manufacturer's instructions. 1 μg of ptdTomato-N1 plasmid alone will be transfected in triplicate as a negative control. Cells will be assayed for EGFP and tdTomato expression at 2 and 5 days post-transfection using a BD FACSAriall flow cytometer.

PCR Amplification and Sequence Verification of Endogenous Human Genes

PCR reactions to amplify targeted loci will be performed using the primers shown in Supplementary Table 5. Standard PCR conditions with Phusion Hot Start II high-fidelity DNA polymerase (Thermo-Fisher) will be performed according to manufacturer's instructions for 35 cycles (98° C., 10 s denaturation; 68° C., 15 s annealing; 72° C., 30 s extension). For loci that do not amplify under standard conditions we will use one of the following modifications: 1) the addition of betaine to a final concentration of 1.8M, 2) touchdown PCR ([98° C., 10 s; 72-62° C., −1° C./cycle, 15 s; 72° C., 30 s]$_{10\ cycles}$, [98° C., 10 s; 62° C., −1° C./cycle, 15 s; 72° C., 30 s]$_{25\ cycles}$) with 1.8M betaine, and 3) the addition of 3% or 5% DMSO and an annealing temperature of 65° C. PCR products will be analyzed for correct size on a QIAxcel capillary electrophoresis system. Correctly sized products will be treated with ExoSap-IT (Affymetrix) to remove unincorporated nucleotides or primers and sent for DNA sequencing to confirm the endogenous gene sequence.

T7 Endonuclease I Assay for Quantifying NHEJ-Mediated Mutation of Endogenous Human Genes U2OS-EGFP cells will be cultured and transfected in duplicate as described above. Genomic DNA was isolated from cells transfected with TALEN-encoding or control plasmids using a high-throughput magnetic-bead based purification system (Agencourt DNAdvance) according to the manufacturer's instructions. PCR to amplify endogenous loci will be performed for 35 cycles as described above and fragments were purified with Ampure XP (Agencourt) according to manufacturer's instructions. 200 ng of purified PCR product will be denatured and reannealed in NEBuffer 2 (New England Biolabs) using a thermocycler with the following protocol (95° C., 5 min; 95-85° C. at −2° C./s; 85-25° C. at −0.1° C./s; hold at 4° C.). 33 Hybridized PCR products were treated with 10 U of T7 Endonuclease I at 37° C. for 15 minutes in a reaction volume of 20 al. Reactions were stopped by the addition of 2 μl 0.5 M EDTA, purified with Ampure XP, and quantified on a QIAxcel capillary electrophoresis system using method OM500. The sum of the area beneath TALEN-specific cleavage peaks (expressed as a percentage of the parent amplicon peak, denoted fraction cleaved) is used to estimate gene modification levels using the following equation as previously described. (% gene modification=100×(1−(1−fraction cleaved)$^2$)

Example 2

Five fragments shown below were synthesized and each cloned into a modified pUC57: pUC57-ΔBsal (vectors as disclosed in Juong et. al. FLASH assembly paper). It contains single basepair change to disrupt a Bsal site) with XbaI and BamHI.

```
RTN1 EBEs:
NK:
XbaI BbsI
ATGCA T^ACTAGA-GAAGACAA^ACTGA-
GCACCGAGCAGGTGGTGGCCATCGCCAGCAACAAGGGCGGCAAGCAGGCC
CTGGAGGCCGTGAAGGCCCACCTGCTGGACCTGCTGGGCGCCCCCTACGA
G-CTGAAAGAGACC-GAGATCC(CGGGC)SEQ ID NO: 26) BsaI
```

-continued

```
BamHI
NN:
ATGCA
TCTAGAGAAGACAACTGAGCACCGAGCAGGTGGTGGCCATCGCCAGCAAC
AACGGCGGCAAGCAGGCCCTGGAGGCCGTGAAGGCCCAGCTGCTGGAGCT
GAGGGCCGCCCCCTACGAGCTGAAGAGACCGGATCC CGGGC
(SEQ ID NO: 27)

NG:
ATGCA
TCTAGAGAAGACAACTGAGCACCGagCAGGTGGTGGCCATCGCCAGCAAC
GGCGGCGGCAAGCAGGCCCTGGAGGGCATCGGCGAGCAGCTGCTGAAGCT
GAGGACCGCCCCCTACGAGCTGAAGAGACCGGATCC CGGGC
(SEQ ID NO: 28)

HD:
ATGCA
TCTAGAGAAGACAACTGAGCACCGagCAGGTGGTGGCCATCGCCAGCCAC
GACGGCGGCAAGCCCGCCCTGGAGGCCGTGTGGGCCAAGCTGCCCGTGCT
GAGGGGCGTGCCCTACGAGCTGAAGAGACCGGATCC CGGGC
(SEQ ID NO: 29)

SI:
ATGCA
TCTAGAGAAGACAACTGAGCACCGAGCAGGTGGTGACCATCGCCAGCAGC
ATCGGCGGCAAGCAGGCCCTGGAGGCCGTGAAGGTGCAGCTGCCCGTGCT
GAGGGCCGCCCCCTACGAGCTGAAGAGACCGGATCC CGGGC
(SEQ ID NO: 30)
```

For proof of principle, these cloned fragments will be used to generate chimeric proteins of six repeat units fused to FokI nuclease, following the exact protocol in Joung's FLASH TALEN paper, i.e. a chimeric protein that targets a string of A (C,T and G) nucleotides. These chimeric proteins will then be tested for binding/targeting efficiency to desired DNA bases using a reporter construct.

Once the binding efficiency of these units are confirmed, a library of *Ralstonia* EBEs will be generated that will be an exact copy of FALSH TALEN's *Xanthomonas* EBE library. This library can then be used to generate *Ralstonia* TALENs following the exact protocol of the FLASH TALEN system.

Example 3. Generating Nucleic Acid Vectors with Methylesterase

Additional sequences cloned from other species or cloned from the same species may be used functionally as an enzyme either by itself or in series as a monomer or polymer (protein fusion) for performing any of the experiments disclosed herein with DNA recognition. A RVD identification consensus sequence was created using sequence optimization techniques known in the art. A BLAST search was performed across methlyesterase sequences in bacterial species (see FIG. 1). The following polypeptides were identified as having DNA base pair recognition capability similar to the nucleic acid sequences and polypeptides disclosed herein SEQ ID NO: 1-19:

TAL EBE against methylesterase

| #1 | | | |
|---|---|---|---|
| *Xanthomonas* Consensus EBEs | | | |
| | | LTPDQVVAIASNGGGKQALETVQRLLPVLCQDHG (SEQ ID NO: 31) | |
| | | LTPEQVVAIANNNGGKQALETVQRLLPVLCQAHG (SEQ ID NO: 32) | |
| | | LTPDQVVAIASHDGGKQALETVQRLLPVLCQAHG (SEQ ID NO: 33) | |
| | | LTPAQVVAIASNIGGKQALETVQRLLPVLCQDHG (SEQ ID NO: 34) | |
| EJO92907 | 166 | TTDRVVALGTSTGGTQALEVVLRQLPVDC (SEQ ID NO: 35) | 194 |
| YP_001187060 | 166 | TTDRVVALGTSTGGTQALEVVLRQLPVDC (SEQ ID NO: 213) | 194 |
| YP_003847734 | 169 | MTSEQIVAIGTSTGGTQALEAVLTALPRVC (SEQ ID NO: 36) | 198 |
| ZP_08780698 | 167 | TTDRVVAIGTSTGGTQALEVVLTALPRVC (SEQ ID NO: 37) | 195 |
| YP_004846745 | 185 | TTERIVAIGTSTGGTQALETVLHRLPATC (SEQ ID NO: 38) | 213 |
| YP_005027668 | 186 | TTDKIIAIGTSTGGTQALEAVLTKLPAVC (SEQ ID NO: 39) | 214 |
| ZP_10991552 | 174 | TTERIVAIGTSTGGTQALETVLTALPRVC (SEQ ID NO: 40) | 202 |
| YP_001792820 | 162 | TTERVVALGTSTGGTQALEVVLRTLPRVC (SEQ ID NO: 58) | 190 |
| EKE17764 | 172 | TTDQLIAIGTSTGGTQALEAILTKLPATC (SEQ ID NO: 62) | 200 |
| ZP_03698248 | 178 | TTERIVAIGTSTGGTQALETVLPRLPATC (SEQ ID NO: 44) | 206 |

-continued

| TAL EBE against methylesterase | | | |
|---|---|---|---|
| EGH48032 | 11 | TTERIVAIGTSTGGTQALEAVLTALPRVC (SEQ ID NO: 136) | 39 |
| ZP_06495900 | 1 | TTERIVAIGTSTGGTQALEAVLTALPRVC (SEQ ID NO: 214) | 29 |
| ZP_10381001 | 76 | TTERIVAIGTSTGGTQALEAVLTALPRVC (SEQ ID NO: 215) | 104 |
| ZP_10442431 | 158 | TSDKVVAIGASTGGTQALELLLTGLPAVC (SEQ ID NO: 45) | 186 |
| #2 | | | |
| ZP_10991552 | 174 | TTERIVAIGTSTGGTQALETVLTALPRVC (SEQ ID NO: 138) | 202 |
| EGH48032 | 11 | TTERIVAIGTSTGGTQALEAVLTALPRVC (SEQ ID NO: 216) | 39 |
| ZP_06495900 | 1 | TTERIVAIGTSTGGTQALEAVLTALPRVC (SEQ ID NO: 217) | 29 |
| EGH61007 | 172 | TTERIVAIGTSTGGTQALEAVLTALPRVC (SEQ ID NO: 218) | 200 |
| EGH06695 | 172 | TTERIVAIGTSTGGTQALEAVLTALPRVC (SEQ ID NO: 219) | 200 |
| EGH31878 | 172 | TTERIVAIGTSTGGTQALEAVLTALPRVC (SEQ ID NO: 220) | 200 |
| EGH66597 | 172 | TTERIVAIGTSTGGTQALEAVLTALPRVC (SEQ ID NO: 221) | 200 |
| ZP_07003572 | 172 | TTERIVAIGTSTGGTQALEAVLTALPRVC (SEQ ID NO: 222) | 200 |
| ZP_06457223 | 172 | TTERIVAIGTSTGGTQALEAVLTALPRVC (SEQ ID NO: 232) | 200 |
| ZP_04590480 | 172 | TTERIVAIGTSTGGTQALEAVLTALPRVC (SEQ ID NO: 224) | 200 |
| ZP_07251539 | 172 | TTERIVAIGTSTGGTQALEAVLTALPRVC (SEQ ID NO: 225) | 200 |
| NP_790747 | 172 | TTERIVAIGTSTGGTQALEAVLTALPRVC (SEQ ID NO: 226) | 200 |
| EGH77388 | 172 | TTERIVAIGTSTGGTQALEAVLTALPRVC (SEQ ID NO: 227) | 200 |
| EFW86187 | 172 | TTERIVAIGTSTGGTQALEAVLTALPRVC (SEQ ID NO: 228) | 200 |
| EGH54563 | 172 | TTERIVAIGTSTGGTQALEAVLTALPRVC (SEQ ID NO: 229) | 200 |
| YP_233877 | 172 | TTERIVAIGTSTGGTQALEAVLTALPRVC (SEQ ID NO: 230) | 200 |
| EGH23390 | 172 | TTERIVAIGTSTGGTQALEAVLTALPRVC (SEQ ID NO: 231) | 200 |
| ZP_05638023 | 172 | TTERIVAIGTSTGGTQALEAVLTALPRVC (SEQ ID NO: 232) | 200 |
| EGH71924 | 106 | TTERIVAIGTSTGGTQALEAVLTALPRVC (SEQ ID NO: 233) | 134 |
| EFW82095 | 172 | TTERIVAIGTSTGGTQALEAVLTALPRVC (SEQ ID NO: 234) | 200 |
| ZP_07265841 | 172 | TTERIVAIGTSTGGTQALEAVLTALPRVC (SEQ ID NO: 235) | 200 |

-continued

| TAL EBE against methylesterase | | | |
|---|---|---|---|
| YP_273082 | 172 | TTERIVAIGTSTGGTQALEAVLTALPRVC (SEQ ID NO: 236) | 200 |
| YP_004030667 | 117 | FSQADIVRIADNIGGAQALKAVLEHGPTL (SEQ ID NO: 46) | 145 |
| YP_004030667 | 186 | ADIVKIASNGGGAQALEAVAMHGSTLCE (SEQ ID NO: 237) | 213 |
| YP_004030667 | 153 | ADIVKIAGNGGGARALKAVVMHGPTLCE (SEQ ID NO: 48) | 180 |
| ZP_10995147 | 155 | TTDRVVALGCSTGGTQALEFILRQLPRDC (SEQ ID NO: 49) | 183 |
| EGH56182 | 30 | ALAAAVGGKGALEVPANLIPANCE (SEQ ID NO: 50) | 53 |
| YP_003907367 | 173 | RIVAIGTSTGGTQALEVVLTALP (SEQ ID NO: 51) | 195 |
| EBE1 | | LTPDQVVAIASNGGGKQALETVQRLLPVLCQDHG (SEQ ID NO: 52) | 34 |
| EBE4 | | LTPAQVVAIASNIGGKQALETVQRLLPVLCQDHG (SEQ ID NO: 53) | 34 |
| EBE3 | | LTPDQVVAIASHDGGKQALETVQRLLPVLCQAHG (SEQ ID NO: 54) | 34 |
| EBE2 | | LTPEQVVAIANNNGGKQALETVQRLLPVLCQAHG (SEQ ID NO: 55) | 34 |
| ZP_07265841_2 | | -TTERIVAIGTSTGGTQALEAVLTALPRVC---- (SEQ ID NO: 235) | 29 |
| YP_2730822 | | -TTERIVAIGTSTGGTQALEAVLTALPRVC---- (SEQ ID NO: 236) | 29 |
| EFW82095_2 | | -TTERIVAIGTSTGGTQALEAVLTALPRVC---- (SEQ ID NO: 234) | 29 |
| EGH71924_2 | | -TTERIVAIGTSTGGTQALEAVLTALPRVC---- (SEQ ID NO: 233) | 29 |
| ZP_05638023 2 | | -TTERIVAIGTSTGGTQALEAVLTALPRVC---- (SEQ ID NO: 232) | 29 |
| EGH23390 _2 | | -TTERIVAIGTSTGGTQALEAVLTALPRVC---- (SEQ ID NO: 231) | 29 |
| YP_233877_2 | | -TTERIVAIGTSTGGTQALEAVLTALPRVC---- (SEQ ID NO: 230) | 29 |
| EGH54563 _2 | | -TTERIVAIGTSTGGTQALEAVLTALPRVC---- (SEQ ID NO: 229) | 29 |
| EFW86187 2 | | -TTERIVAIGTSTGGTQALEAVLTALPRVC---- (SEQ ID NO: 228) | 29 |
| EGH77388_2 | | -TTERIVAIGTSTGGTQALEAVLTALPRVC---- (SEQ ID NO: 227) | 29 |
| NP_7907472 | | -TTERIVAIGTSTGGTQALEAVLTALPRVC---- (SEQ ID NO: 226) | 29 |
| ZP_07251539 2 | | -TTERIVAIGTSTGGTQALEAVLTALPRVC---- (SEQ ID NO: 225) | 29 |
| ZP_04590480 2 | | -TTERIVAIGTSTGGTQALEAVLTALPRVC---- (SEQ ID NO: 224) | 29 |
| ZP_06457223 2 | | -TTERIVAIGTSTGGTQALEAVLTALPRVC---- (SEQ ID NO: 223) | 29 |

-continued

| TAL EBE against methylesterase | | |
|---|---|---|
| ZP_07003572 2 | -TTERIVAIGTSTGGTQALEAVLTALPRVC---- (SEQ ID NO: 222) | 29 |
| EGH66597 2 | -TTERIVAIGTSTGGTQALEAVLTALPRVC---- (SEQ ID NO: 221) | 29 |
| EGH31878 2 | -TTERIVAIGTSTGGTQALEAVLTALPRVC---- (SEQ ID NO: 220) | 29 |
| EGH06695 2 | -TTERIVAIGTSTGGTQALEAVLTALPRVC---- (SEQ ID NO: 219) | 29 |
| EGH61007 2 | -TTERIVAIGTSTGGTQALEAVLTALPRVC---- (SEQ ID NO: 218) | 29 |
| ZP_064959002 | -TTERIVAIGTSTGGTQALEAVLTALPRVC---- (SEQ ID NO: 214) | 29 |
| EGH48032 2 | -TTERIVAIGTSTGGTQALEAVLTALPRVC---- (SEQ ID NO: 136) | 29 |
| ZP_10381001 | -TTERIVAIGTSTGGTQALEAVLTALPRVC---- (SEQ ID NO: 215) | 29 |
| ZP_06495900 | -TTERIVAIGTSTGGTQALEAVLTALPRVC---- (SEQ ID NO: 214) | 29 |
| EGH48032 | -TTERIVAIGTSTGGTQALEAVLTALPRVC---- (SEQ ID NO: 136) | 29 |
| YP_003847734 | MTSEQIVAIGTSTGGTQALEAVLTALPRVC---- (SEQ ID NO: 137) | 30 |
| ZP_10991552 | -TTERIVAIGTSTGGTQALETVLTALPRVC---- (SEQ ID NO: 138) | 29 |
| ZP_10991552 2 | -TTERIVAIGTSTGGTQALETVLTALPRVC---- (SEQ ID NO: 40) | 29 |
| YP_003907367 2 | ----RIVAIGTSTGGTQALEVVLTALP------- (SEQ ID NO: 51) | 23 |
| EJO92907 | -TTDRVVALGTSTGGTQALEVVLRQLPVDC---- (SEQ ID NO: 56) | 29 |
| YP_001187060 | -TTDRVVALGTSTGGTQALEVVLRQLPVDC---- (SEQ ID NO: 237) | 29 |
| ZP_10995147 2 | -TTDRVVALGCSTGGTQALEFILRQLPRDC---- (SEQ ID NO: 57) | 29 |
| YP_001792820 | -TTERVVALGTSTGGTQALEVVLRTLPRVC---- (SEQ ID NO: 58) | 29 |
| ZP_08780698 | -TTDRVVAIGTSTGGTQALEVVLTALPRVC---- (SEQ ID NO: 59) | 29 |
| YP_004846745 | -TTERIVAIGTSTGGTQALETVLHRLPATC---- (SEQ ID NO: 38) | 29 |
| ZP_03698248 | -TTERIVAIGTSTGGTQALETVLPRLPATC---- (SEQ ID NO: 44) | 29 |
| YP_005027668 | -TTDKIIAIGTSTGGTQALEAVLTKLPAVC---- (SEQ ID NO: 61) | 29 |
| EKE17764 | -TTDQLIAIGTSTGGTQALEAILTKLPATC---- (SEQ ID NO: 62) | 29 |
| ZP_10442431 | -TSDKVVAIGASTGGTQALELLLTGLPAVC---- (SEQ ID NO: 63) | 29 |
| YP_004030667_2b | ---ADIVKIASNGGGAQALEAVAMHGSTLCE--- (SEQ ID NO: 64) | 28 |

-continued

| TAL EBE against methylesterase | | |
|---|---|---|
| YP_004030667_2c | ---ADIVKIAGNGGGARALKAVVMHGPTLCE--- (SEQ ID NO: 65) | 28 |
| YP_004030667_2a | FSQADIVRIADNIGGAQALKAVLEHGPTL----- (SEQ ID NO: 66) | 29 |
| EGH56182_2 | -------ALAAAVGGKGALEVPANLIPANCE--- (SEQ ID NO: 67) | 24 |

Example 4

Figure 2:
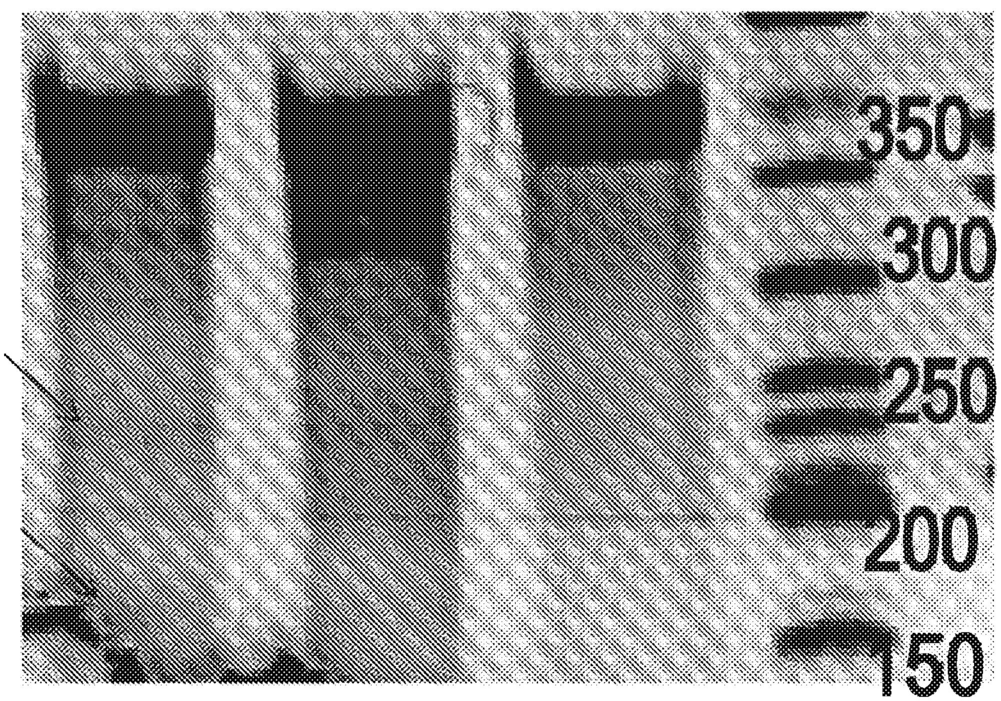
FIG. 2 depicts a gel demonstrating RTN functionality.

A pair of Bmpr2 specific EBEs (*Ralstonia* DNA binding domain, 16 EBEs each) were gene synthesized and cloned into XTN-BB (*Xanthomonas* TAL backbone fused to FokI). These constructs were co-transfected into Rat C6 cells and gDNA extracted after 48 hrs for Cell surveyor nuclease assay. If successful, the assay should produce 240 bp and 150 bp subpopulations from the original 400 bp amplicon of the locus. The results are shown in the FIG. 2.

The assay reveals the expected 250 bp and 150 bp bands in the *Ralstonia* and *Xanthomonas* TALEN transfected cells, which are absent in the WT negative control. This indicates that the *Ralstonia* EBEs target this locus and the fusion of FokI nuclease to *Ralstonia* EBEs lead to targeted digestion of genomic DNA. Using the 250 bp band, 5.75% for XTN, 1.82% for RTN. Using the 150 bp band, 3.66% for XTN, 5.43% for RTN.

Bmpr2 Target site T-T-GATA-GTCG-CCTT-ATG-TtttggatacagaatgtT-GAC-AGGT-AAAC-GAAA-T-A (SEQ ID NO: 141)

Fwd RTN TGATAGTCGCCTTATG (SEQ ID NO: 142)

Rev RTN ATTTGGTTTACCTGTC (SEQ ID NO: 143)

Note:
the first and the last nucleotide of the targeted site (underlined) are not specified by the RTNs. These are specified by the Xanthomonas TALEN backbone.

Bmpr2 FWD RTN EBEs' amino acid sequence:

LSTAQVVAIAS NG GGKQALEGIGEQLLKLRTAPYG (SEQ ID NO: 102)

LSTEQVVAIAS NK GGKQALEAVKAHLLDLLGAPYV (SEQ ID NO: 72)

LSTEQVVAIAS NN GGKQALEAVKAQLLELRAAPYE (SEQ ID NO: 93)

LSTAQVVAIAS NG GGKQALEGIGEQLLKLRTAPYG (SEQ ID NO: 102)

LSTEQVVAIAS NN GGKQALEAVKAQLLELRAAPYE (SEQ ID NO: 93)

LSTEQVVAIAS NK GGKQALEAVKAHLLDLLGAPYV (SEQ ID NO: 72)

LSTAQVVAIAS NG GGKQALEGIGEQLLKLRTAPYG (SEQ ID NO: 102)

LSTAQVVAIAS HD GGKPALEAVWAKLPVLRGVPYA (SEQ ID NO: 134)

LSTEQVVAIAS NK GGKQALEAVKAHLLDLLGAPYV (SEQ ID NO: 72)

LSTAQVVAIAS HD GGKPALEAVWAKLPVLRGVPYA (SEQ ID NO: 134)

LSTAQVVAIAS HD GGKPALEAVWAKLPVLRGVPYA (SEQ ID NO: 134)

LSTAQVVAIAS NG GGKQALEGIGEQLLKLRTAPYG (SEQ ID NO: 102)

LSTAQVVAIAS NG GGKQALEGIGEQLLKLRTAPYG (SEQ ID NO: 102)

LSTEQVVAIAS NN GGKQALEAVKAQLLELRAAPYE (SEQ ID NO: 93)

LSTAQVVAIAS NG GGKQALEGIGEQLLKLRTAPYG (SEQ ID NO: 102)

LSTEQVVAIAS NK GGKQALEAVKAHLLDLLGAPYV (SEQ ID NO: 72)

Bmpr2 FWD RTN DNA sequence:
(Bolded font: synthesized Ralstonia EBEs) This sequence is Contiguous (SEQ ID NO: 145):

GACGGATCGGGAGATCTCCCGATCCCCTATGGTCGACTCTCAGTACAATCTGCTCTGATGCCGCATAGTTAAGCCAGTATCTG

CTCCCTGCTTGTGTGTTGGAGGTCGCTGAGTAGTGCGCGAGCAAAATTTAAGCTACAACAAGGCAAGGCTTGACCGACAATT

-continued

GCATGAAGAATCTGCTTAGGGTTAGGCGTTTTGCGCTGCTTCGCGATGTACGGGCCAGATATACGCGTTGACATTGATTATTG

ACTAGTTATTAATAGTAATCAATTACGGGGTCATTAGTTCATAGCCCATATATGGAGTTCCGCGTTACATAACTTACGGTAAA

TGGCCCGCCTGGCTGACCGCCCAACGACCCCCGCCCATTGACGTCAATAATGACGTATGTTCCCATAGTAACGCCAATAGGG

ACTTTCCATTGACGTCAATGGGTGGAgTATTTACGGTAAACTGCCCACTTGGCAGTACATCAAGTGTATCATATGCCAAGTAC

GCCCCCTATTGACGTCAATGACGGTAAATGGCCCGCCTGGCATTATGCCCAGTACATGACCTTATGGGACTTTCCTACTTGGC

AGTACATCTACGTATTAGTCATCGCTATTACCATGGTGATGCGGTTTTGGCAGTACATCAATGGGCGTGGATAGCGGTTTGAC

TCACGGGGATTTCCAAGTCTCCACCCCATTGACGTCAATGGGAGTTTGTTTTGGCACCAAAATCAACGGGACTTTCCAAAATG

TCGTAACAACTCCGCCCCATTGACGCAAATGGGCGGTAGGCGTGTACGGTGGGAGGTCTATATAAGCAGAGCTCTCTGGCTA

ACTAGAGAACCCACTGCTTACTGGCTTATCGAAATTAATACGACTCACTATAGGGAGACCCAAGCTGGCTAGCACCATGGAC

TACAAAGACCATGACGGTGATTATAAAGATCATGACATCGATTACAAGGATGACGATGACAAGATGGCCCCCAAGAAGAAG

AGGAAGGTGGGCATTCACCGCGGGGTACCTATGGTGGACTTGAGGACACTCGGTTATTCGCAACAGCAACAGGAGAAAATC

AAGCCTAAGGTCAGGAGCACCGTCGCGCAACACCACGAGGCGCTTGTGGGGCATGGCTTCACTCATGCGCATATTGTCGCGC

TTTCACAGCACCCTGCGGCGCTTGGGACGGTGGCTGTCAAATACCAAGATATGATTGCGGCCCTGCCCGAAGCCACGCACGA

GGCAATTGTAGGGGTCGGTAAACAGTGGTCGGGAGCGCGAGCACTTGAGGCGCTGCTGACTGTGGCGGGTGAGCTTAGGGG

GCCTCCGCTCCAGCTCGACACCGGGCAGCTGCTGAAGATCGCGAAGAGAGGGGGAGTAACAGCGGTAGAGGCAGTGCACGC

CTGGCGCAATGCGCTCACCGGGGCCCCCTTGAAC

CTGAGCACCGCCCAGGTGGTGGCCATCGCCAGC AACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGC AACAAG

GGCGGCAAGCAGGCCCTGGAGGCCGTGAAGGCCCACCTGCTGGACCTGCTGGGCGCCCCCTACGTG

CTGAGCACCGAGCAGGTGGTGGCCATCGCCAGC AACAAC

GGCGGCAAGCAGGCCCTGGAGGCCGTGAAGGCCCAGCTGCTGGAGCTGAGGGCCGCCCCCTACGAG

CTGAGCACCGCCCAGGTGGTGGCCATCGCCAGC AACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGC AACAAC

GGCGGCAAGCAGGCCCTGGAGGCCGTGAAGGCCCAGCTGCTGGAGCTGAGGGCCGCCCCCTACGAG

CTGAGCACCGAGCAGGTGGTGGCCATCGCCAGC AACAAG

GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGC AACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGC CACGAC

GGCGGCAAGCCCGCCCTGGAGGCCGTGTGGGCCAAGCTGCCCGTGCTGAGGGGCGTGCCCTACGCC

CTGAGCACCGAGCAGGTGGTGGCCATCGCCAGC AACAAG

GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGC CACGAC

GGCGGCAAGCCCGCCCTGGAGGCCGTGTGGGCCAAGCTGCCCGTGCTGAGGGGCGTGCCCTACGCC

CTGAGCACCGCCCAGGTGGTGGCCATCGCCAGC CACGAC

GGCGGCAAGCCCGCCCTGGAGGCCGTGTGGGCCAAGCTGCCCGTGCTGAGGGGCGTGCCCTACGCC

CTGAGCACCGCCCAGGTGGTGGCCATCGCCAGC AACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGC AACGGC

-continued

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGC AACAAC

GGCGGCAAGCAGGCCCTGGAGGCCGTGAAGGCCCAGCTGCTGGAGCTGAGGGCCGCCCCCTACGAG

CTGAGCACCGCCCAGGTGGTGGCCATCGCCAGC AACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGC AACAAG

GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGCAACGGCGGAGGACGGCCAGCCTTGGAGTCCATCGTAGCCCAATTGTCCA

GGCCCGATCCCGCGTTGGCTGCGTTAACGAATGACCATCTGGTGGCGTTGGCATGTCTTGGTGGACGACCCGCGCTCGATGC

AGTCAAAAAGGGTCTGCCTCATGCTCCCGCATTGATCAAAAGAACCAACCGGCGGATTCCCGAGAGAACTTCCCATCGAGTC

GCGGGATCCCAACTAGTCAAAAGTGAACTGGAGGAGAAGAAATCTGAACTTCGTCATAAATTGAAATATGTGCCTCATGAAT

ATATTGAATTAATTGAAATTGCCAGAAATTCCACTCAGGATAGAATTCTTGAAATGAAGGTAATGGAATTTTTTATGAAAGTT

TATGGATATAGAGGTAAACATTTGGGTGGATCAAGGAAACCGGACGGAGCAATTTATACTGTCGGATCTCCTATTGATTACG

GTGTGATCGTGGATACTAAAGCTTATAGCGGAGGTTATAATCTGCCAATTGGCCAAGCAGATGAAAGTCAACGATATGTCGA

AGAAAATCAAACACGAAACAAACATATCAACCCTAATGAATGGTGGAAAGTCTATCCATCTTCTGTAACGGAATTTAAGTTT

TTATTTGTGAGTGGTCACTTTAAAGGAAACTACAAAGCTCAGCTTACACGATTAAATCATATCACTAATTGTAATGGAGCTGT

TCTTAGTGTAGAAGAGCTTTTAATTGGTGGAGAAATGATTAAAGCCGGCACATTAACCTTAGAGGAAGTCAGACGGAAATTT

AATAACGGCGAGATAAACTTTTAAGGGCCCTTCGAAGGTAAGCCTATCCCTAACCCTCTCCTCGGTCTCGATTCTACGCGTAC

CGGTCATCATCACCATCACCATTGAGTTTAAACCCGCTGATCAGCCTCGACTGTGCCTTCTAGTTGCCAGCCATCTGTTGTTTG

CCCCTCCCCCGTGCCTTCCTTGACCCTGGAAGGTGCCACTCCCACTGTCCTTTCCTAATAAAATGAGGAAATTGCATCGCATT

GTCTGAGTAGGTGTCATTCTATTCTGGGGGGTGGGGTGGGGCAGGACAGCAAGGGGGAGGATTGGGAAGACAATAGCAGGC

ATGCTGGGGATGCGGTGGGCTCTATGGCTTCTGAGGCGGAAAGAACCAGCTGGGGCTCTAGGGGGTATCCCCACGCGCCCTG

TAGCGGCGCATTAAGCGCGGCGGGTGTGGTGCTTACGCGCAGCGTGACCGCTACACTTGCCAGCGCCCTAGCGCCCGCTCCT

TTCGCTTTCTTCCCTTCCTTTCTCGCCACGTTCGCCGGCTTTCCCCGTCAAGCTCTAAATCGGGGCATCCCTTTAGGGTTCCGA

TTTAGTGCTTTACGGCACCTCGACCCCAAAAAACTTGATTAGGGTGATGGTTCACGTAGTGGGCCATCGCCCTGATAGACGG

TTTTTCGCCCTTTGACGTTGGAGTCCACGTTCTTTAATAGTGGACTCTTGTTCCAAACTGGAACAACACTCAACCCTATCTCGG

TCTATTCTTTTGATTTATAAGGGATTTTGGGGATTTCGGCCTATTGGTTAAAAAATGAGCTGATTTAACAAAAATTTAACGCG

AATTAATTCTGTGGAATGTGTGTCAGTTAGGGTGTGGAAAGTCCCCAGGCTCCCCAGGCAGGCAGAAGTATGCAAAGCATGC

ATCTCAATTAGTCAGCAACCAGGTGTGGAAAGTCCCCAGGCTCCCCAGCAGGCAGAAGTATGCAAAGCATGCATCTCAATTA

GTCAGCAACCATAGTCCCGCCCCTAACTCCGCCCATCCCGCCCCTAACTCCGCCCAGTTCCGCCCATTCTCCGCCCCATGGCT

GACTAATTTTTTTTATTTATGCAGAGGCCGAGGCCGCCTCTGCCTCTGAGCTATTCCAGAAGTAGTGAGGAGGCTTTTTTGGA

GGCCTAGGCTTTTGCAAAAAGCTCCCGGGAGCTTGTATATCCATTTTCGGATCTGATCAGCACGTGTTGACAATTAATCATCG

GCATAGTATATCGGCATAGTATAATACGACAAGGTGAGGAACTAAACCATGGCCAAGCCTTTGTCTCAAGAAGAATCCACCC

TCATTGAAAGAGCAACGGCTACAATCAACAGCATCCCCATCTCTGAAGACTACAGCGTCGCCAGCGCAGCTCTCTCTAGCGA

CGGCCGCATCTTCACTGGTGTCAATGTATATCATTTTACTGGGGGACCTTGTGCAGAACTCGTGGTGCTGGGCACTGCTGCTG

CTGCGGCAGCTGGCAACCTGACTTGTATCGTCGCGATCGGAAATGAGAACAGGGGCATCTTGAGCCCCTGCGGACGGTGTCG

ACAGGTGCTTCTCGATCTGCATCCTGGGATCAAAGCGATAGTGAAGGACAGTGATGGACAGCCGACGGCAGTTGGGATTCGT

GAATTGCTGCCCTCTGGTTATGTGTGGGAGGGCTAAGCACTTCGTGGCCGAGGAGCAGGACTGACACGTGCTACGAGATTTC

GATTCCACCGCCGCCTTCTATGAAAGGTTGGGCTTCGGAATCGTTTTCCGGGACGCCGGCTGGATGATCCTCCAGCGCGGGG

ATCTCATGCTGGAGITCTTCGCCCACCCCAACTTGTTTATTGCAGcTTATAATGGTTACAAATAAAGCAATAGCATCACAAAT

-continued

TTCACAAATAAAGCATTTTTTTCACTGCATTCTAGTTGTGGTTTGTCCAAACTCATCAATGTATCTTATCATGTCTGTATACCG

TCGACCTCTAGCTAGAGCTTGGCGTAATCATGGTCATAGCTGTTTCCTGTGTGAAATTGTTATCCGCTCACAATTCCACACAA

CATACGAGCCGGAAGCATAAAGTGTAAAGCCTGGGGTGCCTAATGAGTGAGCTAACTCACATTAATTGCGTTGCGCTCACTG

CCCGCTTTCCAGTCGGGAAACCTGTCGTGCCAGCTGCATTAATGAATCGGCCAACGCGCGGGGAGAGGCGGTTTGCGTATTG

GGCGCTCTTCCGCTTCCTCGCTCACTGACTCGCTGCGCTCGGTCGTTCGGCTGCGGCGAGCGGTATCAGCTCACTCAAAGGCG

GTAATACGGTTATCCACAGAATCAGGGGATAACGCAGGAAAGAACATGTGAGCAAAAGGCCAGCAAAAGGCCAGGAACCG

TAAAAAGGCCGCGTTGCTGGCGTTTTTCCATAGGCTCCGCCCCCCTGACGAGCATCACAAAAATCGACGCTCAAGTCAGAGG

TGGCGAAACCCGACAGGACTATAAAGATACCAGGCGTTTCCCCCTGGAAGCTCCCTCGTGCGCTCTCCTGTTCCGACCCTGCC

GCTTACCGGATACCTGTCCGCCTTTCTCCCTTCGGGAAGCGTGGCGCTTTCTCAATGCTCACGCTGTAGGTATCTCAGTTCGGT

GTAGGTCGTTCGCTCCAAGCTGGGCTGTGTGCACGAACCCCCCGTTCAGCCCGACCGCTGCGCCTTATCCGGTAACTATCGTC

TTGAGTCCAACCCGGTAAGACACGACTTATCGCCACTGGCAGCAGCCACTGGTAACAGGATTAGCAGAGCGAGGTATGTAG

GCGGTGCTACAGAGTTCTTGAAGTGGTGGCCTAACTACGGCTACACTAGAAGGACAGTATTTGGTATCTGCGCTCTGCTGAA

GCCAGTTACCTTCGGAAAAAGAGTTGGTAGCTCTTGATCCGGCAAACAAACCACCGCTGGTAGCGGTGGTTTTTTTGTTTGCA

AGCAGCAGATTACGCGCAGAAAAAAAGGATCTCAAGAAGATCCTTTGATCTTTTCTACGGGGTCTGACGCTCAGTGGAACGA

AAACTCACGTTAAGGGATTTTGGTCATGAGATTATCAAAAAGGATCTTCACCTAGATCCTTTTAAATTAAAAATGAAGTTTTA

AATCAATCTAAAGTATATATGAGTAAACTTGGTCTGACAGTTACCAATGCTTAATCAGTGAGGCACCTATCTCAGCGATCTGT

CTATTTCGITCATCCATAGTTGCCTGACTCCCCGTCGTGTAGATAACTACGATACCGGAGGCCTTACCATCTGGCCCCAGTGC

TGCAATGATACXGCGAGACCCACGCTCACCGGCTCCAGATTTATCAGCAATAAACCAGCCAGCCGGAAGGGCCGAGCGCAG

AAGTGGTCCTGCAACTTTATCCGCCTCCATCCAGTCTATTAATTGTTGCCGGGAAGCTAGACTAAGTACTTCGCCAGTTAATA

GTTTGCGCAACGTTGTTGCCATTGCTACAGGCATCGTGGTGTCACGCTCGTCGTTTGGTATGGCTTCATTCAGCTCCGGTTCCC

AACGATCAAGGCGAGTTACATGATCCCCCATGTTGTGCAAAAAAGCGGTTAGCTCCTTCGGTCCTCCGATCGTTGTCAGAAG

TAAGTTGGCCGCAGTGTTATCACTCATGGTTATGGCAGCACTGCATAATTCTCTTACTGTCATGCCATCCGTAAGATGCTTTTC

TGTGACTGGTGAGTACTCAACCAAGTCATTCTGAGAATAGTGTATGCGGCGACCGAGTTGCTCTTGCCCGOCGTCAATACGG

GATAATACCGCGCCACATAGCAGAACTTTAAAAGTGCTCATCATTGGAAAACGTTCTTCGGGGCGAAAACTCTCAAGGATCT

TACCGCTGTTGAGATCCAGTTCGATGTAACCCACTCGTGCACCCAACTGATCTTCAGCATCTTTTACTTTCACCAGCGTTTCTG

GGTGAGCAAAAACAGGAAGGCAAAATGCCGCAAAAAAGGGAATAAGGGCGACACGGAAATGTTGAATACTCATACTCTTCC

TTTTTCAATATTATTGAAGCATTTATCAGGGTTATTGTCTCATGAGCGGATACATATTTGAATGTATTTAGAAAAATAAACAA

ATAGGGGTTCCGCGCACATTTCCCCGAAAAGTGCCACCTGACGTC

Bmpr2 REV RTN EBEs' amino acid sequence:

LSTEQVVAIAS NN GGKQALEAVKAQLLELRAAPYE (SEQ ID NO: 93)

LSTAQVVAIAS NG GGKQALEGIGEQLLKLRTAPYG (SEQ ID NO: 102)

LSTAQVVAIAS NG GGKQALEGIGEQLLKLRTAPYG (SEQ ID NO: 102)

LSTAQVVAIAS NG GGKQALEGIGEQLLKLRTAPYG (SEQ ID NO: 102)

LSTAQVVAIAS HD GGKPALEAVWAKLPVLRGVPYA (SEQ ID NO: 134)

LSTEQVVAIAS NK GGKQALEAVKAHLLDLLGAPYV (SEQ ID NO: 72)

LSTAQVVAIAS NG GGKQALEGIGEQLLKLRTAPYG (SEQ ID NO: 102)

LSTAQVVAIAS NG GGKQALEGIGEQLLKLRTAPYG (SEQ ID NO: 102)

LSTAQVVAIAS NG GGKQALEGIGEQLLKLRTAPYG (SEQ ID NO: 102)

LSTEQVVAIAS NN GGKQALEAVKAQLLELRAAPYE (SEQ ID NO: 93)

LSTAQVVAIAS HD GGKPALEAVWAKLPVLRGVPYA (SEQ ID NO: 134)

LSTAQVVAIAS HD GGKPALEAVWAKLPVLRGVPYA (SEQ ID NO: 134)

-continued

LSTAQVVAIAS NG GGKQALEGIGEQLLKLRTAPYG (SEQ ID NO: 102)

LSTEQVVAIAS NK GGKQALEAVKAHLLDLLGAPYV (SEQ ID NO: 72)

LSTAQVVAIAS NG GGKQALEGIGEQLLKLRTAPYG (SEQ ID NO: 102)

LSTAQVVAIAS HD GGKPALEAVWAKLPVLRGVPYA (SEQ ID NO: 134)

Bmpr2 REV RTN DNA Sequence:
(Bolded Font: synthesized Ralstonia EBEs)this sequence is
Contiguous (SEQ ID NO: 147):

GACGGATCGGGAGATCTCCCGATCCCCTATGGTCGACTCTCAGTACAATCTGCTCTGATGCCGCATAGTTAAGCCAGTATCTG

CTCCCTGCTTGTGTGTTGGAGGTCGCTGAGTAGTGCGCGAGCAAAATTTAAGCTACAACAAGGCAAGGCTTGACCGACAATT

GCATGAAGAATCTGCTTAGGGTTAGGCGTTTTGCGCTGCTTCGCGATGTACGGGCCAGATATACGCGTTGACATTGATTATTG

ACTAGTTATTAATAGTAATCAATTACGGGGTCATTAGTTCATAGCCCATATATGGAGTTCCGCGTTACATAACTTACGGTAAA

TGGCCCGCCTGGCTGACCGCCCAACGACCCCCGCCCATTGACGTCAATAATGACGTATGTTCCCATAGTAACGCCAATAGGG

ACTTTCCATTGACGTCAATGGGTGGAgTATTTACGGTAAACTGCCCACTTGGCAGTACATCAAGTGTATCATATGCCAAGTAC

GCCCCCTATTGACGTCAATGACGGTAAATGGCCCGCCTGGCATTATGCCCAGTACATGACCTTATGGGACTTTCCTACTTGGC

AGTACATCTACGTATTAGTCATCGCTATTACCATGGTGATGCGGTTTTGGCAGTACATCAATGGGCGTGGATAGCGGTTTGAC

TCACGGGGATTTCCAAGTCTCCACCCCATTGACGTCAATGGGAGTTTGTTTTGGCACCAAAATCAACGGGACTTTCCAAAATG

TCGTAACAACTCCGCCCCATTGACGCAAATGGGCGGTAGGCGTGTACGGTGGGAGGTCTATATAAGCAGAGCTCTCTGGCTA

ACTAGAGAACCCACTGCTTACTGGCTTATCGAAATTAATACGACTCACTATAGGGAGACCCAAGCTGGCTAGCACCATGGAC

TACAAAGACCATGACGGTGATTATAAAGATCATGACATCGATTACAAGGATGACGATGACAAGATGGCCCCCAAGAAGAAG

AGGAAGGTGGGCATTCACCGCGGGGTACCTATGGTGGACTTGAGGACACTCGGTTATTCGCAACAGCAACAGGAGAAAATC

AAGCCTAAGGTCAGGAGCACCGTCGCGCAACACCACGAGGCGCTTGTGGGGCATGGCTTCACTCATGCGCATATTGTCGCGC

TTTCACAGCACCCTGCGGCGCTTGGGACGGTGGCTGTCAAATACCAAGATATGATTGCGGCCCTGCCCGAAGCCACGCACGA

GGCAATTGTAGGGGTCGGTAAACAGTGGTCGGGAGCGCGAGCACTTGAGGCGCTGCTGACTGTGGCGGGTGAGCTTAGGGG

GCCTCCGCTCCAGCTCGACACCGGGCAGCTGCTGAAGATCGCGAAGAGAGGGGGAGTAACAGCGGTAGAGGCAGTGCACGC

CTGGCGCAATGCGCTCACCGGGGCCCCCTT

CTGAGCACCGAGCAGGTGGTGGCCATCGCCAGC AACAAC GGCGGCAAGCAGGCCCTGGAGGCCGTGAAGGCCCAGCTGCTGGAG

CTGAGGGCCGCCCCCTACGAG

CTGAGCACCGCCCAGGTGGTGGCCATCGCCAGC AACGGC GGCGGCAAGCAGGCCCTGGAGGGCATCGGCGAGCAGCTGCTGAAG

CTGAGGACCGCCCCCTACGGC

CTGAGCACCGCCCAGGTGGTGGCCATCGCCAGC AACGGC GGCGGCAAGCAGGCCCTGGAGGGCATCGGCGAGCAGCTGCTGAAG

CTGAGGACCGCCCCCTACGGC

CTGAGCACCGCCCAGGTGGTGGCCATCGCCAGC AACGGC GGCGGCAAGCAGGCCCTGGAGGGCATCGGCGAGCAGCTGCTGAAG

CTGAGGACCGCCCCCTACGGC

CTGAGCACCGCCCAGGTGGTGGCCATCGCCAGC CACGAC GGCGGCAAGCCCGCCCTGGAGGCCGTGTGGGCCAAGCTGCCCGTG

CTGAGGGGCGTGCCCTACGCC

CTGAGCACCGAGCAGGTGGTGGCCATCGCCAGC AACAAG GGCGGCAAGCAGGCCCTGGAGGCCGTGAAGGCCCACCTGCTGGAC

CTGCTGGGCGCCCCCTACGTG

CTGAGCACCGCCCAGGTGGTGGCCATCGCCAGC AACGGC GGCGGCAAGCAGGCCCTGGAGGGCATCGGCGAGCAGCTGCTGAAG

CTGAGGACCGCCCCCTACGGC

CTGAGCACCGCCCAGGTGGTGGCCATCGCCAGC AACGGC GGCGGCAAGCAGGCCCTGGAGGGCATCGGCGAGCAGCTGCTGAAG

CTGAGGACCGCCCCCTACGGC

-continued

CTGAGCACCGCCCAGGTGGTGGCCATCGCCAGC AACGGC GGCGGCAAGCAGGCCCTGGAGGGCATCGGCGAGCAGCTGCTGAAG

CTGAGGACCGCCCCCTACGGC

CTGAGCACCGAGCAGGTGGTGGCCATCGCCAGC AACAAC GGCGGCAAGCAGGCCCTGGAGGCCGTGAAGGCCCAGCTGCTGGAG

CTGAGGGCCGCCCCCTACGAG

CTGAGCACCGCCCAGGTGGTGGCCATCGCCAGC CACGAC GGCGGCAAGCCCGCCCTGGAGGCCGTGTGGGCCAAGCTGCCCGTG

CTGAGGGGCGTGCCCTACGCC

CTGAGCACCGCCCAGGTGGTGGCCATCGCCAGC CACGAC GGCGGCAAGCCCGCCCTGGAGGCCGTGTGGGCCAAGCTGCCCGTG

CTGAGGGGCGTGCCCTACGCC

CTGAGCACCGCCCAGGTGGTGGCCATCGCCAGC AACGGC GGCGGCAAGCAGGCCCTGGAGGGCATCGGCGAGCAGCTGCTGAAG

CTGAGGACCGCCCCCTACGGC

CTGAGCACCGAGCAGGTGGTGGCCATCGCCAGC AACAAG GGCGGCAAGCAGGCCCTGGAGGCCGTGAAGGCCCACCTGCTGGAC

CTGCTGGGCGCCCCCTACGTG

CTGAGCACCGCCCAGGTGGTGGCCATCGCCAGC AACGGC GGCGGCAAGCAGGCCCTGGAGGGCATCGGCGAGCAGCTGCTGAAG

CTGAGGACCGCCCCCTACGGC

CTGAGCACCGCCCAGGTGGTGGCCATCGCCAGC CACGAC GGCGGCAAGCCCGCCCTGGAGGCCGTGTGGGCCAAGCTGCCCGTG

CTGAGGGGCGTGCCCTACGCC

CTGAGCACCGAGCAGGTGOTGACCATCGCCAGC

AGCATCUUAGGACGGCCAGCCTTGGAGTCCATCGTAGCCCAATTGTCCAGGCCCGATCCCGCGTTGGCTGCGTTAACGAATG

ACCATCTGGTGGCGTTGGCATGTCTTGGTGGACGACCCGCGCTCGATGCAGTCAAAAAGGGTCTGCCTCATGCTCCCGCATT

GATCAAAAGAACCAACCGGCGGATTCCCGAGAGAACTTCCCATCGAGTCGCGGGATCCCAACTAGTCAAAAGTGAACTGGA

GGAGAAGAAATCTGAACTTCGTCATAAATTGAAATATGTCCTCATGAATATATTGAATTAATTGAAATTGCCAGAAATTCC

ACTCAGGATAGAATTCTTGAAATGAAGGTAATGGAATTTTTTATGAAAGTTTATGGATATAGAGGTAAACATTTGGGTGGAT

CAAGGAAACCGGACGGAGCAATTTATACTGTCGGATCTCCTATTGATTACGGTGTGATCGTGGATACTAAAGCTTATAGCGG

AGGTTATAATCTGCCAATTGGCCAAGCAGATGAAATGCAACGATATGTCGAAGAAAATCAAACACGAAACAAACATATCAA

CCCTAATGAATGGTGGAAAGTCTATCCATCTTCTGTAACGGAATTTAAGTTTTTATTTGTGAGTGGTCACTTAAAGGAAACT

ACAAAGCTCAGCTACACGATTAAATCATATCACTAATTGTAATGGAGCTGTTCTTAGTGTAGAAGAGCTTTTAATTGGTGGA

GAAATGATTAAAGCCGGCACATTAACCTTAGAGGAAGTCAGACGGAAATTTATAACGGCGAGATAAACTTTTAAGGGCCC

TTCGAAGGTAAGCCTATCCCTAACCCTCTCCTCGGTCTCGATTCTACGCGTACCGGTCATCATCACCATCACCATTGAGTTTA

AACCCGCTGATCAGCCTCGACTGTGCCTTCTAGTTGCCAGCCATCTGTTGTTTGCCCCTCCCCCGTGCCTTCCTTGACCCTGGA

AGGTGCCACTCCCACTGTCCTTTCCTAATAAAATGAGGAAATTGCATCGCATTGTCTGAGTAGGTGTCATTCTATTCTGGGGG

GTGGGGTGGGGCAGGACAGCAAGGGGGAGGATTGGGAAGACAATAGCAGGCATGCTGGGGATGCGGTGGGCTCTATGGCTT

TGGTTACGCGCAGCGTGACCGCTACACTTGCCAGCGCCCTAGCGCCCGCTCCTTTCGCTTTCTTCCCTTCCTTTCTCGCCACGT

TCGCCGGCTTTCCCCGTCAAGCTCTAAATCGGGGCATCCCTTTAGGGTTCCGATTTAGTGCTTTACGGCACCTCGACCCCAAA

AAACTTGATTAGGGTGATGGTTCACGTAGTGGGCCATCGCCCTGATAGACGGTTTTTCGCCCTTTGACGTTGGAGTCCACGTT

CTTTAATAGTGGACTCTTGTTCCAAACTGGAACAACACTCAACCCTATCTCGGTCTATTCTTTTGATTTATAAGGGATTTTGGG

GATTTCGGCCTATTGGTTAAAAAATGAGCTGATTTAACAAAAATTTAACGCGAATTAATTCTGTGGAATGTGTGTCAGTTAGG

GTGTGGAAAGTCCCCAGGCTCCCCAGGCAGGCAGAAGTATGCAAAGCATGCATCTCAATTAGTCAGCAACCAGGTGTGGAA

AGTCCCCAGGCTCCCCAGCAGGCAGAAGTATGCAAAGCATGCATCTCAATTAGTCAGCAACCATAGTCCCGCCCCTAACTCC

GCCCATCCCGCCCCTAACTCCGCCCAGTTCCGCCCATTCTCCGCCCCATGGCTGACTAATTTTTTTTATTTATGCAGAGGCCGA

GGCCGCCTCTGCCTCTGAGCTATTCCAGAAGTAGTGAGGAGGCTTTTTTGGAGGCCTAGGCTTTTGCAAAAAGCTCCCGGGA

-continued

```
GCTTGTATATCCATTTTCGGATCTGATCAGCACGTGTTGACATTAATCATCGGCATAGTATATCGGCATAGTATAATACGAC
AAGGTGAGGAACTAAACCATGGCCAAGCCTTTGTCTCAAGAAGAATCTCACCCTCATTGAAAGAGCAACGGCTACAATCAAC
AGCATCCCCATCTCTGAAGACTACAGCGTCGCCAGCGCAGCTCTCTCTAGCGACGGCCGCATCTTCACTGGTGTCAATGTATA
TCATTTTACTGGGGGACCTTGTGCAGAACTCGTGGTGCTGGGCACTGCTGCTGCTGCGGCAGGTGGCAACCTGACTTGTATCG
TCGCGATCGGAAATGAGAACAGGGGCATCTTGAGCCCCTGCGGACGGTGTCGACAGGTGCTTCTCGATCTGCATCCTGGGAT
CAAAGCGATAGTGAAGGACAGTGATGGACAGCCGACGGCAGTTGGGATTCGTGAATTGCTGCCCTCTGGTTATGTGTGGGAG
GGCTAAGCACTTCGTGGCCGAGGAGCAGGACTGACACGTGCTACGAGATTTCGATTCCACCGCCGCCTTCTATGAAAGGTTG
GGCTTCGGAATCGTTTTCCGGGACGCCGGCTGGATGATCCTCCAGCGCGGGGATCTCATGCTGGAGTTCTTCGCCCACCCCAA
CTTGTTTATTGCAGCTTATAATGGTTACAAATAAAGCAATAGCATCACAAATTTCACAAATAAAGCATTTTTTTCACTGCATT
CTAGTTGTGGTTTGTCCAAACTCATCAATGTATCTTATCATGTCTGTATACCGTCGACCTCTAGCTAGAGCTTGGCGTAATCAT
GGTCATAGCTGTTTCCTGTGTGAAATTGTTATCCGCTCACAATTCCACACAACATACGAGCCGGAAGCATAAAGTGTAAAGC
CTGGGGTGCCTAATGAGTGAGCTAACTCACATTAATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATTGGGCGCTCTTCCGCTTCCTCGCTCACTGACTC
GCTGCGCTCGGTCGTTCGGCTGCGGCGAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGCGTTGCTGGCGTTTTTCCAT
AGGCTCCGCCCCCCTGACGAGCATCACAAAAATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCTGCCGCTTACCGGATACCTGTCCGCCTTTCTCCCT
TCGGGAAGCGTGGCGCTTTCTCAATGCTCACGCTGTAGGTATCTCAGTTCGGTGTAGGTCGTTCGCTCCAAGCTGGGCTGTGT
GCACGAACCCCCCGTTCAGCCCGACCGCTGCGCCTTATCCGGTAACTATCGTCTTGAGTCCAACCCGGTAAGACACGACTTAT
CGCCACTGGCAGCAGCCACTGGTAACAGGATTAGCAGAGCGAGGTATGTAGGCGGTGCTACAGAGTTCTTGAAGTGGTGGC
CTAACTACGGCTACACTAGAAGGACAGTATTTGGTATCTGCGCTCTGCTGAAGCCAGTTACCTTCGGAAAAAGAGTTGGTAG
CTCTTGATCCGGCAAACAAACCACCGCTGGTAGCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGTTCATCCATAGTTGCCTGACTC
CCCGTGTAGATAACTACGATACGGGAGGGCTTACCATCTGGCCCCAGTGCTGcAATGATACCGCGAGACCCACGCTCAC
CGGCTCCAGATTTATCAGCAATAAACCAGCCAGCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTAATAGTTTGCGCAACGTTGTTGCCATTGCTACAG
GCATCGTGGTGTCACGCTCGTCGTTTGGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTTTCTGTGACTGGTGAGTACTCAACCAAGTCAT
TCTGAGAATAGTGTATGCGGCGACCGAGTTGCTCTTGCCCGGCGTCAATACGGGATAATACCGCTTCCACATAGCAGAACTTT
AAAAGTGCTCATCATTGGAAAACGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGAGCAAAAACAGGAAGGCAAAATG
CCGCAAAAAAGGGAATAAGGGCGACACGGAAATGTTGAATACTCATACTCTTCCTTTTTCAATATTATTGAAGCATTTATCA
GGGTTATTGTCTCATGAGCGGATACATATTTGAATGTATTTAGAAAAATAAACAAATAGGGGTTCCGCGCACATTTCCCCGA
AAAGTGCCACCTGACGTC
```

Example 5

A library of *Ralstonia* EBEs and backbone vectors were made which could be used to assemble full length *Ralstonia* DNA binding domains into *Ralstonia* or *Xanthomonas* TALEN backbones, utilizing the golden gate assembly method. The RTNs were co-transfected into the Rat C6 cell line and gDNA extracted for analysis 48 hrs post transfection. A 420 bp gDNA fragment containing the RTN binding site was amplified by PCR. This amplicon was then subjected to the Cell assay using Surveyor Mutation Detection Kit (Transgenomic) as per manufacturer protocol. In brief, the amplicon is denatured into single stranded DNA and slowly re-annealed back to double stranded DNA. During this process, considering the original pool was a mixture of WT and mutated sequences, there will be cross hybridization between WT and mutant strands leading to formation of heteroduplexes. Upon treatment of this re-annealed pool with the Surveyor Nuclease, it recognizes the heteroduplexes and cleaves them, which generated two shorter fragments from (255 bp and 165 bp) the original amplicon (420 bp).

Terminology:

pRVD: plasmid containing a single *Ralstonia* EBE. Individual EBEs were gene synthesized and cloned in FLASH-XTN sub-array backbone (XbaI, BamHI).

pFus X: a sub-array plasmid that holds the first 10 EBEs of any given RTN. The required piece was gene synthesized and cloned into pHSG-298 (Sacl, Sbfl).

pFUS Z: a sub-array plasmid that holds EBE 11 upto the second-last EBE of any given RTN.

Eg: Z4 holds EBEs 11-14, Z5 holds EBEs 11-15 and Z6 holds EBEs 11-16. Gene synthesized and cloned into pHSG-298 (Sacl, Sbfl).

XTN-bb: *Xanthomonas* TAL backbone that contains the N-terminal and C-terminal *Xanthomonas* TAL domains fused to FokI nuclease. This backbone specifies a T nucleotide 5' of the target sequence specified by the EBEs. It also contains the last half EBE that specifies the last nucleotide of the targeted sequence. Therefore there are four XTN-bb plasmids, each specifying a different final nucleotide of the targeted sequence (same as FLASH XTN backbones).

All plasmids are stored at 150 ng/ul in 0.1×TE buffer.

Methods: (building a 16 EBE DNA binding domain and cloning it into a *Xanthomonas* TALEN backbone).

Assembly of a custom TALEN or TAL effector construct involves two steps: (i) assembly of repeat modules (pRVDs) into sub-arrays of 1-10 repeats and (ii) joining of the sub-arrays into a backbone to make the final construct.

We constructed of a TALEN monomer with a 17 RVD array (5'-TGATAGTCGC-CTTATG-T-3', SEQ ID NO: 208). Select from the pRVD plasmids those that encode RVDs 1-10 in the array using plasmids numbered in that order. For example, the plasmid for the first RVD would be gRTN-1T, the second gRTN-2G, the third gRTN-3A etc. Modules from these plasmids will be cloned into sub-array plasmid pFUS-X. Next, select modules for RVDs 11-16 in the 16 RVD array again starting with plasmids numbered from 1. Thus for RVD 11 gRTN-1C would be used, for RVD 12 gRTN-2T, etc. The pFUS-Z plasmids are numbered 1-10 and should be selected according to the number of EBEs going in. Thus, in our example, pFUS-Z6 should be used.

The pRVDs and sub-array plasmids (150 ng each) are subjected to digestion and ligation in a single 20 ul reaction containing 1 ul BsaI (10 U, New England BioLabs) and 1 ul T4 DNA Ligase (2000 U, New England BioLabs) in T4 DNA ligase buffer (New England BioLabs). The reaction is incubated in a thermocycler for 10 cycles of 5 min at 37 C and 10 min at 16 C, then heated to 50 C for 5 min and then 80 C for 5 min. Then, 1 ul 25 mM ATP and 1 ul Plasmid Safe DNase (10 U, Epicentre) are added. The mixture is incubated at 37 C for 1 h, then used to transform *Escherichia coli* cells. Cells are plated on LB agar containing 50 mg/ml Kanamycin, overnight at 37° C.

Up to six colonies from each transformation were screened with M13 fwd and rev primers, via colony PCR, to identify clones that contain a full-length sub-array. Full length pFUS-X sub-array clones should produce a 1.1 kb band and full-length pFUS-Z6 clones should produce a 700 bp band (add or subtract 105 bp for each EBE more or less). Cultures were started overnight cultures of a full-length pFUS-X and a full-length pFUS-Z6 clone.

We isolated plasmid DNA from your pFUS-X and pFUS-Z cultures. Sub-arrays were joined into one of the four backbone plasmids. A 20 ul digestion and ligation reaction mixture is prepared with 150 ng each of the pFUS-X and pFUS-Z plasmids, 150 ng of the backbone plasmid, in this case XTN-bbT, 1 ul Esp3I (10 U, Thermo Scientific) and 1 ul T4 DNA Ligase (2000 U, New England Biolabs) in T4 DNA ligase buffer. The reaction is then incubated in a thermocycler for 3 cycles of 10 min at 37 C and 15 min at 16 C. The reaction is then incubated at 37 C for an additional 30 min and heated to 50 C for 5 min, then 80 C for 5 min. After cooling to room temperature, 1 ul 25 mM ATP and 1 ul Plasmid Safe DNase (10 U, Epicenter) were added and incubated at 37 C for 1 hr. The reaction is then used to transform *E. coli* as above, except that Plasmid Safe. Also, in this step, ampicillin (100 mg/ml) is used in place of Kanamycin for selection of transformants.

We screened up to three colonies from each transformation via colony PCR with XTN-VF and XTN-VR2 primers and started overnight cultures of 1 full length clone for each RTN (2.1 kb band indicates 17 EBE array). We then isolated plasmid DNA and identify clones containing the final, full-length repeat array by DNA sequencing with XTN-VF, XTN-VR1 and XTN-VR2.

```
XbaI and BamHI digested XTN sub-array backbone
(sites underlined):SEQ ID NO: 148:
(BamHI)GGATCCCGGGCCCGTCGACTGCAGAGGCCTGCATGCAAGCTT

GGCGTAATCATGGTCATAGCTGTTTCCTGTGTGAAATTGTTATCCGCTC

ACAATTCCACACAACATACGAGCCGGAAGCATAAAGTGTAAAGCCTGGG

GTGCCTAATGAGTGAGCTAACTCACATTAATTGCGTTGCGCTCACTGCC

CGCTTTCCAGTCGGGAAACCTGTCGTGCCAGCTGCATTAATGAATCGGC

CAACGCGCGGGGAGAGGCGGTTTGCGTATTGGGCGCTCTTCCGCTTCCT

CGCTCACTGACTCGCTGCGCTCGGTCGTTCGGCTGCGGCGAGCGGTATC

AGCTCACTCAAAGGCGGTAATACGGTTATCCACAGAATCAGGGGATAAC

GCAGGAAAGAACATGTGAGCAAAAGGCCAGCAAAAGGCCAGGAACCGTA

AAAAGGCCGCGTTGCTGGCGTTTTTCCATAGGCTCCGCCCCCCTGACGA

GCATCACAAAAATCGACGCTCAAGTCAGAGGTGGCGAAACCCGACAGGA

CTATAAAGATACCAGGCGTTTCCCCCTGGAAGCTCCCTCGTGCGCTCTC

CTGTTCCGACCCTGCCGCTTACCGGATACCTGTCCGCCTTTCTCCCTTC

GGGAAGCGTGGCGCTTTCTCATAGCTCACGCTGTAGGTATCTCAGTTCG

GTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCC

GGTAAGACACGACTTATCGCCACTGGCAGCAGCCACTGGTAACAGGATT

AGCAGAGCGAGGTATGTAGGCGGTGCTACAGAGTTCTTGAAGTGGTGGC

CTAACTACGGCTACACTAGAAGAACAGTATTTGGTATCTGCGCTCTGCT

GAAGCCAGTTACCTTCGGAAAAAGAGTTGGTAGCTCTTGATCCGGCAAA

CAAACCACCGCTGGTAGCGGTGGTTTTTTTGTTTGCAAGCAGCAGATTA

ACGCGCAGAAAAAAAGGATCTCAAGAAGATCCTTTGATCTTTTCTACGGG
```

GTCTGACGCTCAGTGGAACGAAAACTCACGTTAAGGGATTTTGGTCATG

AGATTATCAAAAAGGATCTTCACCTAGATCCTTTTAAATTAAAAATGAA

GTTTTAAATCAATCTAAAGTATATATGAGTAAACTTGGTCTGACAGTTA

CCAATGCTTAATCAGTGAGGCACCTATCTCAGCGATCTGTCTATTTCGT

TCATCCATAGTTGCCTGACTCCCCGTCGTGTAGATAACTACGATACGGG

AGGGCTTACCATCTGGCCCCAGTGCTGCAATGATACCGCGAGgCCACG

CTCACCGGCTCCAGATTTATCAGCAATAAACCAGCCAGCCGGAAGGGCC

GAGCGCAGAAGTGGTCCTGCAACTTTATCCGCCTCCATCCAGTCTATTA

ATTGTTGCCGGGAAGCTAGAGTAAGTAGTTCGCCAGTTAATAGTTTGCG

CAACGTTGTTGCCATTGCTACAGGCATCGTGGTGTCACGCTCGTCGTTT

GGTATGGCTTCATTCAGCTCCGGTTCCCAACGATCAAGGCGAGTTACAT

GATCCCCCATGTTGTGCAAAAAAGCGGTTAGCTCCTTCGGTCCTCCGAT

CGTTGTCAGAAGTAAGTTGGCCGCAGTGTTATCACTCATGGTTATGGCA

GCACTGCATAATTCTCTTACTGTCATGCCATCCGTAAGATGCTTTTCTG

TGACTGGTGAGTACTCAACCAAGTCATTCTGAGAATAGTGTATGCGGCG

ACCGAGTTGCTCTTGCCCGGCGTCAATACGGGATAATACCGCGCCACAT

AGCAGAACTTTAAAAGTGCTCATCATTGGAAAACGTTCTTCGGGGCGAA

AACTCTCAAGGATCTTACCGCTGTTGAGATCCAGTTCGATGTAACCCAC

TCGTGCACCCAACTGATCTTCAGCATCTTTTACTTTCACCAGCGTTTCT

GGGTGAGCAAAAACAGGAAGGCAAAATGCCGCAAAAAAGGGAATAAGGG

CGACACGGAAATGTTGAATACTCATACTCTTCCTTTTTCAATATTATTG

AAGCATTTATCAGGGTTATTGTCTCATGAGCGGATACATATTTGAATGT

ATTTAGAAAAATAAACAAATAGGGGTTCCGCGCACATTTCCCCGAAAAG

TGCCACCTGACGTCTAAGAAACCATTATTATCATGACATTAACCTATAA

AAATAGGCGTATCACGAGGCCCTTTCGTCTCGCGCGTTTCGGTGATGAC

GGTGAAAACCTCTGACACATGCAGCTCCCGGAGACGGTCACAGCTTGTC

TGTAAGCGGATGCCGGGAGCAGACAAGCCCGTCAGGGCGCGTCAGCGGG

TGTTGGCGGGTGTCGGGGCTGGCTTAACTATGCGGCATCAGAGCAGATT

GTACTGAGAGTGCACCATATGCGGTGTGAAATACCGCACAGATGCGTAA

GGAGAAAATACCGCATCAGGCGCCATTCGCCATTCAGGCTGCGCAACTG

TTGGGAAGGGCGATCGGTGCGGGCCTCTTCGCTATTACGCCAGCTGGCG

AAAGGGGGATGTGCTGCAAGGCGATTAAGTTGGGTAACGCCAGGGTTTT

CCCAGTCACGACGTTGTAAAACGACGGCCAGTGAATTCGAGCTCGGTAC

CTCGCGAATGCATCTAGA(XbaI)

XTN-bb (BsmBI digested, sites are self excised from the backbone during digestion):
Undelined sequences overlap with sub-arrays pFUS-X and pFUS-Z.
XTN-bbA: is replaced with TCTAACATC XTN-bbC: is replaced with TCCCACGAC XTN-bbG: is replaced with AATAATAAC XTN-bbT: is replaced with TCTAATGGG SEQ ID NO 149:
pFUS-Z overlap CTGACACCCGAACAGGTGGTCGCCATTGCTNNNNN

NNNNGGAGGACGGCCAGCCTTGGAGTCCATCGTAGCCCAATTGTCCAGGC

CCGATCCCGCGTTGGCTGCGTTAACGAATGACCATCTGGTGGCGTTGGCA

TGTCTTGGTGGACGACCCGCGCTCGATGCAGTCAAAAAGGGTCTGCCTCA

TGCTCCCGCATTGATCAAAAGAACCAACCGGCGGATTCCCGAGAGAACTT

CCCATCGAGTCGCGGGATCCCAACTAGTCAAAAGTGAACTGGAGGAGAAG

AAATCTGAACTTCGTCATAAATTGAAATATGTGCCTCATGAATATATTGA

ATTAATTGAAATTGCCAGAAATTCCACTCAGGATAGAATTCTTGAAATGA

AGGTAATGGAATTTTTTATGAAAGTTTATGGATATAGAGGTAAACATTTG

GGTGGATCAAGGAAACCGGACGGAGCAATTTATACTGTCGGATCTCCTAT

TGATTACGGTGTGATCGTGGATACTAAAGCTTATAGCGGAGGTTATAATC

TGCCAATTGGCCAAGCAGATGAAATGCAACGATATGTCGAAGAAAATCAA

ACACGAAACAAACATATCAACCCTAATGAATGGTGGAAAGTCTATCCATC

TTCTGTAACGGAATTTAAGTTTTTATTTGTGAGTGGTCACTTTAAAGGAA

ACTACAAAGCTCAGCTTACACGATTAAATCATATCACTAATTGTAATGGA

GCTGTTCTTAGTGTAGAAGAGCTTTTAATTGGTGGAGAAATGATTAAAGC

CGGCACATTAACCTTAGAGGAAGTCAGACGGAAATTTAATAACGGCGAGA

TAAACTTTTAAGGGCCCTTCGAAGGTAAGCCTATCCCTAACCCTCTCCTC

GGTCTCGATTCTACGCGTACCGGTCATCATCACCATCACCATTGAGTTTA

AACCCGCTGATCAGCCTCGACTGTGCCTTCTAGTTGCCAGCCATCTGTTG

TTTGCCCCTCCCCCGTGCCTTCCTTGACCCTGGAAGGTGCCACTCCCACT

GTCCTTTCCTAATAAAATGAGGAAATTGCATCGCATTGTCTGAGTAGGTG

TCATTCTATTCTGGGGGGTGGGGTGGGGCAGGACAGCAAGGGGGAGGATT

GGGAAGACAATAGCAGGCATGCTGGGGATGCGGTGGGCTCTATGGCTTCT

GAGGCGGAAAGAACCAGCTGGGGCTCTAGGGGGTATCCCCACGCGCCCTG

TAGCGGCGCATTAAGCGCGGCGGGTGTGGTGGTTACGCGCAGCGTGACCG

CTACACTTGCCAGCGCCCTAGCGCCCGCTCCTTTCGCTTTCTTCCCTTCC

TTTCTCGCCACGTTCGCCGGCTTTCCCCGTCAAGCTCTAAATCGGGGCAT

CCCTTTAGGGTTCCGATTTAGTGCTTTACGGCACCTCGACCCCAAAAAAC

TTGATTAGGGTGATGGTTCACGTAGTGGGCCATCGCCCTGATAGACGGTT

TTTCGCCCTTTGACGTTGGAGTCCACGTTCTTTAATAGTGGACTCTTGTT

CCAAACTGGAACAACACTCAACCCTATCTCGGTCTATTCTTTTGATTTAT

AAGGGATTTTGGGGATTTCGGCCTATTGGTTAAAAAATGAGCTGATTTAA

CAAAAATTTAACGCGAATTAATTCTGTGGAATGTGTGTCAGTTAGGGTGT

GGAAAGTCCCCAGGCTCCCCAGGCAGGCAGAAGTATGCAAAGCATGCATC

TCAATTAGTCAGCAACCAGGTGTGGAAAGTCCCCAGGCTCCCCAGCAGGC

GAAGAAGTATGCAAAGCATGCATCTCAATTAGTCAGCAACCATAGTCCCG

CCCCTAACTCCGCCCATCCCGCCCCTAACTCCGCCCAGTTCCGCCCATTC

TCCGCCCCATGGCTGACTAATTTTTTTTATTTATGCAGAGGCCGAGGCCG

CCTCTGCCTCTGAGCTATTCCAAGTAGTGAGGAGGCTTTTTTGGAGGCCT

-continued

AGGCTTTTGCAAAAAGCTCCCGGGAGCTTGTATATCCATTTTCGGATCTG
ATCAGCACGTGTTGACAATTAATCATCGGCATAGTATATCGGCATAGTAT
AATACGACAAGGTGAGGAACTAAACCATGGCCAAGCCTTTGTCTCAAGAA
GAATCCACCCTCATTGAAAGAGCAACGGCTACAATCAACAGCATCCCCAT
CTCTGAAGACTACAGCGTCGCCAGCGCAGCTCTCTCTAGCGACGGCCGCA
TCTTCACTGGTGTCAATGTATATCATTTTACTGGGGGACCTTGTGCAGAA
CTCGTGGTGCTGGGCACTGCTGCTGCTGCGGCAGCTGGCAACCTGACTTG
TATCGTCGCGATCGGAAATGAGAACAGGGGCATCTTGAGCCCCTGCGGAC
GGTGTCGACAGGTGCTTCTCGATCTGCATCCTGGGATCAAAGCGATAGTG
AAGGACAGTGATGGACAGCCGACGGCAGTTGGGATTCGTGAATTGCTGCC
CTCTGGTTATGTGTGGGAGGGCTAAGCACTTCGTGGCCGAGGAGCAGGAC
TGACACGTGCTACGAGATTTCGATTCCACCGCCGCCTTCTATGAAAGGTT
GGGCTTCGGAATCGTTTTCCGGGACGCCGGCTGGATGATCCTCCAGCGCG
GGGATCTCATGCTGGAGTTCTTCGCCCACCCCAACTTGTTTATTGCAGCT
TATAATGGTTACAAATAAAGCAATAGCATCACAAATTTCACAAATAAAGC
ATTTTTTTCACTGCATTCTAGTTGTGGTTTGTCCAAACTCATCAATGTAT
CTTATCATGTCTGTATACCGTCGACCTCTAGCTAGAGCTTGGCGTAATCA
TGGTCATAGCTGTTTCCTGTGTGAAATTGTTATCCGCTCACAATTCCACA
CAACATACGAGCCGGAAGCATAAAGTGTAAAGCCTGGGGTGCCTAATGAG
TGAGCTAACTCACATTAATTGCGTTGCGCTCACTGCCCGCTTTCCAGTCG
GGAAACCTGTCGTGCCAGCTGCATTAATGAATCGGCCAACGCGCGGGGAG
AGGCGGTTTGCGTATTGGGCGCTCTTCCGCTTCCTCGCTCACTGACTCGC
TGCGCTCGGTCGTTCGGCTGCGGCGAGCGGTATCAGCTCACTCAAAGGCG
GTAATACGGTTATCCACAGAATCAGGGGATAACGCAGGAAAGAACATGTG
AGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGC
TCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCAA
TGCTCACGCTGTAGGTATCTCAGTTCGGTGTAGGTCGTTCGCTCCAAGCT
GGGCTGTGTGCACGAACCCCCCGTTCAGCCCGACCGCTGCGCCTTATCCG
GTAACTATCGTCTTGAGTCCAACCCGGTAAGACACGACTTATCGCCACTG
GCAGCAGCCACTGGTAACAGGATTAGCAGAGCGAGGTATGTAGGCGGTGC
TACAGAGTTCTTGAAGTGGTGGCCTAACTACGGCTACACTAGAAGGACAG
TATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATC
CTTTGATCTTTTCTACGGGGTCTGACGCTCAGTGGAACGAAAACTCACGT
TAAGGGATTTTGGTCATGAGATTATCAAAAAGGATCTTCACCTAGATCCT
TTTAAATTAAAAATGAAGTTTTAAATCAATCTAAAGTATATATGAGTAAA

-continued

CTTGGTCTGACAGTTACCAATGCTTAATCAGTGAGGCACCTATCTCAGCG
ATCTGTCTATTTCGTTCATCCATAGTTGCCTGACTCCCCGTCGTGTAGAT
AACTACGATACGGGAGGGCTTACCATCTGGCCCCAGTGCTGCAATGATAC
CGCGAGACCCACGCTCACCGGCTCCAGATTTATCAGCAATAAACCAGCCA
GCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTA
ATAGTTTGCGCAACGTTGTTGCCATTGCTACAGGCATCGTGGTGTCACGC
TCGTCGTTTGGTATGGCTTCATTCAGCTCCGGTTCCCAACGATCAAGGCG
AGTTACATGATCCCCCATGTTGTGCAAAAAAGCGGTTAGCTCCTTCGGTC
CTCCGATCGTTGTCAGAAGTAAGTTGGCCGCAGTGTTATCACTCATGGTT
ATGGCAGCACTGCATAATTCTCTTACTGTCATGCCATCCGTAAGATGCTT
TTCTGTGACTGGTGAGTACTCAACCAAGTCATTCTGAGAATAGTGTATGC
GGCGACCGAGTTGCTCTTGCCCGGCGTCAATACGGGATAATACCGCGCCA
CATAGCAGAACTTTAAAAGTGCTCATCATTGGAAAACGTTCTTCGGGGCG
AAAACTCTCAAGGATCTTACCGCTGTTGAGATCCAGTTCGATGTAACCCA
CTCGTGCACCCAACTGATCTTCAGCATCTTTTACTTTCACCAGCGTTTCT
GGGTGAGCAAAAACAGGAAGGCAAAATGCCGCAAAAAAGGGAATAAGGGC
GACACGGAAATGTTGAATACTCATACTCTTCCTTTTTCAATATTATTGAA
GCATTTATCAGGGTTATTGTCTCATGAGCGGATACATATTTGAATGTATT
TAGAAAAATAAACAAATAGGGGTTCCGCGCACATTTCCCCGAAAAGTGCC
ACCTGACGTCGACGGATCGGGAGATCTCCCGATCCCCTATGGTCGACTCT
CAGTACAATCTGCTCTGATGCCGCATAGTTAAGCCAGTATCTGCTCCCTG
CTTGTGTGTTGGAGGTCGCTGAGTAGTGCGCGAGCAAAATTTAAGCTACA
ACAAGGCAAGGCTTGACCGACAATTGCATGAAGAATCTGCTTAGGGTTAG
GCGTTTTGCGCTGCTTCGCGATGTACGGGCCAGATATACGCGTTGACATT
GATTATTGACTAGTTATTAATAGTAATCAATTACGGGGTCATTAGTTCAT
AGCCCATATATGGAGTTCCGCGTTACATAACTTACGGTAAATGGCCCGCC
TGGCTGACCGCCCAACGACCCCCGCCCATTGACGTCAATAATGACGTATG
TTCCCATAGTAACGCCAATAGGGACTTTCCATTGACGTCAATGGGTGGAg
TATTTACGGTAAACTGCCCACTTGGCAGTACATCAAGTGTATCATATGCC
AAGTACGCCCCCTATTGACGTCAATGACGGTAAATGGCCCGCCTGGCATT
ATGCCCAGTACATGACCTTATGGGACTTTCCTACTTGGCAGTACATCTAC
GTATTAGTCATCGCTATTACCATGGTGATGCGGTTTTGGCAGTACATCAA
TGGGCGTGGATAGCGGTTTGACTCACGGGGATTTCCAAGTCTCCACCCCA
TTGACGTCAATGGGAGTTTGTTTTGGCACCAAAATCAACGGGACTTTCCA
AAATGTCGTAACAACTCCGCCCCATTGACGCAAATGGGCGGTAGGCGTGT
ACGGTGGGAGGTCTATATAAGCAGAGCTCTCTGGCTAACTAGAGAACCCA
CTGCTTACTGGCTTATCGAAATTAATACGACTCACTATAGGGAGACCCAA
GCTGGCTAGCACCATGGACTACAAAGACCATGACGGTGATTATAAAGATC
ATGACATCGATTACAAGGATGACGATGACAAGATGGCCCCCAAGAAGAAG
AGGAAGGTGGGCATTCACCGCGGGGTACCTATGGTGGACTTGAGGACACT

-continued

CGGTTATTCGCAACAGCAACAGGAGAAAATCAAGCCTAAGGTCAGGAGCA

CCGTCGCGCAACACCACGAGGCGCTTGTGGGGCATGGCTTCACTCATGCG

CATATTGTCGCGCTTTCACAGCACCCTGCGGCGCTTGGGACGGTGGCTGT

CAAATACCAAGATATGATTGCGGCCCTGCCCGAAGCCACGCACGAGGCAA

TTGTAGGGGTCGGTAAACAGTGGTCGGGAGCGCGAGCACTTGAGGCGCTG

CTGACTGTGGCGGGTGAGCTTAGGGGGCCTCCGCTCCAGCTCGACACCGG

GCAGCTGCTGAAGATCGCGAAGAGAGGGGGAGTAACAGCGGTAGAGGCAG

TGCACGCCTGGCGCAATGCGCTCACCGGGGCCCCCTT

GAAC pFUS-X overlap

BamHI and XbaI flanked pRVD fragments
(gene synthesized, BamHI-EBE-XbaI)):

gXTN-1C:
TCTAGAGGTCTCATTGACCCCAGACCAGGTAGTCGCAATCGCGTCAcatg
acGGGGGAAAGCAAGCCCTGGAAACCGTGCAAAGGTTGTTGCCGGTCCTT
TGTCAAGACCACGGCAGAGACCGGATCC (SEQ ID NO: 154)

gXTN-2C:
TCTAGAGGTCTCACGGCctgactcccgatcaagttgtagcgattgcgtcg
CATGACggagggaaacaagcattggagactgtccaacggctccttcccgt
gttgtgtcaagcccacggAGAGACCGGATCC (SEQ ID NO: 155)

gXTN-3C:
TCTAGAGGTCTCAacggtTTGACGCCTGCACAAGTGGTCGCCATCGCCAG
CcatgatGGCGGTAAGCAGGCGCTGGAAACAGTACAGCGCCTGCTGCCTG
TACTGTGCCAGGATCATGAGAGACCGGATCC (SEQ ID NO: 156)

gXTN-4C:
TCTAGAGGTCTCACATGGActgaccccagaccaggtagtcgcaatcgcgt
caCATGACgggggaaagcaagccctggaaaccgtgcaaaggttgttgccg
gtcctttgtcaagaccacAGAGACCGGATCC (SEQ ID NO: 157)

gXTN-5C:
TCTAGAGGTCTCAccacggcCTGACCCCAGACCAGGTAGTCGCAATCGCG
TCAcatgacGGGGGAAAGCAAGCCCTGGAAACCGTGCAAAGGTTGTTGCC
GGTCCTTTGTCAAGACCAAGAGACCGGATCC (SEQ ID NO: 158)

gXTN-6C:
TCTAGAGGTCTCAACCACGGCctgactcccgatcaagttgtagcgattgc
gtcgCATGACggagggaaacaagcattggagactgtccaacggctccttc
ccgtgttgtgtcaagcccAGAGACCGGATCC (SEQ ID NO: 159)

gXTN-7C:
TCTAGAGGTCTCAgcccacggtTTGACGCCTGCACAAGTGGTCGCCATCG
CCAGCCATGATGGCGGTAAGCAGGCGCTGGAAACAGTACAGCGCCTGCTG
CCTGTACTGTGCCAGGATAGAGACCGGATCC (SEQ ID NO: 160)

gXTN-8C:
TCTAGAGGTCTCAGGATCATGGActgaccccagaccaggtagtcgcaatc
gcgtcacatgacgggggaaagcaagccctggaaaccgtgcaaaggttgtt
gccggtcctttgtcaagaAGAGACCGGATCC (SEQ ID NO: 161)

gXTN-9C:
TCTAGAGGTCTCAaagaccacggcCTGACCCCAGACCAGGTAGTCGCAAT
CGCGTCAcatgacGGGGGAAAGCAAGCCCTGGAAACCGTGCAAAGGTTGT
TGCCGGTCCTTTGTCAAGAGAGACCGGATCC (SEQ ID NO: 162)

gXTN-10C:
TCTAGAGGTCTCACAAGACCACGGCctgactcccgatcaagttgtagcga
ttgcgtcgcatgacggagggaaacaagcattggagactgtccaacggctc
cttcccgtgttgtgtcaagcccaTggAAGAGACCGGATCC
(SEQ ID NO: 163)

gXTN-1T:
TCTAGAGGTCTCATTGACCCCAGACCAGGTAGTCGCAATCGCGTCAAACG
GAGGGGGAAAGCAAGCCCTGGAAACCGTGCAAAGGTTGTTGCCGGTCCTT
TGTCAAGACCACGGCAGAGACCGGATCC (SEQ ID NO: 164)

gXTN-2T:
TCTAGAGGTCTCACGGCctgactcccgatcaagttgtagcgattgcgtcg
AACGGTggagggaaacaagcattggagactgtccaacggctccttcccgt
gttgtgtcaagcccacggAGAGACCGGATCC (SEQ ID NO: 165)

gXTN-3T:
TCTAGAGGTCTCAacggtTTGACGCCTGCACAAGTGGTCGCCATCGCCTC
GAATGGCGGCGGTAAGCAGGCGCTGGAAACAGTACAGCGCCTGCTGCCTG
TACTGTGCCAGGATCATGAGAGACCGGATCC (SEQ ID NO: 166)

gXTN-4T:
TCTAGAGGTCTCACATGGActgaccccagaccaggtagtcgcaatcgcgt
caaacggagggggaaagcaagccctggaaaccgtgcaaaggttgttgccg
gtcctttgtcaagaccacAGAGACCGGATCC (SEQ ID NO: 167)

gXTN-5T:
TCTAGAGGTCTCAccacggcCTGACCCCAGACCAGGTAGTCGCAATCGCG
TCAaacggaGGGGGAAAGCAAGCCCTGGAAACCGTGCAAAGGTTGTTGCC
GGTCCTTTGTCAAGACCAAGAGACCGGATCC (SEQ ID NO: 168)

gXTN-6T:
TCTAGAGGTCTCAACCACGGCctgactcccgatcaagttgtagcgattgc
gtcgAACGGTggagggaaacaagcattggagactgtccaacggctccttc
ccgtgttgtgtcaagcccAGAGACCGGATCC (SEQ ID NO: 169)

gXTN-7T:
TCTAGAGGTCTCAgcccacggtTTGACGCCTGCACAAGTGGTCGCCATCG
CCAGCaatggcGGCGGTAAGCAGGCGCTGGAAACAGTACAGCGCCTGCTG
CCTGTACTGTGCCAGGATAGAGACCGGATCC (SEQ ID NO: 170)

gXTN-8T:
TCTAGAGGTCTCAGGATCATGGActgaccccagaccaggtagtcgcaatc
gcgtcaAACGGAgggggaaagcaagccctggaaaccgtgcaaaggttgtt
gccggtcctttgtcaagaAGAGACCGGATCC (SEQ ID NO: 171)

gXTN-9T:
TCTAGAGGTCTCAaagaccacggcCTGACCCCAGACCAGGTAGTCGCAAT
CGCGTCAAACGGAGGGGGAAAGCAAGCCCTGGAAACCGTGCAAAGGTTGT
TGCCGGTCCTTTGTCAAGAGAGACCGGATCC (SEQ ID NO: 172)

gXTN-10T:
TCTAGAGGTCTCACAAGACCACGGCctgactcccgatcaagttgtagcga
ttgcgtccaacggtggagggaaacaagcattggagactgtccaacggctc
cttcccgtgttgtgtcaagcccaTggAAGAGACCGGATCC
(SEQ ID NO: 173)

gXTN-1A:
TCTAGAGGTCTCATTGACCCCAGACCAGGTAGTCGCAATCGCGTCAaaca
ttGGGGGAAAGCAAGCCCTGGAAACCGTGCAAAGGTTGTTGCCGGTCCTT
TGTCAAGACCACGGCAGAGACCGGATCC (SEQ ID NO: 174)

gXTN-2A:
TCTAGAGGTCTCACGGCctgactcccgatcaagttgtagcgattgcgtcg
aacattggagggaaacaagcattggagactgtccaacggctccttcccgt
gttgtgtcaagcccacggAGAGACCGGATCC (SEQ ID NO: 175)

gXTN-3A:
TCTAGAGGTCTCAacggtTTGACGCCTGCACAAGTGGTCGCCATCGCCAG
CaatattGGCGGTAAGCAGGCGCTGGAAACAGTACAGCGCCTGCTGCCTG
TACTGTGCCAGGATCATGAGAGACCGGATCC (SEQ ID NO: 176)

gXTN-4A:
TCTAGAGGTCTCACATGGActgaccccagaccaggtagtcgcaatcgcgt
acAACATTgggggaaagcaagccctggaaaccgtgcaaaggttgttgccg
gtcctttgtcaagaccacAGAGACCGGATCC (SEQ ID NO: 177)

gXTN-5A:
TCTAGAGGTCTCAccacggcCTGACCCCAGACCAGGTAGTCGCAATCGCG
TCGAACATTGGGGGAAAGCAAGCCCTGGAAACCGTGCAAAGGTTGTTGCC
GGTCCTTTGTCAAGACCAAGAGACCGGATCC (SEQ ID NO: 178)

gXTN-6A:
TCTAGAGGTCTCAACCAtGGCctgactcccgatcaagttgtagcgattgc
gtcgaacattggagggaaacaagcattggagactgtccaacggctccttc
ccgtgttgtgtcaagcccAGAGACCGGATCC (SEQ ID NO: 179)

gXTN-7A:
TCTAGAGGTCTCAgcccacggtTTGACGCCTGCACAAGTGGTCGCCATCG
CCTCCAATATTGGCGGTAAGCAGGCGCTGGAAACAGTACAGCGCCTGCTG
CCTGTACTGTGCCAGGATAGAGACCGGATCC (SEQ ID NO: 180)

gXTN-8A:
TCTAGAGGTCTCAGGATCATGGActgaccccagaccaggtagtcgcaatc
gcgtcgaacattgggggaaagcaagccctggaaaccgtgcaaaggttgtt
gccggtcctttgtcaagaAGAGACCGGATCC (SEQ ID NO: 181)

-continued gXTN-9A:
TCTAGAGGTCTCAaagaccacggcCTGACCCCAGACCAGGTAGTCGCAATCGCGTCGAACATTGGGGGAAAGCAAGCCCTGGAAACCGTGCAAAGGTTGTTGCCGGTCCTTTGTCAAGAGAGACCGGATCC (SEQ ID NO: 182)

gXTN-10A:
TCTAGAGGTCTCACAAGACCACGGCctgactcccgatcaagttgtagcgattgcgtcgAACATTggagggaaacaagcattggagactgtccaacggctccttcccgtgttgtgtcaagcccaTggAAGAGACCGGATCC (SEQ ID NO: 183)

gXTN-1G:
TCTAGAGGTCTCATTGACCCCAGACCAGGTAGTCGCAATCGCGaacaataatGGGGGAAAGCAAGCCCTGGAAACCGTGCAAAGGTTGTTGCCGGTCCTTTGTCAAGACCACGGCAGAGACCGGATCC (SEQ ID NO: 184)

gXTN-2G:
TCTAGAGGTCTCACGGCctgactcccgatcaagttgtagcgattgcgaataacaatggagggaaacaagcattggagactgtccaacggctccttcccgtgttgtgtcaagcccacggAGAGACCGGATCC (SEQ ID NO: 185)

gXTN-3G:
TCTAGAGGTCTCAacggtTTGACGCCTGCACAAGTGGTCGCCATCGCCAACAACAACGGCGGTAAGCAGGCGCTGGAAACAGTACAGCGCCTGCTGCCTGTACTGTGCCAGGATCATGAGAGACCGGATCC (SEQ ID NO: 186)

gXTN-4G:
TCTAGAGGTCTCACATGGActgaccccagaccaggtagtcgcaatcgcgaacaataatgggggaaagcaagccctggaaaccgtgcaaaggttgttgccggtcctttgtcaagaccacAGAGACCGGATCC (SEQ ID NO: 187)

gXTN-5G:
TCTAGAGGTCTCAccacggcCTGACCCCAGACCAGGTAGTCGCAATCGCGAACAATAATGGGGGAAAGCAAGCCCTGGAAACCGTGCAAAGGTTGTTGCCGGTCCTTTGTCAAGACCAAGAGACCGGATCC (SEQ ID NO: 188)

gXTN-6G:
TCTAGAGGTCTCAACCAtGGCctgactcccgatcaagttgtagcgattgcgaataacaatggagggaaacaagcattggagactgtccaacggctccttcccgtgttgtgtcaagcccAGAGACCGGATCC (SEQ ID NO: 189)

gXTN-7G:
TCTAGAGGTCTCAgcccacggtTTGACGCCTGCACAAGTGGTCGCCATCGCCAACAACAACGGCGGTAAGCAGGCGCTGGAAACAGTACAGCGCCTGCTGCCTGTACTGTGCCAGGATAGAGACCGGATCC (SEQ ID NO: 190)

gXTN-8G:
TCTAGAGGTCTCAGGATCATGGActgaccccagaccaggtagtcgcaatcgcgaacaataatgggggaaagcaagccctggaaaccgtgcaaaggttgttgccggtcctttgtcaagaAGAGACCGGATCC (SEQ ID NO: 191)

gXTN-9G:
TCTAGAGGTCTCAaagaccacggcCTGACCCCAGACCAGGTAGTCGCAATCGCGAACAATAATGGGGGAAAGCAAGCCCTGGAAACCGTGCAAAGGTTGTTGCCGGTCCTTTGTCAAGAGAGACCGGATCC (SEQ ID NO: 192)

gXTN-10G:
TCTAGAGGTCTCACAAGACCACGGCctgactcccgatcaagttgtagcgattgcgaataacaatggagggaaacaagcattggagactgtccaacggctccttcccgtgttgtgtcaagcccaTggAAGAGACCGGATCC (SEQ ID NO: 193)

SbfI and SacI flanked pFUS fragments
(gene synthesized, SbfI-pFUS-SacI)
pFUS-X:
(SbfI)CCTGCAGGTCGACCGTCTCAGAACTTGAAGAGACCGTACGTGATCGTGGTCTCATggaTTGAAGAGACG GGTACCGAGCTC(SacI) (SEQ ID NO: 194)

pFUS-Z1:
CCTGCAGGTCGACCGTCTCATTGAAGAGACCGTACTGgatcgtGGTCTCACGGCctgaAGAGACGGGTACCGAGCTC (SEQ ID NO: 195)

pFUS-Z2:
CCTGCAGGTCGACCGTCTCATTGAAGAGACCGTACTGgatcgtGGTCTCAacggtctgaAGAGACGGGTACCGAGCTC (SEQ ID NO: 196)

pFUS-Z3:
CCTGCAGGTCGACCGTCTCATTGAAGAGACCGTACTGgatcgtGGTCTCACATGGActgaAGAGACGGGTACCGAGCTC (SEQ ID NO: 197)

pFUS-Z4:
CCTGCAGGTCGACCGTCTCATTGAAGAGACCGTACTGgatcgtGGTCTCAccacggcctgaAGAGACGGGTACCGAGCTC (SEQ ID NO: 198)

pFUS-Z5:
CCTGCAGGTCGACCGTCTCATTGAAGAGACCGTACTGgatcgtGGTCTCAACCACGGCctgaAGAGACGGGTACCGAGCTC (SEQ ID NO: 199)

pFUS-Z6:
CCTGCAGGTCGACCGTCTCATTGAAGAGACCGTACTGgatcgtGGTCTCAgcccacggtctgaAGAGACGGGTACCGAGCTC (SEQ ID NO: 200)

pFUS-Z7:
CCTGCAGGTCGACCGTCTCATTGAAGAGACCGTACTGgatcgtGGTCTCAGGATCATGGActgaAGAGACGGGTACCGAGCTC (SEQ ID NO: 201)

pFUS-Z8:
CCTGCAGGTCGACCGTCTCATTGAAGAGACCGTACTGgatcgtGGTCTCAaagaccacggcctgaAGAGACGGGTACCGAGCTC (SEQ ID NO: 202)

pFUS-Z9:
CCTGCAGGTCGACCGTCTCATTGAAGAGACCGTACTGgatcgtGGTCTCACAAGACCACGGCctgaAGAGACGGGTACCGAGCTC (SEQ ID NO: 203)

pFUS-Z10:
CCTGCAGGTCGACCGTCTCATTGAAGAGACCGTACTGgatcgtGGTCTCATggActgaAGAGACGGGTACCGAGCTC (SEQ ID NO: 204)

Example 7
Methylesterases and Methyltransferases 34aa
Consensus EBE (nn is replaced with relevant RVD):
QTTERIVAIGT (SEQ ID NO: 211)
nnGGTQALEAVLTALPRVCPGMV (SEQ ID NO: 212)

Backtranseq of 34aa
QTTERIVAIGT (SEQ ID NO: 211)
SH GGTQALEAVLTALPRVCPGMV (SEQ ID NO: 212)
(SH is a non-specific RVD)
CAGACCACCGAGAGGATCGTGGCCATCGGCACCAGCCACGGCGGCACCCAGGCCCTGGAGGCCGTGCTGACCGCCCTGCCCAGGGTGTGCCCCGGCATGGTG (SEQ ID NO: 102)

Methylesterase EBE (14EBEs in XTN backbone):
Bold Font: Methylesterse EBEs. All with non-specific RVD SH in this example.
Black Font: FLASH XTN Backbone.
The sequence is contiguous (SEQ ID NO: 207):
GACGGATCGGGAGATCTCCCGATCCCCTATGGTCGACTCTCAGTACAATC

TGCTCTGATGCCGCATAGTTAAGCCAGTATCTGCTCCCTGCTTGTGTGTT

GGAGGTCGCTGAGTAGTGCGCGAGCAAAATTTAAGCTACAACAAGGCAAG

GCTTGACCGACAATTGCATGAAGAATCTGCTTAGGGTTAGGCGTTTTGCG

CTGCTTCGCGATGTACGGGCCAGATATACGCGTTGACATTGATTATTGAC

TAGTTATTAATAGTAATCAATTACGGGGTCATTAGTTCATAGCCCATATA

TGGAGTTCCGCGTTACATAACTTACGGTAAATGGCCCGCCTGGCTGACCG

CCCAACGACCCCCGCCCATTGACGTCAATAATGACGTATGTTCCCATAGT

AACGCCAATAGGGACTTTCCATTGACGTCAATGGGTGGAgTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTGATGCGGTTTTGGCAGTACATCAATGGGCGTGGA

TAGCGGTTTGACTCACGGGGATTTCCAAGTCTCCACCCCATTGACGTCAA

TGGGAGTTTGTTTTGGCACCAAAATCAACGGGACTTTCCAAAATGTCGTA

ACAACTCCGCCCCATTGACGCAAATGGGCGGTAGGCGTGTACGGTGGGAG

-continued

GTCTATATAAGCAGAGCTCTCTGGCTAACTAGAGAACCCACTGCTTACTG

GCTTATCGAAATTAATACGACTCACTATAGGGAGACCCAAGCTGGCTAGC

ACCATGGACTACAAAGACCATGACGGTGATTATAAAGATCATGACATCGA

TTACAAGGATGACGATGACAAGATGGCCCCCAAGAAGAAGAGGAAGGTGG

GCATTCACCGCGGGGTACCTATGGTGGACTTGAGGACACTCGGTTATTCG

CAACAGCAACAGGAGAAAATCAAGCCTAAGGTCAGGAGCACCGTCGCGCA

ACACCACGAGGCGCTTGTGGGGCATGGCTTCACTCATGCGCATATTGTCG

CGCTTTCACAGCACCCTGCGGCGCTTGGGACGGTGGCTGTCAAATACCAA

GATATGATTGCGGCCCTGCCCGAAGCCACGCACGAGGCAATTGTAGGGGT

CGGTAAACAGTGGTCGGGAGCGCGAGCACTTGAGGCGCTGCTGACTGTGG

CGGGTGAGCTTAGGGGGCCTCCGCTCCAGCTCGACACCGGGCAGCTGCTG

AAGATCGCGAAGAGAGGGGGAGTAACAGCGGTAGAGGCAGTGCACGCCTG

GCGCAATGCGCTCACCGGGGCCCCCTTGAAC

CAGACCACCGAGAGGATCGTGGCCATCGGCACCAGCCACGGCGGCACCCA

GGCCCTGGAGGCCGTGCTGACCGCCCTGCCCAGGGTGTGCCCCGGCATGG

TGCAGACCACCGAGAGGATCGTGGCCATCGGCACCAGCCACGGCGGCACC

CAGGCCCTGGAGGCCGTGCTGACCGCCCTGCCCAGGGTGTGCCCCGGCAT

GGTGCAGACCACCGAGAGGATCGTGGCCATCGGCACCAGCCACGGCGGCA

CCCAGGCCCTGGAGGCCGTGCTGACCGCCCTGCCCAGGGTGTGCCCCGGC

ATGGTGCAGACCACCGAGAGGATCGTGGCCATCGGCACCAGCCACGGCGG

CACCCAGGCCCTGGAGGCCGTGCTGACCGCCCTGCCCAGGGTGTGCCCCG

GCATGGTGCAGACCACCGAGAGGATCGTGGCCATCGGCACCAGCCACGGC

GGCACCCAGGCCCTGGAGGCCGTGCTGACCGCCCTGCCCAGGGTGTGCCC

CGGCATGGTGCAGACCACCGAGAGGATCGTGGCCATCGGCACCAGCCACG

GCGGCACCCAGGCCCTGGAGGCCGTGCTGACCGCCCTGCCCAGGGTGTGC

CCCGGCATGGTGCAGACCACCGAGAGGATCGTGGCCATCGGCACCAGCCA

CGGCGGCACCCAGGCCCTGGAGGCCGTGCTGACCGCCCTGCCCAGGGTGT

GCCCCGGCATGGTGCAGACCACCGAGAGGATCGTGGCCATCGGCACCAGC

CACGGCGGCACCCAGGCCCTGGAGGCCGTGCTGACCGCCCTGCCCAGGGT

GTGCCCCGGCATGGTGCAGACCACCGAGAGGATCGTGGCCATCGGCACCA

GCCACGGCGGCACCCAGGCCCTGGAGGCCGTGCTGACCGCCCTGCCCAGG

GTGTGCCCCGGCATGGTGCAGACCACCGAGAGGATCGTGGCCATCGGCAC

CAGCCACGGCGGCACCCAGGCCCTGGAGGCCGTGCTGACCGCCCTGCCCA

GGGTGTGCCCCGGCATGGTGCAGACCACCGAGAGGATCGTGGCCATCGGC

ACCAGCCACGGCGGCACCCAGGCCCTGGAGGCCGTGCTGACCGCCCTGCC

CAGGGTGTGCCCCGGCATGGTGCAGACCACCGAGAGGATCGTGGCCATCG

GCACCAGCCACGGCGGCACCCAGGCCCTGGAGGCCGTGCTGACCGCCCTG

CCCAGGGTGTGCCCCGGCATGGTGCAGACCACCGAGAGGATCGTGGCCAT

CGGCACCAGCCACGGCGGCACCCAGGCCCTGGAGGCCGTGCTGACCGCCC

TGCCCAGGGTGTGCCCCGGCATGGTGCAGACCACCGAGAGGATCGTGGCC

ATCGGCACCAGCCACGGCGGCACCCAGGCCCTGGAGGCCGTGCTGACCGC

CCTGCCCAGGGTGTGCCCCGGCATGGTG

CTGACACCCGAACAGGTGGTCGCCATTGCTAATAATAACGGAGGACGGCC

AGCCTTGGAGTCCATCGTAGCCCAATTGTCCAGGCCCGATCCCGCGTTGG

CTGCGTTAACGAATGACCATCTGGTGGCGTTGGCATGTCTTGGTGGACGA

CCCGCGCTCGATGCAGTCAAAAAGGGTCTGCCTCATGCTCCCGCATTGAT

CAAAAGAACCAACCGGCGGATTCCCGAGAGAACTTCCCATCGAGTCGCGG

GATCCCAACTAGTC

What is claimed is:

1. A fusion protein comprising (a) at least one amino acid sequence having the sequence of LSTEQVVAIAS$X_1X_2$GGKQALEAVKAQLLVLRAAPYE (SEQ ID NO: 1), wherein $X_1X_2$ comprises a repeat variable diresidue (RVD), and wherein the RVD consists of SI, SN, SH, NP, NH, NT, NK, ND, HN, HY, HD, HH, RN, RS, NG or GS and (b) an effector domain, wherein the effector domain comprises a nuclease, a nickase, a transcriptional activator, a transcriptional repressor, a methyltransferase, a deacetylase or any functional fragment thereof and wherein the effector domain is neither isolated nor derived from a *Ralstonia* TALEN.

2. The fusion protein of claim 1, further comprising a second amino acid sequence having the sequence of (SEQ ID NO: 1)
LSTEQVVAIAS$X_1X_2$GGKQALEAVKAQLLVLRAAPYE, wherein $X_1X_2$ comprises a repeat variable diresidue (RVD), and wherein the RVD consists of SI, SN, SH, NP, NH, NT, NK, ND, HN, HY, HD, HH, RN, RS, NG or GS.

3. The fusion protein of claim 1 or 2, wherein the at least one amino acid sequence of (a) or the second amino acid sequence comprises the amino acid sequence of SEQ ID NO: 2, SEQ ID NO:3, SEQ ID NO:4, SEQ ID NO:5, SEQ ID NO:6, SEQ ID NO:7, SEQ ID NO:8, SEQ ID NO:11, SEQ ID NO:12, SEQ ID NO:13, SEQ ID NO: 14, SEQ ID NO:15, SEQ ID NO:16, SEQ ID NO:17, SEQ ID NO:18, or SEQ ID NO: 19.

4. The fusion protein of any one of claims 1 or 2 wherein the effector domain comprises at least one nuclease.

5. The fusion protein of any one of claims 1 or 2 wherein the nuclease comprises an endonuclease.

6. The fusion protein of claim 5, wherein the endonuclease comprises a Fok I endonuclease.

7. The fusion protein of claim 5, wherein the endonuclease comprises an I-SceI endonuclease.

8. The fusion protein of any one of claims 1 or 2 wherein the effector domain comprises a zinc-finger nuclease.

* * * * *